(12) United States Patent
Takeda et al.

(10) Patent No.: US 9,751,887 B2
(45) Date of Patent: Sep. 5, 2017

(54) IMIDAZO[1,2-B]PYRIDAZINE DERIVATIVES AS KINASE INHIBITORS

(71) Applicant: Daiichi Sankyo Company, Limited, Chuo-ku, Tokyo (JP)

(72) Inventors: Yasuyuki Takeda, Shinagawa-ku (JP); Kenji Yoshikawa, Shinagawa-ku (JP); Yoshiko Kagoshima, Shinagawa-ku (JP); Yuko Yamamoto, Shinagawa-ku (JP); Ryoichi Tanaka, Shinagawa-ku (JP); Yuichi Tominaga, Shinagawa-ku (JP); Masaki Kiga, Shinagawa-ku (JP); Yoshito Hamada, Shinagawa-ku (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/926,973

(22) Filed: Oct. 29, 2015

(65) Prior Publication Data
US 2016/0046639 A1 Feb. 18, 2016

Related U.S. Application Data

(63) Continuation of application No. 14/378,318, filed as application No. PCT/JP2013/065328 on Jun. 3, 2013, now Pat. No. 9,187,489.

(30) Foreign Application Priority Data

Jun. 4, 2012 (JP) .................. 2012-127079

(51) Int. Cl.
C07D 487/04 (2006.01)
(52) U.S. Cl.
CPC .................. *C07D 487/04* (2013.01)
(58) Field of Classification Search
CPC .................. C07D 487/01
See application file for complete search history.

(56) References Cited

U.S. PATENT DOCUMENTS

| 8,450,322 B2 | 5/2013 | Andrews |
| 8,507,488 B2 | 8/2013 | Albaugh |
| 8,653,076 B2 | 2/2014 | Prien |
| 2008/0167314 A1 | 7/2008 | Uchikawa |
| 2010/0041662 A1 | 2/2010 | Ferrand |
| 2011/0166122 A1 | 7/2011 | Andrews |
| 2011/0166133 A1 | 7/2011 | Albaugh |

FOREIGN PATENT DOCUMENTS

| JP | 2003-231687 A | 8/2003 |
| JP | 2009-227599 A | 10/2009 |
| JP | 2010-508315 A | 3/2010 |
| JP | 2011-520887 A | 7/2011 |
| JP | 2012-503018 A | 2/2012 |
| WO | 01/14380 A1 | 3/2001 |
| WO | 02/20479 A1 | 3/2002 |
| WO | 02/20513 A1 | 3/2002 |
| WO | 2005/049033 A1 | 6/2005 |
| WO | 2005/103010 A2 | 11/2005 |
| WO | 2006/070943 A1 | 7/2006 |
| WO | 2006/082392 A1 | 8/2006 |
| WO | 2006/087530 A1 | 8/2006 |
| WO | 2006/087538 A1 | 8/2006 |
| WO | 2007/013673 A1 | 2/2007 |
| WO | 2007/025540 A2 | 3/2007 |
| WO | 2007/147646 A1 | 12/2007 |
| WO | 2008/052734 A1 | 5/2008 |
| WO | 2008/072682 A1 | 6/2008 |
| WO | 2011/049332 A2 | 4/2011 |
| WO | 2012/005299 A1 | 1/2012 |
| WO | 2012/125667 A1 | 9/2012 |

OTHER PUBLICATIONS

McMahon et al. (2000).*
Pinedo et al. (2000).*
First Office Action mailed Sep. 22, 2015, issued in corresponding Chinese Application No. 201380041498X, filed Jun. 3, 2013, 14 pages.
Acquaviva, J., et al., "The Multifaceted Roles of the Receptor Tyrosine Kinase ROS in Development and Cancer," Biochimica et Biophysica Acta 1795(1):37-52, Jan. 2009.
Bapat, A.A., et al., "Perineural Invasion and Associated Pain in Pancreatic Cancer," Nature Reviews: Cancer 11(10):695-707, Oct. 2011.
Bardelli, A., et al., "Mutational Analysis of the Tyrosine Kinome in Colorectal Cancers," Science 300(5621):949, May 2003.
Charest, A., et al., "Fusion of FIG to the Receptor Tyrosine Kinase ROS in a Glioblastoma With an Interstitial del(6)(q21q21)," Genes, Chromosomes & Cancer 37(1):58-71, May 2003.
Charest, A., et al., "Oncogenic Targeting of an Activated Tyrosine Kinase to the Golgi Apparatus in a Glioblastoma," Proceedings of the National Academy of Sciences of the U.S.A. (PNAS) 100(3):916-921, Feb. 2003.
Charest, A., et al., "ROS Fusion Tyrosine Kinase Activates a SH2 Domain-Containing Phosphatase-2/Phosphatidylinositol 3-Kinase/Mammalian Target of Rapamycin Signaling Axis to Form Glioblastoma in Mice," Cancer Research 66(15):7473-7481, Aug. 2006.
Davidson, B., et al., "Expression and Activation of the Nerve Growth Factor Receptor TrkA in Serous Ovarian Carcinoma," Clinical Cancer Research 9(6):2248-2259, Jun. 2003.

(Continued)

*Primary Examiner* — Paul V Ward
(74) *Attorney, Agent, or Firm* — Christensen O'Connor Johnson Kindness PLLC

(57) ABSTRACT

The present invention is intended to provide a compound or a pharmacologically acceptable salt thereof which is useful in the treatment of a tumor through its ROS1 kinase enzyme activity inhibitory effect and NTRK kinase enzyme inhibitory effect. The present invention provides a compound having an imidazo[1,2-b]pyridazine structure represented by the general formula (I) or a pharmacologically acceptable salt thereof, and a pharmaceutical composition comprising the compound. In the formula, $R^1$, G, T, $Y^1$, $Y^2$, $Y^3$, and $Y^4$ are as defined herein.

17 Claims, No Drawings

(56) References Cited

OTHER PUBLICATIONS

El-Deeb, I.M., et al., "Design, Synthesis, Screening, and Molecular Modeling Study of a New Series of ROS1 Receptor Tyrosine Kinase Inhibitors," Bioorganic & Medicinal Chemistry Letters 19(19):5622-5626, Oct. 2009.
George, D.J., et al., "Sustained In Vivo Regression of Dunning H Rat Prostate Cancers Treated With Combinations of Androgen Ablation and Trk Tyrosine Kinase Inhibitors, CEP-751 (KT-6587) or CEP-701 (KT-5555)," Cancer Research 59(10):2395-2401, May 1999.
Gu, T.-L., et al., "Survey of Tyrosine Kinase Signaling Reveals ROS Kinase Fusions in Human Cholangiocarcinoma," PLoS ONE 6(1):e15640, Jan. 2011, pp. 1-9.
International Search Report and Written Opinion mailed Jun. 25, 2013, issued in corresponding International Application No. PCT/JP2013/065328, filed Jun. 3, 2012, 19 pages.
Jänne, P.A., and M. Meyerson, "ROS1 Rearrangements in Lung Cancer: A New Genomic Subset of Lung Adenocarcinoma," Journal of Clinical Oncology 30(8):878-879, Mar. 2012.
Jun, H.J., et al., "Epigenetic Regulation of c-ROS Receptor Tyrosine Kinase Expression in Malignant Gliomas," Cancer Research 69(6):2180-2184, Mar. 2009.
Lee, J., et al., "A Novel Role for BDNF-TrkB in the Regulation of Chemotherapy Resistance in Head and Neck Squamous Cell Carcinoma," PLoS ONE 7(1):e30246, Jan. 2012, pp. 1-11.
Light, J.E., et al., "Clinical Significance of NTRK Family Gene Expression in Neuroblastomas," Pediatric Blood Cancer 59(2):226-232, Aug. 2012.
Lippa, B., et al., "Discovery of Novel Isothiazole Inhibitors of the TrkA Kinase: Structure-Activity Relationship, Computer Modeling, Optimization, and Identification of Highly Potent Antagonists," Bioorganic & Medicinal Chemistry Letters 16(13):3444-3448, Jul. 2006.
Patapoutian, A., and L.F. Reichardt, "Trk Receptors: Mediators of Neurotrophin Action," Current Opinion in Neurobiology 11(3)272-280, Jun. 2001.
Rey, V., et al., "Photochemical Cyclization of Thioformanilides by Chloranil: An Approach to 2-Substituted Benzothiazoles," Tetrahedron Letters 50(33):4720-4723, Aug. 2009.
Rikova, K., et al., "Global Survey of Phosphotyrosine Signaling Identifies Oncogenic Kinases in Lung Cancer," Cell 131(6):1190-1203, Dec. 2007.
Tognon, C., et al., "Expression of the ETV6-NTRK3 Gene Fusion as a Primary Event in Human Secretory Breast Carcinoma," Cancer Cell 2(5):367-376, Nov. 2002.
Takeuchi, K., et al., "RET, ROS1 and ALK Fusions in Lung Cancer," Nature Medicine 18(3):378-381, Mar. 2012.
Truzzi, F., et al., "Neurotrophins and Their Receptors Stimulate Melanoma Cell Proliferation and Migration," Journal of Investigative Dermatology 128(8):2031-2040, Aug. 2008.
Weeraratna, A.T., et al., "Rational Basis for Trk Inhibition Therapy for Prostate Cancer," Prostate 45(2):140-148, Oct. 2000.
Park, B.S., et al., "Design, Synthesis and Biological Evaluation of New Potent and Highly Selective ROS1-Tyrosine Kinase Inhibitor," Bioorganic & Medicinal Chemistry Letters 19(16):4720-4723, Aug. 2009.
McMahon, G., "VEGF Reception Signaling in Tumor Angiogenesis," The Oncologist 5(Suppl. 1):3-10, Apr. 2000.
Pinedo, H.M., and D.J. Slamon, "Translational Research: The Role of VEGF in Tumor Angiogenesis," The Oncologist 5(Suppl 1):1-2, Apr. 2000.

* cited by examiner

IMIDAZO[1,2-B]PYRIDAZINE DERIVATIVES AS KINASE INHIBITORS

TECHNICAL FIELD

The present invention relates to compounds having a particular chemical structure or pharmacologically acceptable salts thereof which have a potent inhibitory effect to ROS1 kinase and NTRK kinase.

BACKGROUND ART

The ROS1 gene encodes receptor tyrosine kinase discovered as a human ortholog of the cancer gene product v-ros of avian sarcoma virus UR2 (University of Rochester tumor virus 2) (Non Patent Reference 1). The ROS1 fusion gene resulting from the chromosomal rearrangement containing the ROS1 gene and the subsequent fusion of the ROS1 gene to another gene was discovered in a lioblastoma cell line U118MG. In the U118MG cells, a gene encoding a Golgi protein FIG (fused in glioblastoma) is fused with the ROS1 gene to form a gene encoding FIG-ROS1 fusion protein (Non Patent Reference 2). The fusion between FIG and ROS1 causes structural change that constitutively activates ROS1 kinase enzyme activity, and the FIG-ROS1 fusion protein has cell transformation activity and tumorigenic activity mediated by the activation of the ROS1 signaling pathway involving STAT3, ERK, and SHP2 (Non Patent References 3 and 4).

The chromosomal translocation of the ROS1 gene has also been identified in a non-small cell lung cancer cell line HCC78 and clinical specimens of lung cancers. The fusion gene of the SLC34A2 gene and the ROS1 gene has been reported in the HCC78 cells, while the presence of the transmembrane protein-encoding CD74-ROS1 fusion gene of the CD74 gene and the ROS1 gene has been reported in non-small cell lung cancer patient specimens (Non Patent Reference 5). The fusion gene of the FIG gene and the ROS1 gene has been found in 2 out of 23 patient specimens of bile duct cancer (Non Patent Reference 6).

The large-scale screening of patient specimens using FISH (fluorescent in situ hybridization) has identified fusion genes of the ROS1 gene with SDC, CD74, EZR, SLC34A2, LRIG3, or TPM3. Any of the ROS1 fusion genes SDC-ROS1, CD74-ROS1, EZR-ROS1, SLC34A2-ROS1, LRIG3-ROS1, and TPM3-ROS1 have been detected in 13 out of 1476 non small cell lung cancer patient specimens (Non Patent Reference 7).

Likewise, the large-scale screening of non-small cell lung cancer patient specimens using FISH has found the ROS1 fusion gene in 18 out of 1073 cases (Non Patent Reference 8). In addition, analysis using patient specimens has showed that the ROS1 gene is highly expressed in brain tumor (Non Patent References 1 and 9).

ROS1 has been shown to be activated in cancer expressing the ROS1 fusion gene (e.g., non-small cell lung cancer, bile duct cancer, or brain tumor) (Non Patent References 5 and 6). Thus, a drug that inhibits ROS1 kinase activity can block the downstream of the ROS1 pathway, i.e. STAT3, ERK, SHP2, which contribute the tumor growth and tumor cell survival. Therefore, ROS1 is expected to be useful as a therapeutic drug for cancer (Non Patent References 1, 6, and 8). Compounds such as crizotinib (Non Patent Reference 8), TAE684 (Non Patent Reference 6), pyrazole derivatives (Non Patent References 10 and 11), and aminopyrazine derivatives (Patent Reference 1) have been reported to have a ROS1 kinase enzyme activity inhibitory effect. These compounds, however, differ in structure from the compounds of the present invention.

Neurotrophic tyrosine kinase receptor, also called tropomyosin-related kinase (Trk), is a high-affinity receptor that is activated by a soluble growth factor called neurotrophin (NT). The NTRK receptor family has three members: NTRK1 (also called TrkA), NTRK2 (also called TrkB), and NTRK3 (also called TrkC).

NT includes a plurality of proteins as follows: a nerve growth factor (NGF) which activates NTRK1, a brain-derived neurotrophic factor (BDNF) and NT-4/5 which activate NTRK2, and NT3 which activates NTRK3. Each NTRK receptor contains an extracellular domain (ligand-binding site), a transmembrane domain, and an intracellular domain (containing a kinase domain). Upon binding to a ligand, each kinase catalyzes autophosphorylation and then activates the downstream signal transduction pathway.

NTRK is widely expressed in nerve tissues during their development period and plays an important role for the maintenance and survival of these cells. The previous study shows that NTRK plays an important role in both the development and function of the nervous system (Non Patent Reference 12).

A large number of references state that NTRK signal transduction is associated with cancer. For example, NTRK exists at a low expression level in regions other than the nervous system in adult humans, whereas the expression of NTRK is increased at the late stage of prostate cancer. In normal prostate tissues and androgen-dependent prostate tumor at the early state, NTRK1 is expressed only at a low level or an undetectable level, but neither NTRK2 nor NTRK3 is expressed. In androgen-independent prostate cancer at the late stage, however, all isoforms of the NTRK receptors and their ligands are overexpressed. The evidence shows that these late-stage prostate cancer cells depend on NTRK for their tumor survival. Thus, NTRK inhibitors may induce apoptosis for androgen-independent prostate cancer (Non Patent Reference 13). In addition, recent references also show that the overexpression, activation, amplification, fusion gene formation, or mutation of NTRK is related to neuroblastoma (Non Patent Reference 14), secretory breast cancer (Non Patent Reference 15), colorectal cancer (Non Patent Reference 16), ovary cancer (Non Patent Reference 17), head and neck cancer (Non Patent Reference 18), pancreatic cancer (Non Patent Reference 19), and melanoma (Non Patent Reference 20).

Selective NTRK tyrosine kinase inhibitors have been reported, including CEP-751, CEP-701 (Non Patent Reference 21), indolocarbazole compounds (Patent Reference 2), oxindole compounds (Patent References 3 and 4), pyrazolyl condensed-ring compounds (Patent Reference 5), isothiazole compounds (Non Patent Reference 22), and other various compounds (Patent References 6, 7, 8, 9, and 10). These compounds, however, differ in structure from the compound of the present invention.

Lck inhibitors (Patent Reference 11), PKC inhibitors (Patent References 12 and 13), and NTRK inhibitors (Patent References 14 and 15) are known as compounds having an imidazopyridazine skeleton. Nevertheless, none of the known compounds having an imidazopyridazine skeleton exhibit ROS1 kinase enzyme inhibitory activity and NTRK inhibitory activity.

CITATION LIST

Patent References

Patent Reference 1: WO2012/005299
Patent Reference 2: WO01/14380

Patent Reference 3: WO02/20479
Patent Reference 4: WO02/20513
Patent Reference 5: Japanese Patent Laid-Open No. 15-231687
Patent Reference 6: WO2005/049033
Patent Reference 7: WO2005/103010
Patent Reference 8: WO2006/082392
Patent Reference 9: WO2006/087530
Patent Reference 10: WO2006/087538
Patent Reference 11: WO2007/013673
Patent Reference 12: WO2007/025540
Patent Reference 13: WO2007/147646
Patent Reference 14: WO2008/052734
Patent Reference 15: WO2012/125667

Non Patent References

Non Patent Reference 1: Biochim. Biophys. Acta, 1795, 37-52 (2009)
Non Patent Reference 2: Genes Chromosomes Cancer, 37, 58-71 (2003)
Non Patent Reference 3: Proc. Natl. Acad. Sci. USA, 100, 916-921 (2003)
Non Patent Reference 4: Cancer Res., 66, 7473-7481 (2006)
Non Patent Reference 5: Cell, 131, 1190-1203 (2007)
Non Patent Reference 6: PLoS One, 6 (1), e15640 (2011)
Non Patent Reference 7: Nat. Medicine, 2658 (2012)
Non Patent Reference 8: J. Clin. Oncol., 2011. 39. 4197 (2012)
Non Patent Reference 9: Cancer Res., 69, 2180-2184 (2009)
Non Patent Reference 10: Bioorg. Med. Chem. Lett., 19, 4720-4723 (2009)
Non Patent Reference 11: Bioorg. Med. Chem. Lett., 19, 5622-5626 (2009)
Non Patent Reference 12: Current Opinion in Neurobiology, 11, 272-280 (2001)
Non Patent Reference 13: The Prostate, 45, 140-148 (2000)
Non Patent Reference 14: Pediatr Blood Cancer, 59, 226-232 (2012)
Non Patent Reference 15: Cancer Cell, 2, 367-376 (2002)
Non Patent Reference 16: Science, 300, 949-949 (2003)
Non Patent Reference 17: Clinical Cancer Research, 9, 2248-2259 (2003)
Non Patent Reference 18: PLos ONE 7 (1), e30246 (2012)
Non Patent Reference 21: Cancer Research, 59, 2395-2341 (1999)
Non Patent Reference 22: Bioorg. Med. Chem. Lett., 16, 3444-3448 (2006)

SUMMARY OF INVENTION

Technical Problem

An object of the present invention is to provide a novel low-molecular-weight compound that has a potent ROS1 kinase enzyme activity inhibitory effect and NTRK kinase enzyme inhibitory activity and exhibits an antitumor effect.

Solution to Problem

The present invention relates to the following (1) to (47):
(1) A compound represented by the general formula (I) or a pharmacologically acceptable salt thereof:

[Formula 1]

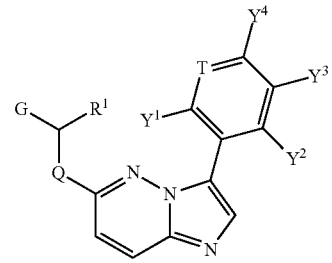

(I)

wherein
$R^1$ represents a hydrogen atom, a $C_1$-$C_6$ alkyl group, a fluoro-$C_1$-$C_6$ alkyl group, or a hydroxy-$C_1$-$C_6$ alkyl group;
Q represents an oxygen atom or $R^a$N, wherein
$R^a$ represents a hydrogen atom or a $C_1$-$C_6$ alkyl group;
G represents a phenyl group or a 5- or 6-membered heteroaryl group having, in the ring, 1 to 3 heteroatoms independently selected from the group consisting of a nitrogen atom, an oxygen atom, and a sulfur atom, wherein the 5-membered heteroaryl group optionally has 1 or 2 substituents independently selected from the group consisting of a halogen atom, a cyano group, a $C_1$-$C_6$ alkyl group, a $C_1$-$C_6$ alkoxy group, a dihalo-$C_1$-$C_6$ alkyl group, and a trihalo-$C_1$-$C_6$ alkyl group, and
the phenyl group and the 6-membered heteroaryl group each optionally have 1 to 3 substituents independently selected from the group consisting of a 5- or 6-membered heteroaryl group having, in the ring, 1 to 3 heteroatoms independently selected from the group consisting of a nitrogen atom, an oxygen atom, and a sulfur atom, a halogen atom, a cyano group, a $C_1$-$C_6$ alkyl group, a $C_1$-$C_6$ alkoxy group, and a trihalo-$C_1$-$C_6$ alkyl group;
T represents a nitrogen atom or $CR^b$, wherein
$R^b$ represents a hydrogen atom, a halogen atom, a $C_1$-$C_6$ alkyl group, a $C_1$-$C_6$ alkoxy group, or a cyano group;
$Y^1$ and $Y^2$ each independently represents a hydrogen atom, a halogen atom, a $C_1$-$C_6$ alkyl group, a $C_1$-$C_6$ alkoxy group, or a cyano group; and
$Y^3$ and $Y^4$ each independently represents a hydrogen atom, a group selected from group A described below, or a group represented by the following formula (II):

[Formula 2]

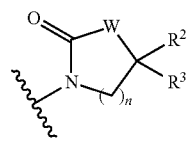

(II)

wherein
W represents an oxygen atom or $CR^cR^d$, wherein
$R^c$ and $R^d$ each independently represents a hydrogen atom, a $C_1$-$C_6$ alkyl group, or an amino group, or
$R^c$ and $R^d$ optionally form a $C_3$-$C_6$ cycloalkyl group together with the carbon atom bonded to $R^c$ and $R^d$; n represents 0, 1, or 2;
$R^2$ and $R^3$ each independently represents a hydrogen atom, an amino group, a $C_1$-$C_6$ alkyl group, an amino-$C_1$-$C_6$ alkyl group, a $C_1$-$C_6$ alkylamino group, or a di-$C_1$-$C_6$ alkylamino group (provided that any one of $Y^3$ and $Y^4$ inevitably represents a hydrogen atom, and the other group represents a group other than a hydrogen atom), group A: —O-M, —S-M, and —NH-M (M represents a $C_1$-$C_6$ alkyl group having 1 or 2 substituents independently selected from group B described below, an amino-$C_3$-$C_6$ cycloalkyl group, a 4- to 6-membered aliphatic heterocyclic group having one nitrogen atom in the ring, or a 5- or 6-membered aliphatic heterocyclic group having 1 or 2 substituents independently selected from group D described below and having one nitrogen atom in the ring), group B: an amino group, a hydroxy group, a $C_1$-$C_6$ alkylamino group, a di-$C_1$-$C_6$ alkylamino group, a $C_3$-$C_6$ cycloalkylamino group, an amino-$C_3$-$C_6$ cycloalkyl group, a hydroxy-$C_1$-$C_6$ alkylamino group, a 4- to 6-membered aliphatic heterocyclic group having one nitrogen atom in the ring, and a 6-membered aliphatic heterocyclic group having one nitrogen atom and one oxygen atom in the ring (the 4- to 6-membered aliphatic heterocyclic group having one nitrogen atom in the ring and the 6-membered aliphatic heterocyclic group having one nitrogen atom and one oxygen atom in the ring each optionally having 1 or 2 substituents independently selected from group C described below), group C: a halogen atom, a $C_1$-$C_6$ alkyl group, and a hydroxy-$C_1$-$C_6$ alkyl group, and group D: an amino group and a halogen atom.

(2) A compound according to (1) or a pharmacologically acceptable salt thereof, wherein in the formula (I),
Q represents an oxygen atom.

(3) A compound according to (1) or a pharmacologically acceptable salt thereof, wherein in the formula (I),
Q represents $R^a$N, wherein
$R^a$ represents a hydrogen atom or a $C_1$-$C_6$ alkyl group.

(4) A compound according to any one of (1) to (3) or a pharmacologically acceptable salt thereof, wherein in the formula (I),
$Y^3$ represents a hydrogen atom.

(5) A compound according to any one of (1) to (4) or a pharmacologically acceptable salt thereof, wherein in the formula (I),
G is represented by the following formula (III):

[Formula 3]

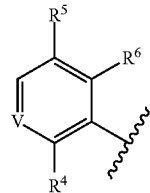

(III)

wherein
V represents $CR^e$ or a nitrogen atom; and
$R^4$, $R^5$, $R^6$, and $R^e$ each independently represent a hydrogen atom, a halogen atom, a cyano group, or a 5- or 6-membered heteroaryl group having, in the ring, 1 to 3 heteroatoms independently selected from the group consisting of a nitrogen atom, an oxygen atom, and a sulfur atom (provided that when V represents $CR^e$, at least one of $R^4$, $R^5$, $R^6$, and $R^e$ represents a hydrogen atom).

(6) A compound according to any one of (1) to (4) or a pharmacologically acceptable salt thereof, wherein in the formula (I), G is represented by the following formula (IV):

[Formula 4]

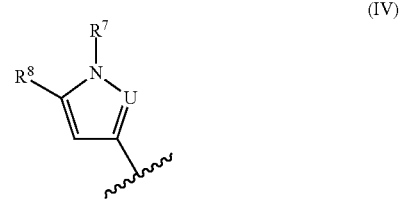

(IV)

wherein
U represents a nitrogen atom or CH;
$R^7$ represents a hydrogen atom or a $C_1$-$C_6$ alkyl group; and
$R^8$ represents a hydrogen atom, a $C_1$-$C_6$ alkyl group, or a halogen atom.

(7) A compound according to any one of (1) to (4) or a pharmacologically acceptable salt thereof, wherein in the formula (I),
G is any of the following $G^a$ to $G^e$:

[Formula 5]

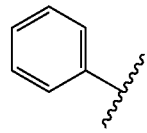

$G^a$

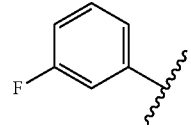

$G^b$

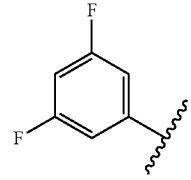

$G^c$

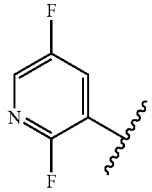

$G^d$

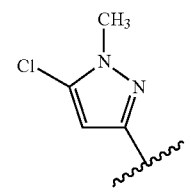

$G^e$ (8) A compound according to any one of (1) to (7) or a pharmacologically acceptable salt thereof, wherein in the formula (I), $Y^4$ represents a group selected from group $A^1$:

group $A^1$: —O-$M^1$, —S-$M^1$, and —NH-$M^1$ ($M^1$ represents a $C_1$-$C_6$ alkyl group having 1 or 2 substituents independently selected from group $B^1$ described below, an amino-$C_3$-$C_6$ cycloalkyl group, a 4- to 6-membered aliphatic heterocyclic group having one nitrogen atom in the ring, or a 5- or 6-membered aliphatic heterocyclic group substituted by 1 or 2 halogen atoms and having one nitrogen atom in the ring), group $B^1$: an amino group, a hydroxy group, a $C_1$-$C_6$ alkylamino group, a di-$C_1$-$C_6$ alkylamino group, a $C_3$-$C_6$ cycloalkylamino group, an amino-$C_3$-$C_6$ cycloalkyl group, a hydroxy-$C_1$-$C_6$ alkylamino group, and a 4- to 6-membered aliphatic heterocyclic group having one nitrogen atom in the ring (the 4- to 6-membered aliphatic heterocyclic group having one nitrogen atom in the ring optionally having 1 or 2 substituents independently selected from group $C^1$ described below), and group $C^1$: a halogen atom, a $C_1$-$C_6$ alkyl group, and a hydroxy-$C_1$-$C_6$ alkyl group.

(9) A compound according to any one of (1) to (7) or a pharmacologically acceptable salt thereof, wherein in the formula (I), $Y^4$ represents —O-$M^2$, wherein $M^2$ is any of the following $M^{2a}$ to $M^{2l}$:

[Formula 6]

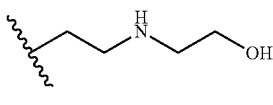
$M^{2a}$

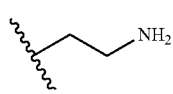
$M^{2b}$

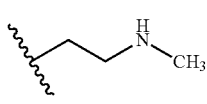
$M^{2c}$

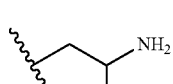
$M^{2d}$

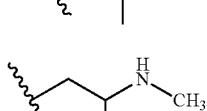
$M^{2e}$

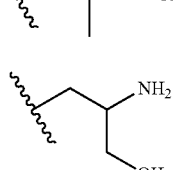
$M^{2f}$

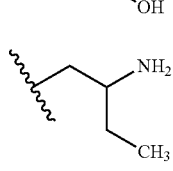
$M^{2g}$

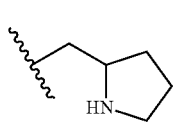
$M^{2h}$

-continued

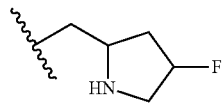
$M^{2i}$

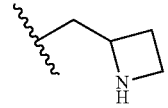
$M^{2j}$

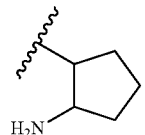
$M^{2k}$

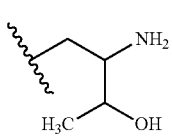
$M^{2l}$

(10) A compound according to any one of (1) to (7) or a pharmacologically acceptable salt thereof, wherein in the formula (I), $Y^4$ is represented by the following formula (V):

[Formula 7]

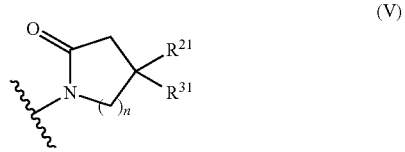
(V)

wherein n represents 1 or 2; and $R^{21}$ and $R^{31}$ each independently represents a hydrogen atom, an amino group, a $C_1$-$C_6$ alkyl group, an amino-$C_1$-$C_6$ alkyl group, or a $C_1$-$C_6$ alkylamino group.

(11) A compound according to any one of (1) to (7) or a pharmacologically acceptable salt thereof, wherein in the formula (I), $Y^4$ is the following $Y^a$ or $Y^b$:

[Formula 8]

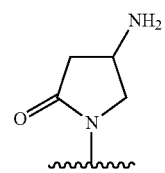
$Y^a$

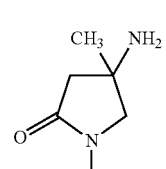
$Y^b$

(12) Any one compound or pharmacologically acceptable salt thereof selected from the following group:

N-[(1R)-1-(3-fluorophenyl)ethyl]-3-[4-[[(2S)-pyrrolidin-2-yl]methoxy]phenyl]imidazo[1,2-b]pyridazin-6-amine, N-[(1R)-1-(3-fluorophenyl)ethyl]-3-[4-[2-(methylamino)ethoxy]phenyl]imidazo[1,2-b]pyridazin-6-amine, 3-[4-[[(2S)-azetidin-2-yl]methoxy]phenyl]-N-[(1R)-1-(3-fluorophenyl)ethyl]imidazo[1,2-b]pyridazin-6-amine, 3-[4-[(2R)-2-aminopropoxy]phenyl]-N-[(1R)-1-(3-fluorophenyl)ethyl]imidazo[1,2-b]pyridazin-6-amine, 3-[4-[(2S)-2-aminopropoxy]phenyl]-N-[(1R)-1-(3-fluorophenyl)ethyl]imidazo[1,2-b]pyridazin-6-amine, (4S)-4-amino-1-[4-[6-[(1R)-1-(3-fluorophenyl)ethoxy]imidazo[1,2-b]pyridazin-3-yl]phenyl]pyrrolidin-2-one, (4S)-4-amino-1-[4-[6-[[(1R)-1-(3-fluorophenyl)ethyl]amino]imidazo[1,2-b]pyridazin-3-yl]phenyl]pyrrolidin-2-one, (4S)-4-amino-1-[5-[6-[(1R)-1-(3-fluorophenyl)ethoxy]imidazo[1,2-b]pyridazin-3-yl]-2-pyridyl]pyrrolidin-2-one, (4S)-4-amino-1-[4-[6-[(3-fluorophenyl)methyl-methylamino]imidazo[1,2-b]pyridazin-3-yl]phenyl]pyrrolidin-2-one, and (4S)-4-amino-1-[4-[6-[(3-fluorophenyl)methyl-methylamino]imidazo[1,2-b]pyridazin-3-yl]-3-methoxyphenyl]pyrrolidin-2-one.

(13) N-[(1R)-1-(3-Fluorophenyl)ethyl]-3-[4-[[(2S)-pyrrolidin-2-yl]methoxy]phenyl]imidazo[1,2-b]pyridazin-6-amine.

(14) 3-[4-[(2R)-2-Aminopropoxy]phenyl]-N-[(1R)-1-(3-fluorophenyl)ethyl]imidazo[1,2-b]pyridazin-6-amine.

(15) (4S)-4-Amino-1-[4-[6-[(1R)-1-(3-fluorophenyl)ethoxy]imidazo[1,2-b]pyridazin-3-yl]phenyl]pyrrolidin-2-one.

(16) (4S)-4-Amino-1-[4-[6-[(3-fluorophenyl)methyl-methylamino]imidazo[1,2-b]pyridazin-3-yl]phenyl]pyrrolidin-2-one.

(17) N-[(1R)-1-(3-Fluorophenyl)ethyl]-3-[4-[[(2S)-pyrrolidin-2-yl]methoxy]phenyl]imidazo[1,2-b]pyridazin-6-amine maleate.

(18) N-[(1R)-1-(3-Fluorophenyl)ethyl]-3-[4-[[(2S)-pyrrolidin-2-yl]methoxy]phenyl]imidazo[1,2-b]pyridazin-6-amine adipate.

(19) 3-[4-[(2R)-2-Aminopropoxy]phenyl]-N-[(1R)-1-(3-fluorophenyl)ethyl]imidazo[1,2-b]pyridazin-6-amine methanesulfonate.

(20) 3-[4-[(2R)-2-Aminopropoxy]phenyl]-N-[(1R)-1-(3-fluorophenyl)ethyl]imidazo[1,2-b]pyridazin-6-amine adipate.

(21) (4S)-4-Amino-1-[4-[6-[(1R)-1-(3-fluorophenyl)ethoxy]imidazo[1,2-b]pyridazin-3-yl]phenyl]pyrrolidin-2-one benzenesulfonate.

(22) (4S)-4-Amino-1-[4-[6-[(1R)-1-(3-fluorophenyl)ethoxy]imidazo[1,2-b]pyridazin-3-yl]phenyl]pyrrolidin-2-one hydrochloride.

(23) (4S)-4-Amino-1-[4-[6-[(1R)-1-(3-fluorophenyl)ethoxy]imidazo[1,2-b]pyridazin-3-yl]phenyl]pyrrolidin-2-one adipate.

(24) (4S)-4-Amino-1-[4-[6-[(1R)-1-(3-fluorophenyl)ethoxy]imidazo[1,2-b]pyridazin-3-yl]phenyl]pyrrolidin-2-one lactate.

(25) (4S)-4-Amino-1-[4-[6-[(1R)-1-(3-fluorophenyl)ethoxy]imidazo[1,2-b]pyridazin-3-yl]phenyl]pyrrolidin-2-one benzoate.

(26) (4S)-4-Amino-1-[4-[6-[(3-fluorophenyl)methyl-methylamino]imidazo[1,2-b]pyridazin-3-yl]phenyl]pyrrolidin-2-one benzenesulfonate.

(27) (4S)-4-Amino-1-[4-[6-[(3-fluorophenyl)methyl-methylamino]imidazo[1,2-b]pyridazin-3-yl]phenyl]pyrrolidin-2-one adipate.

(28) (4S)-4-Amino-1-[4-[6-[(3-fluorophenyl)methyl-methylamino]imidazo[1,2-b]pyridazin-3-yl]phenyl]pyrrolidin-2-one camphorate.

(29) A ROS1 kinase enzyme activity inhibitor comprising a compound according to any one of (1) to (28) or a pharmacologically acceptable salt thereof as an active ingredient.

(30) An NTRK kinase enzyme activity inhibitor comprising a compound according to any one of (1) to (28) or a pharmacologically acceptable salt thereof as an active ingredient.

(31) A pharmaceutical composition comprising a compound according to any one of (1) to (28) or a pharmacologically acceptable salt thereof as an active ingredient.

(32) An antitumor agent comprising a compound according to any one of (1) to (28) or a pharmacologically acceptable salt thereof as an active ingredient.

(33) An antitumor agent according to (32), wherein the tumor is hematological malignant tumor (leukemia, lymphoma, or multiple myeloma), brain tumor, head and neck cancer, esophageal cancer, gastric cancer, appendix cancer, colon cancer, anus cancer, gallbladder cancer, bile duct cancer, pancreatic cancer, gastrointestinal stromal tumor, lung cancer, liver cancer, mesothelioma, thyroid cancer, kidney cancer, prostate cancer, neuroendocrine tumor, melanoma, breast cancer, uterine body cancer, uterine cervical cancer, ovary cancer, osteosarcoma, soft tissue sarcoma, Kaposi's sarcoma, myosarcoma, kidney cancer, urinary bladder cancer, or testicular cancer.

(34) A therapeutic agent for a tumor having a detectable increase in the expression level of ROS1 gene, comprising a compound according to any one of (1) to (28) or a pharmacologically acceptable salt thereof as an active ingredient.

(35) A therapeutic agent for a tumor having a detectable increase in the expression level of NTRK gene, comprising a compound according to any one of (1) to (28) or a pharmacologically acceptable salt thereof as an active ingredient.

(36) A therapeutic agent for a tumor having a detectable expression of ROS1 fusion gene, comprising a compound according to any one of (1) to (28) or a pharmacologically acceptable salt thereof as an active ingredient.

(37) A therapeutic agent for a tumor having a detectable expression of NTRK fusion gene, comprising a compound according to any one of (1) to (28) or a pharmacologically acceptable salt thereof as an active ingredient.

(38) A therapeutic agent for a tumor that is treatable by the inhibition of ROS1 kinase enzyme activity, comprising a compound according to any one of (1) to (28) or a pharmacologically acceptable salt thereof as an active ingredient.

(39) A therapeutic agent for a tumor that is treatable by the inhibition of NTRK kinase enzyme activity, comprising a compound according to any one of (1) to (28) or a pharmacologically acceptable salt thereof as an active ingredient.

(40) A method for treating a tumor, comprising administering a compound according to any one of (1) to (28) or a pharmacologically acceptable salt thereof.

(41) A method for treating a tumor according to (40), wherein the tumor is hematological malignant tumor (leukemia, lymphoma, or multiple myeloma), brain tumor, head and neck cancer, esophageal cancer, gastric cancer, appendix cancer, colon cancer, anus cancer, gallbladder cancer, bile duct cancer, pancreatic cancer, gastrointestinal stromal tumor, lung cancer, liver cancer, mesothelioma, thyroid cancer, prostate cancer, neuroendocrine tumor, melanoma, breast cancer, uterine body cancer, uterine cervical cancer, ovary cancer, osteosarcoma, soft tissue sarcoma, Kaposi's sarcoma, myosarcoma, kidney cancer, urinary bladder cancer, or testicular cancer.

(42) A method for treating a tumor having a detectable increase in the expression level of ROS1 gene, comprising administering a compound according to any one of (1) to (28) or a pharmacologically acceptable salt thereof as an active ingredient.

(43) An agent for treating a tumor having a detectable increase in the expression level of NTRK gene, comprising a compound according to any one of (1) to (28) or a pharmacologically acceptable salt thereof as an active ingredient.

(44) A method for treating a tumor having a detectable expression of ROS1 fusion gene, comprising administering a compound according to any one of (1) to (28) or a pharmacologically acceptable salt thereof.

(45) A method for treating a tumor having a detectable expression of NTRK fusion gene, comprising administering a compound according to any one of (1) to (28) or a pharmacologically acceptable salt thereof.

(46) A method for treating a tumor that is treatable by the inhibition of ROS1 kinase enzyme activity, comprising administering a compound according to any one of (1) to (28) or a pharmacologically acceptable salt thereof.

(47) A method for treating a tumor that is treatable by the inhibition of NTRK kinase enzyme activity, comprising a compound according to any one of (1) to (28) or a pharmacologically acceptable salt thereof as an active ingredient.

Advantageous Effects of Invention

The compounds of the present invention or pharmacologically acceptable salts thereof have a potent ROS1 kinase enzyme activity inhibitory effect and NTRK kinase enzyme inhibitory activity and suppress cell growth. Thus, the compounds of the present invention or pharmacologically acceptable salts thereof are useful as antitumor agents, particularly, therapeutic agents for a tumor such as hematological malignant tumor (leukemia, lymphoma, or multiple myeloma), brain tumor, head and neck cancer, esophageal cancer, gastric cancer, appendix cancer, colon cancer, anus cancer, gallbladder cancer, bile duct cancer, pancreatic cancer, gastrointestinal stromal tumor, lung cancer, liver cancer, mesothelioma, thyroid cancer, prostate cancer, neuroendocrine tumor, melanoma, breast cancer, uterine body cancer, uterine cervical cancer, ovary cancer, osteosarcoma, soft tissue sarcoma, Kaposi's sarcoma, myosarcoma, kidney cancer, urinary bladder cancer, and testicular cancer. The compounds of the present invention or pharmacologically acceptable salts thereof are effective as therapeutic drugs for tumors having a detectable increase in the expression level of ROS1 gene and/or having a detectable expression of ROS1 fusion gene, or tumors having a detectable increase in the expression level of NTRK gene and/or having a detectable expression of NTRK fusion gene, among these tumors.

DESCRIPTION OF EMBODIMENTS

In the present invention, "halogen atom" refers to a fluorine atom, a chlorine atom, a bromine atom, or an iodine atom.

In the present invention, "$C_1$-$C_6$ alkyl group" refers to a linear or branched alkyl group having 1 to 6 carbon atoms. Examples thereof include a methyl group, an ethyl group, a propyl group, an isopropyl group, a butyl group, an isobutyl group, a s-butyl group, a t-butyl group, a pentyl group, an isopentyl group, a 2-methylbutyl group, a neopentyl group, a 1-ethylpropyl group, a hexyl group, an isohexyl group, and a 4-methylpentyl group.

In the present invention, "$C_1$-$C_6$ alkoxy group" refers to a $C_1$-$C_6$ alkoxy group formed from the above-described $C_1$-$C_6$ alkyl group. Examples thereof include a methoxy group, an ethoxy group, a n-propoxy group, an isopropoxy group, a butoxy group, an isobutoxy group, a s-butoxy group, a t-butoxy group, a pentoxy group, an isopentoxy group, a 2-methylbutoxy group, hexyloxy, and an isohexyloxy group.

In the present invention, "amino-$C_1$-$C_6$ alkyl group" means the above-described $C_1$-$C_6$ alkyl group substituted by one amino group. Examples thereof include an aminomethyl group, a 1-aminoethyl group, a 2-aminoethyl group, a 1-aminopropyl group, a 2-aminopropyl group, a 3-aminopropyl group, a 1-aminobutyl group, a 2-aminobutyl group, a 3-aminobutyl group, and a 4-aminobutyl group.

In the present invention, "halo-$C_1$-$C_6$ alkyl group" means the above-described $C_1$-$C_6$ alkyl group substituted by one above-described halogen atom. Examples thereof include a fluoromethyl group, a chloromethyl group, a bromomethyl group, a 2-fluoroethyl group, a 2-chloroethyl group, a 3-fluoropropyl group, and a 3-chloropropyl group.

In the present invention, "fluoro-$C_1$-$C_6$ alkyl group" means the above-described $C_1$-$C_6$ alkyl group substituted by one fluorine atom. Examples thereof include a fluoromethyl group, a 2-fluoroethyl group, and a 3-fluoropropyl group.

In the present invention, "dihalo-$C_1$-$C_6$ alkyl group" means the above-described $C_1$-$C_6$ alkyl group substituted by two identical or different above-described halogen atoms. Examples thereof include a difluoromethyl group, a dichloromethyl group, a dibromomethyl group, a 2,2-difluoroethyl group, a 2,2-dichloroethyl group, a 3,3-difluoropropyl group, and a 3,3-dichloropropyl group.

In the present invention, "trihalo-$C_1$-$C_6$ alkyl group" means the above-described $C_1$-$C_6$ alkyl group substituted by three identical or different above-described halogen atoms. Examples thereof include a trifluoromethyl group, a trichloromethyl group, a tribromomethyl group, a 2,2,2-trifluoroethyl group, a 2,2,2-trichloroethyl group, a 3,3,3-trifluoropropyl group, and a 3,3,3-trichloropropyl group.

In the present invention, examples of a "$C_3$-$C_6$ cycloalkyl group" include a cyclopropyl group, a cyclobutyl group, a cyclopentyl group, and a cyclohexyl group.

In the present invention, "$C_1$-$C_6$ alkylamino group" means an amino group substituted by one above-described $C_1$-$C_6$ alkyl group. Examples thereof include a methylamino group, an ethylamino group, a propylamino group, an isopropylamino group, a butylamino group, an isobutylamino group, a s-butylamino group, a t-butylamino group, a pentylamino group, an isopentylamino group, a 2-methylbutylamino group, a neopentylamino group, a 1-ethylpropylamino group, a hexylamino group, and an isohexylamino group.

In the present invention, "di-$C_1$-$C_6$ alkylamino group" means an amino group substituted by two identical or different above-described $C_1$-$C_6$ alkyl groups. Examples thereof include a dimethylamino group, a diethylamino group, a dipropylamino group, a diisopropylamino group, a dibutylamino group, a diisobutylamino group, a dipentylamino group, a dineopentylamino group, a dihexylamino group, a N-ethyl-N-methylamino group, a N-methyl-N-propylamino group, a N-isopropyl-N-methylamino group, a N-butyl-N-methylamino group, a N-isobutyl-N-methylamino group, a N-ethyl-N-propylamino group, a N-ethyl-N-isopropylamino group, a N-butyl-N-ethylamino group, and a N-ethyl-N-isopentylamino group.

In the present invention, "$C_3$-$C_6$ cycloalkylamino group" means an amino group substituted by one above-described $C_3$-$C_6$ cycloalkyl group. Examples thereof include a cyclopropylamino group, a cyclobutylamino group, a cyclopentylamino group, and a cyclohexylamino group.

In the present invention, "amino-$C_3$-$C_6$ cycloalkyl group" means one above-described $C_3$-$C_6$ cycloalkyl group substituted by one amino group. Examples thereof include a 1-aminocyclopropyl group, a 2-aminocyclopropyl group, a 1-aminocyclobutyl group, a 2-aminocyclobutyl group, a 3-aminocyclobutyl group, a 1-aminocyclopentyl group, a 2-aminocyclopentyl group, a 3-aminocyclopentyl group, a 1-aminocyclohexyl group, a 2-aminocyclohexyl group, a 3-aminocyclohexyl group, and a 4-aminocyclohexyl group.

In the present invention, "hydroxy-$C_1$-$C_6$ alkyl group" means the above-described $C_1$-$C_6$ alkyl group substituted by one hydroxy group. Examples thereof include a hydroxymethyl group, a 1-hydroxyethyl group, a 2-hydroxyethyl group, a 1-hydroxypropyl group, a 2-hydroxypropyl group, a 3-hydroxypropyl group, a 1-hydroxy-1-methyl-ethyl group, a 2-hydroxy-methyl-ethyl group, a 1-hydroxybutyl group, a 2-hydroxybutyl group, a 3-hydroxybutyl group, a 4-hydroxybutyl group, a 1-hydroxy-2-methyl-propyl group, a 2-hydroxy-2-methyl-propyl group, a 3-hydroxy-2-methyl-propyl group, a 1-hydroxy-1-methyl-propyl group, a 1-(hydroxymethyl)propyl group, a 2-hydroxy-1-methyl-propyl group, a 3-hydroxy-1-methyl-propyl group, a 1-hydroxypentyl group, a 2-hydroxypentyl group, a 3-hydroxypentyl group, a 4-hydroxypentyl group, and a 5-hydroxypentyl group.

In the present invention, "hydroxy-$C_1$-$C_6$ alkylamino group" means an amino group substituted by one above-described hydroxy-$C_1$-$C_6$ alkyl group. Examples thereof include a hydroxymethylamino group, a 2-hydroxyethylamino group, and a 3-hydroxypropylamino group.

In the present invention, "heteroaryl group" means a group derived from a 5- or 6-membered monocyclic aromatic compound containing 1 or 4 atoms each independently selected from the group consisting of a nitrogen atom, an oxygen atom, and a sulfur atom as ring-constituting atoms other than carbon. Examples thereof include a furyl group, a thienyl group, a pyrrolyl group, an oxazolyl group, an isoxazolyl group, a thiazolyl group, an isothiazolyl group, an imidazolyl group, a pyrazolyl group, a pyridyl group, a pyrazyl group, a pyrimidinyl group, and a pyridazinyl group.

In the present invention, "heteroarylene group" means a divalent group derived from the above-described heteroaryl group. Examples thereof include a thienylene group, a pyrrolylene group, a thiazolylene group, an imidazolylene group, a pyrazolylene group, a pyridylene group, a pyrazylene group, a pyrimidylene group, and a pyridazylene group.

In the present invention, "aliphatic heterocyclic group" means a group derived from an aliphatic cyclic compound containing 1 or 4 atoms each independently selected from the group consisting of a nitrogen atom, an oxygen atom, and a sulfur atom as ring-constituting atoms other than carbon. Examples thereof include an oxiranyl group, an aziridinyl group, a thiiranyl group, an oxetanyl group, an azetidinyl group, a thietanyl group, a tetrahydrofuranyl group, a pyrrolidinyl group, a tetrahydrothiophenyl group, a tetrahydropyranyl group, a tetrahydrothiopyranyl group, a morpholino group, a morpholinyl group, and a piperazinyl group.

In the present invention, the term "tumor" is not limited to malignant tumor and includes every type of tumor, for example, carcinoma, sarcoma, and benign tumor. Particularly, a malignant tumor may be expressed as "cancer".

In the present invention, "increase in the expression level of ROS1 gene" means that the mRNA expression level or protein expression level of the ROS1 gene has been increased by enhanced gene transcription activity, promoted translation, suppressed proteolysis, improved protein stabilization, etc.

In the present invention, "expression of ROS1 fusion gene" means that the ROS1 fusion gene has been formed and expressed as a result of the fusion between the ROS1 gene and another gene (e.g., FIG gene, SLC34A2 gene, or CD74 gene).

In the present invention, "chromosomal translocation of ROS1 gene" refers to a positional mutation in a chromosome containing the ROS1 gene.

In the present invention, "ROS1 pathway" refers to a pathway through which ROS1 and subsequently STAT3, ERK, SHP2, and the like are phosphorylated, leading to the growth, survival, etc. of cancer cells.

In the present invention, "ROS1 kinase enzyme activity inhibitory effect" is indicated by the inhibition of ROS1 kinase and/or the inhibition of ROS1 autophosphorylation activity.

In the present invention, "increase in the expression level of NTRK gene" means that the mRNA expression level or protein expression level of the NTRK gene has been increased by enhanced gene transcription activity, promoted translation, suppressed proteolysis, improved protein stabilization, etc.

In the present invention, "expression of NTRK fusion gene" means that the NTRK fusion gene has been formed and expressed as a result of the fusion between the NTRK gene and another gene (e.g., TPM3 gene, TPR gene, or ETV6 gene).

In the present invention, "NTRK kinase enzyme activity inhibitory effect" is indicated by an NTRK autophosphorylation activity inhibitory effect.

Next, each substituent in the general formula (I) will be described.

$R^1$ represents a hydrogen atom or a $C_1$-$C_6$ alkyl group.

Preferably, $R^1$ is a hydrogen atom or a methyl group.

Q represents an oxygen atom or $R^aN$.

In this context, $R^a$ represents a hydrogen atom or a $C_1$-$C_6$ alkyl group.

Preferably, $R^a$ is a hydrogen atom or a methyl group.

G represents a phenyl group or a 5- or 6-membered heteroaryl group having, in the ring, 1 or 2 heteroatoms independently selected from the group consisting of a nitrogen atom, an oxygen atom, and a sulfur atom. The phenyl group and the 6-membered heteroaryl group may have 1 to 3 substituents independently selected from the group consisting of a halogen atom, a cyano group, a $C_1$-$C_6$ alkyl group, a $C_1$-$C_6$ alkoxy group, and a trihalo-$C_1$-$C_6$ alkyl group. The 5-membered heteroaryl group may have 1 or 2 substituents independently selected from the group consisting of a halogen atom, a cyano group, a $C_1$-$C_6$ alkyl group, a $C_1$-$C_6$ alkoxy group, a monohalo-$C_1$-$C_6$ alkyl group, a dihalo-$C_1$-$C_6$ alkyl group, and a trihalo-$C_1$-$C_6$ alkyl group.

In one aspect, G is a phenyl group, a pyridyl group, or a pyrazyl group. The phenyl group, the pyridyl group, or the pyrazyl group is unsubstituted or may have 1 to 3 substituents independently selected from the group consisting of a halogen atom, a cyano group, a $C_1$-$C_6$ alkyl group, a $C_1$-$C_6$ alkoxy group, and a trihalo-$C_1$-$C_6$ alkyl group.

Preferably, G is a phenyl group, a pyridyl group or a pyrazyl group. The phenyl group, the pyridyl group, or the pyrazyl group is unsubstituted or substituted by one fluorine atom, two fluorine atoms, one chlorine atom, one fluorine atom and one chlorine atom, one fluorine atom and one methyl group, a cyano group, a methyl group, or a trifluoromethyl group.

In another aspect, G is a thiazolyl group, or a pyrazolyl group. The thiazolyl group or the pyrazolyl group is unsubstituted or may have 1 or 2 substituents independently selected from the group consisting of a halogen atom, a cyano group, a $C_1$-$C_6$ alkyl group, a $C_1$-$C_6$ alkoxy group, a monohalo-$C_1$-$C_6$ alkyl group, a dihalo-$C_1$-$C_6$ alkyl group, and a trihalo-$C_1$-$C_6$ alkyl group.

Preferably, G is a pyrazolyl group. The pyrazolyl group is substituted by one fluorine atom, one chlorine atom, one methyl group, one difluoromethyl group, one trifluoromethyl group, two methyl groups, one chlorine atom and one methyl group, one methyl group and one difluoromethyl group, or one methyl group and one trifluoromethyl group.

In a more preferred aspect, G is any one of the following $G^a$ to $G^e$:

[Formula 9]

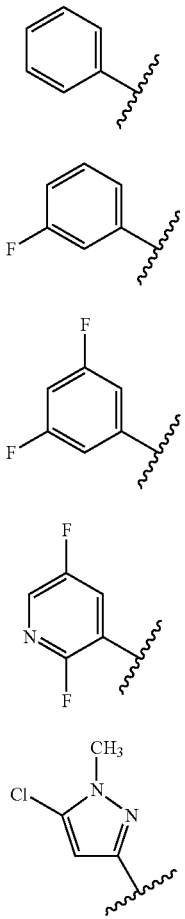

T represents a nitrogen atom or $CR^b$.

In this context, $R^b$ represents a hydrogen atom, a halogen atom, a $C_1$-$C_6$ alkyl group, a $C_1$-$C_6$ alkoxy group, or a cyano group.

Preferably, T is $CR^b$, and $R^b$ is a hydrogen atom or a fluorine atom.

$Y^1$ and $Y^2$ each independently represents a hydrogen atom, a halogen atom, a $C_1$-$C_6$ alkyl group, a $C_1$-$C_6$ alkoxy group, or a cyano group.

Preferably, $Y^1$ and $Y^2$ are each independently a hydrogen atom or a fluorine atom.

$Y^3$ and $Y^4$ each independently represents a hydrogen atom, a group selected from the above-described group A, or a group represented by the above-described formula (II), provided that any one of $Y^3$ and $Y^4$ inevitably represents a hydrogen atom, and the other group represents a group other than a hydrogen atom.

In a preferred aspect, for example, $Y^3$ represents a hydrogen atom, and $Y^4$ represents —O-$M^2$. In this context, $M^2$ is any one of the following $M^{2a}$ to $M^{2i}$:

[Formula 10]

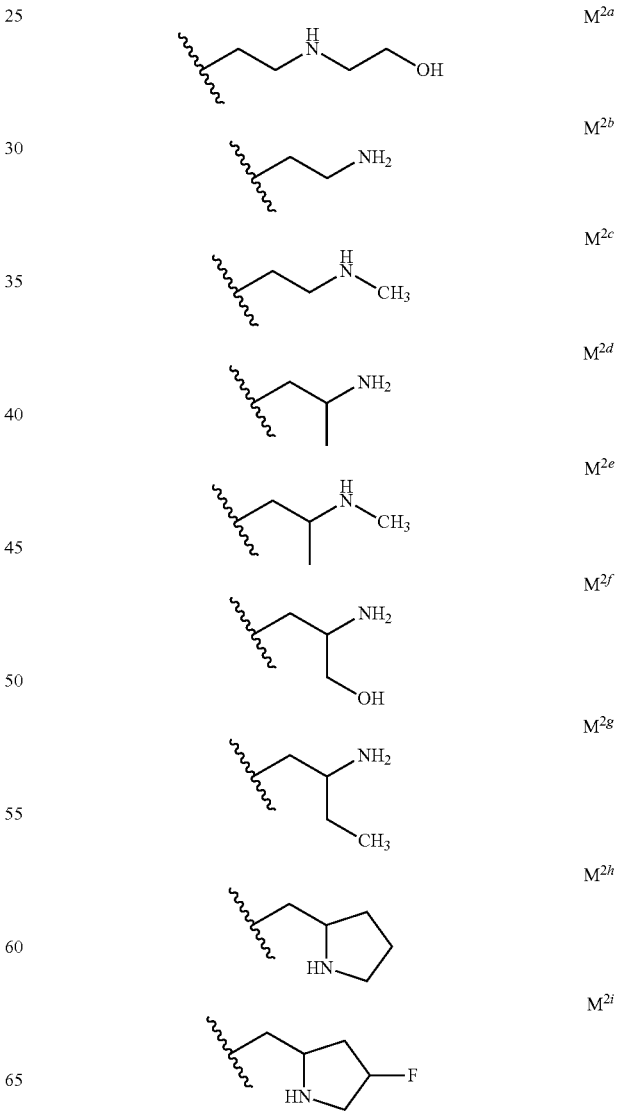

-continued
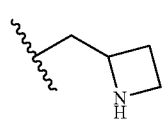 M²ʲ
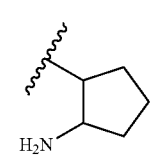 M²ᵏ
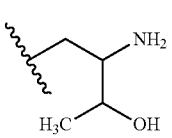 M²ˡ
In a more preferred aspect, for example, Y³ represents a hydrogen atom, and Y⁴ represents —O-M³. In this context, M³ is any one of the following M³ᵃ to M³ᵠ:
[Formula 11]
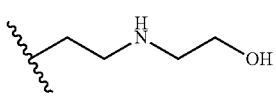 M³ᵃ
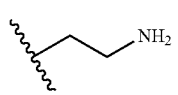 M³ᵇ
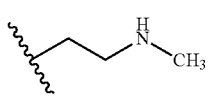 M³ᶜ
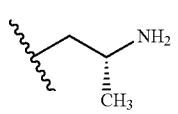 M³ᵈ
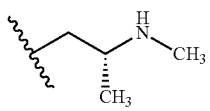 M³ᵉ
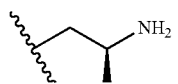 M³ᶠ
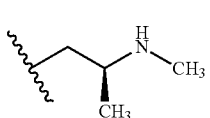 M³ᵍ
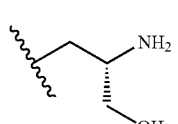 M³ʰ
-continued
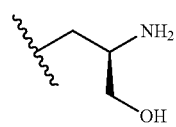 M³ⁱ
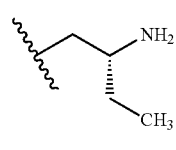 M³ʲ
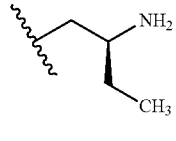 M³ᵏ
M³ˡ
M³ᵐ
M³ⁿ
M³ᵒ
M³ᵖ
M³ᵠ
In another preferred aspect, Y³ represents a hydrogen atom, and Y⁴ is the following Yᵃ or Yᵇ:
[Formula 12]
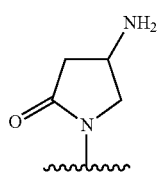 Yᵃ

-continued

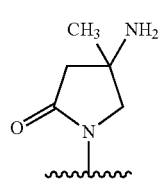
$Y^b$

In a more preferred aspect, $Y^3$ represents a hydrogen atom, and $Y^4$ is the following $Y^c$ or $Y^d$:

[Formula 13]

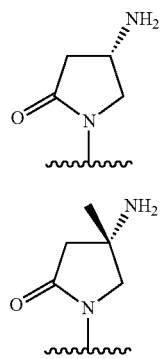

$Y^c$ $Y^d$

According to a preferred aspect, the compound represented by the general formula (I) is any one compound selected from the following group or a pharmacologically acceptable salt thereof:

N-[(1R)-1-(3-fluorophenyl)ethyl]-3-[4-[[(2S)-pyrrolidin-2-yl]methoxy]phenyl]imidazo[1,2-b]pyridazin-6-amine,
N-[(1R)-1-(3-fluorophenyl)ethyl]-3-[4-[2-(methylamino)ethoxy]phenyl]imidazo[1,2-b]pyridazin-6-amine,
3-[4-[[(2S)-azetidin-2-yl]methoxy]phenyl]-N-[(1R)-1-(3-fluorophenyl)ethyl]imidazo[1,2-b]pyridazin-6-amine,
3-[4-[(2R)-2-aminopropoxy]phenyl]-N-[(1R)-1-(3-fluorophenyl)ethyl]imidazo[1,2-b]pyridazin-6-amine,
3-[4-[(2S)-2-aminopropoxy]phenyl]-N-[(1R)-1-(3-fluorophenyl)ethyl]imidazo[1,2-b]pyridazin-6-amine,
(4S)-4-amino-1-[4-[6-[(1R)-1-(3-fluorophenyl)ethoxy]imidazo[1,2-b]pyridazin-3-yl]phenyl]pyrrolidin-2-one,
(4S)-4-amino-1-[4-[6-[[(1R)-1-(3-fluorophenyl)ethyl]amino]imidazo[1,2-b]pyridazin-3-yl]phenyl]pyrrolidin-2-one,
(4S)-4-amino-1-[5-[6-[(1R)-1-(3-fluorophenyl)ethoxy]imidazo[1,2-b]pyridazin-3-yl]-2-pyridyl]pyrrolidin-2-one,
(4S)-4-amino-1-[4-[6-[(3-fluorophenyl)methyl-methylamino]imidazo[1,2-b]pyridazin-3-yl]phenyl]pyrrolidin-2-one, and
(4S)-4-amino-1-[4-[6-[(3-fluorophenyl)methyl-methylamino]imidazo[1,2-b]pyridazin-3-yl]-3-methoxyphenyl]pyrrolidin-2-one.

The compounds represented by the general formula (I) of the present invention can form pharmaceutically acceptable salts, if desired. The term pharmaceutically acceptable salt refers to a salt that has no significant toxicity and can be used as a medicine. A compound represented by the general formula (I) of the present invention can be converted to a salt through reaction with an acid, when having a basic group.

Examples of the salt based on the basic group can include: inorganic acid salts such as hydrohalides (e.g., hydrofluoride, hydrochloride, hydrobromide, and hydroiodide), nitrate, perchlorate, sulfate, and phosphate; organic acid salts such as $C_1$-$C_6$ alkylsulfonates (e.g., methanesulfonate, trifluoromethanesulfonate, and ethanesulfonate), arylsulfonates (e.g., benzenesulfonate and p-toluenesulfonate), acetate, malate, fumarate, succinate, citrate, ascorbate, tartrate, oxalate, adipate, and maleate; and amino acid salts such as glycine salt, lysine salt, arginine salt, ornithine salt, glutamate, and aspartate.

The compounds represented by the general formula (I) of the present invention or salts thereof, when left in the atmosphere or recrystallized, may form a hydrate by absorbing water molecules. Such hydrates are also included in the salts of the present invention.

The compounds represented by the general formula (I) of the present invention or salts thereof, when left in a solvent or recrystallized, may form a solvate by absorbing a certain kind of solvent. Such solvates are also included in the salts of the present invention.

The compounds represented by the general formula (I) of the present invention or pharmacologically acceptable salts thereof encompass all isomers (diastereomers, optical isomers, geometric isomers, rotational isomers, etc.).

These isomers of the compounds of the present invention and mixtures of these isomers are all represented by a single formula, i.e., the general formula (I). Thus, the present invention encompasses all of these isomers and even mixtures of these isomers at any ratio.

The compounds of the present invention may contain isotope(s) of one or more atoms constituting such compounds at a nonnatural ratio. Examples of the isotope include deuterium ($^2$H), tritium ($^3$H), iodine-125 ($^{125}$I), and carbon-14 ($^{14}$C). Alternatively, the compounds may be radiolabeled with a radioisotope, for example, tritium ($^3$H), iodine-125 ($^{125}$I), or carbon-14 ($^{14}$C). Such radiolabeled compounds are useful as therapeutic or prophylactic agents, research reagents, for example, assay reagents, and diagnostic agents, for example, in vivo diagnostic imaging agents. All isotopic variants of the compounds of the present invention fall within the scope of the present invention, regardless of being radioactive or not.

The ROS1 kinase enzyme activity inhibitory effect of the compounds of the present invention can be assayed by the methods of Test Example 1 or 2. The NTRK activity inhibitory effect of the compounds of the present invention can be assayed by the method of Test Example 3.

The cell growth inhibitory activity of the compounds of the present invention can be examined using a growth inhibition test method usually used by those skilled in the art. The cell growth inhibitory activity can be determined, for example, as described below in Test Example 4, by the comparison of the degree of cell growth in the presence of and in the absence of a test compound. The degree of growth can be examined using, for example, a test system for assaying live cells. Examples of the method for assaying live cells include a [$^3$H]-thymidine uptake test, a BrdU method, and MTT assay.

Also, the in vivo antitumor activity of the compounds of the present invention can be examined using an antitumor test method usually used by those skilled in the art. For example, various tumor cells are transplanted to mice, rats, or the like. After confirmation of successful engraftment of the transplanted cells, the compound of the present invention is administered, for example, orally or intravenously, to the animals. A few days to a few weeks later, tumor growth in a drug-unadministered group can be compared with tumor growth in the compound-administered group to confirm the in vivo antitumor activity of the compound of the present invention.

The compounds of the present invention can be used in the treatment of a tumor, for example, hematological malignant tumor (leukemia, lymphoma, or multiple myeloma), brain tumor, head and neck cancer, esophageal cancer, gastric cancer, appendix cancer, colon cancer, anus cancer, gallbladder cancer, bile duct cancer, pancreatic cancer, gastrointestinal stromal tumor, lung cancer, liver cancer, mesothelioma, thyroid cancer, kidney cancer, prostate cancer, neuroendocrine tumor, melanoma, breast cancer, uterine body cancer, uterine cervical cancer, ovary cancer, osteosarcoma, soft tissue sarcoma, Kaposi's sarcoma, myosarcoma, kidney cancer, urinary bladder cancer, or testicular cancer. Preferably, the compounds of the present invention are used in the treatment of non-small cell lung cancer, bile duct cancer, or brain tumor.

It has been suggested that the ROS1 pathway is involved in the growth, survival, etc. of cancer. Hence, the compounds of the present invention are preferably used for a tumor with an activated ROS1 pathway.

Examples of a tumor with an activated ROS1 pathway include a tumor having increase in the expression level of ROS1 gene, a tumor in which the chromosomal translocation of ROS1 has occurred, and a tumor in which ROS1 fusion gene has been formed and activated as a result of the fusion between the ROS1 gene and another gene (e.g., FIG gene, SLC34A2 gene, or CD74 gene). Non-small cell lung cancer, bile duct cancer, and brain tumor are known as tumors with an activated ROS1 pathway.

It has also been suggested that the overexpression, fusion gene, and activation, etc. of NTRK is involved in the growth, survival, etc. of cancer. Hence, the compounds of the present invention are preferably used for a tumor with activated NTRK.

Examples of a tumor with activated NTRK include a tumor having an increase in the expression level of NTRK gene. Prostate cancer and the like are known as tumors with activated NTRK.

The activated ROS1 pathway can be confirmed on the basis of gene/protein amplification or mutation of ROS1, ROS1 fusion gene, or the like, ROS1 phosphorylation, STAT3 phosphorylation, ERK phosphorylation, SHP2 phosphorylation, AKT phosphorylation, or the like in the test tissues (collected by, for example, blood collection or biopsy) of patients, or the activated NTRK can be confirmed on the basis of gene/protein amplification, etc. of NTRK or NTRK fusion gene in the test tissues (collected by, for example, blood collection or biopsy) of patients, using methods known in the art such as Southern blotting, Northern blotting, Western blotting, ELISA, DNA chips, FISH assay, histological immunostaining, and analysis using other gene analysis methods known in the art {e.g., PCR, LCR (ligase chain reaction), SDA (strand displacement amplification), NASBA (nucleic acid sequence-based amplification), ICAN (isothermal and chimeric primer-initiated amplification), and LAMP (loop-mediated isothermal amplification)}, or pathological approaches.

The compounds of the present invention may be used in combination with an additional antitumor agent. Examples thereof include antitumor antibiotics, antitumor plant constituents, BRMs (biological response modifiers), hormones, vitamins, antitumor antibodies, molecular target drugs, and other antitumor agents.

More specifically, examples of alkylating agents include: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and other agents such as busulfan, improsulfan tosylate, and dacarbazine.

Examples of various metabolic antagonists include: purine metabolic antagonists such as 6-mercaptopurine, 6-thioguanine, and thioinosine; pyrimidine metabolic antagonists such as fluorouracil, tegafur, tegafur-uracil, carmofur, doxifluridine, broxuridine, cytarabine, and enocitabine; and folic acid metabolic antagonists such as methotrexate and trimetrexate.

Examples of antitumor antibiotics include: antitumor anthracycline antibiotics such as mitomycin C, bleomycin, peplomycin, daunorubicin, aclarubicin, doxorubicin, pirarubicin, THP-adriamycin, 4'-epidoxorubicin, and epirubicin; and other antibiotics such as chromomycin A3 and actinomycin D.

Examples of antitumor plant constituents include: *vinca* alkaloids such as vindesine, vincristine, and vinblastine; taxanes such as paclitaxel and docetaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, and medroxyprogesterone.

Examples of vitamins include vitamin C and vitamin A.

Examples of antitumor antibodies and molecular target drugs include trastuzumab, rituximab, cetuximab, nimotuzumab, denosumab, bevacizumab, infliximab, imatinib mesilate, gefitinib, erlotinib, sunitinib, lapatinib, and sorafenib.

Examples of other antitumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, and krestin.

Next, a typical method for producing the compounds represented by the general formula (I) will be described. The compounds of the present invention can be produced by various production methods. The production method shown below is given for illustrative purposes. It should be understood that the present invention is not limited by this example. The compounds represented by the general formula (I) and intermediates for production thereof can be produced through the use of various reactions known in the art as described below. In this respect, functional groups in starting materials or intermediates may be protected with appropriate protective groups. Examples of such functional groups can include a hydroxy group, a carboxy group, and an amino group. For the types of the protective groups and conditions for the introduction and removal of these protective groups, see, for example, Protective Groups in Organic Synthesis (T. W. Greene and P. G. M. Wuts, John Wiley & Sons, Inc., New York, 1991).

[Production Method]

[Formula 14]

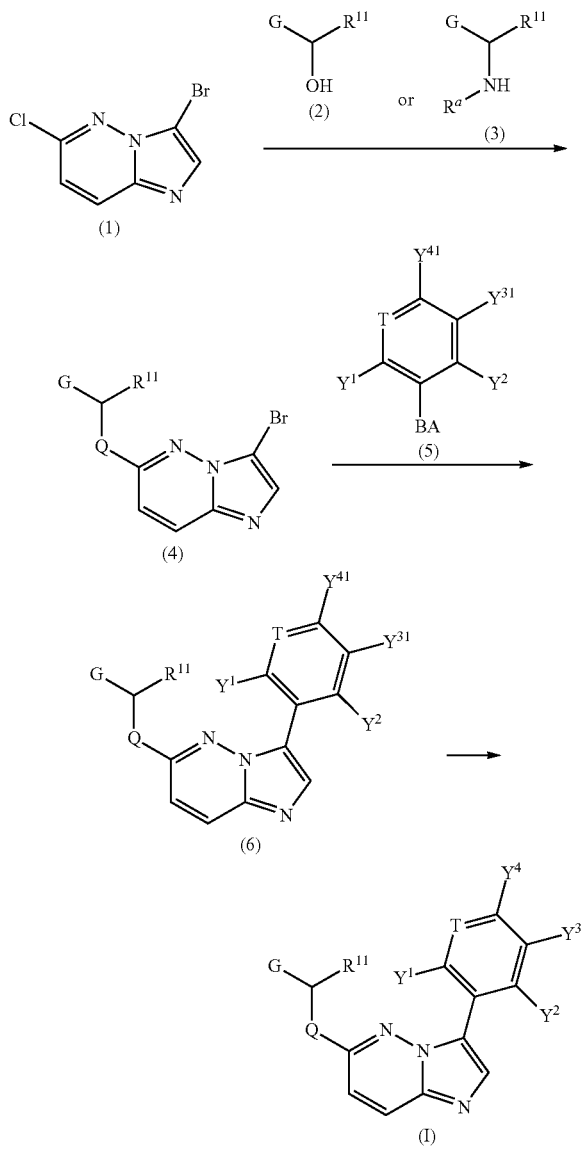

In the reaction scheme, $R^a$, G, Q, T, $Y^1$, and $Y^2$ are as defined above. In the reaction scheme, BA represents boronic acid or boronic acid ester, organic tin, or the like.

In the reaction scheme, $R^{11}$ represents a hydrogen atom, a $C_1$-$C_6$ alkyl group, a fluoro-$C_1$-$C_6$ alkyl group, or $R^{12}$. In this context, $R^{12}$ represents a $C_1$-$C_6$ alkyl group having a hydroxy group protected with a protective group. Examples of the protective group include a tert-butyldimethylsilyl group, a benzyl group, and an acetyl group.

In the reaction scheme, $Y^{31}$ represents $Y^3$ mentioned above, or when $Y^3$ has an amino group and/or a hydroxy group, $Y^{31}$ represents an optionally protected amino group and/or hydroxy group in $Y^3$. In the reaction scheme, $Y^{41}$ represents $Y^4$ mentioned above, or when $Y^4$ has an amino group and/or a hydroxy group, $Y^{41}$ represents an optionally protected amino group and/or hydroxy group in $Y^4$. Examples of the protective group for the amino group include a benzyloxycarbonyl group, a tert-butoxycarbonyl group, and a trityl group. Examples of the protective group for the hydroxy group include a tert-butyldimethylsilyl group, a benzyl group, and an acetyl group.

1. Conversion of Compound (1) to Compound (4)

The conversion of compound (1) to compound (4) is carried out through a nucleophilic substitution reaction between the compound (1) and alcohol (2) or amine (3). The alcohol (2) or the amine (3) used in this reaction is commercially available or can be produced by a method known in the art.

For the substitution reaction using alcohol (2), the compound (1) can be treated with a stoichiometric amount of the alcohol (2) in the presence of a base to obtain compound (4).

Examples of the base used can include inorganic bases (sodium hydride, etc.). The amount of the base used can be 1 to excess molar equivalents with respect to the compound (1) and is preferably 1 to 2 molar equivalents. The amount of the alcohol (2) used can be 1 to excess molar equivalents with respect to the compound (1) and is preferably 1 to 1.5 molar equivalents.

The solvent used in the reaction is an appropriate solvent that has no adverse effect on the reaction (e.g., N,N-dimethylformamide, N-methyl-2-pyrrolidone, tetrahydrofuran, or dimethyl sulfoxide) or a mixed solvent thereof. The reaction temperature is preferably 0° C. to 100° C., more preferably 0° C. to room temperature. The reaction time is usually preferably 1 minute to 24 hours, more preferably 10 minutes to 2 hours.

For the above-described reaction using amine (3), the compound (1) can be treated with a stoichiometric amount of the amine (3) in the presence of a base or using an excessive amount of the amine (3) to obtain compound (4).

Examples of the base used can include organic bases (e.g., triethylamine and diisopropylethylamine) and inorganic bases (potassium fluoride, etc.). The amount of the base used is preferably in the range of 2 to 10 molar equivalents with respect to the compound (1). The amount of the amine (3) used may be 1 to 2 molar equivalents in the presence of the base and is preferably in the range of 2 to 30 molar equivalents with respect to the compound (1) in the absence of the base.

The solvent used in the reaction is an appropriate solvent that has no adverse effect on the reaction (e.g., N,N-dimethylformamide, N-methyl-2-pyrrolidone, or dimethyl sulfoxide) or a mixed solvent thereof. The reaction temperature is preferably in the range of 80 to 160° C. The reaction may be carried out by treatment in a sealed tube or under microwave irradiation. The reaction time is usually preferably approximately 1 to 24 hours.

2. Conversion of Compound (4) to Compound (6)

The conversion of compound (4) to compound (6) is carried out through a coupling reaction between the compound (4) and compound (5) using an organic chemical approach known in the art.

The coupling reaction is performed in the presence of an appropriate organic boronic acid, organic tin, organic zinc, or organic magnesium derivative, or the like (e.g., compound (5)) and an appropriate transition metal catalyst (the transition metal catalyst is preferably a palladium catalyst, and examples thereof include a [1,1'-bis(diphenylphosphino)ferrocene]dichloropalladium(II)-dichloromethane complex, dichlorobis(triphenylphosphine)palladium(II), and tetrakis(triphenylphosphine)palladium(0)) by the addition of, if necessary, an inorganic base or organic base (examples thereof include sodium carbonate, potassium carbonate, tripotassium phosphate, cesium carbonate, and diisopropylethylamine), a ligand (examples thereof include organic phosphorus compounds such as 1,1'-bis(diphenylphosphino) ferrocene (dppf) and triphenylphosphine), and a reaction-promoting additive known in the art (examples thereof include lithium chloride and copper iodide) to the compound (4). The organic boronic acid derivative (5) is commercially available or can be produced by a method known in the art. Examples of references for the method for producing the organic boronic acid derivative (5) and the coupling reaction can include "Chemical Reviews, 1995, 95, 2457-2483".

The solvent used in the coupling reaction is an appropriate solvent that has no adverse effect on the reaction (e.g., N,N-dimethylformamide, tetrahydrofuran, toluene, 1,4-dioxane, or water) or a mixed solvent thereof. The reaction temperature is preferably 0° C. to 300° C., more preferably room temperature to 200° C. (optimum temperature: 80° C. to 100° C.). The coupling reaction may be performed by treatment in a sealed tube or under microwave irradiation. The organic boronic acid or the like and the base are each preferably used at 1 to excess molar equivalents with respect to the compound (4). The organic boronic acid or the like is more preferably used at 1 to 1.5 molar equivalents, and the base is more preferably used at 1 to 5 molar equivalents. The reaction time is preferably 1 minute to 60 hours, more preferably 5 minutes to 24 hours.

3. Conversion of Compound (6) to Compound (I)

When the groups $Y^{31}$ and/or $Y^{41}$ in the compound (6) obtained by this production method have functional groups such as an amino group or a hydroxy group and/or when the compound (6) has a hydroxy group on the group $R^{11}$, the functional groups such as an amino group or a hydroxy group are preferably protected. The protective groups therefor can be removed using methods generally used, as mentioned above. The amino group on the groups $Y^{31}$ or/and $Y^{41}$ can be converted to a substituted amino group through alkylation or the like by a general method.

In the present invention, stereoisomers of the compounds represented by the general formula (I) can be obtained using optically active starting compounds or by the synthesis of the compounds according to the present invention using an asymmetric synthesis or asymmetric induction approach. Alternatively, the stereoisomers may be obtained by the isolation of the synthesized compounds according to the present invention using a conventional optical resolution or isolation method, if desired.

In the present invention, the compounds represented by the general formula (I) encompass compounds labeled with isotopes or radioisotopes. Such labeled compounds can be produced, for example, using starting materials labeled with isotopes instead of the starting materials in the production method of the present invention.

The compounds represented by the general formula (I) of the present invention can be converted to salts through reaction with an acid, when having a basic group.

The compounds represented by the general formula (I) of the present invention or the salts thereof, when left in the atmosphere or recrystallized, may form a hydrate by absorbing water molecules.

The compounds represented by the general formula (I) of the present invention or the salts thereof, when left in a solvent or recrystallized in a solvent, may form a solvate by absorbing a certain kind of solvent.

The compounds of the present invention or pharmacologically acceptable salts thereof can be administered in various forms. Examples of the dosage form can include tablets, capsules, granules, emulsions, pills, powders, and syrups (solutions) for oral administration and injections (intravenous, intramuscular, subcutaneous, or intraperitoneal administration), drip infusions, and suppositories (rectal administration) for parenteral administration. These various preparations can be formulated according to routine methods using aids that may be conventionally used in the field of pharmaceutical formulation techniques such as excipients, binders, disintegrants, lubricants, corrigents, solubilizers, suspending agents, and coating agents, in addition to the active ingredient.

For use as a tablet, examples of carriers that can be used include: excipients such as lactose, saccharose, sodium chloride, glucose, urea, starch, calcium carbonate, kaolin, crystalline cellulose, and silicic acid; binders such as water, ethanol, propanol, simple syrup, glucose solutions, starch solutions, gelatin solutions, carboxymethylcellulose, shellac, methylcellulose, potassium phosphate, and polyvinylpyrrolidone; disintegrants such as dry starch, sodium alginate, agar powder, laminaran powder, sodium bicarbonate, calcium carbonate, polyoxyethylene sorbitan fatty acid esters, sodium lauryl sulfate, monoglyceride stearate, starch, and lactose; disintegration inhibitors such as saccharose, stearin, cocoa butter, and hydrogenated oil; absorption promoters such as quaternary ammonium salts and sodium lauryl sulfate; moisturizing agents such as glycerin and starch; adsorbents such as starch, lactose, kaolin, bentonite, and colloidal silicic acid; and lubricants such as purified talc, stearate, boric acid powder, and polyethylene glycol. Alternatively, tablets coated in a conventional manner, for example, sugar-coated tablets, gelatin-coated tablets, enteric-coated tablets, film-coated tablets, double-layer tablets, and multilayered tablets may be prepared, if necessary.

For use as a pill, examples of carriers that can be used include: excipients such as glucose, lactose, cocoa butter, starch, hydrogenated plant oil, kaolin, and talc; binders such as gum arabic powder, powdered tragacanth, gelatin, and ethanol; and disintegrants such as laminaran and agar.

For use as a suppository, conventional carriers known in the art can be widely used. Examples thereof can include polyethylene glycol, cocoa butter, higher alcohols, esters of higher alcohols, gelatin, and semisynthetic glyceride.

For use as an injection, solutions, emulsions, or suspensions can be used. These solutions, emulsions, or suspensions are preferably sterilized and adjusted to be isotonic to blood. Any solvent that can be used as a medical diluent can be used without limitation in the production of these solutions, emulsions, or suspensions. Examples thereof can include water, ethanol, propylene glycol, ethoxylated isostearyl alcohol, polyoxylated isostearyl alcohol, and polyoxyethylene sorbitan fatty acid esters. In this case, each preparation may contain common salt, glucose, or glycerin in an amount sufficient for preparing an isotonic solution. Also, each preparation may contain a conventional solubilizer, buffer, soothing agent, and the like.

These preparations may also contain a colorant, a preservative, a fragrance, a flavor, a sweetener, and the like, if necessary, and may further contain an additional pharmaceutical product.

The amount of the active ingredient compound contained in the preparation is not particularly limited and is appropriately selected in a wide range. The composition usually contains 0.5 to 70% by weight, preferably 1 to 30% by weight of the compound with respect to the total weight.

The amount of the compound used differs depending on the symptoms, age, etc. of the patient (warm-blooded animal, particularly, a human). The daily dose for oral administration to an adult human is 2000 mg (preferably 100 mg) as the upper limit and 0.1 mg (preferably 1 mg, more preferably 10 mg) as the lower limit and is desirably administered once to 6 times a day according to the symptoms.

EXAMPLES

Hereinafter, the present invention will be described in more detail with reference to Reference Examples, Examples, and Test Examples. However, the scope of the present invention is not intended to be limited by these examples.

Elution for column chromatography in the Reference Examples and Examples was performed under observation by thin layer chromatography (TLC). In the TLC observation, silica gel $60F_{254}$ or silica gel $60NH_2F_{254}S$ manufactured by Merck & Co., Inc. was used as a TLC plate; the solvent used as an elution solvent in column chromatography was used as a developing solvent; and a UV detector was adopted for a detection method. Silica gel SK-85 (230 to 400 mesh) manufactured by Merck & Co., Inc. or Chromatorex NH (200 to 350 mesh) manufactured by Fuji Silysia Chemical Ltd. was used as a silica gel for columns. In addition to conventional column chromatography apparatus, an automated purification apparatus (YFLC-5404-FC) manufactured by Yamazen Corp. or an automated purification apparatus (HORIZON, SP1 or Isolera) manufactured by Biotage AB was appropriately used. Solvents designated in each Reference Example and Example were used as elution solvents. The abbreviations used in Reference Examples and Examples have the following meanings:

mg: milligram, g: gram, μl: microliter, ml: milliliter, L: liter, and MHz: megahertz.

In the Examples below, nuclear magnetic resonance (hereinafter, referred to as $^1$H NMR; 400 MHz) spectra were indicated by chemical shift δ values (ppm) using tetramethylsilane as a standard. Fragmentation patterns were indicated by s for a singlet, d for a doublet, t for a triplet, q for a quadruplet, m for a multiplet, and br for broad.

Reference Example 1 tert-Butyl (2S)-2-[[4-(4,4,5,5-tetramethyl-1,3,2-dioxaborolan-2-yl)phenoxy]methyl]pyrrolidine-1-carboxylate

[Formula 15]

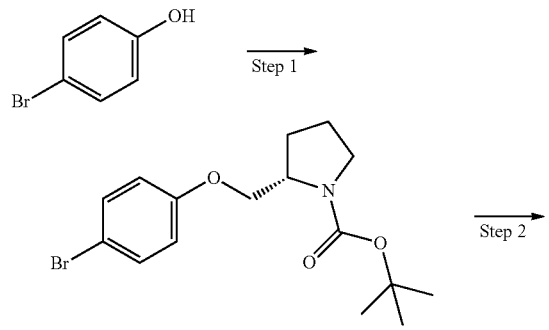

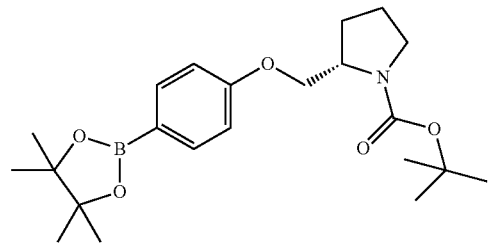

Step 1 tert-Butyl (2S)-2-[(4-bromophenoxy)methyl]pyrrolidine-1-carboxylate

To a solution of 4-bromophenol (1.73 g) and tert-butyl (2S)-2-(hydroxymethyl)pyrrolidine-1-carboxylate (4.0 g) in tetrahydrofuran (50 ml), triphenylphosphine (3.1 g) and a solution of diisopropyl azodicarboxylate (2.4 g) in tetrahydrofuran (10 ml) were added, and the mixture was heated to reflux for 2 hours. After cooling, the reaction solution was concentrated under reduced pressure. The obtained residue was purified by silica gel column chromatography (n-hexane-ethyl acetate) to obtain the title compound (3.5 g).

$^1$H-NMR (CDCl$_3$) δ: 1.47 (9H, s), 1.81-2.06 (4H, m), 3.27-3.46 (2H, m), 3.70-3.94 (1H, m), 4.03-4.17 (2H, m), 6.81 (2H, br s), 7.35 (2H, d, J=8.7 Hz).

Step 2 tert-Butyl (2S)-2-[[4-(4,4,5,5-tetramethyl-1,3,2-dioxaborolan-2-yl)phenoxy]methyl]pyrrolidine-1-carboxylate To a solution of the compound (3.5 g) obtained in the preceding step 1 in 1,4-dioxane (30 ml), bis(pinacolato)diborane (3.0 g), potassium acetate (2.9 g), and a [1,1'-bis(diphenylphosphino)ferrocene]dichloropalladium(II)-dichloromethane adduct (0.8 g) were added, and the mixture was stirred at 80° C. for 4 hours under a nitrogen atmosphere. After cooling, ethyl acetate was added to the reaction solution, and the insoluble matter was filtered off. The filtrate was concentrated under reduced pressure. Then, the obtained residue was purified by silica gel column chromatography (n-hexane-ethyl acetate) to obtain the title compound (3.4 g).

$^1$H-NMR (CDCl$_3$) δ: 1.33 (12H, s), 1.47 (9H, s), 1.79-2.08 (4H, m), 3.40 (2H, br s), 3.75-4.20 (3H, m), 6.91 (2H, d, J=7.8 Hz), 7.73 (2H, d, J=8.3 Hz).

The following compounds were obtained by the same procedures as in Reference Example 1.

TABLE 1-1

| Reference Example | Structure and name | Instrumental data |
|---|---|---|
| 2 | 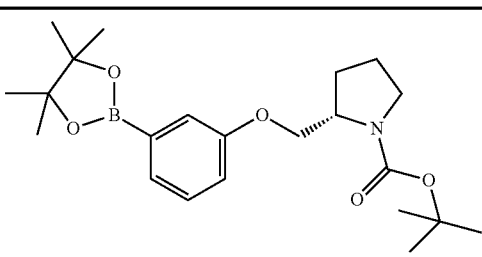<br>tert-Butyl (2S)-2-[[3-(4,4,5,5-tetramethyl-1,3,2-dioxaborolan-2-yl)phenoxy]methyl]pyrrolidine-1-carboxylate | $^1$H-NMR (CDCl$_3$) δ: 1.34 (12H, s), 1.47 (9H, s), 1.79-2.08 (4H, m), 3.41 (2H, br s), 3.75-4.21 (3H, m), 7.02 (1H, d, J = 8.3 Hz), 7.27-7.40 (3H, m). |
| 3 | 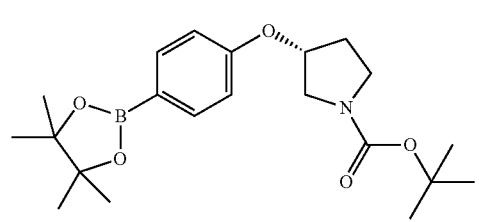<br>tert-Butyl (3R)-3-[4-(4,4,5,5-tetramethyl-1,3,2-dioxaborolan-2-yl)phenoxy]pyrrolidine-1-carboxylate | $^1$H-NMR (CDCl$_3$) δ: 1.33 (12H, s), 1.45 (9H, br s), 2.06-2.21 (2H, m), 3.41-3.67 (4H, m), 4.93 (1H, br s), 6.86 (2H, d, J = 8.6 Hz), 7.74 (2H, br s). |
| 4 | 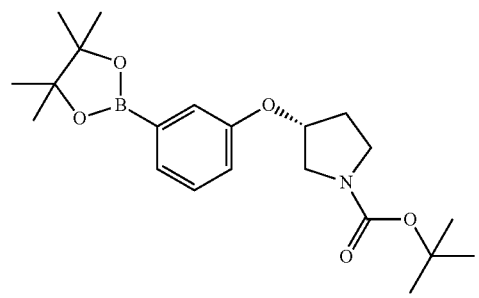<br>tert-Butyl (3R)-3-[3-(4,4,5,5-tetramethyl-1,3,2-dioxaborolan-2-yl)phenoxy]pyrrolidine-1-carboxylate | $^1$H-NMR (CDCl$_3$) δ: 1.34 (12H, s), 1.47 (9H, s), 2.04-2.20 (2H, m), 3.45-3.65 (4H, m), 4.95 (1H, br s), 6.97 (1H, d, J = 9.2 Hz), 7.25-7.32 (2H, m), 7.41 (1H, br s). |
| 5 | 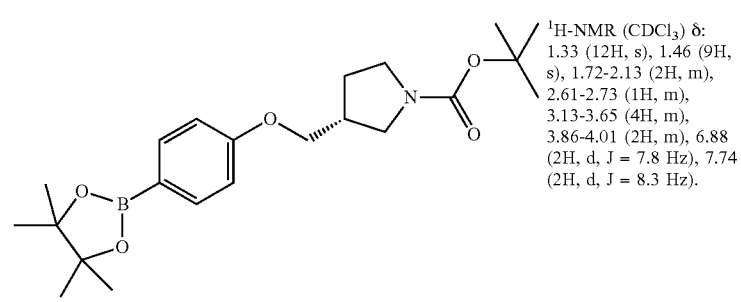<br>tert-Butyl (3R)-3-[[4-(4,4,5,5-tetramethyl-1,3,2-dioxaborolan-2-yl)phenoxy]methyl]pyrrolidine-1-carboxylate | $^1$H-NMR (CDCl$_3$) δ: 1.33 (12H, s), 1.46 (9H, s), 1.72-2.13 (2H, m), 2.61-2.73 (1H, m), 3.13-3.65 (4H, m), 3.86-4.01 (2H, m), 6.88 (2H, d, J = 7.8 Hz), 7.74 (2H, d, J = 8.3 Hz). |
| 6 | 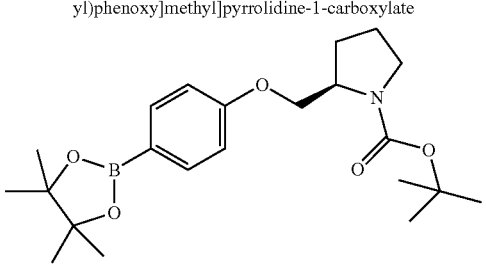<br>tert-Butyl (2R)-2-[[4-(4,4,5,5-tetramethyl-1,3,2-dioxaborolan-2-yl)phenoxy]methyl]pyrrolidine-1-carboxylate | $^1$H-NMR (CDCl$_3$) δ: 1.33 (12H, s), 1.47 (9H, s), 1.79-2.08 (4H, m), 3.40 (2H, br s), 3.75-4.20 (3H, m), 6.91 (2H, d, J = 7.8 Hz), 7.73 (2H, d, J = 8.3 Hz). |

TABLE 1-2

| | | |
|---|---|---|
| 7 | 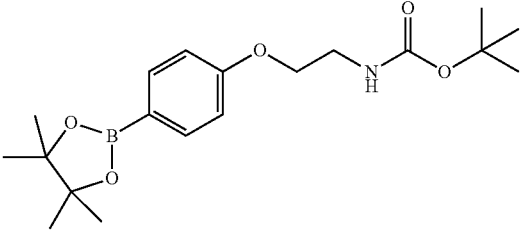 [SMILES: CN(CCOc1ccc(B2OC(C)(C)C(C)(C)O2)cn1)C(=O)OC(C)(C)C]<br>tert-Butyl N-[2-[4-(4,4,5,5-tetramethyl-1,3,2-dioxaborolan-2-yl)phenoxy]ethyl]carbamate | ¹H-NMR (CDCl₃) δ: 1.33 (12H, s), 1.45 (9H, s), 3.54 (2H, q, J = 5.0 Hz), 4.04 (2H, t, J = 5.0 Hz), 4.99 (1H, s), 6.88 (2H, d, J = 9.0 Hz), 7.74 (2H, d, J = 9.0 Hz). |
| 8 | 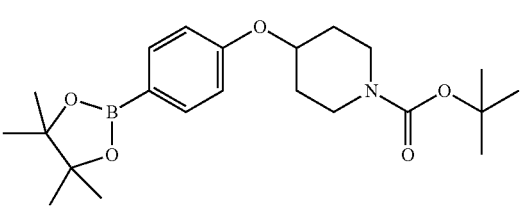<br>tert-Butyl 4-[4-(4,4,5,5-tetramethyl-1,3,2-dioxaborolan-2-yl)phenoxy]piperidine-1-carboxylate | ¹H-NMR (CDCl₃) δ: 1.33 (12H, s), 1.47 (9H, s), 1.71-1.81 (2H, m), 1.87-1.96 (2H, m), 3.31-3.39 (2H, m), 3.64-3.72 (2H, m), 4.51-4.57 (1H, m), 6.90 (2H, d, J = 8.3 Hz), 7.74 (2H, d, J = 7.8 Hz). |
| 9 | 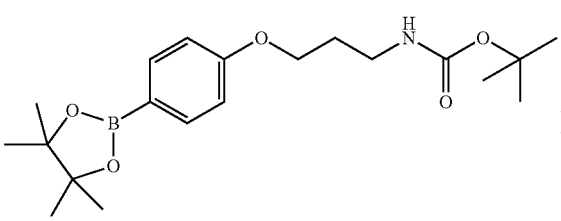<br>tert-Butyl N-[3-[4-(4,4,5,5-tetramethyl-1,3,2-dioxaborolan-2-yl)phenoxy]propyl]carbamate | ¹H-NMR (CDCl₃) δ: 1.33 (12H, s), 1.44 (9H, s), 1.95-2.01 (2H, m), 3.33 (2H, q, J = 6.3 Hz), 4.05 (2H, t, J = 6.1 Hz), 4.75 (1H, br s), 6.88 (2H, d, J = 8.6 Hz), 7.74 (2H, d, J = 8.6 Hz). |
| 10 | 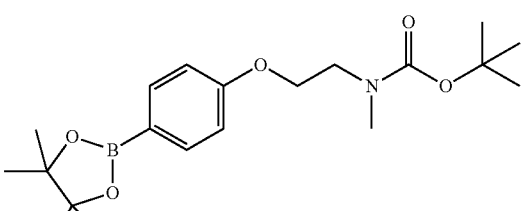<br>tert-Butyl N-methyl-N-[2-[4-(4,4,5,5-tetramethyl-1,3,2-dioxaborolan-2-yl)phenoxy]ethyl]carbamate | ¹H-NMR (CDCl₃) δ: 1.33 (12H, s), 1.46 (9H, s), 2.98 (3H, s), 3.60 (2H, br s), 4.11 (2H, br s), 6.88 (2H, d, J = 8.6 Hz), 7.74 (2H, d, J = 8.6 Hz). |
| 11 | 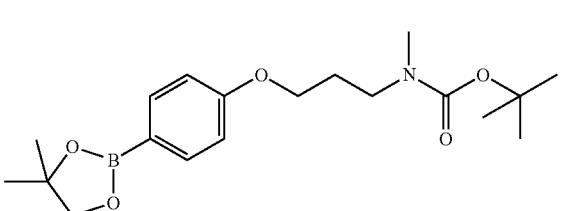<br>tert-Butyl N-methyl-N-[3-[4-(4,4,5,5-tetramethyl-1,3,2-dioxaborolan-2-yl)phenoxy]propyl]carbamate | ¹H-NMR (CDCl₃) δ: 1.33 (12H, s), 1.43 (9H, s), 1.99-2.01 (2H, br m), 2.87 (3H, s), 3.40 (2H, t, J = 6.8 Hz), 4.00 (2H, t, J = 6.3 Hz), 6.88 (2H, d, J = 8.6 Hz), 7.74 (2H, d, J = 8.6 Hz). |

TABLE 1-2-continued

| 12 | tert-Butyl N-[1-methyl-2-[4-(4,4,5,5-tetramethyl-1,3,2-dioxaborolan-2-yl)phenoxy]ethyl]carbamate | $^1$H-NMR (CDCl$_3$) δ: 1.29 (3H, d, J = 7.0 Hz), 1.33 (12H, s), 1.45 (9H, s), 3.95 (2H, d, J = 3.9 Hz), 4.06 (1H, br s), 4.79 (1H, br s), 6.89 (2H, d, J = 8.6 Hz), 7.74 (2H, d, J = 8.6 Hz). |

TABLE 1-3

| 13 | tert-Butyl N-[(1S,2R)-2-[4-(4,4,5,5-tetramethyl-1,3,2-dioxaborolan-2-yl)phenoxy]cyclopentyl]carbamate | $^1$H-NMR (CDCl$_3$) δ: 1.33 (12H, s), 1.46 (9H, s), 1.54-2.11 (6H, m), 4.10 (1H, br s), 4.67 (1H, br s), 5.03 (1H, d, J = 8.5 Hz), 6.88 (2H, d, J = 8.5 Hz), 7.73 (2H, d, J = 8.5 Hz). |
| 14 | tert-Butyl N-[(1R,2S)-2-[4-(4,4,5,5-tetramethyl-1,3,2-dioxaborolan-2-yl)phenoxy]cyclopentyl]carbamate | $^1$H-NMR (CDCl$_3$) δ: 1.21-2.10 (6H, m), 1.33 (12H, s), 1.42 (9H, s), 4.07 (1H, br s), 4.65-4.68 (1H, m), 5.03 (1H, d, J = 8.5 Hz), 6.87 (2H, d, J = 8.5 Hz), 7.73 (2H, d, J = 8.5 Hz). |
| 15 | tert-Butyl N-[(1R)-1-methyl-2-[4-(4,4,5,5-tetramethyl-1,3,2-dioxaborolan-2-yl)phenoxy]ethyl]carbamate | $^1$H-NMR (CDCl$_3$) δ: 1.29 (3H, d, J = 6.7 Hz), 1.33 (12H, s), 1.45 (9H, s), 3.94 (2H, d, J = 3.6 Hz), 4.06 (1H, br s), 4.78 (1H, br s), 6.89 (2H, d, J = 8.5 Hz), 7.74 (2H, d, J = 8.5 Hz). |

TABLE 1-3-continued

| | | |
|---|---|---|
| 16 | 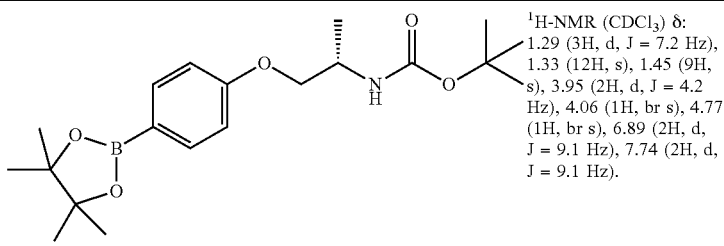<br>tert-Butyl N-[(1S)-1-methyl-2-[4-(4,4,5,5-tetramethyl-1,3,2-dioxaborolan-2-yl)phenoxy]ethyl]carbamate | $^1$H-NMR (CDCl$_3$) δ: 1.29 (3H, d, J = 7.2 Hz), 1.33 (12H, s), 1.45 (9H, s), 3.95 (2H, d, J = 4.2 Hz), 4.06 (1H, br s), 4.77 (1H, br s), 6.89 (2H, d, J = 9.1 Hz), 7.74 (2H, d, J = 9.1 Hz). |
| 17 | 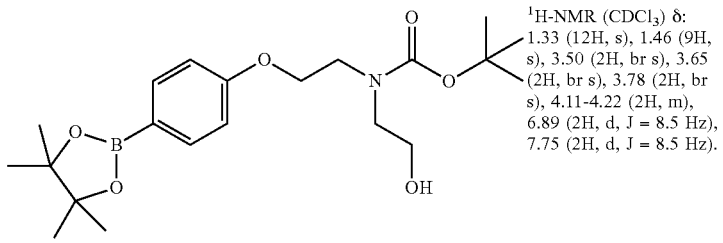<br>tert-Butyl N-(2-hydroxyethyl)-N-[2-[4-(4,4,5,5-tetramethyl-1,3,2-dioxaborolan-2-yl)phenoxy]ethyl]carbamate | $^1$H-NMR (CDCl$_3$) δ: 1.33 (12H, s), 1.46 (9H, s), 3.50 (2H, br s), 3.65 (2H, br s), 3.78 (2H, br s), 4.11-4.22 (2H, m), 6.89 (2H, d, J = 8.5 Hz), 7.75 (2H, d, J = 8.5 Hz). |
| 18 | 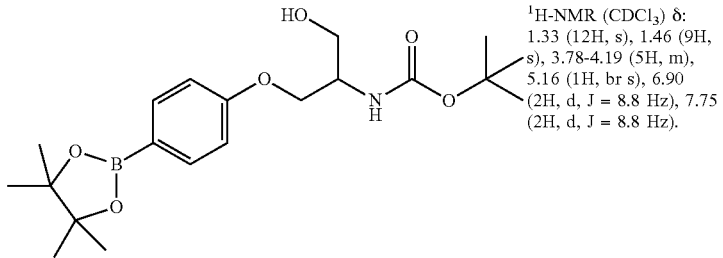<br>tert-Butyl N-[1-(hydroxymethyl)-2-[4-(4,4,5,5-tetramethyl-1,3,2-dioxaborolan-2-yl)phenoxy]ethyl]carbamate | $^1$H-NMR (CDCl$_3$) δ: 1.33 (12H, s), 1.46 (9H, s), 3.78-4.19 (5H, m), 5.16 (1H, br s), 6.90 (2H, d, J = 8.8 Hz), 7.75 (2H, d, J = 8.8 Hz). |

TABLE 1-4

| | | |
|---|---|---|
| 19 | 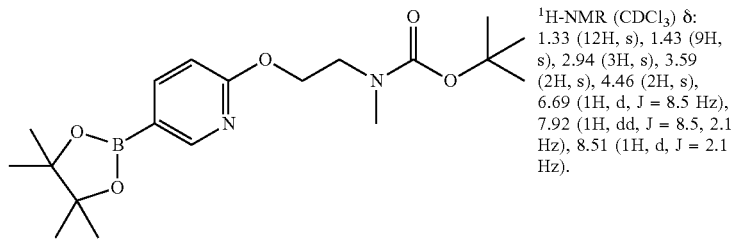<br>tert-Butyl N-methyl-N-[2-[[5-(4,4,5,5-tetramethyl-1,3,2-dioxaborolan-2-yl)-2-pyridyl]oxy]ethyl]carbamate | $^1$H-NMR (CDCl$_3$) δ: 1.33 (12H, s), 1.43 (9H, s), 2.94 (3H, s), 3.59 (2H, s), 4.46 (2H, s), 6.69 (1H, d, J = 8.5 Hz), 7.92 (1H, dd, J = 8.5, 2.1 Hz), 8.51 (1H, d, J = 2.1 Hz). |
| 20 | 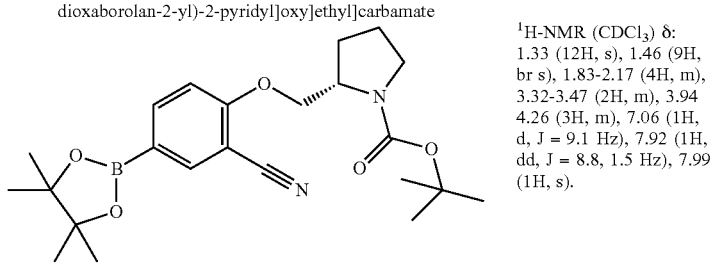<br>tert-Butyl (2S)-2-[[2-cyano-4-(4,4,5,5-tetramethyl-1,3,2-dioxaborolan-2-yl)phenoxy]methyl]pyrrolidine-1-carboxylate | $^1$H-NMR (CDCl$_3$) δ: 1.33 (12H, s), 1.46 (9H, br s), 1.83-2.17 (4H, m), 3.32-3.47 (2H, m), 3.94-4.26 (3H, m), 7.06 (1H, d, J = 9.1 Hz), 7.92 (1H, dd, J = 8.8, 1.5 Hz), 7.99 (1H, s). |

TABLE 1-4-continued

| | | |
|---|---|---|
| 21 | *tert*-Butyl N-[(1S)-1-[[4-(4,4,5,5-tetramethyl-1,3,2-dioxaborolan-2-yl)phenoxy]methyl]propyl]carbamate | ¹H-NMR (CDCl₃) δ: 0.97 (3H, t, J = 7.6 Hz), 1.33 (12H, s), 1.45 (9H, s), 1.61-1.76 (2H, m), 3.84 (1H, br s), 3.99 (2H, d, J = 3.6 Hz), 4.77 (1H, d, J = 6.7 Hz), 6.88 (2H, d, J = 8.5 Hz), 7.74 (2H, d, J = 8.5 Hz). |
| 22 | *tert*-Butyl N-[3-trans-[4-(4,4,5,5-tetramethyl-1,3,2-dioxaborolan-2-yl)phenoxy]cyclobutyl]carbamate | ¹H-NMR (CDCl₃) δ: 1.33 (12H, s), 1.45 (9H, s), 2.35-2.41 (2H, m), 2.53-2.59 (2H, m), 4.28 (1H, br s), 4.72-4.85 (2H, m), 6.76 (2H, d, J = 9.1 Hz), 7.72 (2H, d, J = 8.5 Hz). |
| 23 | *tert*-Butyl N-[(1R)-1-[[4-(4,4,5,5-tetramethyl-1,3,2-dioxaborolan-2-yl)phenoxy]methyl]propyl]carbamate | ¹H-NMR (CDCl₃) δ: 0.97 (3H, t, J = 7.6 Hz), 1.33 (12H, s), 1.45 (9H, s), 1.61-1.76 (2H, m), 3.84 (1H, br s), 3.99 (2H, d, J = 3.6 Hz), 4.77 (1H, d, J = 6.7 Hz), 6.88 (2H, d, J = 8.5 Hz), 7.74 (2H, d, J = 8.5 Hz). |
| 24 | *tert*-Butyl N-[(1S)-1-methyl-2-[3-(4,4,5,5-tetramethyl-1,3,2-dioxaborolan-2-yl)phenoxy]ethyl]carbamate | ¹H-NMR (CDCl₃) δ: 1.29 (3H, d, J = 6.7 Hz), 1.34 (12H, s), 1.45 (9H, s), 3.91-4.08 (3H, m), 4.80 (1H, br s), 6.99-7.01 (1H, m), 7.27-7.33 (2H, m), 7.40 (1H, d, J = 7.3 Hz). |

Reference Example 25 tert-Butyl 4-[[4-(4,4,5,5-tetramethyl-1,3,2-dioxaborolan-2-yl)phenoxy]methyl]piperidine-1-carboxylate

[Formula 16]

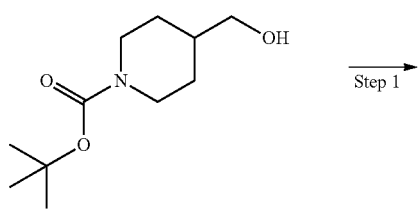

Step 1 →

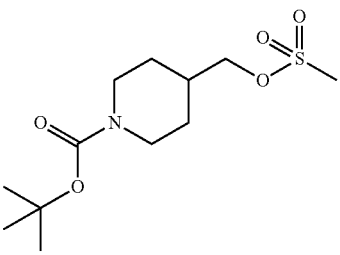

Step 2 →

-continued

-continued

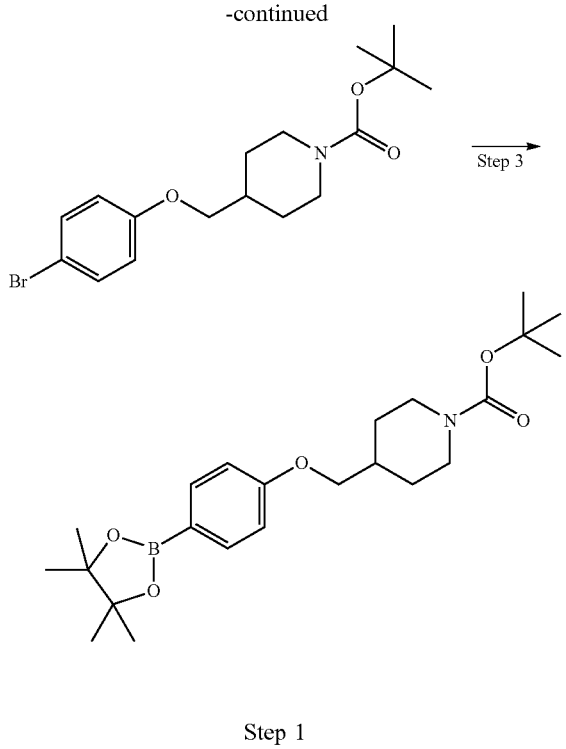

Step 1 tert-Butyl 4-(methylsulfonyloxymethyl)piperidine-1-carboxylate

To a solution of tert-butyl 4-(hydroxymethyl)piperidine-1-carboxylate (2.5 g) in dichloromethane (40 ml), triethylamine (2.8 ml) and methanesulfonyl chloride (1.2 ml) were added under ice cooling, and the mixture was stirred at room temperature for 3 hours. Water was added to the reaction solution to separate two layers. Then, the aqueous layer was subjected to extraction with chloroform. The organic layers were combined, washed with saturated saline and then dried over anhydrous sodium sulfate. The solvent was distilled off under reduced pressure. The obtained residue was purified by silica gel column chromatography (n-hexane-ethyl acetate) to obtain the title compound (2.8 g).

$^1$H-NMR (CDCl$_3$) δ: 1.16-1.29 (2H, m), 1.46 (9H, s), 1.74 (2H, d, J=12.8 Hz), 1.86-1.97 (1H, m), 2.71 (2H, t, J=12.4 Hz), 3.02 (3H, s), 4.07 (2H, d, J=6.4 Hz), 4.05-4.22 (2H, m).

Step 2 tert-Butyl 4-[(4-bromophenoxy)methyl]piperidine-1-carboxylate

To a solution of the compound (1.9 g) obtained in the preceding step 1 in N,N-dimethylformamide (30 ml), sodium iodide (0.97 g), cesium carbonate (4.2 g), and 4-bromophenol (0.75 g) were added, and the mixture was stirred at 70° C. for 2 hours. After cooling, water was added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) to obtain a crude product of the title compound. The crude product of the title compound was dissolved in ethyl acetate. The organic layer was washed with a 1 N aqueous sodium hydroxide solution and saturated saline in this order and then dried over anhydrous sodium sulfate. The solvent was distilled off under reduced pressure to obtain the title compound (0.7 g).

$^1$H-NMR (CDCl$_3$) δ: 1.20-1.32 (2H, m), 1.46 (9H, s), 1.80 (2H, d, J=13.3 Hz), 1.89-1.98 (1H, m), 2.74 (2H, t, J=11.7 Hz), 3.76 (2H, d, J=6.4 Hz), 4.15 (2H, br s), 6.76 (2H, d, J=8.3 Hz), 7.36 (2H, d, J=8.7 Hz).

Step 3 tert-Butyl 4-[[4-(4,4,5,5-tetramethyl-1,3,2-dioxaborolan-2-yl)phenoxy]methyl]piperidine-1-carboxylate The title compound (0.9 g) was obtained by the same procedures as in step 2 of Reference Example 1 using the compound (0.7 g) obtained in the preceding step 2.

$^1$H-NMR (CDCl$_3$) δ: 1.21-1.30 (2H, m), 1.33 (12H, s), 1.46 (9H, s), 1.78-1.99 (3H, m), 2.68-2.80 (2H, m), 3.83 (2H, d, J=6.4 Hz), 4.08-4.23 (2H, m), 6.87 (2H, d, J=7.8 Hz), 7.74 (2H, d, J=7.8 Hz).

The following compounds were obtained by the same procedures as in Reference Example 25.

TABLE 2-1

| Reference Example | Structure and name | Instrumental data |
|---|---|---|
| 26 | ![structure] <br> tert-Butyl (2S)-2-[[4-(4,4,5,5-tetramethyl-1,3,2-dioxaborolan-2-yl)phenoxy]methyl]azetidine-1-carboxylate | $^1$H-NMR (CDCl$_3$) δ: 1.31 (12H, s), 1.38 (9H, s), 2.19-2.35 (2H, m), 3.81-3.90 (2H, m), 4.08-4.13 (1H, m), 4.20-4.28 (1H, br m), 4.43-4.51 (1H, br m), 6.90 (2H, d, J = 8.6 Hz), 7.71 (2H, d, J= 8.6 Hz). |

TABLE 2-1-continued

| Reference Example | Structure and name | Instrumental data |
|---|---|---|
| 27 | 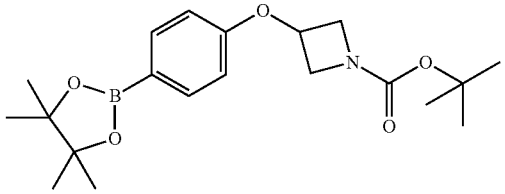 [SMILES: CC(C)(C)OC(=O)N1CC(Oc2ccc(B3OC(C)(C)C(C)(C)O3)cc2)C1]<br>tert-Butyl 3-[4-(4,4,5,5-tetramethyl-1,3,2-dioxaborolan-2-yl)phenoxy]azetidine-1-carboxylate | $^1$H-NMR (CDCl$_3$) δ: 1.29 (12H, s), 1.41 (9H, s), 3.94-3.98 (2H, m), 4.24-4.29 (2H, m), 4.84-4.91 (1H, m), 6.69 (2H, d, J = 8.6 Hz), 7.71 (2H, d, J = 8.6 Hz). |
| 28 | 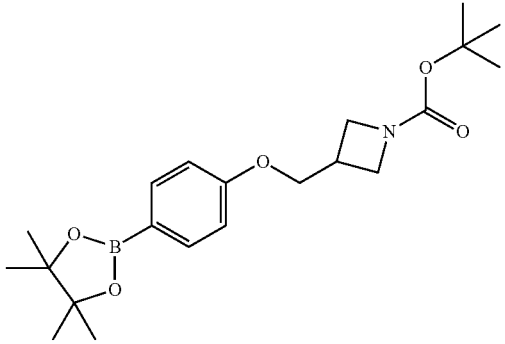 [SMILES: CC(C)(C)OC(=O)N1CC(COc2ccc(B3OC(C)(C)C(C)(C)O3)cc2)C1]<br>tert-Butyl 3-[[4-(4,4,5,5-tetramethyl-1,3,2-dioxaborolan-2-yl)phenoxy]methyl]azetidine-1-carboxylate | $^1$H-NMR (CDCl$_3$) δ: 1.30 (12H, s), 1.41 (9H, s), 2.89-2.98 (1H, m), 3.76 (2H, dd, J = 9.0, 4.7 Hz), 4.02-4.12 (4H, m), 6.86 (2H, d, J = 8.9 Hz), 7.72 (2H, d, J = 8.9 Hz). |
| 29 | 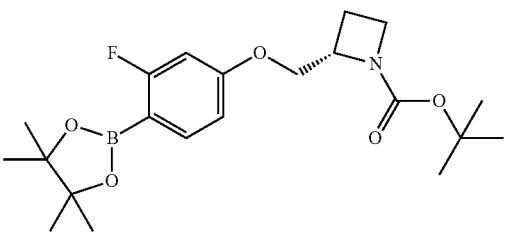 [SMILES: CC(C)(C)OC(=O)N1CC[C@H]1COc1ccc(B2OC(C)(C)C(C)(C)O2)c(F)c1]<br>tert-Butyl (2S)-2-[[3-fluoro-4-(4,4,5,5-tetramethyl-1,3,2-dioxaborolan-2-yl)phenoxy]methyl]azetidine-1-carboxylate | $^1$H-NMR (CDCl$_3$) δ: 1.35 (12H, s), 1.42 (9H, s), 2.20-2.39 (2H, m), 3.88 (2H, t, J = 7.9 Hz), 4.07-4.15 (1H, m), 4.27 (1H, br s), 4.46-4.53 (1H, m), 6.61 (1H, dd, J = 10.9, 2.4 Hz), 6.72 (1H, dd, J = 8.5, 3.0 Hz), 7.65 (1H, t, J = 7.6 Hz). |
| 30 | 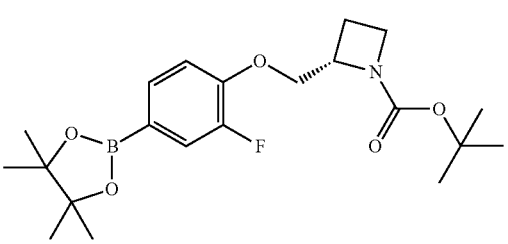 [SMILES: CC(C)(C)OC(=O)N1CC[C@H]1COc1ccc(B2OC(C)(C)C(C)(C)O2)cc1F]<br>tert-Butyl (2S)-2-[[2-fluoro-4-(4,4,5,5-tetramethyl-1,3,2-dioxaborolan-2-yl)phenoxy]methyl]azetidine-1-carboxylate | $^1$H-NMR (CDCl$_3$) δ: 1.33 (12H, s), 1.41 (9H, s), 2.31-2.38 (2H, m), 3.86-3.93 (2H, m), 4.19 (1H, dd, J = 10.0, 2.7 Hz), 4.37 (1H, s), 4.49-4.53 (1H, m), 7.00 (1H, t, J = 8.2 Hz), 7.47-7.53 (2H, m). |

TABLE 2-2

| 31 | tert-Butyl (2S)-2-[[3-(4,4,5,5-tetramethyl-1,3,2-dioxaborolan-2-yl)phenoxy]methyl]azetidine-1-carboxylate | $^1$H-NMR (CDCl$_3$) δ: 1.34 (12H, s), 1.42 (9H, s), 2.26-2.37 (2H, m), 3.85-3.94 (2H, m), 4.11-4.15 (1H, m), 4.28 (1H, br s), 4.49 (1H, br s), 7.04 (1H, dd, J = 8.5, 2.4 Hz), 7.27-7.31 (1H, m), 7.37-7.40 (2H, m). |
|---|---|---|
| 32 | tert-Butyl (2S)-2-[[3-fluoro-5-(4,4,5,5-tetramethyl-1,3,2-dioxaborolan-2-yl)phenoxy]methyl]azetidine-1-carboxylate | $^1$H-NMR (CDCl$_3$) δ: 1.34 (12H, s), 1.42 (9H, s), 2.21-2.37 (2H, m), 3.85-3.91 (2H, m), 4.10 (1H, dd, J = 10.0, 2.7 Hz), 4.28 (1H, br s), 4.47-4.50 (1H, m), 6.73-6.76 (1H, m), 7.09 (1H, dd, J = 8.5, 1.8 Hz), 7.15 (1H, d, J = 1.8 Hz). |
| 33 | tert-Butyl (2S)-2-[[2-fluoro-5-(4,4,5,5-tetramethyl-1,3,2-dioxaborolan-2-yl)phenoxy]methyl]azetidine-1-carboxylate | $^1$H-NMR (CDCl$_3$) δ: 1.34 (12H, s), 1.42 (9H, s), 2.26-2.40 (2H, m), 3.85-3.96 (2H, m), 4.20 (1H, dd, J = 9.7, 3.0 Hz), 4.36-4.40 (1H, br m), 4.50-4.54 (1H, br m), 7.06 (1H, dd, J = 11.5, 7.9 Hz), 7.36-7.44 (2H, m). |

Reference Example 34 tert-Butyl N-[cis-2-[4-(4,4,5,5-tetramethyl-1,3,2-dioxaborolan-2-yl)phenoxy]cyclopentyl]carbamate

[Formula 17]

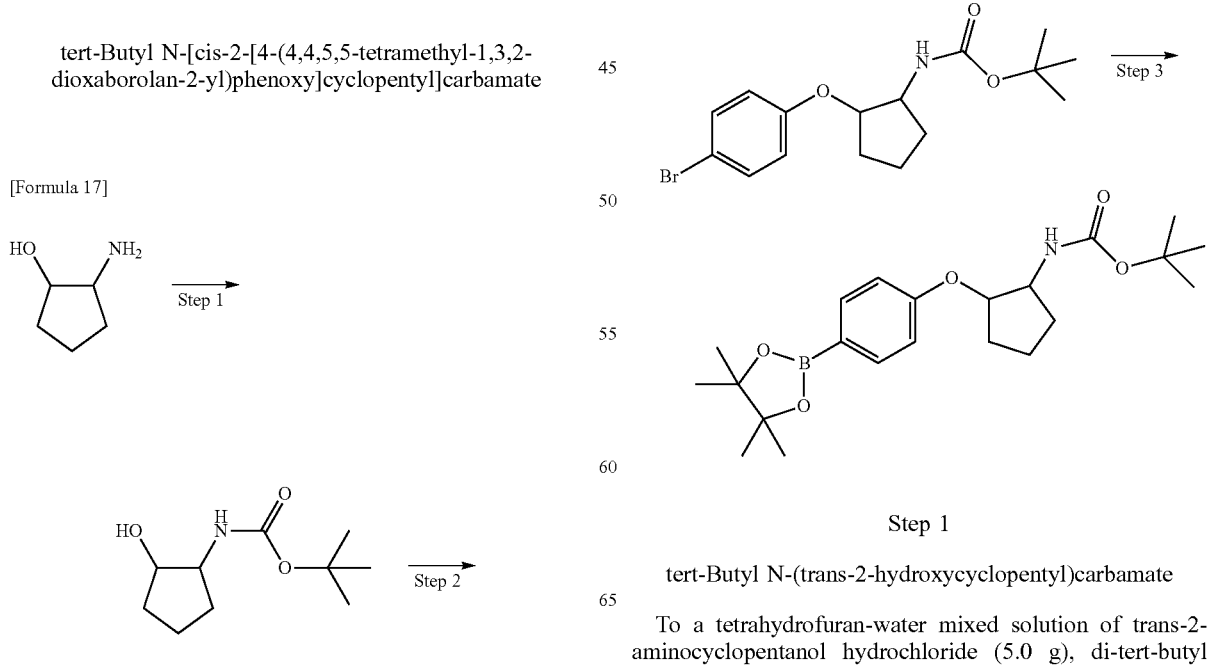

Step 1 tert-Butyl N-(trans-2-hydroxycyclopentyl)carbamate

To a tetrahydrofuran-water mixed solution of trans-2-aminocyclopentanol hydrochloride (5.0 g), di-tert-butyl dicarbonate (7.92 g) and potassium carbonate (10 g) were added, and the mixture was stirred at room temperature for 45 minutes. Water was added to the obtained reaction solution, followed by extraction with ethyl acetate. The extract was washed with water and saturated saline in this order and then dried over anhydrous sodium sulfate. The solvent was distilled off under reduced pressure. The obtained residue was washed with n-hexane-ethyl acetate to obtain the title compound (7.21 g).

$^1$H-NMR (CDCl$_3$) δ: 1.28-1.40 (2H, m), 1.45 (9H, s), 1.59-1.81 (2H, m), 2.00-2.12 (2H, m), 3.59-3.66 (1H, m), 3.98 (1H, q, J=6.5 Hz), 4.04 (1H, s), 4.70 (1H, br s).

Step 2 tert-Butyl N-[cis-2-(4-bromophenoxy)cyclopentyl]carbamate

The title compound (1.35 g) was obtained by the same procedures as in step 1 of Reference Example 1 with 4-bromophenol as the starting material using the compound (3.37 g) obtained in the preceding step 1 instead of tert-butyl (2S)-2-(hydroxymethyl)pyrrolidine-1-carboxylate.

$^1$H-NMR (CDCl$_3$) δ: 1.18-2.11 (6H, m), 1.46 (9H, s), 4.06 (1H, br s), 4.58 (1H, t, J=4.5 Hz), 4.97 (1H, d, J=8.6 Hz), 6.77 (2H, d, J=8.6 Hz), 7.36 (2H, d, J=8.6 Hz).

Step 3 tert-Butyl N-[cis-2-[4-(4,4,5,5-tetramethyl-1,3,2-dioxaborolan-2-yl)phenoxy]cyclopentyl]carbamate The title compound (1.18 g) was obtained by the same procedures as in step 2 of Reference Example 1 using the compound (1.35 g) obtained in the preceding step 2.

$^1$H-NMR (CDCl$_3$) δ: 1.17-2.08 (6H, m), 1.26 (12H, s), 1.42 (9H, s), 4.10 (1H, br s), 4.66-4.67 (1H, m), 5.03 (1H, d, J=8.6 Hz), 6.87 (2H, d, J=8.6 Hz), 7.73 (2H, d, J=8.6 Hz).

The following compound was obtained by the same procedures as in Reference Example 34.

Reference Example 36 tert-Butyl (2S,4S)-4-fluoro-2-[[4-(4,4,5,5-tetramethyl-1,3,2-dioxaborolan-2-yl)phenoxy]methyl]pyrrolidine-1-carboxylate

[Formula 18]

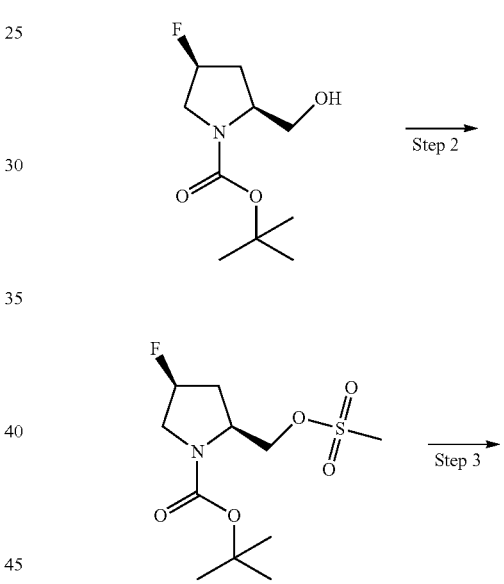

TABLE 3

| Reference Example | Structure and name | Instrumental data |
|---|---|---|
| 35 | 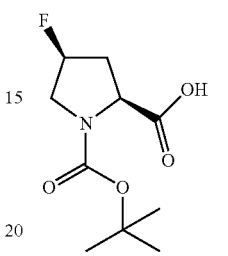<br>tert-Butyl N-[trans-2-[4-(4,4,5,5-tetramethyl-1,3,2-dioxaborolan-2-yl)phenoxy]cyclopentyl]carbamate | $^1$H-NMR (CDCl$_3$) δ: 1.33 (12H, s), 1.45 (9H, s), 1.48-2.20 (6H, m), 4.03 (1H, br s), 4.51 (1H, br s), 4.61 (1H, br s), 6.95 (2H, d, J = 8.9 Hz), 7.73 (2H, d, J = 8.9 Hz). |

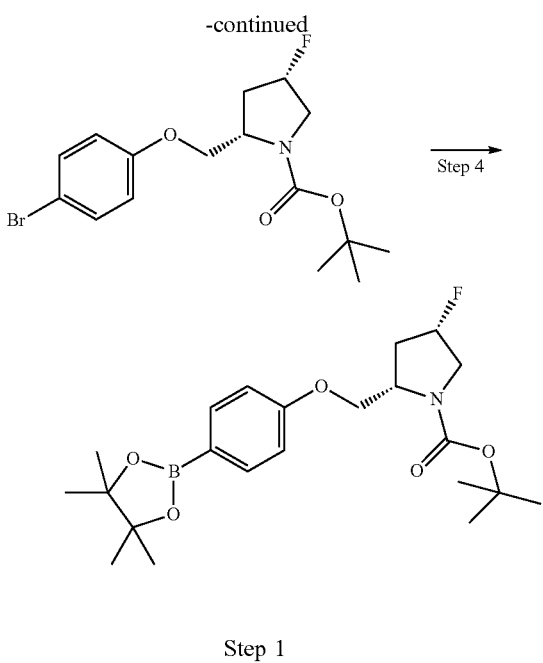

Step 1 tert-Butyl (2S,4S)-4-fluoro-2-(hydroxymethyl)pyrrolidine-1-carboxylate

To a solution of (2S,4S)-1-tert-butoxycarbonyl-4-fluoropyrrolidine-2-carboxylic acid (4.7 g) in tetrahydrofuran (40 ml), a borane-tetrahydrofuran complex (0.95 M solution in tetrahydrofuran, 31.6 ml) was added under ice cooling, and the mixture was stirred at room temperature for 1 hour. Ice water and a saturated aqueous solution of sodium bicarbonate were added to the reaction solution, followed by extraction with ethyl acetate. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (4.2 g).

$^1$H-NMR (CDCl$_3$) δ: 1.46 (9H, s), 1.91-2.32 (2H, m), 3.44-3.87 (4H, m), 4.10-4.25 (1H, m), 5.03-5.23 (1H, m).

Step 2 tert-Butyl (2S,4S)-4-fluoro-2-(methylsulfonyloxymethyl)pyrrolidine-1-carboxylate The title compound (5.4 g) was obtained by the same procedures as in step 1 of Reference Example 25 with the compound (4.2 g) obtained in the preceding step 1 as the starting material.

$^1$H-NMR (CDCl$_3$) δ: 1.45 (9H, s), 2.02-2.44 (2H, m), 3.01 (3H, s), 3.44-3.73 (2H, m), 3.98-4.25 (2H, m), 4.45-4.51 (1H, m), 5.22 (1H, d, J=53.2 Hz).

Step 3 tert-Butyl (2S,4S)-2-[(4-bromophenoxy)methyl]-4-fluoropyrrolidine-1-carboxylate

The title compound (2.0 g) was obtained by the same procedures as in step 2 of Reference Example 25 with the compound (5.4 g) obtained in the preceding step 2 as the starting material.

$^1$H-NMR (CDCl$_3$) δ: 1.45 (9H, s), 2.05-2.15 (1H, m), 2.38-2.49 (1H, m), 3.47-3.83 (3H, m), 4.12-4.35 (2H, m), 5.21 (1H, d, J=52.4 Hz), 6.81 (2H, d, J=7.8 Hz), 7.33 (2H, d, J=8.6 Hz).

Step 4 tert-Butyl (2S,4S)-4-fluoro-2-[[4-(4,4,5,5-tetramethyl-1,3,2-dioxaborolan-2-yl)phenoxy]methyl]pyrrolidine-1-carboxylate The title compound (1.8 g) was obtained by the same procedures as in step 2 of Reference Example 1 using the compound (1.9 g) obtained in the preceding step 3.

$^1$H-NMR (CDCl$_3$) δ: 1.29 (12H, s), 1.46 (9H, s), 2.00-2.21 (2H, m), 2.39-2.53 (1H, m), 3.46-3.92 (2H, m), 4.14-4.42 (2H, m), 5.10-5.30 (1H, m), 6.90 (2H, d, J=8.6 Hz), 7.71 (2H, d, J=7.8 Hz).

Reference Example 37 tert-Butyl N-cyclopropyl-N-[2-[4-(4,4,5,5-tetramethyl-1,3,2-dioxaborolan-2-yl)phenoxy]ethyl]carbamate

[Formula 19]

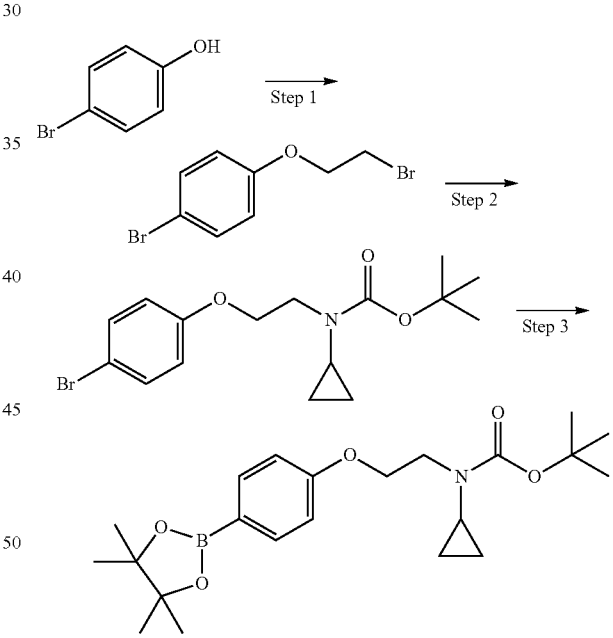

Step 1

1-Bromo-4-(2-bromoethoxy)benzene

The title compound (2.7 g) was obtained by the same procedures as in step 1 of Reference Example 1 with 4-bromophenol as the starting material using 2-bromoethanol (1.9 g) instead of tert-butyl (2S)-2-(hydroxymethyl)pyrrolidine-1-carboxylate.

$^1$H-NMR (CDCl$_3$) δ: 3.63 (2H, t, J=5.4 Hz), 4.26 (2H, t, J=6.0 Hz), 6.80 (2H, d, J=9.1 Hz), 7.39 (2H, d, J=9.1 Hz).

Step 2 tert-Butyl N-[2-(4-bromophenoxy)ethyl]-N-cyclopropylcarbamate

To a solution of the compound (2.7 g) obtained in the preceding step 1 in N,N-dimethylformamide (20 ml), cyclopropylamine (2.0 ml) was added, and the mixture was stirred at room temperature for 2.5 hours. Water was added to the reaction solution, followed by extraction with ethyl acetate. The extract was washed with water and saturated saline in this order and then dried over anhydrous sodium sulfate. The solvent was distilled off under reduced pressure. The obtained residue was dissolved in ethanol (30 ml). To this solution, di-tert-butyl dicarbonate (2.2 g) was added, and the mixture was stirred at room temperature for 1.5 hours. The reaction solution was concentrated under reduced pressure. The obtained residue was purified by silica gel column chromatography (n-hexane-ethyl acetate) to obtain the title compound (1.0 g).

$^1$H-NMR (CDCl$_3$) δ: 0.62-0.78 (4H, m), 1.46 (9H, s), 2.56-2.63 (1H, m), 3.59 (2H, t, J=5.4 Hz), 4.06 (2H, t, J=5.4 Hz), 6.77 (2H, d, J=9.1 Hz), 7.36 (2H, d, J=8.5 Hz).

Step 3 tert-Butyl N-cyclopropyl-N-[2-[4-(4,4,5,5-tetramethyl-1,3,2-dioxaborolan-2-yl)phenoxy]ethyl]carbamate The title compound (1.2 g) was obtained by the same procedures as in step 2 of Reference Example 1 using the compound (1.0 g) obtained in the preceding step 2.

$^1$H-NMR (CDCl$_3$) δ: 0.63-0.78 (4H, m), 1.33 (12H, s), 1.46 (9H, s), 2.56-2.65 (1H, m), 3.61 (2H, t, J=6.0 Hz), 4.12 (3H, t, J=6.0 Hz), 6.88 (2H, d, J=7.3 Hz), 7.74 (2H, d, J=7.3 Hz).

Reference Example 38 tert-Butyl N-methyl-N-[1-methyl-2-[4-(4,4,5,5-tetramethyl-1,3,2-dioxaborolan-2-yl)phenoxy]ethyl]carbamate

[Formula 20]

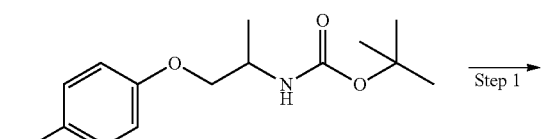

Step 1→

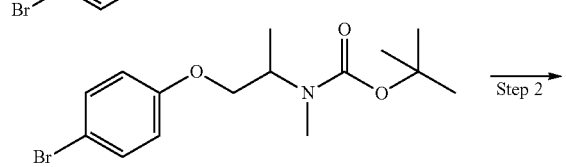

Step 2→

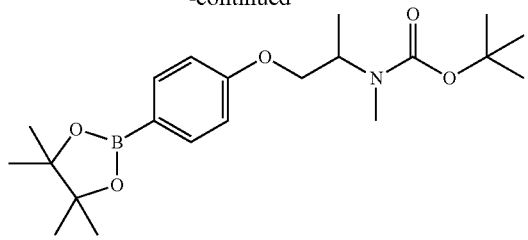

Step 1 tert-Butyl N-[2-(4-bromophenoxy)-1-methyl-ethyl]-N-methylcarbamate

To a solution of the compound (3.80 g) obtained in step 1 of Reference Example 12 by the same procedures as in step 1 of Reference Example 1 in N,N-dimethylformamide (40 ml), sodium hydride (55% oil, 0.57 g) was added, and the mixture was stirred at room temperature for 20 minutes. Then, methyl iodide (2.83 g) was added thereto, and the mixture was further stirred at room temperature for 40 minutes. After ice cooling, water was added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) to obtain the title compound (3.79 g).

$^1$H-NMR (CDCl$_3$) δ: 1.23 (3H, d, J=6.7 Hz), 1.46 (9H, s), 2.79 (3H, s), 3.87 (1H, br s), 3.93 (1H, dd, J=9.7, 7.3 Hz), 4.41-4.57 (1H, m), 6.77 (2H, d, J=9.1 Hz), 7.36 (2H, d, J=9.1 Hz).

Step 2 tert-Butyl N-methyl-N-[1-methyl-2-[4-(4,4,5,5-tetramethyl-1,3,2-dioxaborolan-2-yl)phenoxy]ethyl]carbamate The title compound (0.78 g) was obtained by the same procedures as in step 2 of Reference Example 1 using the compound (1.29 g) obtained in the preceding step 1.

$^1$H-NMR (CDCl$_3$) δ: 1.24 (3H, d, J=6.8 Hz), 1.33 (12H, s), 1.46 (9H, s), 2.80 (3H, s), 3.93 (1H, br s), 3.99 (1H, dd, J=9.7, 6.7 Hz), 4.44-4.59 (1H, m), 6.87 (2H, d, J=8.5 Hz), 7.73 (2H, d, J=8.5 Hz).

Reference Example 39 tert-Butyl N-[1-[[4-(4,4,5,5-tetramethyl-1,3,2-dioxaborolan-2-yl)phenoxy]methyl]cyclopropyl]carbamate

[Formula 21]

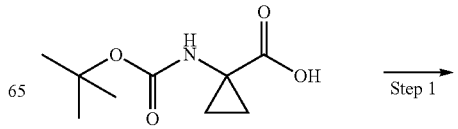

Step 1→

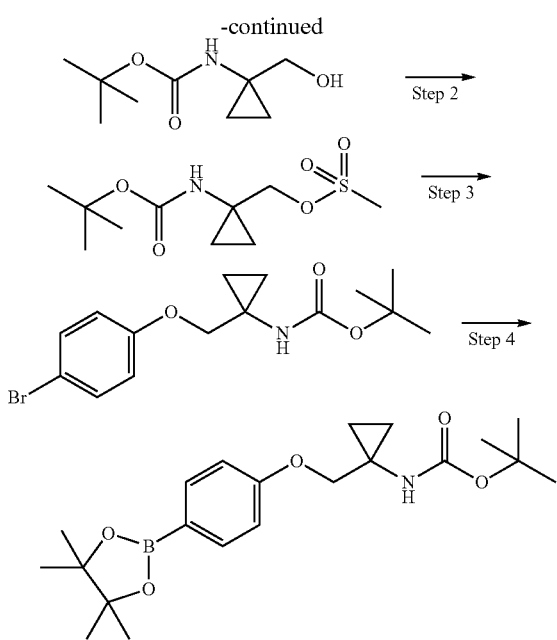

Step 1 tert-Butyl N-[1-(hydroxymethyl)cyclopropyl]carbamate

A solution of 1-(N-tert-butoxycarbonylamino)cyclopropanecarboxylic acid (5 g) in tetrahydrofuran was cooled to −20° C. Isobutyl chloroformate (3.24 ml) and N-methylmorpholine (2.74 ml) were added thereto, and the mixture was stirred at the same temperature as above for 20 minutes. Then, sodium borohydride (1.12 g) and water (1 ml) were added thereto, and the mixture was further stirred at room temperature for 40 minutes. Water was added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) to obtain the title compound (4.24 g).

$^1$H-NMR (CDCl$_3$) δ: 0.81-0.85 (4H, m), 1.44 (9H, s), 3.43 (1H, br s), 3.59 (2H, d, J=4.8 Hz), 5.07 (1H, br s).

Step 2

[1-(tert-Butoxycarbonylamino)cyclopropyl]methyl methanesulfonate

The title compound (3.93 g) was obtained by the same procedures as in step 1 of Reference Example 25 using the compound (3.21 g) obtained in the preceding step 1.

$^1$H-NMR (CDCl$_3$) δ: 0.92-0.96 (4H, m), 1.44 (9H, s), 3.03 (3H, s), 4.25 (2H, s), 5.06 (1H, br s).

Step 3 tert-Butyl N-[1-[(4-bromophenoxy)methyl]cyclopropyl]carbamate

The title compound (0.43 g) was obtained by the same procedures as in step 2 of Reference Example 25 using the compound (2.05 g) obtained in the preceding step 2.

$^1$H-NMR (CDCl$_3$) δ: 0.89-0.92 (4H, m), 1.43 (9H, s), 3.94 (2H, s), 5.11 (1H, br s), 6.77 (2H, d, J=9.1 Hz), 7.36 (2H, d, J=9.1 Hz).

Step 4 tert-Butyl N-[1-[[4-(4,4,5,5-tetramethyl-1,3,2-dioxaborolan-2-yl)phenoxy]methyl]cyclopropyl]carbamate The title compound (0.39 g) was obtained by the same procedures as in step 2 of Reference Example 1 using the compound (0.43 g) obtained in the preceding step 3.

$^1$H-NMR (CDCl$_3$) δ: 0.89-0.92 (4H, m), 1.33 (12H, s), 1.42 (9H, s), 3.99 (2H, s), 5.14 (1H, br s), 6.88 (2H, d, J=8.5 Hz), 7.73 (2H, d, J=8.5 Hz).

Reference Example 40 tert-Butyl (2S,4S)-4-fluoro-2-[[5-(4,4,5,5-tetramethyl-1,3,2-dioxaborolan-2-yl)-2-pyridyl]oxymethyl]pyrrolidine-1-carboxylate

[Formula 22]

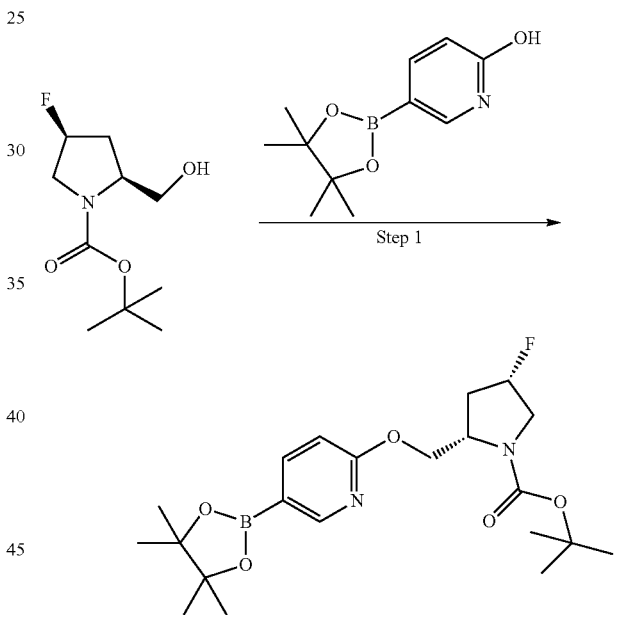

Step 1 tert-Butyl (2S,4S)-4-fluoro-2-[[5-(4,4,5,5-tetramethyl-1,3,2-dioxaborolan-2-yl)-2-pyridyl]oxymethyl]pyrrolidine-1-carboxylate The title compound (1.0 g) was obtained by the same procedures as in step 1 of Reference Example 1 with the compound (1.25 g) obtained in step 1 of Reference Example 36 as the starting material using 5-(4,4,5,5-tetramethyl-1,3,2-dioxaborolan-2-yl)pyridin-2-ol (1.26 g) instead of 4-bromophenol.

$^1$H-NMR (CDCl$_3$) δ: 1.33 (12H, s), 1.47 (9H, s), 2.06-2.24 (1H, m), 2.45 (1H, dd, J=20.0, 14.5 Hz), 3.66-3.74 (2H, m), 4.18 (1H, br s), 4.32 (1H, br s), 4.66 (1H, br s), 5.23 (1H, d, J=52.6 Hz), 6.71 (1H, d, J=8.5 Hz), 7.92 (1H, dd, J=8.5, 1.2 Hz), 8.52 (1H, d, J=1.2 Hz).

The following compounds were obtained by the same procedures as in Reference Example 40.

TABLE 4

| Reference Example | Structure and name | Instrumental data |
|---|---|---|
| 41 | ![structure] <br> tert-Butyl N-[(1R)-1-methyl-2-[[5-(4,4,5,5-tetramethyl-1,3,2-dioxaborolan-2-yl)-2-pyridyl]oxy]ethyl]carbamate | $^1$H-NMR (CDCl$_3$) δ: 1.25 (3H, d, J = 7.3 Hz), 1.33 (12H, s), 1.44 (9H, s), 4.07 (1H, br s), 4.25-4.33 (2H, m), 4.87 (1H, br s), 6.72 (1H, d, J = 8.2 Hz), 7.93 (1H, dd, J = 8.2, 2.1 Hz), 8.51 (1H, d, J = 2.1 Hz). |
| 42 | ![structure] <br> tert-Butyl N-[(1S)-1-methyl-2-[[5-(4,4,5,5-tetramethyl-1,3,2-dioxaborolan-2-yl)-2-pyridyl]oxy]ethyl]carbamate | $^1$H-NMR (CDCl$_3$) δ: 1.25 (3H, d, J = 7.3 Hz), 1.33 (12H, s), 1.44 (9H, s), 4.08 (1H, br s), 4.25-4.33 (2H, m), 4.93-5.03 (1H, m), 6.72 (1H, d, J = 8.2 Hz), 7.93 (1H, dd, J = 8.2, 1.8 Hz), 8.51 (1H, d, J = 1.8 Hz). |

Reference Example 43 tert-Butyl N-[(1R,2R)-2-hydroxy-1-[[4-(4,4,5,5-tetramethyl-1,3,2-dioxaborolan-2-yl)phenoxy]methyl]propyl]carbamate

[Formula 23]

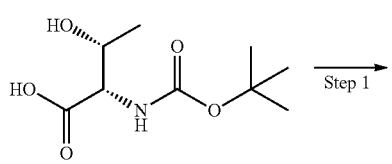

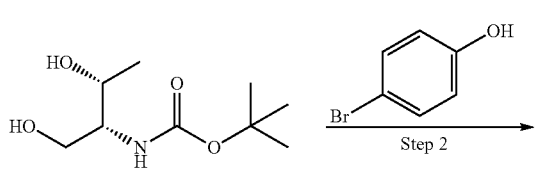

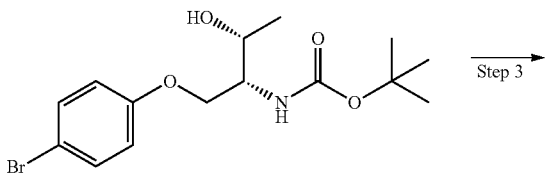

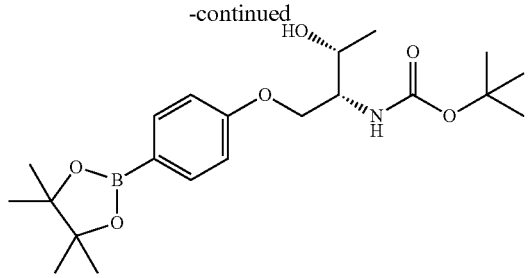

Step 1 tert-Butyl N-[(1R,2R)-2-hydroxy-1-(hydroxymethyl)propyl]carbamate

The title compound (1.58 g) was obtained by the same procedures as in step 1 of Reference Example 39 with (2S,3R)-2-(tert-butoxycarbonylamino)-3-hydroxybutyric acid (3.42 g) as the starting material.

$^1$H-NMR (CDCl$_3$) δ: 1.23 (3H, d, J=6.7 Hz), 1.46 (9H, s), 2.35 (1H, br s), 2.44 (1H, br s), 3.53 (1H, br s), 3.82-3.85 (2H, br m), 4.15 (2H, br s), 5.22 (1H, br s).

Step 2 tert-Butyl N-[(1R,2R)-1-[(4-bromophenoxy)methyl]-2-hydroxypropyl]carbamate

The title compound (1.09 g) was obtained by the same procedures as in step 1 of Reference Example 1 with 4-bromophenol (0.87 g) as the starting material using the compound (1.58 g) obtained in the preceding step 1 instead of tert-butyl (2S)-2-(hydroxymethyl)pyrrolidine-1-carboxylate.

$^1$H-NMR (CDCl$_3$) δ: 1.27 (3H, d, J=6.7 Hz), 1.46 (9H, s), 2.30 (1H, br s), 3.81 (1H, br s), 4.07 (2H, d, J=4.8 Hz), 4.18-4.21 (1H, m), 5.13 (1H, d, J=8.5 Hz), 6.80 (2H, d, J=9.1 Hz), 7.38 (2H, d, J=9.1 Hz).

Step 3 tert-Butyl N-[(1R,2R)-2-hydroxy-1-[[4-(4,4,5,5-tetramethyl-1,3,2-dioxaborolan-2-yl)phenoxy]methyl]propyl]carbamate The title compound (1.07 g) was obtained by the same procedures as in step 2 of Reference Example 1 using the compound (1.09 g) obtained in the preceding step 2.

$^1$H-NMR (CDCl$_3$) δ: 1.26 (3H, d, J=6.7 Hz), 1.33 (12H, s), 1.46 (9H, s), 3.83 (1H, br s), 4.14 (2H, br s), 4.21 (1H, br s), 5.18 (1H, d, J=8.5 Hz), 6.89 (2H, d, J=8.8 Hz), 7.75 (2H, d, J=8.8 Hz).

Reference Example 44 tert-Butyl N-[(1S,2S)-2-hydroxy-1-[[4-(4,4,5,5-tetramethyl-1,3,2-dioxaborolan-2-yl)phenoxy]methyl]propyl]carbamate

[Formula 24]

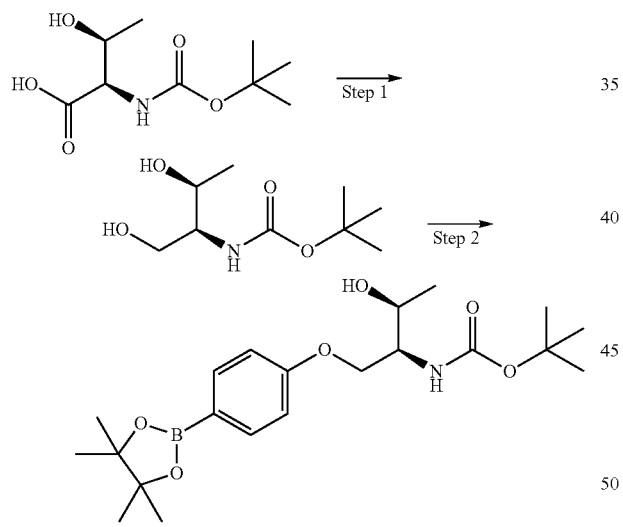

Step 1 tert-Butyl N-[(1S,2S)-2-hydroxy-1-(hydroxymethyl)propyl]carbamate

The title compound (2.24 g) was obtained by the same procedures as in step 1 of Reference Example 39 with (2R,3S)-2-(tert-butoxycarbonylamino)-3-hydroxybutyric acid (4.28 g) as the starting material.

$^1$H-NMR (CDCl$_3$) δ: 1.23 (3H, d, J=6.7 Hz), 1.46 (9H, s), 2.41 (1H, br s), 2.49 (1H, br s), 3.52 (1H, br s), 3.83 (2H, d, J=3.0 Hz), 4.15 (2H, br s), 5.21 (1H, br s).

Step 2 tert-Butyl N-[(1S,2S)-2-hydroxy-1-[[4-(4,4,5,5-tetramethyl-1,3,2-dioxaborolan-2-yl)phenoxy]methyl]propyl]carbamate The title compound (0.97 g) was obtained by the same procedures as in step 1 of Reference Example 1 with 4-(4,4,5,5-tetramethyl-1,3,2-dioxaborolan-2-yl)phenol (1.54 g) as the starting material using the compound (2.24 g) obtained in the preceding step 1 instead of tert-butyl (2S)-2-(hydroxymethyl)pyrrolidine-1-carboxylate.

$^1$H-NMR (CDCl$_3$) δ: 1.27 (3H, d, J=6.7 Hz), 1.33 (12H, s), 1.46 (9H, s), 2.44 (1H, br s), 3.82 (1H, br s), 4.13 (2H, br s), 4.19-4.23 (1H, m), 5.18 (1H, d, J=9.1 Hz), 6.90 (2H, d, J=8.5 Hz), 7.75 (2H, d, J=8.5 Hz).

Reference Example 45 tert-Butyl N-[(1R)-1-[[tert-butyldimethylsilyl]oxymethyl]-2-[4-(4,4,5,5-tetramethyl-1,3,2-dioxaborolan-2-yl)phenoxy]ethyl]carbamate

[Formula 25]

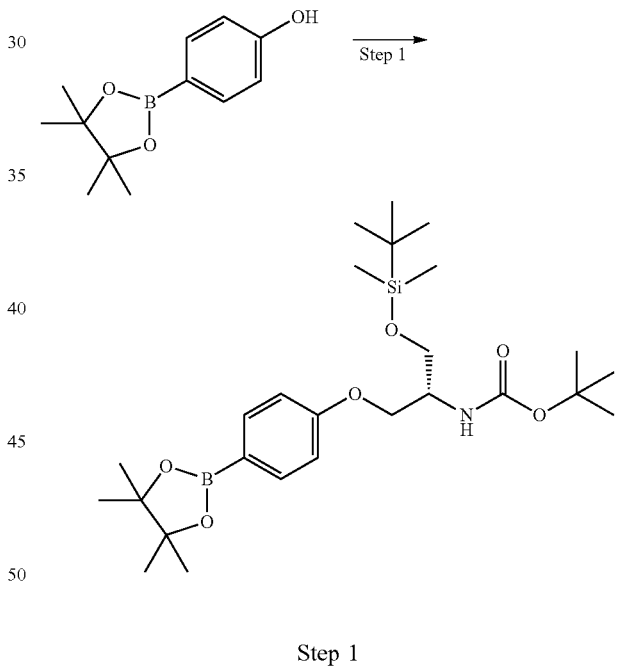

Step 1 tert-Butyl N-[(1R)-1-[[tert-butyldimethylsilyl]oxymethyl]-2-[4-(4,4,5,5-tetramethyl-1,3,2-dioxaborolan-2-yl)phenoxy]ethyl]carbamate The title compound (3.34 g) was obtained by the same procedures as in step 1 of Reference Example 1 with 4-(4,4,5,5-tetramethyl-1,3,2-dioxaborolan-2-yl)phenol (2.86 g) as the starting material using tert-butyl N-[(1R)-1-[[tert-butyldimethylsilyl]oxymethyl]-2-hydroxyethyl]carbamate (5.0 g) instead of tert-butyl (2S)-2-(hydroxymethyl)pyrrolidine-1-carboxylate.

$^1$H-NMR (CDCl$_3$) δ: 0.02 (6H, s), 0.86 (9H, s), 1.33 (12H, s), 1.46 (9H, s), 3.69 (1H, dd, J=10.3, 5.4 Hz), 3.84 (1H, dd,

J=10.3, 3.3 Hz), 3.98 (2H, br s), 4.11 (1H, br s), 4.96 (1H, d, J=6.0 Hz), 6.90 (2H, d, J=8.5 Hz), 7.73 (2H, d, J=8.5 Hz).

The following compounds were obtained by the same procedures as in Reference Example 45.

TABLE 5

| Reference Example | Structure and name | Instrumental data |
|---|---|---|
| 46 | 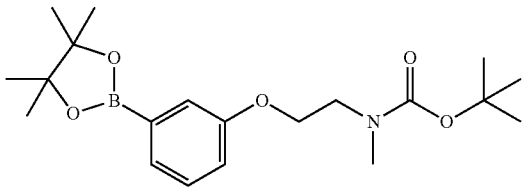 [SMILES: CN(CCOc1cccc(B2OC(C)(C)C(C)(C)O2)c1)C(=O)OC(C)(C)C]<br>tert-Butyl N-methyl-N-[2-[3-(4,4,5,5-tetramethyl-1,3,2-dioxaborolan-2-yl)phenoxy]ethyl]carbamate | $^1$H-NMR (CDCl$_3$) δ: 1.34 (12H, s), 1.46 (9H, s), 2.99 (3H, s), 3.60 (2H, br s), 4.10 (3H, br s), 6.98-7.00 (1H, m), 7.27-7.32 (2H, m), 7.40 (1H, d, J = 7.3 Hz). |
| 47 | 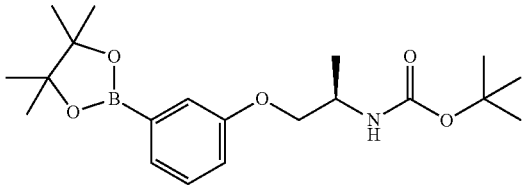 [SMILES: C[C@H](COc1cccc(B2OC(C)(C)C(C)(C)O2)c1)NC(=O)OC(C)(C)C]<br>tert-Butyl N-[(1R)-1-methyl-2-[3-(4,4,5,5-tetramethyl-1,3,2-dioxaborolan-2-yl)phenoxy]ethyl]carbamate | $^1$H-NMR (CDCl$_3$) δ: 1.29 (3H, d, J = 6.7 Hz), 1.34 (12H, s), 1.45 (9H, s), 3.95-3.97 (2H, m), 4.05 (1H, br s), 4.80 (1H, br s), 6.99-7.01 (1H, m), 7.28 (1H, d, J = 7.3 Hz), 7.32-7.32 (1H, m), 7.40 (1H, d, J = 6.7 Hz). |
| 48 | 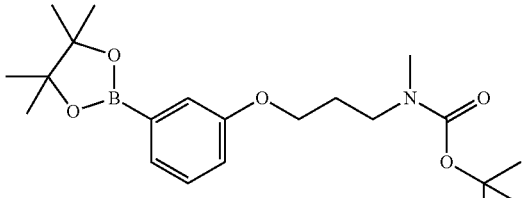<br>tert-Butyl N-methyl-N-[3-[3-(4,4,5,5-tetramethyl-1,3,2-dioxaborolan-2-yl)phenoxy]propyl]carbamate | $^1$H-NMR (CDCl$_3$) δ: 1.34 (12H, s), 1.44 (9H, s), 1.97-2.01 (2H, m), 2.87 (3H, s), 3.40 (2H, t, J = 7.0 Hz), 4.00 (2H, t, J = 6.3 Hz), 6.98-7.00 (1H, m), 7.29-7.32 (2H, m), 7.39 (1H, d, J = 7.3 Hz). |
| 49 | 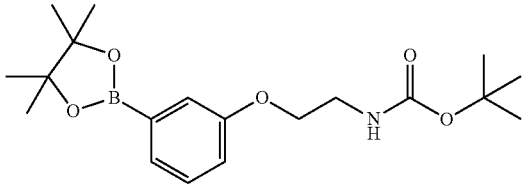<br>tert-Butyl N-[2-[3-(4,4,5,5-tetramethyl-1,3,2-dioxaborolan-2-yl)phenoxy]ethyl]carbamate | $^1$H-NMR (CDCl$_3$) δ: 1.33 (12H, s), 1.45 (9H, s), 3.53 (2H, q, J = 5.0 Hz), 4.05 (2H, t, J = 5.1 Hz), 4.99 (1H, br s), 6.93-7.01 (1H, m), 7.22-7.32 (2H, m), 7.39 (1H, dd, J = 14.5, 7.3 Hz). |
| 50 | 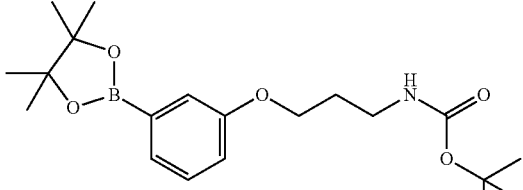<br>tert-Butyl N-[3-[3-(4,4,5,5-tetramethyl-1,3,2-dioxaborolan-2-yl)phenoxy]propyl]carbamate | $^1$H-NMR (CDCl$_3$) δ: 1.34 (12H, s), 1.44 (9H, s), 1.94-2.00 (2H, m), 3.32 (2H, q, J = 6.3 Hz), 4.06 (2H, t, J = 5.7 Hz), 4.77 (1H, br s), 6.99-7.01 (1H, m), 7.27-7.33 (2H, m), 7.40 (1H, d, J = 7.3 Hz). |

Reference Example 51 tert-Butyl (2S)-2-[[4-(4,4,5,5-tetramethyl-1,3,2-dioxaborolan-2-yl)phenyl]sulfanylmethyl]pyrrolidine-1-carboxylate

[Formula 26]

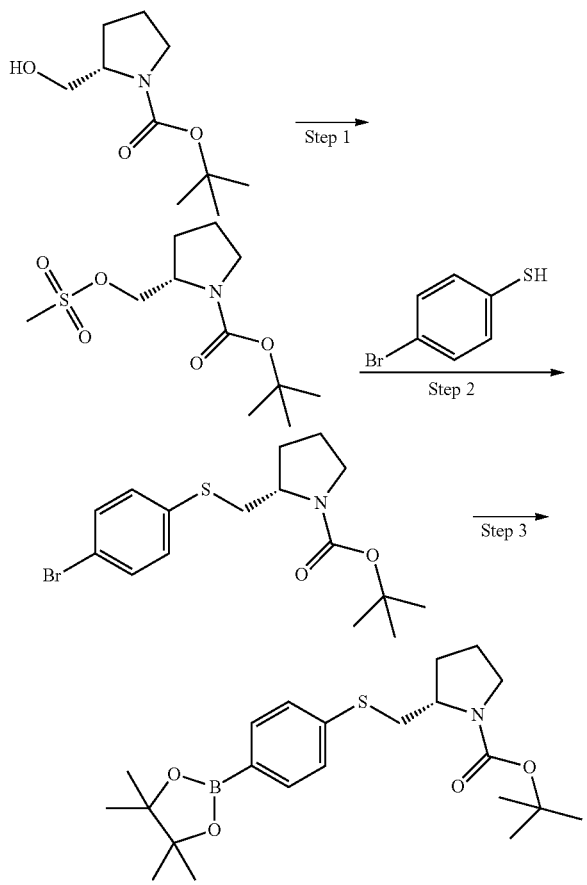

Step 1 tert-Butyl (2S)-2-(methylsulfonyloxymethyl)pyrrolidine-1-carboxylate

The title compound (1.4 g) was obtained by the same procedures as in step 1 of Reference Example 25 with tert-butyl (2S)-2-(hydroxymethyl)pyrrolidine-1-carboxylate (1.0 g) as the starting material.

$^1$H-NMR (CDCl$_3$) δ: 1.46 (9H, br s), 1.79-2.09 (4H, m), 3.01 (3H, s), 3.31-3.46 (2H, m), 3.96-4.36 (3H, m).

Step 2 tert-Butyl (2S)-2-[(4-bromophenyl)sulfanylmethyl]pyrrolidine-1-carboxylate

To a solution of the compound (1.4 g) obtained in the preceding step 1 in N,N-dimethylformamide (20 ml), potassium carbonate (1.1 g) and 4-bromobenzenethiol (0.76 g) were added, and the mixture was stirred at room temperature for 19 hours. Water was added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) to obtain the title compound (0.9 g).

$^1$H-NMR (CDCl$_3$) δ: 1.45 (9H, s), 1.76-2.05 (4H, m), 2.61-2.83 (1H, m), 3.28-3.51 (3H, m), 3.87-4.06 (1H, m), 7.31 (2H, d, J=7.9 Hz), 7.39 (2H, d, J=8.5 Hz).

Step 3 tert-Butyl (2S)-2-[[4-(4,4,5,5-tetramethyl-1,3,2-dioxaborolan-2-yl)phenyl]sulfanylmethyl]pyrrolidine-1-carboxylate The title compound (0.7 g) was obtained by the same procedures as in step 2 of Reference Example 1 using the compound (0.9 g) obtained in the preceding step 2.

$^1$H-NMR (CDCl$_3$) δ: 1.33 (12H, s), 1.45 (9H, br s), 1.75-2.04 (4H, m), 2.61-2.87 (1H, m), 3.28-3.56 (3H, m), 3.90-4.08 (1H, m), 7.35 (2H, d, J=7.9 Hz), 7.69 (2H, d, J=7.9 Hz).

Reference Example 52

(2R)-3-[4-(4,4,5,5-Tetramethyl-1,3,2-dioxaborolan-2-yl)phenoxy]-2-(tritylamino)propan-1-ol

[Formula 27]

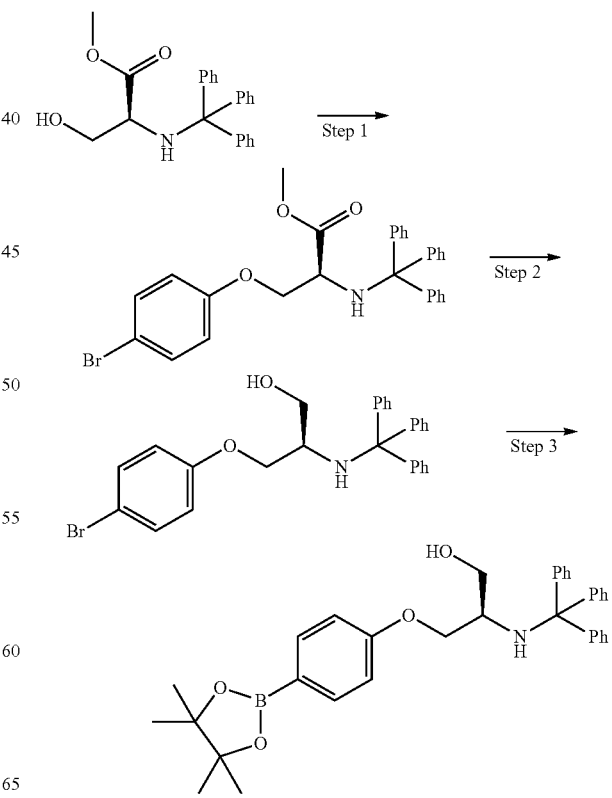

Step 1

Methyl (2S)-3-(4-bromophenoxy)-2-(tritylamino)propanoate

The title compound (4.80 g) was obtained by the same procedures as in step 1 of Reference Example 1 with 4-bromophenol (3.46 g) as the starting material using methyl (2S)-3-hydroxy-2-(tritylamino)propanoate (7.26 g) instead of tert-butyl (2S)-2-(hydroxymethyl)pyrrolidine-1-carboxylate.

$^1$H-NMR (CDCl$_3$) δ: 2.87 (1H, d, J=10.3 Hz), 3.23 (3H, s), 3.68-3.74 (1H, m), 3.97 (1H, dd, J=9.7, 6.7 Hz), 4.20 (1H, dd, J=9.7, 4.8 Hz), 6.75 (2H, d, J=9.1 Hz), 7.16-7.55 (17H, m).

Step 2

(2R)-3-(4-Bromophenoxy)-2-(tritylamino)propan-1-ol

To a solution of the compound (4.80 g) obtained in the preceding step 1 in tetrahydrofuran (50 ml), lithium aluminum hydride (189 mg) was added under ice cooling, and the mixture was stirred at 0° C. for 2 hours. Water was added to the reaction solution to separate two layers. Then, the aqueous layer was subjected to extraction with ethyl acetate. The organic layers were combined, washed with saturated saline and then dried over anhydrous magnesium sulfate. The solvent was distilled off under reduced pressure. The obtained residue was purified by silica gel column chromatography (n-hexane-ethyl acetate) to obtain the title compound (4.14 g).

$^1$H-NMR (CDCl$_3$) δ: 1.79 (1H, t, J=5.7 Hz), 2.42 (1H, br s), 3.02-3.12 (3H, m), 3.55-3.62 (2H, m), 6.55 (2H, d, J=9.1 Hz), 7.17-7.59 (17H, m).

Step 3

(2R)-3-[4-(4,4,5,5-Tetramethyl-1,3,2-dioxaborolan-2-yl)phenoxy]-2-(tritylamino)propan-1-ol The title compound (1.08 g) was obtained by the same procedures as in step 2 of Reference Example 1 using the compound (1.18 g) obtained in the preceding step 2.

$^1$H-NMR (CDCl$_3$) δ: 1.33 (12H, s), 1.83 (1H, br s), 2.46 (1H, br s), 3.06 (2H, br s), 3.17 (1H, dd, J=9.4, 6.0 Hz), 3.58-3.61 (1H, m), 3.65 (1H, dd, J=9.4, 3.3 Hz), 6.67 (2H, d, J=8.8 Hz), 7.18-7.20 (3H, m), 7.22-7.30 (6H, m), 7.52-7.62 (6H, m), 7.67 (2H, d, J=8.8 Hz).

Reference Example 53 tert-Butyl N-[3-cis-[4-(4,4,5,5-Tetramethyl-1,3,2-dioxaborolan-2-yl)phenoxy]cyclobutyl]carbamate

[Formula 28]

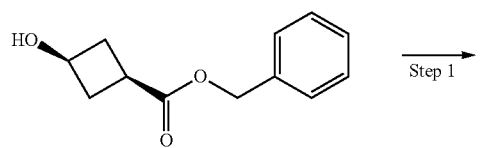

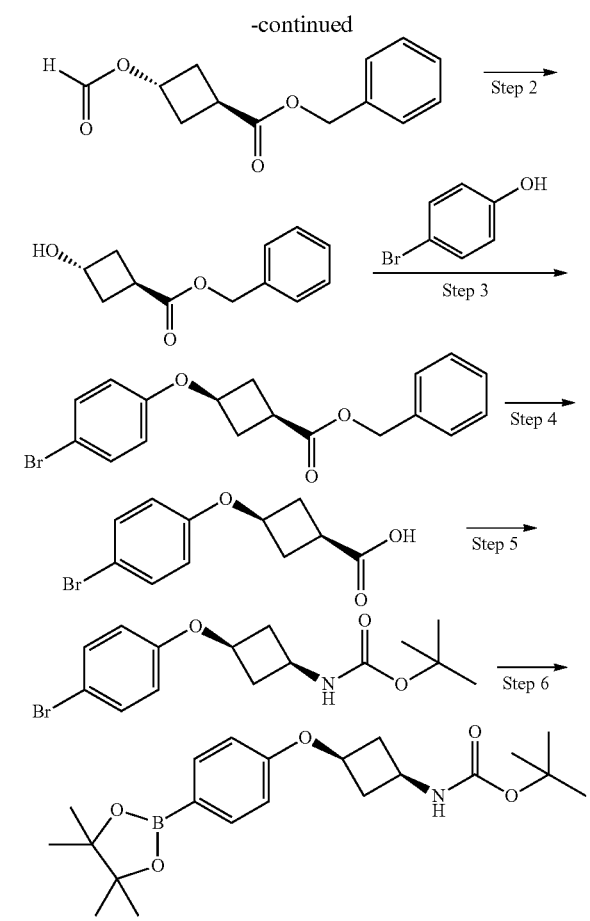

Step 1

Benzyl 3-cis-formyloxycyclobutanecarboxylate

To a solution of benzyl 3-cis-hydroxycyclobutanecarboxylate (7.40 g) and formic acid (1.62 ml) in tetrahydrofuran (80 ml), triphenylphosphine (11.28 g) and a solution of diethyl azodicarboxylate in toluene (40%, 19.5 ml) were added, and the mixture was stirred at room temperature for 2 hours. The reaction solution was concentrated under reduced pressure. The obtained residue was purified by silica gel column chromatography (n-hexane-ethyl acetate) to obtain the title compound (8.59 g).

$^1$H-NMR (CDCl$_3$) δ: 2.38-2.46 (2H, m), 2.69-2.75 (2H, m), 3.17-3.24 (1H, m), 5.15 (2H, s), 5.30-5.33 (1H, m), 7.32-7.40 (5H, m), 7.97 (1H, s).

Step 2

Benzyl 3-trans-hydroxycyclobutanecarboxylate

To the compound (8.59 g) obtained in the preceding step 1, dimethylamine (2 M solution in tetrahydrofuran, 50 ml) was added, and the mixture was stirred at room temperature for 5 hours. The reaction solution was concentrated under reduced pressure. The obtained residue was purified by silica gel column chromatography (n-hexane-ethyl acetate) to obtain the title compound (5.36 g).

¹H-NMR (CDCl₃) δ: 1.81 (1H, d, J=5.4 Hz), 2.19-2.27 (2H, m), 2.56-2.63 (2H, m), 3.05-3.11 (1H, m), 4.55-4.60 (1H, m), 5.13 (2H, s), 7.30-7.39 (5H, m).

Step 3

Benzyl 3-cis-(4-bromophenoxy)cyclobutanecarboxylate

The title compound (6.03 g) was obtained by the same procedures as in step 1 of Reference Example 1 with 4-bromophenol (4.84 g) as the starting material using the compound (5.36 g) obtained in the preceding step 2 instead of tert-butyl (2S)-2-(hydroxymethyl)pyrrolidine-1-carboxylate.

¹H-NMR (CDCl₃) δ: 2.41-2.50 (2H, m), 2.69-2.77 (2H, m), 2.81-2.88 (1H, m), 4.50-4.58 (1H, m), 5.14 (2H, s), 6.68 (2H, d, J=9.1 Hz), 7.30-7.39 (7H, m).

Step 4

3-cis-(4-Bromophenoxy)cyclobutanecarboxylic acid

To a solution of the compound (6.03 g) obtained in the preceding step 3 in ethanol (40 ml), a 1 N aqueous sodium hydroxide solution (40 ml) was added, and the mixture was stirred at room temperature for 2.5 hours. 1 N hydrochloric acid (60 ml) was added to the reaction solution. The aqueous layer was subjected to extraction with ethyl acetate. The organic layers were combined, washed with saturated saline and then dried over anhydrous magnesium sulfate. The solvent was distilled off under reduced pressure to obtain the title compound (4.30 g).

¹H-NMR (CDCl₃) δ: 2.43-2.52 (2H, m), 2.73-2.80 (2H, m), 2.84-2.89 (1H, m), 4.53-4.60 (1H, m), 6.68 (2H, d, J=8.8 Hz), 7.36 (2H, d, J=8.8 Hz).

Step 5 tert-Butyl N-[3-cis-(4-bromophenoxy)cyclobutyl]carbamate

To a solution of the compound (4.3 g) obtained in the preceding step 4 in toluene (50 ml), triethylamine (2.40 g) and diphenylphosphoryl azide (4.09 ml) were added, and the mixture was heated at 90° C. for 1 hour. Tert-butanol (15 ml) was added to the mixture, and the resulting mixture was further stirred at the same temperature as above for 3 hours. After cooling, ethyl acetate was added to the reaction solution. The organic layer was washed with water and saturated saline in this order and dried over anhydrous magnesium sulfate. The solvent was distilled off under reduced pressure. The obtained residue was purified by silica gel column chromatography (n-hexane-ethyl acetate) to obtain the title compound (2.11 g).

¹H-NMR (CDCl₃) δ: 1.44 (9H, s), 1.95-2.05 (2H, m), 2.91-2.96 (2H, m), 3.91 (1H, br s), 4.29-4.36 (1H, m), 4.68 (1H, br s), 6.67 (2H, d, J=9.1 Hz), 7.35 (2H, d, J=9.1 Hz).

Step 6 tert-Butyl N-[3-cis-[4-(4,4,5,5-tetramethyl-1,3,2-dioxaborolan-2-yl)phenoxy]cyclobutyl]carbamate The title compound (0.84 g) was obtained by the same procedures as in step 2 of Reference Example 1 using the compound (0.85 g) obtained in the preceding step 5.

¹H-NMR (CDCl₃) δ: 1.32 (12H, s), 1.44 (9H, s), 1.95-2.03 (2H, m), 2.95 (2H, br s), 3.91 (1H, br s), 4.38-4.45 (1H, m), 4.67-4.69 (1H, br m), 6.78 (2H, d, J=8.9 Hz), 7.72 (2H, d, J=8.9 Hz).

Reference Example 54

(+)-1-(2,5-Difluoro-3-pyridyl)ethanol

[Formula 29]

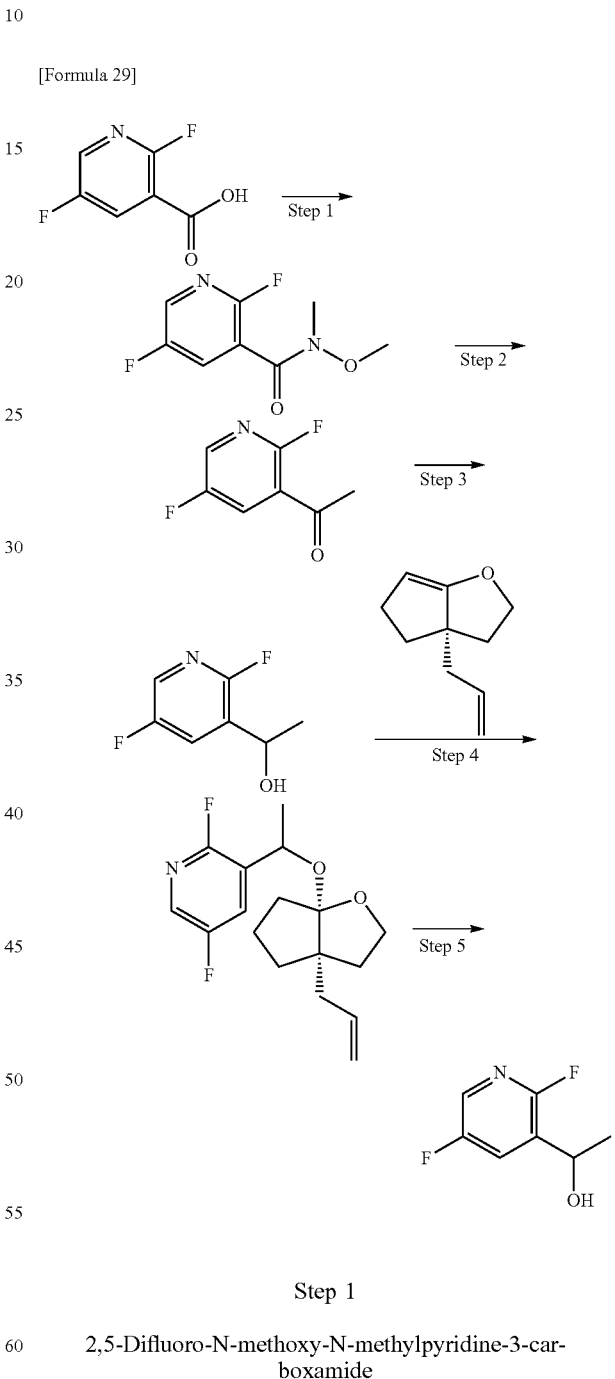

Step 1

2,5-Difluoro-N-methoxy-N-methylpyridine-3-carboxamide

To a solution of 2,5-difluoropyridine-3-carboxylic acid (3.00 g), 1-ethyl-3-(3-dimethylaminopropyl)carbodiimide hydrochloride (4.34 g), 1-hydroxybenzotriazole (127 mg), and N,O-dimethylhydroxylamine hydrochloride (1.93 g) in N,N-dimethylformamide (30 ml), diisopropylethylamine (7.42 ml) was added, and the mixture was stirred overnight at room temperature. Ethyl acetate and water were added to the reaction solution to separate the aqueous and organic layers. The aqueous layer was subjected to extraction with ethyl acetate. The organic layers were combined, washed with saturated saline, dried over anhydrous sodium sulfate and then concentrated under reduced pressure. The obtained residue was purified by silica gel column chromatography (hexane-ethyl acetate) to obtain the title compound (2.42 g).

$^1$H-NMR (CDCl$_3$) δ: 3.37 (3H, s), 3.59 (3H, s), 7.64 (1H, td, J=6.7, 3.0 Hz), 8.11-8.13 (1H, m).

ESI-MS (m/z): 203 (M+H)$^+$.

Step 2

1-(2,5-Difluoro-3-pyridyl)ethanone

The compound (2.40 g) obtained in the preceding step 1 was dissolved in tetrahydrofuran (50 ml). To the solution, methyl magnesium bromide (1 M solution in tetrahydrofuran, 17.8 ml) was added under ice cooling, and the mixture was then stirred at room temperature for 45 minutes. Methyl magnesium bromide (1 M solution in tetrahydrofuran, 5.9 ml) was further added thereto, and the mixture was stirred at room temperature for 30 minutes, followed by addition of a saturated aqueous solution of ammonium chloride. Ethyl acetate was added to the reaction solution to separate the aqueous and organic layers. The organic layer was dried over anhydrous sodium sulfate and then concentrated under reduced pressure. The obtained residue was purified by silica gel column chromatography (n-hexane-ethyl acetate) to obtain the title compound (1.36 g).

$^1$H-NMR (CDCl$_3$) δ: 2.70 (3H, d, J=4.8 Hz), 8.05 (1H, td, J=7.3, 3.9 Hz), 8.22-8.24 (1H, m).

Step 3

1-(2,5-Difluoro-3-pyridyl)ethanol (+)-B-Chlorodiisopinocampheylborane (1.6 M solution in n-hexane, 7.7 ml) was diluted with tetrahydrofuran (25 ml). To the dilution, a solution of the compound (878 mg) obtained in the preceding step 2 in tetrahydrofuran (10 ml) was added under ice cooling. After stirring at 0° C. for 5 hours, the solvent was distilled off under reduced pressure, and diethyl ether (100 ml) was added to the residue. Diethanolamine (1.29 g) was added thereto, and the mixture was stirred at room temperature for 2.5 hours. The deposited solid was collected by filtration. The obtained solid was dissolved in water, followed by extraction with ethyl acetate. The extract and the filtrate were combined, dried over anhydrous sodium sulfate and then concentrated under reduced pressure. The obtained residue was purified by silica gel column chromatography (n-hexane-ethyl acetate; and subsequently basic silica gel, n-hexane-ethyl acetate) to obtain the title compound (647 mg).

$^1$H-NMR (CDCl$_3$) δ: 1.53 (3H, d, J=6.7 Hz), 2.03 (1H, d, J=4.2 Hz), 5.09-5.15 (1H, m), 7.73 (1H, td, J=7.9, 3.0 Hz), 7.91-7.93 (1H, m).

Step 4

3-[1-[[(3a5,6aS)-3a-Allyl-3,4,5,6-tetrahydro-2H-cyclopenta[b]furan-6a-yl]oxy]ethyl]-2,5-difluoropyridine The compound (644 mg) obtained in the preceding step 3 and (3aS)-3a-allyl-2,3,4,5-tetrahydrocyclopenta[b]furan (730 mg) were dissolved in toluene (20 ml). To the solution, p-toluenesulfonic acid pyridine salt (712 mg) was added, and the mixture was stirred at room temperature for 3 days. Ethyl acetate and a saturated aqueous solution of sodium bicarbonate were added to the reaction solution to separate the aqueous and organic layers. The organic layer was dried over anhydrous sodium sulfate and then concentrated under reduced pressure. The obtained residue was purified by silica gel column chromatography (n-hexane-ethyl acetate) to obtain the title compound (926 mg).

$^1$H-NMR (CDCl$_3$) δ: 1.40 (3H, d, J=6.7 Hz), 1.49-1.74 (6H, m), 1.89-1.95 (1H, m), 2.19-2.25 (2H, m), 2.33 (1H, dd, J=13.9, 7.9 Hz), 3.33 (1H, q, J=7.9 Hz), 3.64 (1H, td, J=8.5, 4.2 Hz), 5.02-5.15 (3H, m), 5.82-5.92 (1H, m), 7.62 (1H, td, J=7.9, 3.0 Hz), 7.88-7.89 (1H, m).

Step 5

(+)-1-(2,5-Difluoro-3-pyridyl)ethanol

The compound (902 mg) obtained in the preceding step 4 was dissolved in methanol (20 ml). To the solution, p-toluenesulfonic acid monohydrate (55 mg) was added, and the mixture was stirred at 50° C. for 1 hour. A saturated aqueous solution of sodium bicarbonate and ethyl acetate were added to the reaction solution to separate the aqueous and organic layers. The aqueous layer was subjected to extraction with ethyl acetate. The organic layers were combined, dried over anhydrous sodium sulfate and then concentrated under reduced pressure. The obtained residue was purified by silica gel column chromatography (n-hexane-ethyl acetate) to obtain the title compound (375 mg).

$^1$H-NMR (CDCl$_3$) δ: 1.52 (3H, d, J=6.7 Hz), 2.21 (1H, d, J=4.2 Hz), 5.08-5.15 (1H, m), 7.73 (1H, td, J=7.9, 3.0 Hz), 7.91-7.92 (1H, m).

[α]$_D$+55.90° (c=0.916, methanol, 25.0° C.)

Reference Example 55

(+)-1-(5-Chloro-1-methylpyrazol-3-yl)ethanol

[Formula 30]

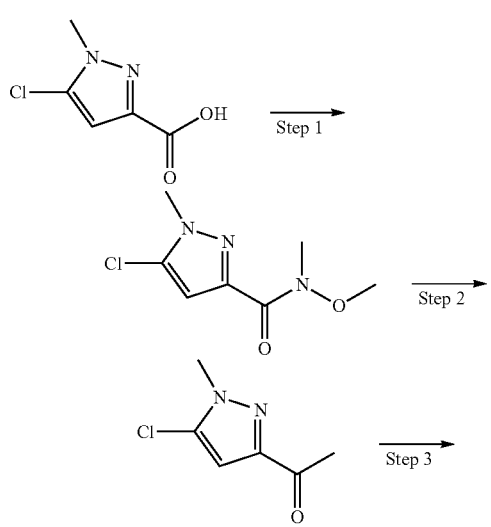

-continued

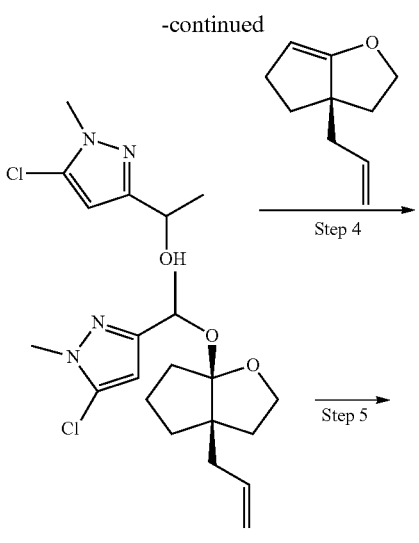

isomer A
isomer B

Step 1

5-Chloro-N-methoxy-N,1-dimethylpyrazole-3-carboxamide

5-Chloro-1-methyl-1H-pyrazole-3-carboxylic acid (982 mg) was added to a solution of 1-ethyl-3-(3-dimethylaminopropyl)carbodiimide hydrochloride (2.39 g), 1-hydroxybenzotriazole (252 mg), and N,O-dimethylhydroxylamine hydrochloride (1.21 g) in dichloromethane (50 ml). Triethylamine (2.4 ml) was added dropwise to the mixture, and the resulting mixture was stirred overnight at room temperature. The reaction solution was diluted with dichloromethane (20 ml). Water (50 ml) was added to the dilution to separate the aqueous and organic layers. The organic layer was washed with water (50 ml). The organic layer was dried over anhydrous magnesium sulfate. After filtration, the solvent was distilled off under reduced pressure. The obtained residue was purified by silica gel column chromatography (n-hexane-ethyl acetate) to obtain the title compound (1.14 g).

$^1$H-NMR (CDCl$_3$) δ: 3.37 (3H, s), 3.71-3.71 (3H, m), 3.87-3.88 (3H, m), 6.67 (1H, s).

ESI-MS (m/z): 203 (M+H)$^+$.

Step 2

1-(5-Chloro-1-methylpyrazol-3-yl)ethanone

A solution of the compound (1.14 g) obtained in the preceding step 1 in tetrahydrofuran (15 ml) was cooled in ice, and methyl magnesium bromide (0.99 M solution in tetrahydrofuran, 12.5 ml) was added dropwise thereto over 5 minutes. The reaction solution was stirred for 2 hours under ice cooling and then at room temperature for 30 minutes. The reaction solution was diluted with ethyl acetate (30 ml). After ice cooling, 1 N hydrochloric acid (6.7 ml) was added dropwise to the reaction solution. Then, a saturated aqueous solution of sodium bicarbonate (12 ml) and an aqueous sodium hydroxide solution (4 ml) were further added to the mixture, and the resulting mixture was stirred at room temperature for 30 minutes. The insoluble matter was filtered off through celite, and the filtrate was then separated into the aqueous and organic layers. The aqueous layer was subjected to extraction with ethyl acetate (20 ml). The organic layer was dried over anhydrous magnesium sulfate. After filtration, the solvent was distilled off under reduced pressure. The obtained residue was purified by silica gel column chromatography (n-hexane-ethyl acetate) to obtain the title compound (752 mg).

$^1$H-NMR (CDCl$_3$) δ: 2.50 (3H, s), 3.88 (3H, s), 6.68 (1H, s).

Step 3

1-(5-Chloro-1-methylpyrazol-3-yl)ethanol

A solution of the compound (741 mg) obtained in the preceding step 2 in methanol (12 ml) was cooled in ice, and sodium borohydride (230 mg) was added thereto. The mixture was stirred for 4 hours under ice cooling. A saturated ammonium chloride solution (0.8 ml) was added dropwise to the reaction solution, and the mixture was stirred for 5 minutes and then further stirred at room temperature for 10 minutes. The solvent was distilled off under reduced pressure, and the residue was diluted with ethyl acetate (50 ml). A saturated aqueous solution of sodium bicarbonate (15 ml) was added to the dilution to separate the aqueous and organic layers. The aqueous layer was subjected to extraction with ethyl acetate (20 ml). The organic layer was dried over anhydrous magnesium sulfate. After filtration, the solvent was distilled off under reduced pressure. The obtained residue was purified by silica gel column chromatography (n-hexane:ethyl acetate) to obtain the title compound (685 mg).

$^1$H-NMR (CDCl$_3$) δ: 1.46 (3H, d, J=6.6 Hz), 2.43 (1H, d, J=4.3 Hz), 3.76 (3H, s), 4.81-4.83 (1H, m), 6.13 (1H, s).

Step 4

3-[1-[[(3aR,6aR)-3a-Allyl-3,4,5,6-tetrahydro-2H-cyclopenta[b]furan-6a-yl]oxy]ethyl]-5-chloro-1-methylpyrazole To a solution of the compound (1.355 g) obtained in the preceding step 3 in toluene (36 ml), a solution of (3aR)-3a-allyl-2,3,4,5-tetrahydrocyclopenta[b]furan (1.52 g) in toluene (6 ml) was added. To this solution, p-toluenesulfonic acid pyridine salt (1.48 g) was added, and the mixture was stirred for 3 hours. The reaction solution was fractionated with ethyl acetate and a saturated aqueous solution of sodium bicarbonate. The organic layer was washed with saturated saline and then dried over anhydrous magnesium sulfate. After filtering off the insoluble matter, the solvent in the filtrate was distilled off under reduced pressure. The obtained residue was purified by silica gel column chromatography (n-hexane-ethyl acetate) to obtain low polar isomer A (1.108 g) and highly polar isomer B (1.017 g).

Low polar isomer A (Rf=0.60, n-hexane:ethyl acetate=3:1)

$^1$H-NMR (CDCl$_3$) δ: 1.38-1.59 (5H, m), 1.42 (3H, d, J=6.7 Hz), 1.67-1.74 (1H, m), 1.94-2.03 (2H, m), 2.09 (1H, dd, J=13.9, 7.3 Hz), 2.32 (1H, dd, J=13.9, 7.3 Hz), 3.78 (3H, s), 3.81-3.90 (2H, m), 4.89 (1H, q, J=6.7 Hz), 5.00-5.10 (2H, m), 5.81-5.91 (1H, m), 6.15 (1H, s).

Highly polar isomer B (Rf=0.51, n-hexane:ethyl acetate=3:1)

$^1$H-NMR (CDCl$_3$) δ: 1.42 (3H, d, J=6.7 Hz), 1.48-1.71 (6H, m), 1.88-1.94 (1H, m), 2.13 (1H, dd, J=13.9, 7.3 Hz), 2.17-2.22 (1H, m), 2.28 (1H, dd, J=13.9, 7.3 Hz), 3.58 (1H, q, J=7.9 Hz), 3.72 (1H, td, J=7.9, 4.2 Hz), 3.78 (3H, s), 4.87 (1H, q, J=6.7 Hz), 5.01-5.10 (2H, m), 5.80-5.91 (1H, m), 6.16 (1H, s).

Step 5

(+)-1-(5-Chloro-1-methylpyrazol-3-yl)ethanol

The low polar isomer A (1.48 g) obtained in the preceding step 4 was dissolved in methanol (45 ml). To the solution, p-toluenesulfonic acid monohydrate (91 mg) was added at room temperature. After stirring at room temperature for 3 hours, the solvent was distilled off under reduced pressure. Ethyl acetate and a saturated aqueous solution of sodium bicarbonate were added to the residue to separate the aqueous and organic layers. The organic layer was dried over anhydrous sodium sulfate. Then, the solvent was distilled off under reduced pressure. The obtained residue was purified by silica gel column chromatography (n-hexane-ethyl acetate) to obtain the title compound (647 mg).

$^1$H-NMR (CDCl$_3$) δ: 1.49 (3H, d, J=6.7 Hz), 2.37 (1H, d, J=3.6 Hz), 3.79 (3H, s), 4.84-4.89 (1H, m), 6.16 (1H, s).

[α]$_D$ +16.7° (c=1.08, chloroform, 25.0° C.)

The following compounds were obtained by the same procedures as in Reference Example 55.

TABLE 6

| Reference Example | Structure and name | Instrumental data |
|---|---|---|
| 56 | 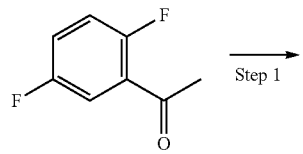<br>(+)-1-(5-Fluoro-3-pyridyl)ethanol | $^1$H-NMR (CDCl$_3$) δ: 1.46 (3H, d, J = 6.6 Hz), 2.75 (1H, br s), 4.94-4.97 (1H, m), 7.44-7.48 (1H, m), 8.30-8.32 (2H, m). [α]$_D$ +43.44° (c = 0.32, chloroform, 29.2° C.) |
| 57 | (+)-1-(5-Chloro-3-pyridyl)ethanol | $^1$H-NMR (CDCl$_3$) δ: 1.52 (3H, d, J = 6.7 Hz), 2.82-2.85 (1H, br m), 4.94-4.97 (1H, m), 7.75-7.75 (1H, m), 8.42-8.43 (2H, m). [α]$_D$ +44.44° (c = 0.18, chloroform, 22.6° C.) |

Reference Example 58

1-[5-Fluoro-2-(triazol-2-yl)phenyl]ethanol

[Formula 31]

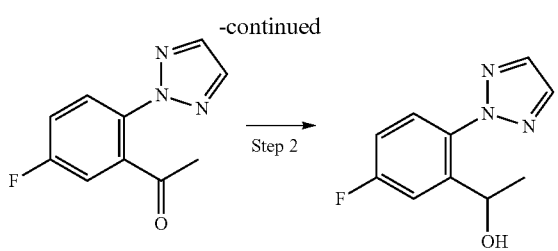

Step 1

1-[5-Fluoro-2-(triazol-2-yl)phenyl]ethanone 1-(2,5-Difluorophenyl)ethanone (3.00 g) and 1H-triazole (1.99 g) were dissolved in N-methylpyrrolidone (5 ml). To the solution, potassium carbonate (2.66 g) was added, and the mixture was stirred at 140° C. for 4.5 hours. After standing to cool, water and ethyl acetate were added to the reaction solution to separate the aqueous and organic layers. The aqueous layer was subjected to extraction with ethyl acetate. The organic layers were combined, washed three times with saturated saline, dried over anhydrous sodium sulfate and then concentrated under reduced pressure. The obtained residue was purified by silica gel column chromatography (n-hexane-ethyl acetate) to obtain the title compound (1.05 g).

$^1$H-NMR (CDCl$_3$) δ: 2.16 (3H, s), 7.22-7.31 (2H, m), 7.83-7.87 (3H, m).

1-[5-Fluoro-2-(triazol-2-yl)phenyl]ethanol

The compound (310 mg) obtained in the preceding step 1 was dissolved in methanol (10 ml). To the solution, sodium borohydride (86 mg) was added, and the mixture was stirred at room temperature for 15 minutes. The reaction solution was quenched by the addition of acetone. Water and ethyl acetate were added to the reaction solution to separate the aqueous and organic layers. The organic layer was washed with saturated saline, dried over anhydrous sodium sulfate and then concentrated under reduced pressure. The obtained residue was purified by silica gel column chromatography (n-hexane-ethyl acetate) to obtain the title compound (296 mg).

$^1$H-NMR (CDCl$_3$) δ: 1.46 (3H, d, J=6.0 Hz), 3.94 (1H, d, J=4.2 Hz), 4.83-4.89 (1H, m), 7.09-7.14 (1H, m), 7.39 (1H, dd, J=9.7, 3.0 Hz), 7.62 (1H, dd, J=9.1, 5.4 Hz), 7.88 (2H, s).

Reference Example 59

1-[1-(Difluoromethyl)triazol-4-yl]ethanol

[Formula 32]

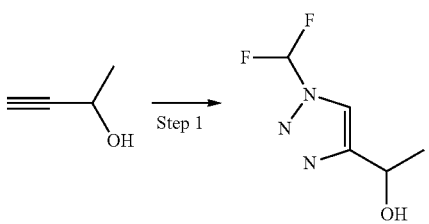

Step 1

Step 1

1-[1-(Difluoromethyl)triazol-4-yl]ethanol

Tert-butanol (17.4 ml), water (17.4 ml), and a 1 M aqueous copper(II) sulfate solution (4.64 ml) were added to sodium chlorodifluoroacetate (3.54 g), but-3-yn-2-ol (2.00 ml), sodium azide (1.66 g), cesium carbonate (11.3 g), and copper (1.18 g), and the mixture was reacted for 30 minutes using a microwave reaction apparatus (300 W, 125° C.). The reaction solution was diluted with ethyl acetate. While being washed, the dilution was filtered to remove the aqueous layer. The organic layer was dried over anhydrous sodium sulfate and then filtered. The solvent was distilled off under reduced pressure. The obtained residue was purified by silica gel column chromatography (n-hexane-methyl acetate) to obtain the title compound (196 mg).

$^1$H-NMR (CDCl$_3$) δ: 1.64 (3H, d, J=6.0 Hz), 2.35-2.39 (1H, m), 5.11-5.19 (1H, m), 7.54 (1H, t, J=59.2 Hz), 7.90 (1H, s).

Reference Example 60

(+)-5-(1-Hydroxyethyl)-2-methylpyrazole-3-carbonitrile

[Formula 33]

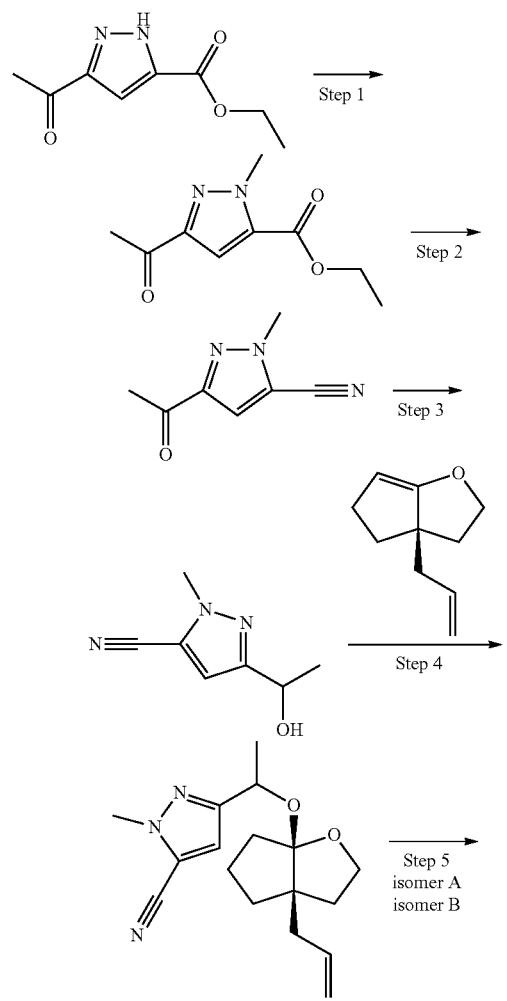

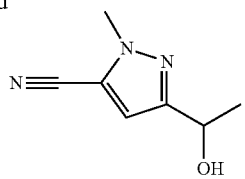

Step 1

Ethyl 5-acetyl-2-methylpyrazole-3-carboxylate

Ethyl 3-acetyl-1H-pyrazole-5-carboxylate (Chem. Commun., 2004, 394-395) (4.82 g) was dissolved in N,N-dimethylformamide (80 ml). To the solution, potassium carbonate (4.39 g) and iodomethane (1.98 ml) were added under ice cooling, and the mixture was stirred at room temperature for 3 hours and 50 minutes. The reaction solution was diluted with ethyl acetate. The organic layer was washed with saturated saline, water, and saturated saline in this order and then dried over anhydrous sodium sulfate. The solvent was distilled off under reduced pressure. The obtained residue was purified by silica gel column chromatography (n-hexane-ethyl acetate) to obtain the title compound (3.38 g).

$^1$H-NMR (CDCl$_3$) δ: 1.38 (3H, t, J=7.1 Hz), 2.58 (3H, s), 4.24 (3H, s), 4.36 (2H, q, J=7.1 Hz), 7.32 (1H, s).

Step 2

5-Acetyl-2-methylpyrazole-3-carbonitrile

The compound (3.38 g) obtained in the preceding step 1 was dissolved in tetrahydrofuran (170 ml). To the solution, an aqueous solution (35 ml) of lithium hydroxide monohydrate (1.45 g) was added under ice cooling, and the mixture was stirred at room temperature for 2 hours and 45 minutes. The reaction solution was rendered acidic by the addition of 1 N hydrochloric acid under ice cooling, followed by extraction with dichloromethane. The extract was dried over anhydrous sodium sulfate. The solvent was distilled off under reduced pressure. The obtained residue was dissolved in N,N-dimethylformamide (60 ml). To this solution, 1-hydroxybenzotriazole (3.49 g) was added. Subsequently, 1-ethyl-3-(3-dimethylaminopropyl)carbodiimide hydrochloride (4.95 g) and an aqueous ammonia solution (28%, 2.79 ml) were added to the mixture under ice cooling, and the resulting mixture was stirred overnight at room temperature. Ethyl acetate and saturated saline were added to the reaction solution to separate two layers. Then, the aqueous layer was subjected to extraction with ethyl acetate. The organic layers were combined and dried over anhydrous sodium sulfate. The solvent was distilled off under reduced pressure. The obtained residue was dissolved in tetrahydrofuran (70 ml). To this solution, triethylamine (6.24 ml) and a solution of trifluoroacetic anhydride in tetrahydrofuran (22 ml) were added at −5° C. under a nitrogen atmosphere, and the mixture was stirred for 3 hours and 40 minutes under ice cooling. Water was added to the reaction solution, followed by extraction with ethyl acetate. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (2.36 g).

¹H-NMR (CDCl₃) δ: 2.59 (3H, s), 4.13 (3H, s), 7.26 (1H, s).

Step 3

5-(1-Hydroxyethyl)-2-methylpyrazole-3-carbonitrile

The compound (2.36 g) obtained in the preceding step 2 was dissolved in methanol (170 ml). To this solution, sodium borohydride (658 mg) was added, and the mixture was stirred for 50 minutes. The reaction solution was concentrated under reduced pressure. The obtained residue was purified by silica gel column chromatography (n-hexane-ethyl acetate) to obtain the title compound (1.75 g).
¹H-NMR (CDCl₃) δ:1.53 (3H, d, J=6.6 Hz), 2.15 (1H, d, J=4.3 Hz), 4.03 (3H, s), 4.92-4.99 (1H, m), 6.74 (1H, s).

Step 4

5-[1-[[(3aR,6aR)-3a-Allyl-3,4,5,6-tetrahydro-2H-cyclopenta[b]furan-6a-yl]oxy]ethyl]-2-methylpyrazole-3-carbonitrile The compound (1.75 g) obtained in the preceding step 3 was dissolved in dichloromethane (60 ml). To the solution, p-toluenesulfonic acid pyridine salt (232 mg) was added under ice cooling. A solution of (3aR)-3a-allyl-2,3,4,5-tetrahydrocyclopenta[b]furan (2.09 g) in dichloromethane (35 ml) was further added to the mixture, and the resulting mixture was stirred at room temperature for 2 hours and 20 minutes. A saturated aqueous solution of sodium bicarbonate was added to the reaction solution, followed by extraction with dichloromethane. The extract was dried over anhydrous sodium sulfate. The solvent was distilled off under reduced pressure. The obtained residue was purified by silica gel column chromatography (n-hexane-ethyl acetate) to obtain low polar isomer A (1.56 g) and highly polar isomer B (1.62 g).
Low polar isomer A (Rf=0.70, n-hexane:ethyl acetate=7:3)
¹H-NMR (CDCl₃) δ: 1.26-1.37 (1H, m), 1.44 (3H, d, J=6.7 Hz), 1.47-1.62 (4H, m), 1.68-1.76 (1H, m), 1.93-2.11 (3H, m), 2.28-2.35 (1H, m), 3.80-3.91 (2H, m), 4.00 (3H, s), 4.97-5.10 (3H, m), 5.79-5.90 (1H, m), 7.26 (1H, s).
Highly polar isomer B (Rf=0.63, n-hexane:ethyl acetate=7:3)
¹H-NMR (CDCl₃) δ: 1.43 (3H, d, J=6.7 Hz), 1.47-1.73 (6H, m), 1.88-1.94 (1H, m), 2.10-2.31 (3H, m), 3.46-3.55 (1H, m), 3.67-3.74 (1H, m), 4.00 (3H, s), 4.96 (1H, q, J=6.7 Hz), 5.02-5.11 (2H, m), 5.80-5.90 (1H, m), 6.73 (1H, s).

Step 5

(+)-5-(1-Hydroxyethyl)-2-methylpyrazole-3-carbonitrile

The low polar isomer A (1.56 g) obtained in the preceding step 4 was dissolved in methanol (52 ml). To the solution, p-toluenesulfonic acid monohydrate (1.48 g) was added at room temperature. After stirring at 50° C. for 2 hours, the solvent was distilled off under reduced pressure. Dichloromethane and a saturated aqueous solution of sodium bicarbonate were added to the residue to separate the aqueous and organic layers. The organic layer was dried over anhydrous sodium sulfate. Then, the solvent was distilled off under reduced pressure. The obtained residue was purified by silica gel column chromatography (n-hexane-ethyl acetate) to obtain the title compound (709 mg).
¹H-NMR (CDCl₃) δ: 1.53 (3H, d, J=6.6 Hz), 2.15 (1H, d, J=4.3 Hz), 4.03 (3H, s), 4.92-4.99 (1H, m), 6.74 (1H, s).
[α]_D+19.0° (c=1.05, chloroform, 25.0° C.)

Reference Example 61 tert-Butyl N-[5-oxo-1-[4-(4,4,5,5-tetramethyl-1,3,2-dioxaborolan-2-yl)phenyl]pyrrolidin-3-yl]carbamate

[Formula 34]

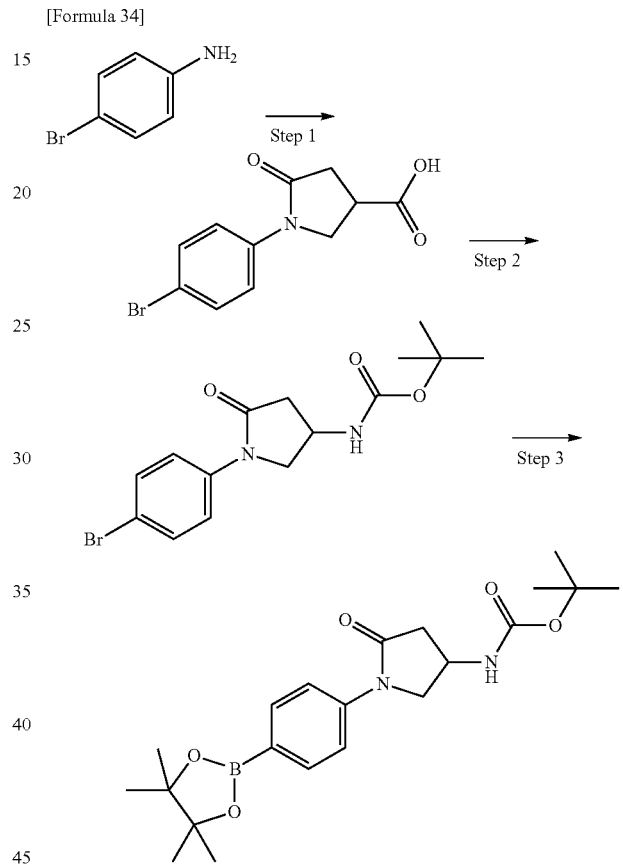

Step 1

1-(4-Bromophenyl)-5-oxopyrrolidine-3-carboxylic acid

A mixture of 4-bromoaniline (8.6 g) and itaconic acid (6.5 g) was stirred at 130° C. for 50 minutes. After cooling, a n-hexane-ethyl acetate mixed solution was added to the resulting solid. The compound was collected by filtration to obtain the title compound (13.5 g).
¹H-NMR (CDCl₃) δ: 2.89-3.03 (2H, m), 3.38-3.47 (1H, m), 4.02-4.16 (2H, m), 7.49 (4H, s).

Step 2 tert-Butyl N-[1-(4-bromophenyl)-5-oxopyrrolidin-3-yl]carbamate

To a solution of the compound (2.8 g) obtained in the preceding step 1 in tert-butanol (40 ml), triethylamine (2.1 ml) and diphenylphosphoryl azide (2.6 ml) were added, and the mixture was stirred at room temperature for 1 hour and then stirred at 80° C. for 3 hours. After cooling, the reaction solution was concentrated under reduced pressure, and a saturated aqueous solution of sodium bicarbonate was added to the residue, followed by extraction with ethyl acetate. The extract was washed with saturated saline and then dried over anhydrous sodium sulfate. The solvent was distilled off under reduced pressure. The obtained residue was purified by silica gel column chromatography (chloroform) to obtain the title compound (2.0 g).

$^1$H-NMR (CDCl$_3$) δ: 1.45 (9H, s), 2.48 (1H, dd, J=17.2, 4.6 Hz), 2.97 (1H, dd, J=17.2, 8.0 Hz), 3.70 (1H, d, J=10.9 Hz), 4.14 (1H, t, J=8.0 Hz), 4.41 (1H, br s), 4.85 (1H, br s), 7.46-7.52 (4H, m).

Step 3 tert-Butyl N-[5-oxo-1-[4-(4,4,5,5-tetramethyl-1,3,2-dioxaborolan-2-yl)phenyl]pyrrolidin-3-yl]carbamate To a solution of the compound (0.9 g) obtained in the preceding step 2 in 1,4-dioxane (20 ml), bis(pinacolato)diborane (0.77 g), potassium acetate (0.75 g), and a [1,1'-bis(diphenylphosphino)ferrocene]dichloropalladium(II)-dichloromethane adduct (0.21 g) were added, and the mixture was stirred at 80° C. for 6 hours under a nitrogen atmosphere. After cooling, ethyl acetate was added to the reaction solution, and the insoluble matter was filtered off. The filtrate was concentrated under reduced pressure. Then, the obtained residue was purified by silica gel column chromatography (n-hexane-ethyl acetate) to obtain the title compound (1.0 g).

$^1$H-NMR (CDCl$_3$) δ: 1.34 (12H, s), 1.45 (9H, s), 2.49 (1H, dd, J=17.8, 4.6 Hz), 2.98 (1H, dd, J=17.2, 8.0 Hz), 3.74 (1H, d, J=6.9 Hz), 4.15-4.21 (1H, m), 4.37-4.47 (1H, m), 4.85 (1H, br s), 7.61 (2H, d, J=8.6 Hz), 7.81 (2H, d, J=8.6 Hz).

Reference Example 62 tert-Butyl N-[(3R)-5-oxo-1-[4-(4,4,5,5-tetramethyl-1,3,2-dioxaborolan-2-yl)phenyl]pyrrolidin-3-yl]carbamate

[Formula 35]

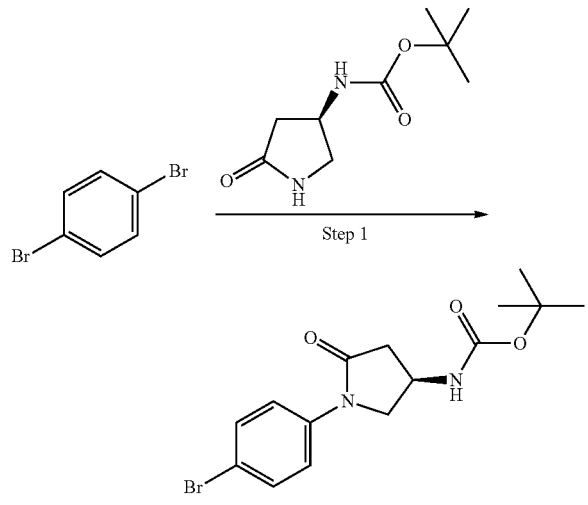

Step 1 tert-Butyl N-[(3R)-1-(4-bromophenyl)-5-oxopyrrolidin-3-yl]carbamate 1,4-Dioxane (8 ml) was added to 1,4-dibromobenzene (176 mg), t-butyl N-[(3R)-5-oxopyrrolidin-3-yl]carbamate (100 mg), tris(dibenzylideneacetone)dipalladium(0) (23 mg), 4,5-bis(diphenylphosphino)-9,9-dimethylxanthene (29 mg), and cesium carbonate (244 mg), and the mixture was stirred at 90° C. for 1 hour under an argon atmosphere and then further heated to reflux for 1 hour. Dichloromethane and water were added to the reaction solution to separate the aqueous and organic layers. The organic layer was dried over anhydrous sodium sulfate and then concentrated under reduced pressure. The obtained residue was purified by silica gel column chromatography (n-hexane-ethyl acetate) to obtain the title compound (24 mg).

$^1$H-NMR (CDCl$_3$) δ: 1.45 (9H, s), 2.49 (1H, dd, J=17.2, 4.6 Hz), 2.96 (1H, dd, J=17.2, 8.0 Hz), 3.69 (1H, dd, J=10.0, 3.2 Hz), 4.12 (1H, dd, J=10.0, 7.2 Hz), 4.41 (1H, br s), 4.96 (1H, d, J=7.2 Hz), 7.46-7.50 (4H, m).

ESI-MS (m/z): 355, 357 (M+H)$^+$.

Reference Example 63 tert-Butyl N-[[5-oxo-1-[4-(4,4,5,5-tetramethyl-1,3,2-dioxaborolan-2-yl)phenyl]pyrrolidin-3-yl]methyl]carbamate

[Formula 36]

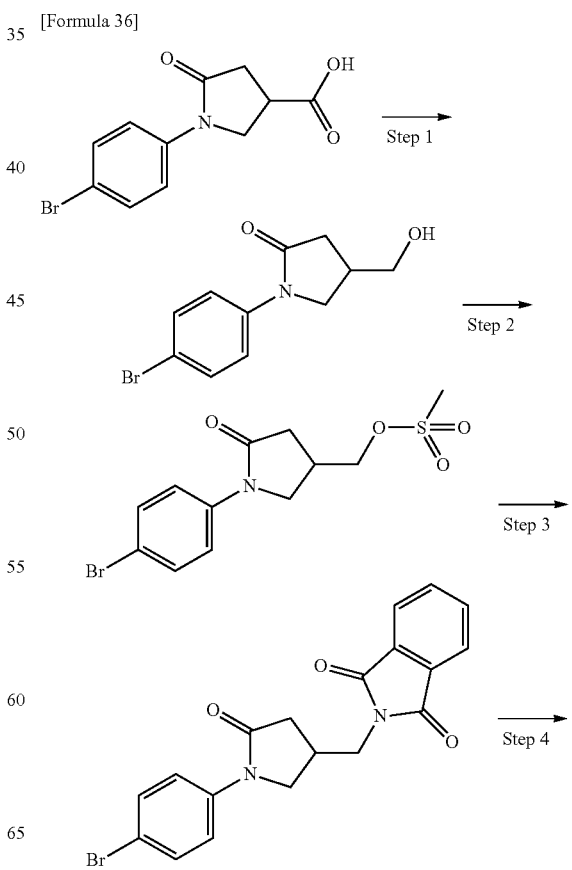

-continued

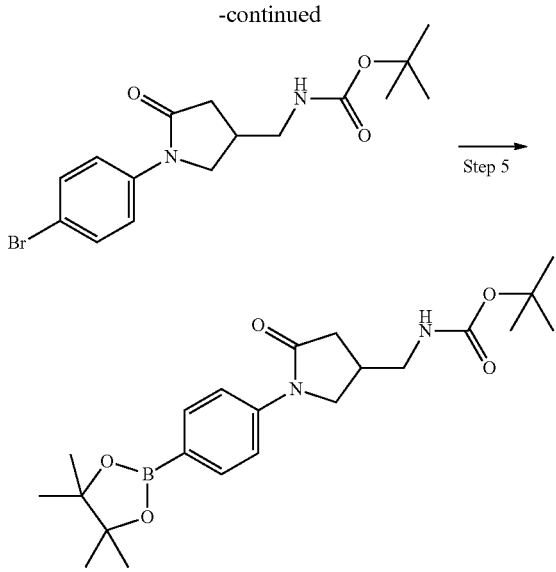

Step 5

Step 1

1-(4-Bromophenyl)-4-(hydroxymethyl)pyrrolidin-2-one

To a solution of the compound (2.8 g) obtained in step 1 of Reference Example 61 in tetrahydrofuran (30 ml), a borane-tetrahydrofuran complex (0.98 M solution in tetrahydrofuran, 20.4 ml) was added under ice cooling, and the mixture was stirred at the same temperature as above for 1 hour. A saturated aqueous solution of sodium bicarbonate was added to the reaction solution, followed by extraction with ethyl acetate. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (1.3 g).

$^1$H-NMR (CDCl$_3$) δ: 1.67 (1H, br s), 2.39-2.49 (1H, m), 2.65-2.77 (2H, m), 3.67-3.81 (3H, m), 3.93 (1H, dd, J=9.6, 7.8 Hz), 7.47 (2H, d, J=9.2 Hz), 7.54 (2H, d, J=8.7 Hz).

Step 2

[1-(4-Bromophenyl)-5-oxo-pyrrolidin-3-yl]methyl methanesulfonate

To a solution of the compound (1.3 g) obtained in the preceding step 1 in dichloromethane (30 ml), triethylamine (1.3 ml) and methanesulfonyl chloride (0.56 ml) were added under ice cooling, and the mixture was stirred at room temperature for 4 hours. Water was added to the reaction solution to separate two layers. Then, the aqueous layer was subjected to extraction with chloroform. The organic layers were combined, washed with saturated saline and then dried over anhydrous sodium sulfate. The solvent was distilled off under reduced pressure to obtain the title compound (1.6 g).

$^1$H-NMR (CDCl$_3$) δ: 2.46 (1H, dd, J=17.8, 6.9 Hz), 2.82 (1H, dd, J=17.2, 9.2 Hz), 2.91-3.00 (1H, m), 3.06 (3H, s), 3.73 (1H, dd, J=10.3, 5.7 Hz), 4.00 (1H, dd, J=9.7, 8.0 Hz), 4.26 (1H, dd, J=10.0, 7.7 Hz), 4.34 (1H, dd, J=10.3, 5.7 Hz), 7.46-7.53 (4H, m).

Step 3

2-[[1-(4-Bromophenyl)-5-oxo-pyrrolidin-3-yl]methyl]isoindoline-1,3-dione

To a solution of the compound (0.5 g) obtained in the preceding step 2 in N,N-dimethylformamide (20 ml), sodium iodide (0.26 g) and phthalimide potassium (0.32 g) were added, and the mixture was stirred at 70° C. for 4 hours. After cooling, water was added to the reaction solution, followed by extraction with ethyl acetate. The extract was washed with water and saturated saline in this order and then dried over anhydrous sodium sulfate. The solvent was distilled off under reduced pressure. The obtained residue was washed with an ethyl acetate-diethyl ether mixed solvent to obtain the title compound (0.38 g).

$^1$H-NMR (CDCl$_3$) δ: 2.50 (1H, dd, J=17.0, 7.3 Hz), 2.77 (1H, dd, J=17.0, 8.7 Hz), 2.88-3.01 (1H, m), 3.73 (1H, dd, J=10.1, 6.0 Hz), 3.82-3.91 (3H, m), 7.43-7.51 (4H, m), 7.74-7.79 (2H, m), 7.85-7.91 (2H, m).

Step 4 tert-Butyl N-[[1-(4-bromophenyl)-5-oxopyrrolidin-3-yl]methyl]carbamate

To a solution of the compound (0.38 g) obtained in the preceding step 3 in ethanol (20 ml), hydrazine hydrate (0.11 ml) was added, and the mixture was stirred at room temperature for 24 hours. The reaction solution was concentrated under reduced pressure. Then, chloroform was added to the residue, and the insoluble matter was filtered off. The filtrate was concentrated under reduced pressure. Ethanol (10 ml) and di-tert-butyl dicarbonate (0.33 g) were added to the obtained residue, and the mixture was stirred at room temperature for 1 hour. The reaction solution was concentrated under reduced pressure. Then, the obtained residue was purified by silica gel column chromatography (n-hexane-ethyl acetate) to obtain the title compound (0.31 g).

$^1$H-NMR (CDCl$_3$) δ: 1.44 (9H, s), 2.34-2.40 (1H, m), 2.65-2.76 (2H, m), 3.27 (2H, br s), 3.60 (1H, dd, J=10.3, 5.7 Hz), 3.90 (1H, dd, J=9.7, 6.9 Hz), 4.75 (1H, s), 7.47 (2H, d, J=8.6 Hz), 7.51 (2H, d, J=9.2 Hz).

Step 5 tert-Butyl N-[[5-oxo-1-[4-(4,4,5,5-tetramethyl-1,3,2-dioxaborolan-2-yl)phenyl]pyrrolidin-3-yl]methyl]carbamate The title compound (0.33 g) was obtained by the same procedures as in step 3 of Reference Example 61 using the compound (0.31 g) obtained in the preceding step 4.

$^1$H-NMR (CDCl$_3$) δ: 1.24 (12H, s), 1.44 (9H, s), 2.39 (1H, dd, J=16.0, 5.7 Hz), 2.67-2.78 (2H, m), 3.27 (2H, br s), 3.63 (1H, dd, J=9.7, 5.7 Hz), 3.94 (1H, dd, J=9.7, 8.0 Hz), 4.75 (1H, s), 7.62 (2H, d, J=8.6 Hz), 7.80 (2H, d, J=8.0 Hz).

Reference Example 64 tert-Butyl N-[2-oxo-1-[4-(4,4,5,5-tetramethyl-1,3,2-dioxaborolan-2-yl)phenyl]pyrrolidin-3-yl]carbamate

[Formula 37]

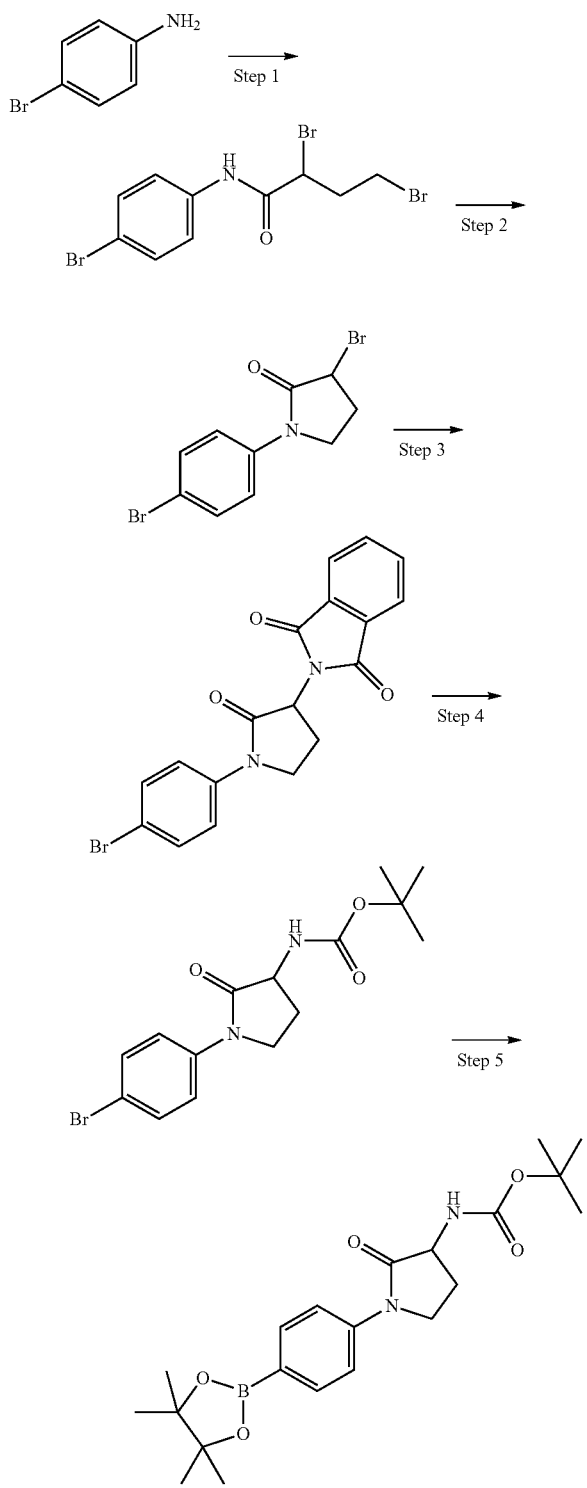

Step 1

2,4-Dibromo-N-(4-bromophenyl)butanamide

To a solution of 4-bromoaniline (1.73 g) in dichloromethane (40 ml), triethylamine (2.8 ml) and a solution of 2,4-dibromobutyryl chloride (3.2 g) in dichloromethane (10 ml) were added under ice cooling, and the mixture was stirred at room temperature for 5 hours. After addition of 1 N hydrochloric acid to the reaction solution, the mixture was separated into two layers. The aqueous layer was subjected to extraction with chloroform. The organic layers were combined, washed with a saturated aqueous solution of sodium bicarbonate and saturated saline in this order and then dried over anhydrous sodium sulfate. The solvent was distilled off under reduced pressure to obtain a crude product of the title compound, which was used in the next reaction without being purified.

Step 2

3-Bromo-1-(4-bromophenyl)pyrrolidin-2-one

To a solution of the compound obtained in the preceding step 1 in N,N-dimethylformamide (30 ml), sodium hydride (55% oil, 0.65 g) was added under ice cooling, and the mixture was stirred at the same temperature as above for 1 hour. A saturated aqueous solution of sodium chloride was added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) and then washed with n-hexane to obtain the title compound (1.2 g).
$^1$H-NMR (CDCl$_3$) δ: 2.43-2.50 (1H, m), 2.69-2.77 (1H, m), 3.78-3.83 (1H, m), 4.00-4.06 (1H, m), 4.58 (1H, dd, J=6.9, 2.9 Hz), 7.51 (2H, d, J=9.2 Hz), 7.56 (2H, d, J=9.2 Hz).

Step 3

2-[1-(4-Bromophenyl)-2-oxo-pyrrolidin-3-yl]isoindoline-1,3-dione

To a solution of the compound (0.7 g) obtained in the preceding step 2 in N,N-dimethylformamide (20 ml), phthalimide potassium (0.51 g) was added, and the mixture was stirred at 70° C. for 1 hour. After cooling, water was added to the reaction solution, followed by extraction with ethyl acetate. The extract was washed with water and saturated saline in this order and then dried over anhydrous sodium sulfate. The solvent was distilled off under reduced pressure. The obtained residue was washed with diethyl ether to obtain the title compound (0.35 g).
$^1$H-NMR (CDCl$_3$) δ: 2.53-2.67 (2H, m), 3.87-4.02 (2H, m), 5.14 (1H, t, J=9.9 Hz), 7.51 (2H, d, J=9.5 Hz), 7.59 (2H, d, J=9.5 Hz), 7.73-7.78 (2H, m), 7.85-7.90 (2H, m).

Step 4 tert-Butyl N-[1-(4-bromophenyl)-2-oxopyrrolidin-3-yl]carbamate

The title compound (0.39 g) was obtained by the same procedures as in step 4 of Reference Example 63 using the compound (0.35 g) obtained in the preceding step 3.

¹H-NMR (CDCl₃) δ: 1.47 (9H, s), 1.96-2.07 (2H, m), 2.79 (1H, br s), 3.74-3.80 (1H, m), 4.34 (1H, br s), 5.20 (1H, s), 7.49 (2H, d, J=9.2 Hz), 7.55 (2H, d, J=9.7 Hz).

Step 5 tert-Butyl N-[2-oxo-1-[4-(4,4,5,5-tetramethyl-1,3,2-dioxaborolan-2-yl)phenyl]pyrrolidin-3-yl]carbamate The title compound (0.52 g) was obtained by the same procedures as in step 3 of Reference Example 61 using the compound (0.39 g) obtained in the preceding step 4.

¹H-NMR (CDCl₃) δ: 1.24 (12H, s), 1.47 (9H, s), 1.96-2.04 (1H, m), 2.80 (1H, br s), 3.80 (1H, d, J=5.0 Hz), 3.83 (1H, d, J=4.1 Hz), 4.36 (1H, br s), 5.22 (1H, br s), 7.66 (2H, d, J=8.3 Hz), 7.82 (2H, d, J=9.2 Hz).

Reference Example 65 tert-Butyl N-[(3S)-5-oxo-1-[4-(4,4,5,5-tetramethyl-1,3,2-dioxaborolan-2-yl)phenyl]pyrrolidin-3-yl]carbamate

[Formula 38]

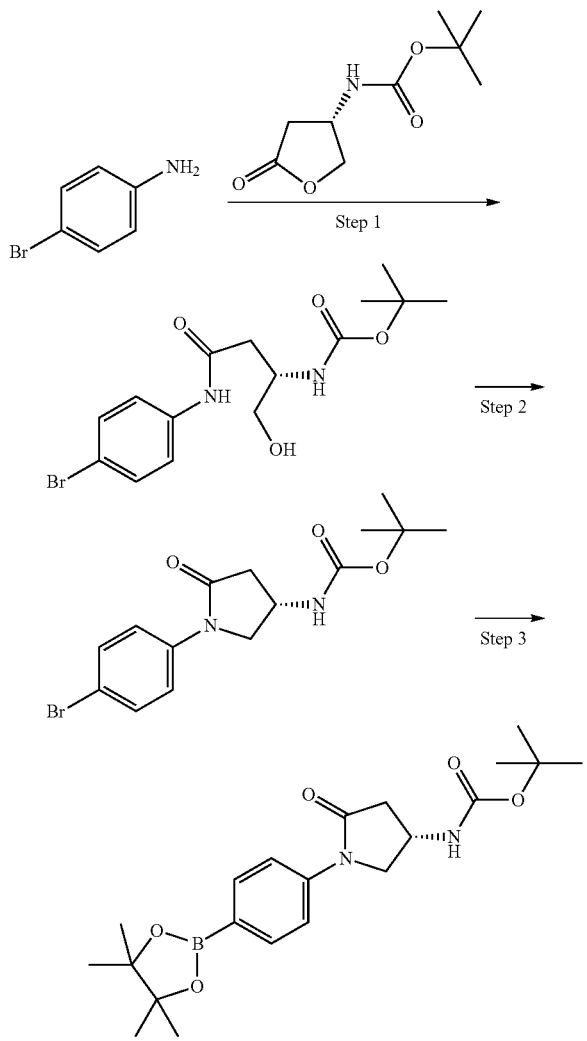

Step 1 tert-Butyl N-[(1S)-3-(4-bromoanilino)-1-(hydroxymethyl)-3-oxopropyl]carbamate

4-Bromoaniline (172 mg) was dissolved in dichloromethane (5 ml). To the solution, trimethylaluminum (1.8 M solution in toluene, 0.556 ml) was added, and the mixture was stirred at room temperature for 15 minutes. Tert-butyl N-[(3S)-5-oxotetrahydrofuran-3-yl]carbamate (201 mg) was added to the reaction solution, and the mixture was stirred overnight at room temperature, then stirred at 60° C. for 1 hour, and then further heated to reflux for 1 hour.

The same procedures as above were performed using 4-bromoaniline (2.56 g), and two lots were combined. Water was added to the reaction solution, followed by extraction from the aqueous layer with ethyl acetate. The aqueous layer was filtered through celite. After extraction from the filtrate with dichloromethane, these two organic layers were combined, dried over anhydrous sodium sulfate and then concentrated under reduced pressure. The obtained residue was purified by silica gel column chromatography (n-hexane-ethyl acetate) to obtain the title compound (3.82 g).

¹H-NMR (DMSO-d₆) δ: 1.34 (9H, s), 2.39 (1H, dd, J=14.9, 7.4 Hz), 2.54 (1H, dd, J=14.9, 5.7 Hz), 3.28-3.35 (1H, m), 3.36-3.41 (1H, m), 3.82-3.88 (1H, m), 4.70-4.78 (1H, m), 6.59 (1H, d, J=8.6 Hz), 7.45-7.48 (2H, m), 7.54-7.57 (2H, m), 9.97 (1H, s).

ESI-MS (m/z): 373, 375 (M+H)⁺.

Step 2 tert-Butyl N-[(3S)-1-(4-bromophenyl)-5-oxopyrrolidin-3-yl]carbamate

The compound (100 mg) obtained in the preceding step 1 was dissolved in tetrahydrofuran (5 ml). To the solution, di-tert-butyl azodicarboxylate (74 mg) and tributylphosphine (80 μl) were added, and the mixture was stirred at 60° C. for 1 hour and then heated to reflux for 2 hours. Di-tert-butyl azodicarboxylate (148 mg) and tributylphosphine (160 μl) were further added thereto, and the mixture was further heated to reflux for 1.5 hours.

The same procedures as above were performed using the compound (3.09 g) obtained in the preceding step 1, and two lots were combined. The reaction solution was concentrated under reduced pressure. The obtained residue was purified by silica gel column chromatography (n-hexane-ethyl acetate) to obtain the title compound (1.78 g).

¹H-NMR (CDCl₃) δ: 1.45 (9H, s), 2.49 (1H, dd, J=17.5, 4.6 Hz), 2.97 (1H, dd, J=17.5, 8.0 Hz), 3.70 (1H, dd, J=10.3, 3.4 Hz), 4.14 (1H, dd, J=10.3, 6.9 Hz), 4.42 (1H, br s), 4.87 (1H, br s), 7.46-7.51 (4H, m).

ESI-MS (m/z): 355, 357 (M+H)⁺.

Step 3 tert-Butyl N-[(3S)-5-oxo-1-[4-(4,4,5,5-tetramethyl-1,3,2-dioxaborolan-2-yl)phenyl]pyrrolidin-3-yl]carbamate The title compound (0.148 g) was obtained by the same procedures as in step 3 of Reference Example 61 using the compound (0.200 g) obtained in the preceding step 2.

¹H-NMR (CDCl₃) δ: 1.34 (12H, s), 1.45 (9H, s), 2.49 (1H, dd, J=17.2, 4.6 Hz), 2.98 (1H, dd, J=17.2, 8.0 Hz), 3.73 (1H, dd, J=10.3, 3.4 Hz), 4.18 (1H, dd, J=10.3, 6.3 Hz), 4.42 (1H, br s), 4.85 (1H, br s), 7.59-7.62 (2H, m), 7.80-7.82 (2H, m).

ESI-MS (m/z): 403 (M+H)⁺.

The following compounds were obtained by the same procedures as in Reference Example 65.

TABLE 7

| Reference Example | Structure and name | Instrumental data |
|---|---|---|
| 66 | 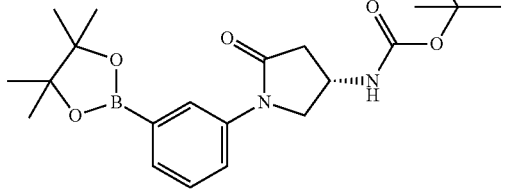<br>tert-Butyl N-[(3S)-5-oxo-1-[3-(4,4,5,5-tetramethyl-1,3,2-dioxaborolan-2-yl)phenyl]pyrrolidin-3-yl]carbamate | $^1$H-NMR (CDCl$_3$) δ: 1.34 (12H, s), 1.46 (9H, s), 2.48 (1H, dd, J = 17.2, 4.1 Hz), 2.97 (1H, dd, J = 17.2, 7.8 Hz), 3.77 (1H, d, J = 9.8 Hz), 4.20-4.23 (1H, m), 4.43 (1H, br s), 4.86 (1H, br s), 7.39 (1H, t, J = 7.6 Hz), 7.61 (1H, d, J = 6.8 Hz), 7.69 (1H, s), 7.93-7.96 (1H, m). |
| 67 | 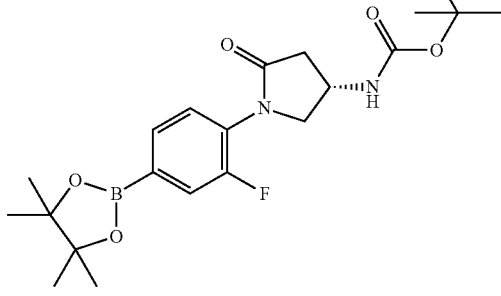<br>tert-Butyl N-[(3S)-1-[2-fluoro-4-(4,4,5,5-tetramethyl-1,3,2-dioxaborolan-2-yl)phenyl]-5-oxopyrrolidin-3-yl]carbamate | $^1$H-NMR (CDCl$_3$) δ: 1.33 (12H, s), 1.46 (9H, s), 2.45 (1H, dd, J = 17.3, 4.6 Hz), 2.92 (1H, dd, J = 17.3, 8.1 Hz), 3.70 (1H, dd, J = 10.7, 3.4 Hz), 4.12-4.16 (1H, m), 4.46 (1H, br s), 4.89 (1H, br s), 7.45 (1H, t, J = 7.6 Hz), 7.56 (1H, d, J = 11.2 Hz), 7.59 (1H, dd, J = 7.6, 1.0 Hz). |
| 68 | 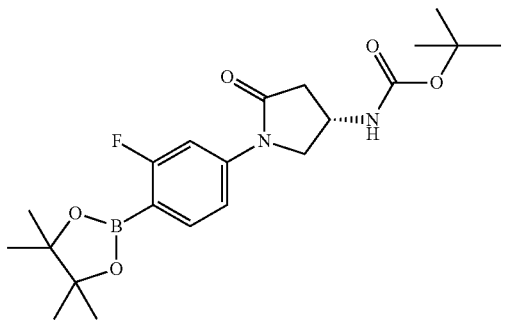 [SMILES: CC(C)(C)OC(=O)N[C@H]1CC(=O)N(c2ccc(B3OC(C)(C)C(C)(C)O3)c(F)c2)C1]<br>tert-Butyl N-[(3S)-1-[3-fluoro-4-(4,4,5,5-tetramethyl-1,3,2-dioxaborolan-2-yl)phenyl]-5-oxopyrrolidin-3-yl]carbamate | $^1$H-NMR (CDCl$_3$) δ: 1.36 (12H, s), 1.46 (9H, s), 2.51 (1H, dd, J = 17.3, 4.6 Hz), 2.98 (1H, dd, J = 17.3, 8.1 Hz), 3.70-3.73 (1H, m), 4.10-4.16 (1H, m), 4.42 (1H, br s), 4.92 (1H, br s), 7.32 (1H, dd, J = 8.3, 2.0 Hz), 7.51 (1H, t, J = 8.3 Hz), 7.72 (1H, t, J = 7.6 Hz). |
| 69 | 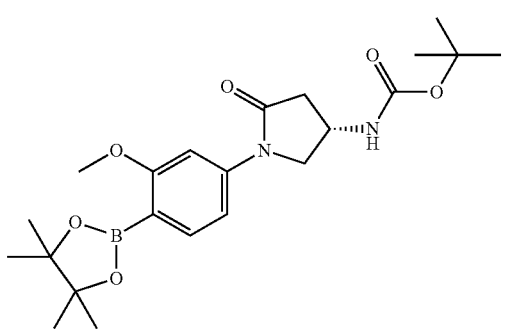 [SMILES: COc1cc(N2C[C@@H](NC(=O)OC(C)(C)C)CC2=O)ccc1B1OC(C)(C)C(C)(C)O1]<br>tert-Butyl N-[(3S)-1-[3-methoxy-4-(4,4,5,5-tetramethyl-1,3,2-dioxaborolan-2-yl)phenyl]-5-oxopyrrolidin-3-yl]carbamate | $^1$H-NMR (CDCl$_3$) δ: 1.34 (12H, s), 1.45 (9H, s), 2.46-2.53 (1H, m), 2.94-3.02 (1H, m), 3.69-3.75 (1H, m), 3.85 (3H, s), 4.09-4.19 (1H, m), 4.37-4.46 (1H, br m), 4.84-4.90 (1H, br m), 6.85-6.90 (1H, m), 7.56 (1H, d, J = 1.8 Hz), 7.66 (1H, d, J = 8.5 Hz). |

Reference Example 70 tert-Butyl N-[(3S)-5-oxo-1-[5-(4,4,5,5-tetramethyl-1,3,2-dioxaborolan-2-yl)-2-pyridyl]pyrrolidin-3-yl]carbamate

[Formula 39]

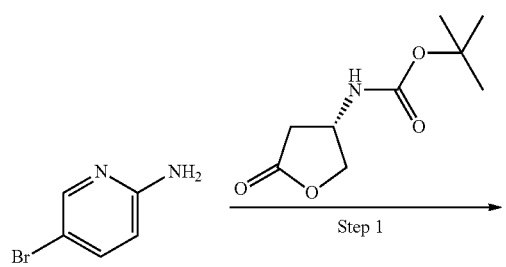

Step 1 tert-Butyl N-[(1S)-3-[(5-bromo-2-pyridyl)amino]-1-(hydroxymethyl)-3-oxopropyl]carbamate The title compound (0.53 g) was obtained by the same procedures as in step 1 of Reference Example 65 using 2-amino-5-bromopyridine (0.66 g) instead of 4-bromoaniline.

$^1$H-NMR (CDCl$_3$) δ: 1.42 (9H, s), 2.76-2.80 (2H, m), 3.56 (1H, br s), 3.72-3.78 (1H, m), 3.80-3.87 (1H, m), 4.02-4.10 (1H, m), 5.64-5.67 (1H, m), 7.79 (1H, dd, J=9.0, 2.6 Hz), 8.12 (1H, d, J=9.0 Hz), 8.33 (1H, d, J=2.6 Hz), 8.87 (1H, s).
ESI-MS (m/z): 374, 376 (M+H)$^+$.

Step 2 tert-Butyl N-[(3S)-1-(5-bromo-2-pyridyl)-5-oxopyrrolidin-3-yl]carbamate

The title compound (0.59 g) was obtained by the same procedures as in step 2 of Reference Example 65 using the compound (0.53 g) obtained in the preceding step 1.

$^1$H-NMR (CDCl$_3$) δ: 1.43 (9H, s), 2.55 (1H, dd, J=17.6, 4.3 Hz), 2.99 (1H, dd, J=17.6, 7.8 Hz), 3.91-3.97 (1H, m), 4.28 (1H, dd, J=11.9, 6.8 Hz), 4.37 (1H, br s), 4.81 (1H, br s), 7.76 (1H, dd, J=9.0, 2.3 Hz), 8.29 (1H, d, J=9.0 Hz), 8.35 (1H, d, J=2.3 Hz).
ESI-MS (m/z): 356, 358 (M+H)$^+$.

Reference Example 71 tert-Butyl N-methyl-N-[(3S)-5-oxo-1-[4-(4,4,5,5-tetramethyl-1,3,2-dioxaborolan-2-yl)phenyl]pyrrolidin-3-yl]carbamate

[Formula 40]

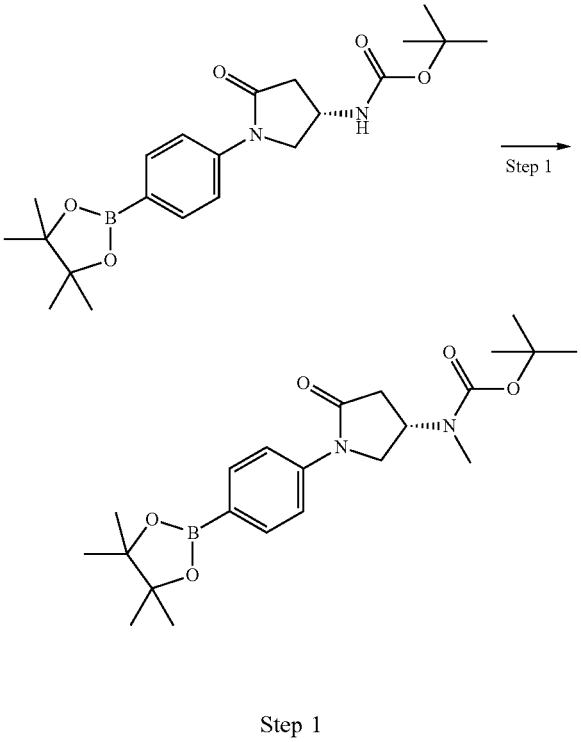

Step 1 tert-Butyl N-methyl-N-[(3S)-5-oxo-1-[4-(4,4,5,5-tetramethyl-1,3,2-dioxaborolan-2-yl)phenyl]pyrrolidin-3-yl]carbamate To a solution of the compound (500 mg) obtained in step 3 of Reference Example 65 in N,N-dimethylformamide (10 ml), cesium carbonate (405 mg) and iodomethane (77 μl) were added, and the mixture was stirred at room temperature for 1 hour. Sodium hydride (55% oil, 60 mg) was added thereto, and the mixture was stirred at room temperature for 2 hours. Sodium hydride (60 mg) and iodomethane (77 μl) were further added thereto, and the mixture was further stirred at room temperature for 1 hour. Ethyl acetate and water were added to the reaction solution to separate the aqueous and organic layers. The aqueous layer was subjected to extraction with ethyl acetate. The organic layers were combined, dried over anhydrous sodium sulfate and then concentrated under reduced pressure. The obtained residue was purified by silica gel column chromatography (n-hexane-ethyl acetate) to obtain the title compound (192 mg).

$^1$H-NMR (CDCl$_3$) δ: 1.34 (12H, s), 1.47 (9H, s), 2.68 (1H, dd, J=17.5, 5.4 Hz), 2.85 (3H, s), 2.89-2.96 (1H, m), 3.73-3.79 (1H, m), 4.10-4.15 (1H, m), 4.41-4.83 (1H, m), 7.64 (2H, d, J=8.5 Hz), 7.82 (2H, d, J=8.5 Hz).
ESI-MS (m/z): 417 (M+H)$^+$.

Reference Example 72 tert-Butyl N-[(3S)-1-[3-methyl-4-(4,4,5,5-tetramethyl-1,3,2-dioxaborolan-2-yl)phenyl]-5-oxopyrrolidin-3-yl]carbamate

[Formula 41]

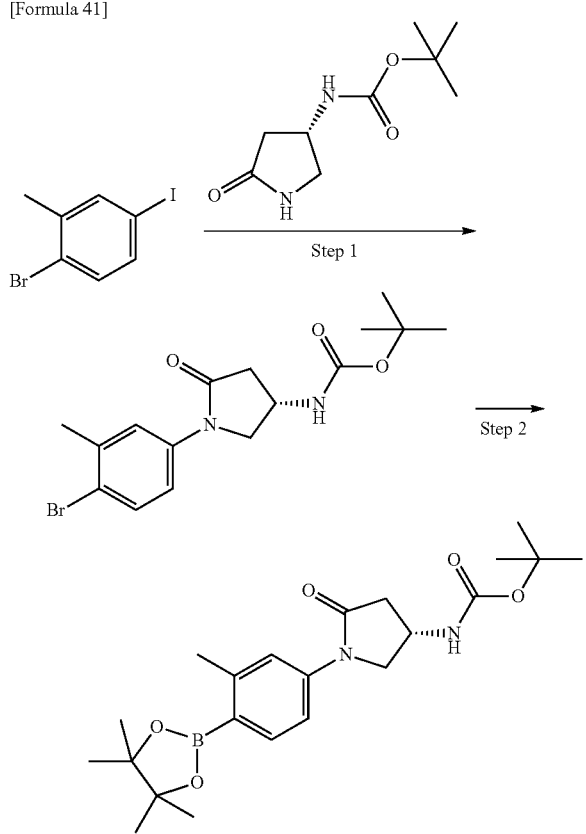

Step 1 tert-Butyl N-[(3S)-1-(4-bromo-3-methylphenyl)-5-oxopyrrolidin-3-yl]carbamate

A suspension of 2-bromo-5-iodotoluene (1.5 g), tert-butyl ((S)-5-oxopyrrolidin-3-yl)carbamate (2.7 g), copper iodide (95 mg), cesium fluoride (1.9 g), and N,N-dimethylethylenediamine (0.11 ml) in acetonitrile (20 ml) was stirred at 100° C. for 3 hours under a nitrogen atmosphere. After cooling, a saturated aqueous solution of ammonium chloride was added to the reaction solution, followed by extraction with ethyl acetate. The extract was washed with a 10% aqueous sodium thiosulfate solution and saturated saline in this order and then dried over anhydrous sodium sulfate. The solvent was distilled off under reduced pressure. The obtained residue was purified by silica gel column chromatography (chloroform-methanol) to obtain the title compound (1.8 g).

$^1$H-NMR (CDCl$_3$) δ: 1.45 (9H, s), 2.40 (3H, s), 2.47 (1H, dd, J=17.2, 4.5 Hz), 2.96 (1H, dd, J=17.2, 8.2 Hz), 3.69 (1H, d, J=9.7 Hz), 4.13 (1H, dd, J=9.7, 6.7 Hz), 4.41 (1H, br s), 4.83 (1H, br s), 7.29 (1H, d, J=8.5 Hz), 7.47-7.52 (2H, m).

Step 2 tert-Butyl N-[(3S)-1-[3-methyl-4-(4,4,5,5-tetramethyl-1,3,2-dioxaborolan-2-yl)phenyl]-5-oxopyrrolidin-3-yl]carbamate The title compound (1.5 g) was obtained by the same procedures as in step 3 of Reference Example 61 using the compound (1.0 g) obtained in the preceding step 1.

$^1$H-NMR (CDCl$_3$) δ: 1.33 (12H, s), 1.45 (9H, s), 2.48 (1H, dd, J=17.2, 4.5 Hz), 2.54 (3H, s), 2.97 (1H, dd, J=17.2, 8.2 Hz), 3.71 (1H, d, J=7.3 Hz), 4.10-4.18 (1H, m), 4.42 (1H, br s), 4.85 (1H, br s), 7.34-7.44 (2H, m), 7.76 (1H, d, J=8.5 Hz).

The following compounds were obtained by the same procedures as in Reference Example 72.

TABLE 8

| Reference Example | Structure and name | Instrumental data |
|---|---|---|
| 73 | tert-Butyl N-[7-methyl-4-oxo-5-[4-(4,4,5,5-tetramethyl-1,3,2-dioxaborolan-2-yl)phenyl]-5-azaspiro[2.4]heptan-7-yl]carbamate | $^1$H-NMR (CDCl$_3$) δ: 1.04-1.30 (4H, m), 1.26 (3H, s), 1.27 (12H, s), 1.40 (9H, s), 3.75 (1H, d, J = 10.3 Hz), 4.62 (2H, br s), 7.66 (2H, d, J = 8.5 Hz), 7.81 (2H, d, J = 8.5 Hz). |

TABLE 8-continued

| Reference Example | Structure and name | Instrumental data |
|---|---|---|
| 74 | tert-Butyl N-[(3S)-1-[2-methyl-4-(4,4,5,5-tetramethyl-1,3,2-dioxaborolan-2-yl)phenyl]-5-oxopyrrolidin-3-yl]carbamate | $^1$H-NMR (CDCl$_3$) δ: 1.33 (12H, s), 1.46 (9H, s), 2.24 (3H, s), 2.44 (1H, dd, J = 17.5, 4.8 Hz), 2.94 (1H, dd, J = 17.5, 7.9 Hz), 3.59 (1H, dd, J = 10.3, 4.2 Hz), 3.97-4.05 (1H, m), 4.45 (1H, br s), 4.91 (1H, d, J = 6.0 Hz), 7.13 (1H, d, J = 7.9 Hz), 7.67 (1H, d, J = 7.9 Hz), 7.73 (1H, s). |

Reference Example 75 tert-Butyl N-[3-methyl-5-oxo-1-[4-(4,4,5,5-tetramethyl-1,3,2-dioxaborolan-2-yl)phenyl]pyrrolidin-3-yl]carbamate

[Formula 42]

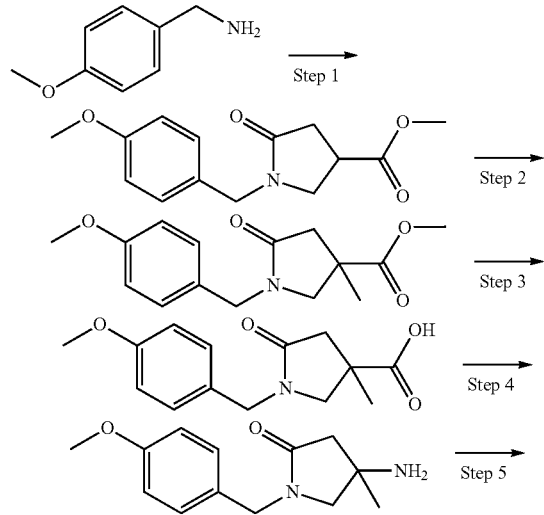

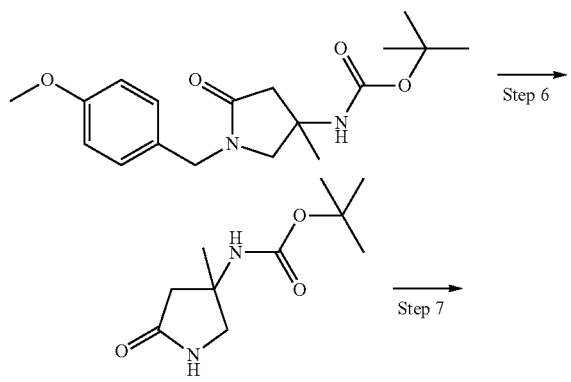

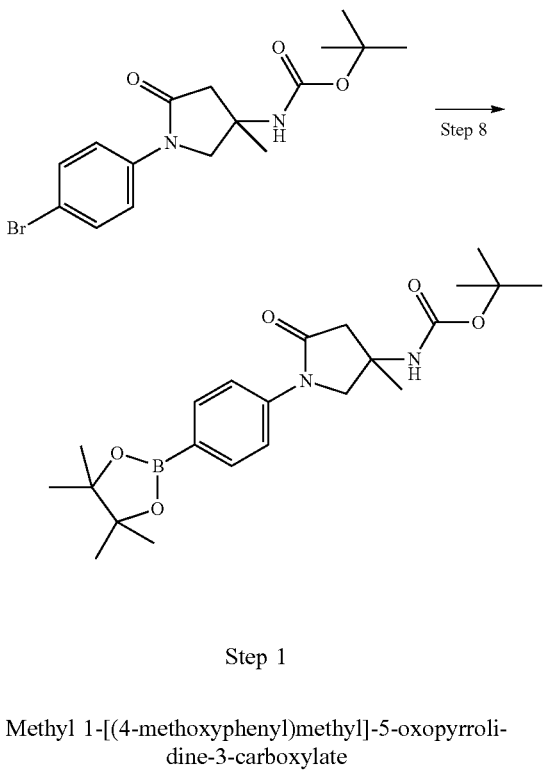

Step 1

Methyl 1-[(4-methoxyphenyl)methyl]-5-oxopyrrolidine-3-carboxylate

A mixture of (4-methoxyphenyl)methanamine (6.9 g) and dimethyl itaconate (7.9 g) was stirred at 120° C. for 2 hours. After cooling, ethyl acetate was added to the reaction solution. The organic layer was washed with 1 N hydrochloric acid, a saturated aqueous solution of sodium bicarbonate, and saturated saline in this order and then dried over anhydrous sodium sulfate. The solvent was distilled off under reduced pressure to obtain the title compound (12.7 g).

$^1$H-NMR (CDCl$_3$) δ: 2.62-2.77 (2H, m), 3.10-3.20 (1H, m), 3.41 (1H, d, J=7.8 Hz), 3.67 (3H, s), 3.75 (1H, d, J=8.6 Hz), 3.76 (3H, s), 4.32 (1H, d, J=15.2 Hz), 4.40 (1H, d, J=15.6 Hz), 6.83 (2H, d, J=8.2 Hz), 7.13 (2H, d, J=8.7 Hz).

Step 2

Methyl 1-[(4-methoxyphenyl)methyl]-3-methyl-5-oxopyrrolidine-3-carboxylate

To a solution of the compound (9.8 g) obtained in the preceding step 1 in N,N-dimethylformamide (100 ml), methyl iodide (23.2 ml) and sodium hydride (55% oil, 6.5 g) were added, and the mixture was stirred at room temperature for 7.5 hours. Water was added to the reaction solution, followed by extraction with ethyl acetate. The extract was washed with water and saturated saline in this order and then dried over anhydrous sodium sulfate. The solvent was distilled off under reduced pressure to obtain a crude product of the title compound, which was used directly in the next reaction.

Step 3

1-[(4-Methoxyphenyl)methyl]-3-methyl-5-oxopyrrolidine-3-carboxylic acid

To a methanol (50 ml)-tetrahydrofuran (50 ml) mixed solution of the compound obtained in the preceding step 2, a 1 N aqueous sodium hydroxide solution (50 ml) was added, and the mixture was stirred at room temperature for 3.5 hours. The reaction solution was concentrated under reduced pressure. Then, the residue was made acidic by the addition of concentrated hydrochloric acid, followed by extraction with ethyl acetate. The extract was washed with saturated saline and then dried over anhydrous sodium sulfate. The solvent was distilled off under reduced pressure. The obtained residue was washed with a n-hexane-diethyl ether mixed solution to obtain the title compound (7.3 g).

$^1$H-NMR (CDCl$_3$) δ: 1.38 (3H, s), 2.38 (1H, d, J=17.1 Hz), 3.02 (1H, d, J=17.1 Hz), 3.02 (1H, d, J=9.8 Hz), 3.66 (1H, d, J=10.4 Hz), 3.80 (3H, s), 4.31 (1H, d, J=14.6 Hz), 4.49 (1H, d, J=14.6 Hz), 6.86 (2H, d, J 9.2 Hz), 7.16 (2H, d, J=8.5 Hz).

Step 4

4-Amino-1-[(4-methoxyphenyl)methyl]-4-methylpyrrolidin-2-one

To a solution of the compound (4.5 g) obtained in the preceding step 3 in toluene (50 ml), triethylamine (4.8 ml) and diphenylphosphoryl azide (4.4 ml) were added, and the mixture was heated to reflux for 3 hours. After cooling, the reaction solution was concentrated under reduced pressure. 1,4-Dioxane (40 ml), water (20 ml), and concentrated hydrochloric acid (20 ml) were added to the obtained residue, and the mixture was stirred at 50° C. for 5 hours. After cooling, water was added to the reaction solution, and the aqueous layer was washed with ethyl acetate. The aqueous layer was made alkaline by the addition of a 10 N aqueous sodium hydroxide solution, followed by extraction with chloroform. The extract was washed with saturated saline and then dried over anhydrous sodium sulfate. The solvent was distilled off under reduced pressure to obtain a crude product of the title compound (4.0 g), which was used directly in the next reaction.

$^1$H-NMR (CDCl$_3$) δ: 1.28 (3H, s), 1.57 (2H, br s), 2.39 (1H, d, J=16.9 Hz), 2.46 (1H, d, J=16.9 Hz), 3.04 (1H, d, J=9.7 Hz), 3.12 (1H, d, J=9.7 Hz), 3.80 (3H, s), 4.35 (1H, d, J=14.5 Hz), 4.43 (1H, d, J=15.1 Hz), 6.86 (2H, d, J=8.5 Hz), 7.17 (2H, d, J=9.1 Hz).

Step 5 tert-Butyl N-[1-[(4-methoxyphenyl)methyl]-3-methyl-5-oxopyrrolidin-3-yl]carbamate To a solution of the compound (4.0 g) obtained in the preceding step 4 in ethanol (50 ml), di-tert-butyl dicarbonate (5.6 g) was added, and the mixture was stirred at room temperature for 2 hours. The reaction solution was concentrated under reduced pressure. The obtained residue was purified by silica gel column chromatography (n-hexane-ethyl acetate) to obtain the title compound (2.8 g).

$^1$H-NMR (CDCl$_3$) δ: 1.39 (3H, s), 1.40 (9H, s), 2.40 (1H, d, J=16.9 Hz), 2.78 (1H, d, J=16.9 Hz), 3.15 (1H, d, J=10.3 Hz), 3.57 (1H, d, J=10.9 Hz), 3.79 (3H, s), 4.31 (1H, d, J=14.5 Hz), 4.48 (1H, d, J=14.5 Hz), 4.61 (1H, br s), 6.85 (2H, d, J=8.5 Hz), 7.16 (2H, d, J=8.5 Hz).

Step 6 tert-Butyl N-(3-methyl-5-oxopyrrolidin-3-yl)carbamate

To a solution of the compound (0.55 g) obtained in the preceding step 5 in toluene (20 ml), methanesulfonic acid (0.43 ml) was added, and the mixture was heated to reflux for 5 hours. After cooling, the reaction solution was concentrated under reduced pressure. The obtained residue was dissolved in 1,4-dioxane (10 ml). To this solution, a saturated aqueous solution of sodium bicarbonate was added to make the solution alkaline. Then, di-tert-butyl dicarbonate (0.53 g) was added to the mixture, and the resulting mixture was stirred at room temperature for 22 hours. The reaction solution was concentrated under reduced pressure. The obtained residue was purified by silica gel column chromatography (chloroform-methanol) to obtain the title compound (0.2 g).

$^1$H-NMR (CDCl$_3$) δ: 1.44 (9H, s), 1.50 (3H, s), 2.28 (1H, d, J=16.3 Hz), 2.75 (1H, d, J=16.3 Hz), 3.30 (1H, d, J=9.7 Hz), 3.74 (1H, d, J=9.7 Hz), 4.70 (1H, br s), 5.47 (1H, br s).

Step 7 tert-Butyl N-[1-(4-bromophenyl)-3-methyl-5-oxopyrrolidin-3-yl]carbamate

The title compound (0.65 g) was obtained by the same procedures as in step 1 of Reference Example 72 using the compound (0.9 g) obtained in the preceding step 6.

$^1$H-NMR (CDCl$_3$) δ: 1.44 (9H, s), 1.56 (3H, s), 2.56 (1H, d, J=16.9 Hz), 3.00 (1H, d, J=16.3 Hz), 3.72 (1H, d, J=10.3 Hz), 4.22 (1H, d, J=9.1 Hz), 4.75 (1H, br s), 7.47 (2H, d, J=9.1 Hz), 7.51 (2H, d, J=9.1 Hz).

Step 8 tert-Butyl N-[3-methyl-5-oxo-1-[4-(4,4,5,5-tetramethyl-1,3,2-dioxaborolan-2-yl)phenyl]pyrrolidin-3-yl]carbamate A crude product of the title compound (1.0 g) was obtained by the same procedures as in step 3 of Reference Example 61 using the compound (0.65 g) obtained in the preceding step 7.

$^1$H-NMR (CDCl$_3$) δ: 1.34 (12H, s), 1.44 (9H, s), 1.56 (3H, s), 2.58 (1H, d, J=16.9 Hz), 3.00 (1H, d, J=16.9 Hz), 3.78

(1H, d, J=10.3 Hz), 4.23 (1H, d, J=10.3 Hz), 4.76 (1H, br s), 7.62 (2H, d, J=9.1 Hz), 7.80 (2H, d, J=8.5 Hz).

Reference Example 76 tert-Butyl N-[(3S)-1-(4-bromo-2-cyanophenyl)-5-oxopyrrolidin-3-yl]carbamate

[Formula 43]

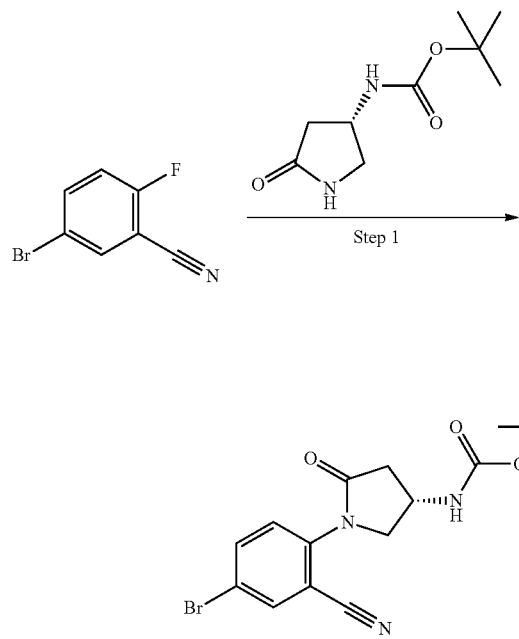

Step 1 tert-Butyl N-[(3S)-1-(4-bromo-2-cyanophenyl)-5-oxopyrrolidin-3-yl]carbamate

To a solution of tert-butyl ((S)-5-oxopyrrolidin-3-yl)carbamate (2.0 g) in N,N-dimethylformamide (50 ml), sodium hydride (55% oil, 0.65 g) was added under ice cooling, and the mixture was stirred at the same temperature as above for 10 minutes. 5-Bromo-2-fluorobenzonitrile (3.0 g) was added to the reaction solution, and the mixture was stirred at room temperature for 1 hour. Ice water and a saturated aqueous solution of ammonium chloride were added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) to obtain the title compound (1.5 g).

$^1$H-NMR (CDCl$_3$) δ: 1.46 (9H, s), 2.52 (1H, dd, J=17.5, 4.8 Hz), 2.96 (1H, dd, J=17.5, 7.9 Hz), 3.81 (1H, d, J=6.7 Hz), 4.19 (1H, dd, J=10.0, 6.3 Hz), 4.49 (1H, br s), 4.98 (1H, br s), 7.32 (1H, d, J=8.5 Hz), 7.76 (1H, dd, J=8.8, 2.1 Hz), 7.83 (1H, d, J=2.4 Hz).

Reference Example 77 tert-Butyl 1-[(1S)-1-(4-methoxyphenyl)ethyl]-3-methyl-5-oxopyrrolidine-3-carboxylate

[Formula 44]

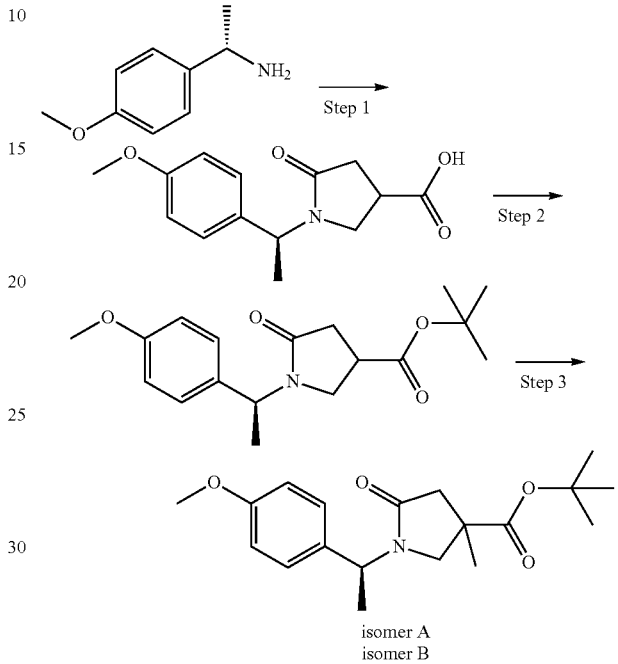

isomer A
isomer B

Step 1

1-[(1S)-1-(4-Methoxyphenyl)ethyl]-5-oxopyrrolidine-3-carboxylic acid

A mixture of (1S)-1-(4-methoxyphenyl)ethanamine (7.6 g) and itaconic acid (6.5 g) was stirred at 130° C. for 1 hour. After cooling, chloroform was added to the reaction solution. The organic layer was washed with 1 N hydrochloric acid and saturated saline in this order and then dried over anhydrous sodium sulfate. The solvent was distilled off under reduced pressure to obtain a stereoisomeric mixture (12.7 g) related to the 3-position of the title compound.

Step 2 tert-Butyl 1-[(1S)-1-(4-methoxyphenyl)ethyl]-5-oxopyrrolidine-3-carboxylate

To a tetrahydrofuran (50 ml)-tert-butanol (50 ml) mixed solution of the compound (12.7 g) obtained in the preceding step 1, di-tert-butyl dicarbonate (16.4 g) and 4-dimethylaminopyridine (1.2 g) were added, and the mixture was stirred at room temperature for 4 hours. The reaction solution was concentrated under reduced pressure. The obtained residue was purified by silica gel column chromatography (n-hexane-ethyl acetate) to obtain a stereoisomeric mixture (13.9 g) related to the 3-position of the title compound.

Step 3 tert-Butyl 1-[(1S)-1-(4-methoxyphenyl)ethyl]-3-methyl-5-oxopyrrolidine-3-carboxylate

To a solution of the compound (13.9 g) obtained in the preceding step 2 in N,N-dimethylformamide (100 ml), methyl iodide (27.1 ml) and sodium hydride (55% oil, 7.6 g) were added, and the mixture was stirred at room temperature for 19 hours. Water was added to the reaction solution under ice cooling, followed by extraction with ethyl acetate. The extract was washed with water and saturated saline in this order and then dried over anhydrous sodium sulfate. The solvent was distilled off under reduced pressure. The obtained residue was purified by silica gel column chromatography (n-hexane-ethyl acetate) to obtain low polar isomer A (3.9 g) and highly polar isomer B (5.0 g).

Low polar isomer A (Rf=0.45, n-hexane:ethyl acetate=1:1)

$^1$H-NMR (CDCl$_3$) δ: 1.17 (3H, s), 1.44 (9H, s), 1.49 (3H, d, J=7.3 Hz), 2.24 (1H, d, J=16.9 Hz), 2.66 (1H, d, J=9.7 Hz), 2.90 (1H, d, J=16.9 Hz), 3.61 (1H, d, J=9.7 Hz), 3.81 (3H, s), 5.46 (1H, q, J=7.1 Hz), 6.87 (2H, d, J=9.1 Hz), 7.23 (2H, d, J=8.5 Hz).

Highly polar isomer B (Rf=0.35, n-hexane:ethyl acetate=1:1)

$^1$H-NMR (CDCl$_3$) δ: 1.34 (3H, s), 1.35 (9H, s), 1.49 (3H, d, J=7.3 Hz), 2.26 (1H, d, J=16.9 Hz), 2.90 (1H, d, J=16.3 Hz), 3.02 (1H, d, J=9.7 Hz), 3.29 (1H, d, J=9.7 Hz), 3.79 (3H, s), 5.45 (1H, q, J=7.3 Hz), 6.86 (2H, d, J=8.5 Hz), 7.21 (2H, d, J=8.5 Hz).

Reference Example 78 tert-Butyl N-[3-methyl-5-oxo-1-[4-(4,4,5,5-tetramethyl-1,3,2-dioxaborolan-2-yl)phenyl]pyrrolidin-3-yl]carbamate

[Formula 45]

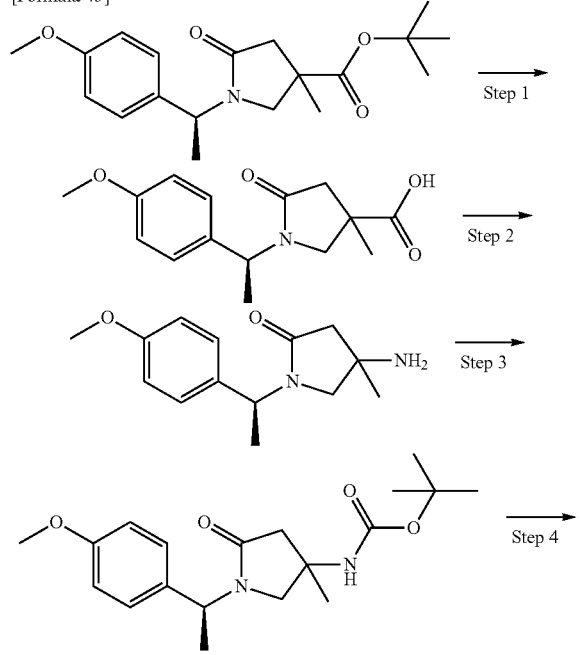

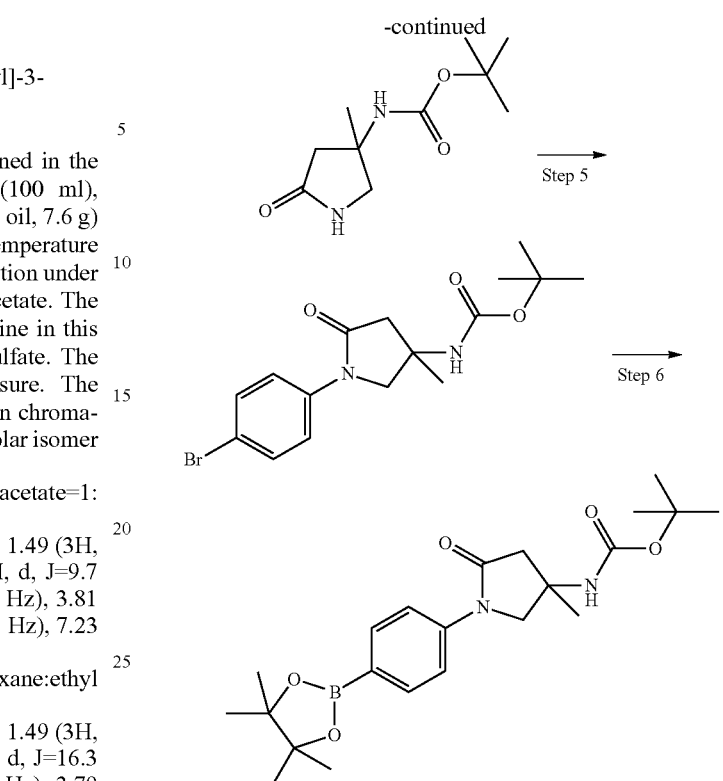

Step 1

1-[(1S)-1-(4-Methoxyphenyl)ethyl]-3-methyl-5-oxopyrrolidine-3-carboxylic acid

To a solution of the low polar isomer A (3.8 g) obtained in step 3 of Reference Example 77 in dichloromethane (50 ml), trifluoroacetic acid (10 ml) was added, and the mixture was stirred at room temperature for 24 hours. Water was added to the reaction solution to separate two layers. Then, the aqueous layer was subjected to extraction with chloroform. The organic layers were combined, washed with saturated saline and then dried over anhydrous sodium sulfate. The solvent was distilled off under reduced pressure. The obtained residue was washed with n-hexane to obtain the title compound (2.7 g).

$^1$H-NMR (CDCl$_3$) δ: 1.25 (3H, s), 1.50 (3H, d, J=6.7 Hz), 2.36 (1H, d, J=16.9 Hz), 2.74 (1H, d, J=10.3 Hz), 3.01 (1H, d, J=16.9 Hz), 3.72 (1H, d, J=10.3 Hz), 3.81 (3H, s), 5.47 (1H, q, J=7.1 Hz), 6.88 (2H, d, J 8.5 Hz), 7.22 (2H, d, J=8.5 Hz).

Step 2

4-Amino-1-[(1S)-1-(4-methoxyphenyl)ethyl]-4-methylpyrrolidin-2-one

To a solution of the compound (2.7 g) obtained in the preceding step 1 in toluene (30 ml), triethylamine (2.7 ml) and diphenylphosphoryl azide (2.5 ml) were added, and the mixture was heated to reflux for 3 hours. After cooling, the reaction solution was concentrated under reduced pressure. 1,4-Dioxane (10 ml), water (5 ml), and concentrated hydrochloric acid (5 ml) were added to the obtained residue, and the mixture was stirred at 50° C. for 2.5 hours. After cooling, water was added to the reaction solution, and the aqueous layer was washed with ethyl acetate. The aqueous layer was made alkaline by the addition of a 10 N aqueous sodium hydroxide solution, followed by extraction with chloroform. The extract was washed with saturated saline and then dried over anhydrous sodium sulfate. The solvent was distilled off under reduced pressure to obtain a crude product of the title compound, which was used directly in the next reaction.

$^1$H-NMR (CDCl$_3$) δ: 1.17 (3H, s), 1.50 (3H, d, J=7.3 Hz), 1.64 (2H, br s), 2.37 (1H, d, J=16.3 Hz), 2.42 (1H, d, J=16.3 Hz), 2.82 (1H, d, J=9.7 Hz), 3.07 (1H, d, J 9.7 Hz), 3.80 (3H, s), 5.50 (1H, q, J=7.1 Hz), 6.87 (2H, d, J=8.5 Hz), 7.22 (2H, d, J=7.9 Hz).

Step 3 tert-Butyl N-[1-[(1S)-1-(4-methoxyphenyl)ethyl]-3-methyl-5-oxopyrrolidin-3-yl]carbamate To a solution of the compound obtained in the preceding step 2 in ethanol (30 ml), di-tert-butyl dicarbonate (3.3 g) was added, and the mixture was stirred at room temperature for 16 hours. The reaction solution was concentrated under reduced pressure. The obtained residue was purified by silica gel column chromatography (n-hexane-ethyl acetate) to obtain the title compound (1.2 g).

$^1$H-NMR (CDCl$_3$) δ: 1.25 (3H, s), 1.43 (9H, s), 1.49 (3H, d, J=7.9 Hz), 2.34 (1H, d, J=16.3 Hz), 2.76 (1H, d, J=16.3 Hz), 2.88 (1H, d, J=9.7 Hz), 3.65 (1H, d, J 9.7 Hz), 3.80 (3H, s), 4.62 (1H, br s), 5.49 (1H, q, J 7.1 Hz), 6.86 (2H, d, J=8.5 Hz), 7.22 (2H, d, J=8.5 Hz).

Step 4 tert-Butyl N-(3-methyl-5-oxopyrrolidin-3-yl)carbamate

Trifluoroacetic acid (10 ml) was added to the compound (1.2 g) obtained in the preceding step 3, and the mixture was stirred at 80° C. for 7 hours. After cooling, the reaction solution was concentrated under reduced pressure. The obtained residue was dissolved in 1,4-dioxane (20 ml). To this solution, a saturated aqueous solution of sodium bicarbonate was added to make the solution alkaline. Then, di-tert-butyl dicarbonate (1.1 g) was added to the mixture, and the resulting mixture was stirred at room temperature for 23 hours. The reaction solution was concentrated under reduced pressure. The obtained residue was purified by silica gel column chromatography (chloroform-methanol) to obtain the title compound (0.65 g).

$^1$H-NMR (CDCl$_3$) δ: 1.44 (9H, s), 1.50 (3H, s), 2.28 (1H, d, J=16.3 Hz), 2.75 (1H, d, J=16.3 Hz), 3.30 (1H, d, J=9.7 Hz), 3.74 (1H, d, J=9.7 Hz), 4.71 (1H, br s), 5.52 (1H, br s).

Step 5 tert-Butyl N-[1-(4-bromophenyl)-3-methyl-5-oxopyrrolidin-3-yl]carbamate

The title compound (0.8 g) was obtained by the same procedures as in step 1 of Reference Example 72 using the compound (0.65 g) obtained in the preceding step 4.

$^1$H-NMR (CDCl$_3$) δ: 1.44 (9H, s), 1.56 (3H, s), 2.56 (1H, d, J=16.9 Hz), 3.00 (1H, d, J=16.3 Hz), 3.72 (1H, d, J=10.3 Hz), 4.22 (1H, d, J=9.1 Hz), 4.73 (1H, br s), 7.47 (2H, d, J=9.1 Hz), 7.51 (2H, d, J=9.1 Hz).

Step 6 tert-Butyl N-[3-methyl-5-oxo-1-[4-(4,4,5,5-tetramethyl-1,3,2-dioxaborolan-2-yl)phenyl]pyrrolidin-3-yl]carbamate The title compound (0.65 g) was obtained by the same procedures as in step 3 of Reference Example 61 using the compound (0.8 g) obtained in the preceding step 5.

$^1$H-NMR (CDCl$_3$) δ: 1.34 (12H, s), 1.56 (3H, s), 1.44 (9H, s), 2.58 (1H, d, J=16.9 Hz), 3.00 (1H, d, J=16.9 Hz), 3.78 (1H, d, J=10.3 Hz), 4.23 (1H, d, J=10.3 Hz), 4.74 (1H, br s), 7.62 (2H, d, J=9.1 Hz), 7.80 (2H, d, J=8.5 Hz).

Reference Example 79 tert-Butyl N-[3-methyl-5-oxo-1-[4-(4,4,5,5-tetramethyl-1,3,2-dioxaborolan-2-yl)phenyl]pyrrolidin-3-yl]carbamate

[Formula 46]

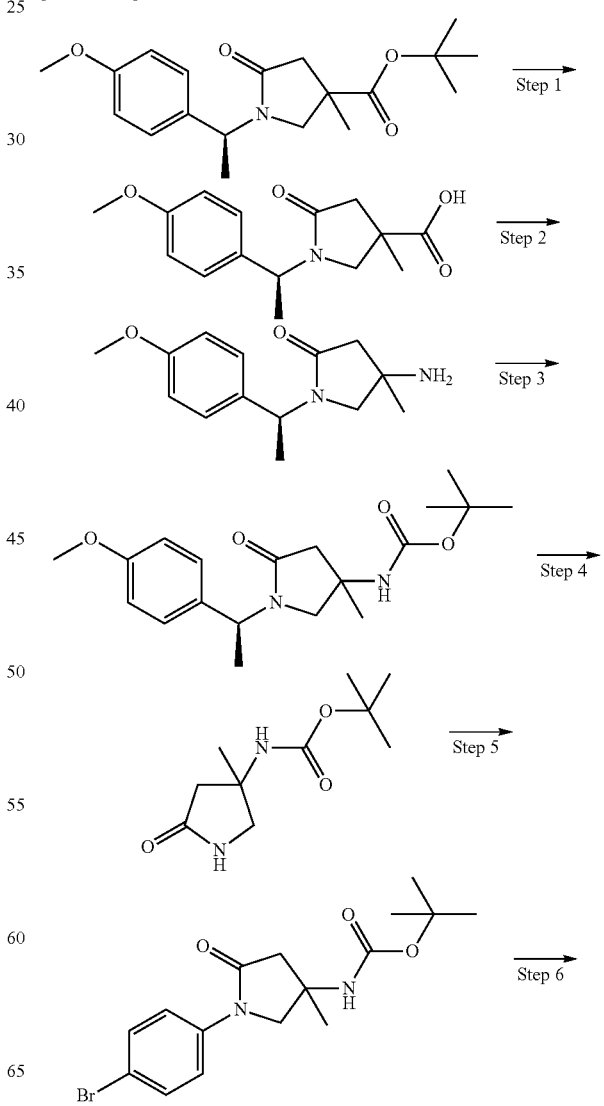

-continued

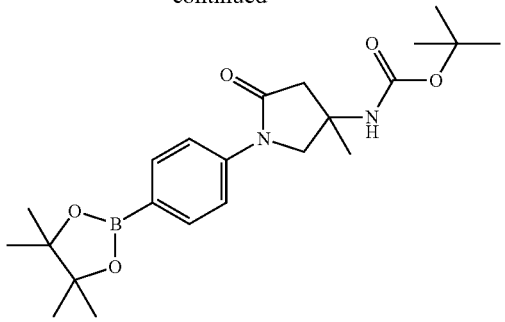

Step 1

1-[(1S)-1-(4-Methoxyphenyl)ethyl]-3-methyl-5-oxopyrrolidine-3-carboxylic acid The title compound (2.7 g) was obtained by the same procedures as in step 1 of Reference Example 78 using the highly polar isomer B (5.0 g) obtained in step 3 of Reference Example 77.

$^1$H-NMR (CDCl$_3$) δ: 1.42 (3H, s), 1.50 (3H, d, J=7.3 Hz), 2.36 (1H, d, J=16.9 Hz), 2.96 (1H, d, J=16.9 Hz), 3.07 (1H, d, J=10.3 Hz), 3.33 (1H, d, J=10.9 Hz), 3.78 (3H, s), 5.46 (1H, q, J=7.1 Hz), 6.84 (2H, d, J 8.5 Hz), 7.19 (2H, d, J=8.5 Hz).

Step 2

4-Amino-1-[(1S)-1-(4-methoxyphenyl)ethyl]-4-methylpyrrolidin-2-one

A crude product of the title compound was obtained by the same procedures as in step 2 of Reference Example 78 using the compound (2.7 g) obtained in the preceding step 1 and used directly in the next reaction.

$^1$H-NMR (CDCl$_3$) δ: 1.31 (3H, s), 1.48 (3H, d, J=6.7 Hz), 2.32 (1H, d, J=16.9 Hz), 2.47 (1H, d, J=16.3 Hz), 2.74 (1H, d, J=9.7 Hz), 3.18 (1H, d, J=9.7 Hz), 3.80 (3H, s), 5.49 (1H, q, J=7.1 Hz), 6.87 (2H, d, J=9.1 Hz), 7.24 (2H, d, J=9.1 Hz).

Step 3 tert-Butyl N-[1-[(1S)-1-(4-methoxyphenyl)ethyl]-3-methyl-5-oxopyrrolidin-3-yl]carbamate The title compound (1.0 g) was obtained by the same procedures as in step 3 of Reference Example 78 using the compound obtained in the preceding step 2.

$^1$H-NMR (CDCl$_3$) δ: 1.35 (9H, s), 1.47 (3H, s), 1.48 (3H, d, J=6.7 Hz), 2.42 (1H, d, J=16.3 Hz), 2.64 (1H, d, J=16.3 Hz), 3.18-3.30 (2H, m), 3.79 (3H, s), 4.54 (1H, br s), 5.47 (1H, q, J=6.7 Hz), 6.85 (2H, d, J=8.5 Hz), 7.22 (2H, d, J=8.5 Hz).

Step 4 tert-Butyl N-(3-methyl-5-oxopyrrolidin-3-yl)carbamate

The title compound (0.4 g) was obtained by the same procedures as in step 4 of Reference Example 78 using the compound (1.0 g) obtained in the preceding step 3.

$^1$H-NMR (CDCl$_3$) δ: 1.44 (9H, s), 1.50 (3H, s), 2.28 (1H, d, J=16.3 Hz), 2.75 (1H, d, J=16.3 Hz), 3.30 (1H, d, J=9.7 Hz), 3.74 (1H, d, J=9.7 Hz), 4.70 (1H, br s), 5.46 (1H, br s).

Step 5 tert-Butyl N-[1-(4-bromophenyl)-3-methyl-5-oxopyrrolidin-3-yl]carbamate

The title compound (0.4 g) was obtained by the same procedures as in step 1 of Reference Example 72 using the compound (0.4 g) obtained in the preceding step 4.

$^1$H-NMR (CDCl$_3$) δ: 1.44 (9H, s), 1.56 (3H, s), 2.56 (1H, d, J=16.9 Hz), 3.00 (1H, d, J=16.3 Hz), 3.72 (1H, d, J=9.7 Hz), 4.22 (1H, d, J=9.1 Hz), 4.73 (1H, br s), 7.47 (2H, d, J=9.1 Hz), 7.51 (2H, d, J=9.1 Hz).

Step 6 tert-Butyl N-[3-methyl-5-oxo-1-[4-(4,4,5,5-tetramethyl-1,3,2-dioxaborolan-2-yl)phenyl]pyrrolidin-3-yl]carbamate The title compound (0.35 g) was obtained by the same procedures as in step 3 of Reference Example 61 using the compound (0.4 g) obtained in the preceding step 5.

$^1$H-NMR (CDCl$_3$) δ: 1.34 (12H, s), 1.44 (9H, s), 1.56 (3H, s), 2.58 (1H, d, J=16.9 Hz), 3.00 (1H, d, J=16.9 Hz), 3.78 (1H, d, J=10.3 Hz), 4.23 (1H, d, J=10.3 Hz), 4.73 (1H, br s), 7.62 (2H, d, J=9.1 Hz), 7.80 (2H, d, J=8.5 Hz).

The present invention will be described specifically with reference to the Examples shown below. However, these Examples are neither intended to limit the present invention nor be construed as being limited in any sense. In the present specification, reagents, solvents, and starting materials can be obtained easily from commercially available supply sources or can be produced by methods known in the art, unless otherwise specified.

Example 1

N-Benzyl-3-[4-[[(2S)-pyrrolidin-2-yl]methoxy]phenyl]imidazo[1,2-b]pyridazin-6-amine

[Formula 47]

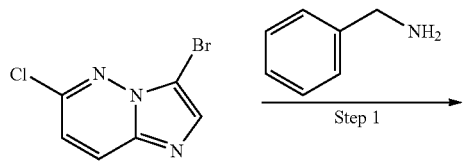

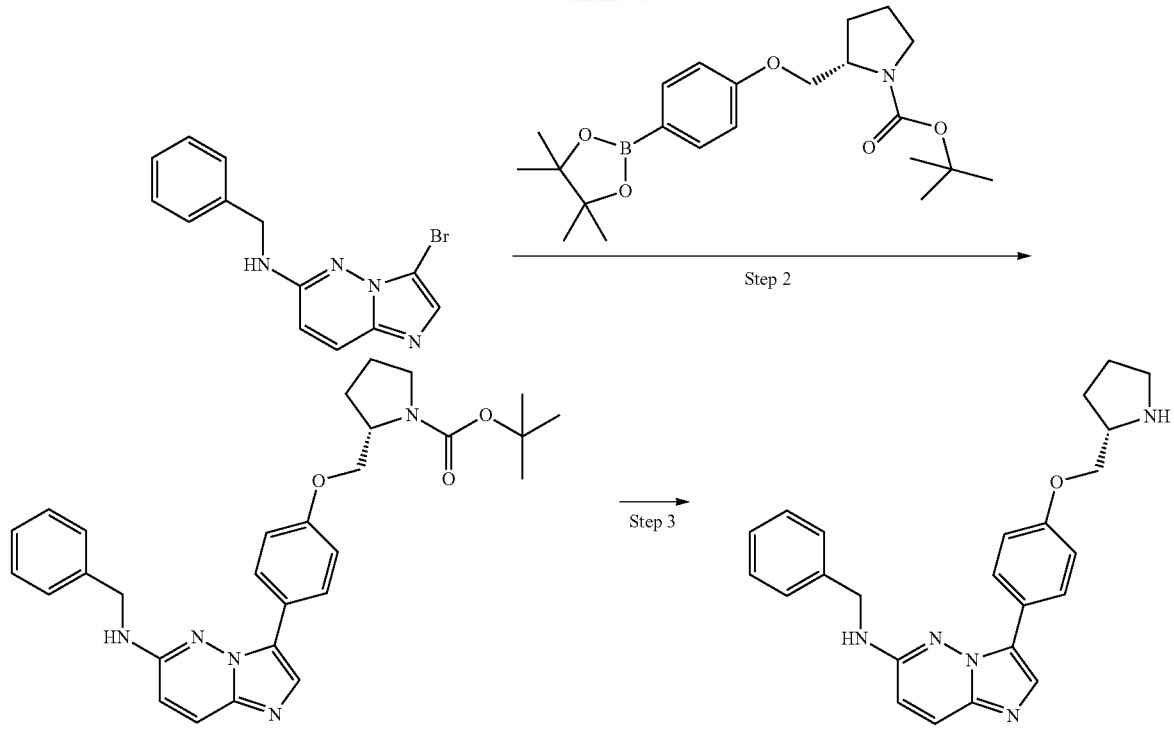

Step 1

N-Benzyl-3-bromoimidazo[1,2-b]pyridazin-6-amine

3-Bromo-6-chloroimidazo[1,2-b]pyridazine (20.0 g), phenylmethanamine (11.3 ml), and potassium fluoride (12.0 g) were dissolved in dimethyl sulfoxide (400 ml), and the solution was stirred at 130° C. for 24 hours. After standing to cool to room temperature, the reaction solution was poured into ice water (2.0 L). The resulting solid was collected by filtration and dried under reduced pressure. The obtained solid was dissolved in hot ethyl acetate, and the insoluble matter was filtered under heating. After distilling off the solvent, the solid was recrystallized from ethyl acetate to obtain the title compound (21.0 g).

$^1$H-NMR (CDCl$_3$) δ: 4.61 (2H, d, J=5.2 Hz), 4.75 (1H, br s), 6.45 (1H, d, J=9.7 Hz), 7.31 (1H, td, J=6.4, 2.9 Hz), 7.36-7.39 (2H, m), 7.45 (2H, d, J=7.4 Hz), 7.49 (1H, s), 7.60 (1H, d, J=9.7 Hz).

Step 2 tert-Butyl (2S)-2-[[4-[6-(Benzylamino)imidazo[1,2-b]pyridazin-3-yl]phenoxy]methyl]pyrrolidine-1-carboxylate 1,4-Dioxane (10 ml) and water (5 ml) were added to the compound (107 mg) obtained in the preceding step 1, the compound (170 mg) obtained in step 2 of Reference Example 1, sodium carbonate (56 mg), and a [1,1'-bis(diphenylphosphino)ferrocene]dichloropalladium(II)-dichloromethane adduct (29 mg), and the mixture was heated to reflux for 1 hour under a nitrogen atmosphere. After cooling, water was added to the reaction solution, followed by extraction with ethyl acetate. The extract was washed with saturated saline and then dried over anhydrous sodium sulfate. The solvent was distilled off under reduced pressure. The obtained residue was purified by silica gel column chromatography (ethyl acetate) to obtain the title compound (65 mg).

$^1$H-NMR (CDCl$_3$) δ: 1.48 (9H, s), 1.81-2.13 (4H, m), 3.29-3.51 (2H, m), 3.75-4.02 (1H, m), 4.09-4.26 (2H, m), 4.59 (2H, d, J=5.0 Hz), 6.46 (1H, d, J=10.1 Hz), 6.98 (2H, d, J=7.3 Hz), 7.28-7.44 (5H, m), 7.65-7.73 (2H, m), 7.88 (2H, br s).

Step 3

N-Benzyl-3-[4-[[(2S)-pyrrolidin-2-yl]methoxy]phenyl]imidazo[1,2-b]pyridazin-6-amine To a solution of the compound (65 mg) obtained in the preceding step 2 in dichloromethane (5 ml), trifluoroacetic acid (1 ml) was added, and the mixture was stirred at room temperature for 2.5 hours. A saturated aqueous solution of sodium bicarbonate was added to the reaction solution, followed by extraction with chloroform. The extract was washed with saturated saline and then dried over anhydrous sodium sulfate. The solvent was distilled off under reduced pressure. The obtained residue was purified by silica gel column chromatography (basic silica gel, chloroform-methanol) to obtain the title compound (40 mg).

$^1$H-NMR (CDCl$_3$) δ: 1.70-2.02 (3H, m), 2.91-3.09 (2H, m), 3.48-3.59 (1H, m), 3.87-4.00 (2H, m), 4.59 (2H, d, J=5.0 Hz), 4.69 (1H, br s), 6.46 (1H, d, J=9.6 Hz), 6.95 (2H, d, J=7.8 Hz), 7.29-7.44 (5H, m), 7.68 (1H, d, J=9.6 Hz), 7.71 (1H, s), 7.87 (2H, d, J=7.8 Hz).

The following compounds were obtained by the same procedures as in Example 1 with the compound obtained in step 1 of Example 1 as the starting material using the compounds obtained in the Reference Examples (the column "Reference Example" represents Reference Example No. of each compound used in the synthesis of the compound of the corresponding Example).

TABLE 9

| Example | Reference Example | Structure and name | Instrumental data |
|---|---|---|---|
| 2 | 2 | 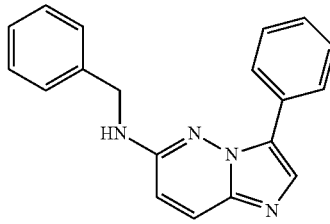<br>N-Benzyl-3-[3-[[(2S)-pyrrolidin-2-yl]methoxy]phenyl]imidazo[1,2-b]pyridazin-6-amine | $^1$H-NMR (CDCl$_3$) δ: 1.47-1.94 (4H, m), 2.87-3.02 (2H, m), 3.89 (1H, t, J = 8.0 Hz), 3.96 (1H, dd, J = 8.6, 5.2 Hz), 4.62 (2H, d, J = 5.2 Hz), 4.64-4.73 (1H, m), 6.48 (1H, d, J = 9.7 Hz), 6.88 (1H, dd, J = 8.0, 4.0 Hz), 7.28-7.44 (6H, m), 7.58 (1H, d, J = 8.0 Hz), 7.70 (1H, d, J = 9.7 Hz), 7.76 (1H, br s), 7.81 (1H, s). |
| 3 | 3 | 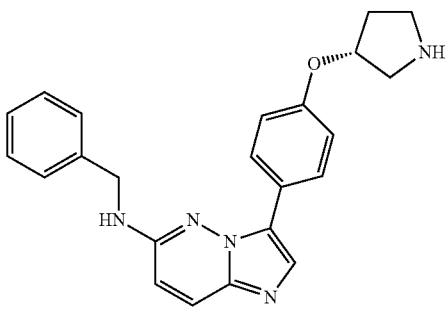 [SMILES: c1ccc(CNc2ccc3ncc(-c4ccc(O[C@@H]5CCNC5)cc4)n3n2)cc1]<br>N-Benzyl-3-[4-[(3R)-pyrrolidin-3-yl]oxyphenyl]imidazo[1,2-b]pyridazin-6-amine | $^1$H-NMR (CDCl$_3$) δ: 2.00-2.21 (2H, m), 2.98-3.32 (4H, m), 4.59 (2H, d, J = 5.5 Hz), 4.71 (1H, t, J = 5.0 Hz), 4.91 (1H, t, J = 5.3 Hz), 6.47 (1H, d, J = 9.6 Hz), 6.90 (2H, d, J = 8.7 Hz), 7.29-7.43 (5H, m), 7.69 (1H, d, J = 9.6 Hz), 7.71 (1H, s), 7.87 (2H, d, J = 9.2 Hz).<br>ESI-MS (m/z): 386 (M + H)$^+$. |
| 4 | 4 | 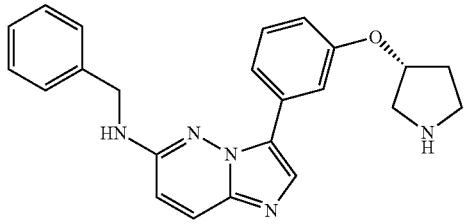 [SMILES: c1ccc(CNc2ccc3ncc(-c4cccc(O[C@@H]5CCNC5)c4)n3n2)cc1]<br>N-Benzyl-3-[3-[(3R)-pyrrolidin-3-yl]oxyphenyl]imidazo[1,2-b]pyridazin-6-amine | $^1$H-NMR (CDCl$_3$) δ: 1.92-2.08 (2H, m), 2.82-2.90 (1H, m), 2.95 (1H, dd, J = 12.8, 4.6 Hz), 3.12-3.23 (2H, m), 4.63 (2H, d, J = 5.0 Hz), 4.70 (1H, t, J = 5.0 Hz), 4.80-4.86 (1H, m), 6.49 (1H, d, J = 9.6 Hz), 6.83 (1H, dd, J = 8.5, 2.5 Hz), 7.27-7.42 (6H, m), 7.56 (1H, d, J = 7.8 Hz), 7.64 (1H, t, J = 2.1 Hz), 7.71 (1H, d, J = 9.6 Hz), 7.80 (1H, s). |
| 5 | 5 | 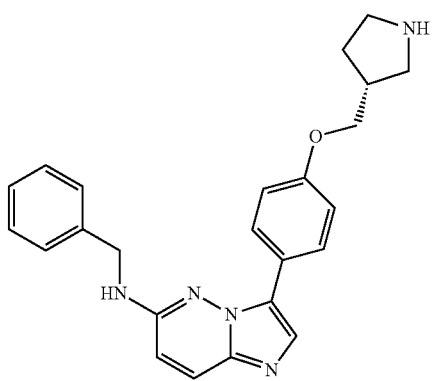 [SMILES: c1ccc(CNc2ccc3ncc(-c4ccc(OC[C@@H]5CCNC5)cc4)n3n2)cc1]<br>N-Benzyl-3-[4-[[(3R)-pyrrolidin-3-yl]methoxy]phenyl]imidazo[1,2-b]pyridazin-6-amine | $^1$H-NMR (CDCl$_3$) δ: 2.01-2.12 (2H, m), 2.61-2.73 (1H, m), 2.93 (1H, dd, J = 11.5, 6.0 Hz), 2.99-3.17 (2H, m), 3.23 (1H, dd, J = 11.5, 8.7 Hz), 3.93 (1H, dd, J = 10.1, 7.3 Hz), 3.99 (1H, dd, J = 9.2, 6.0 Hz), 4.59 (2H, t, J = 5.0 Hz), 4.68 (1H, br s), 6.47 (1H, d, J = 10.1 Hz), 6.93 (2H, d, J = 8.7 Hz), 7.26-7.43 (5H, m), 7.70 (1H, d, J = 10.1 Hz), 7.72 (1H, s), 7.89 (2H, d, J = 8.7 Hz). |

Example 6

N-Benzyl-3-[4-[2-[(2S)-pyrrolidin-2-yl]ethoxy]phenyl]imidazo[1,2-b]pyridazin-6-amine

[Formula 48]

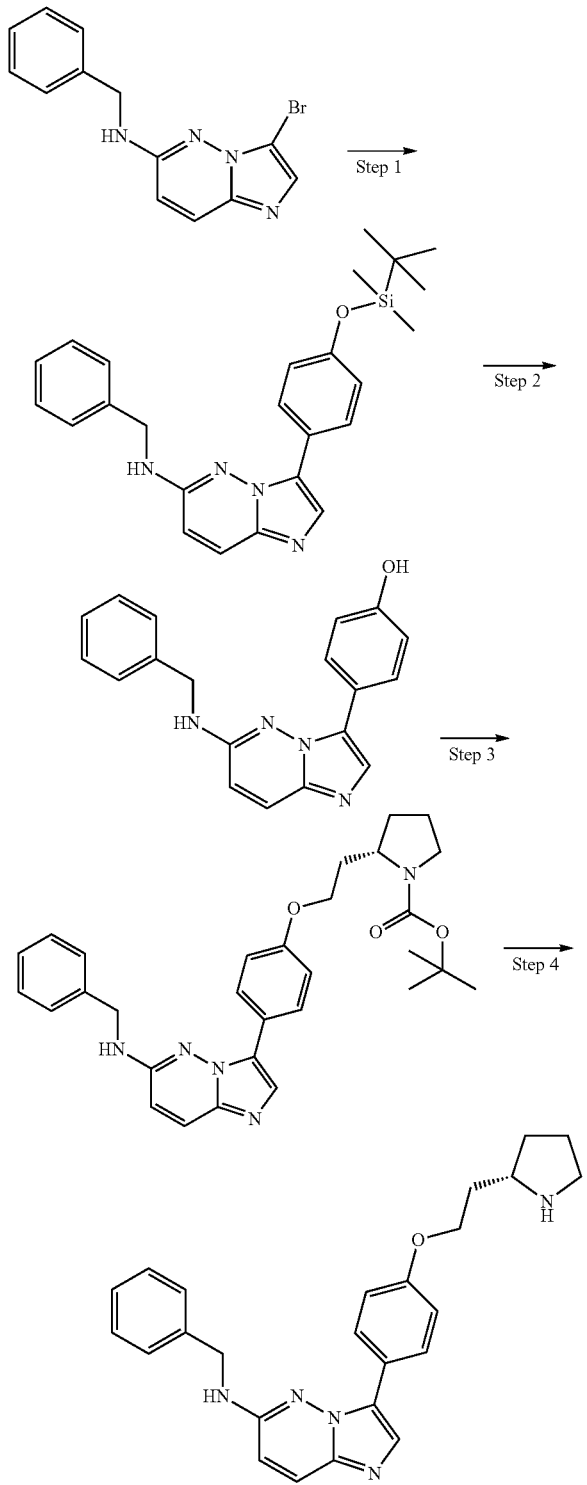

Step 1

N-Benzyl-3-[4-[tert-butyldimethylsilyl]oxyphenyl]imidazo[1,2-b]pyridazin-6-amine The title compound (634 mg) was obtained by the same procedures as in step 2 of Example 1 with the compound (606 mg) obtained in step 1 of Example 1 as the starting material using [4-[t-butyldimethylsilyl]oxyphenyl]boronic acid (327 mg).

$^1$H-NMR (CDCl$_3$) δ: 0.24 (6H, s), 1.01 (9H, s), 4.59 (2H, d, J=5.2 Hz), 4.70 (1H, t, J=5.2 Hz), 6.46 (1H, d, J=9.7 Hz), 6.86-6.89 (2H, m), 7.29-7.33 (1H, m), 7.36-7.39 (2H, m), 7.40-7.43 (2H, m), 7.68 (1H, d, J=9.7 Hz), 7.72 (1H, s), 7.83-7.86 (2H, m).

ESI-MS (m/z): 431 (M+H)$^+$.

Step 2

4-[6-(Benzylamino)imidazo[1,2-b]pyridazin-3-yl]phenol

The compound (634 mg) obtained in the preceding step 1 was dissolved in tetrahydrofuran (5 ml). To the solution, tetrabutylammonium fluoride (1.0 M solution in tetrahydrofuran, 1.5 ml) was added, and the mixture was stirred at room temperature for 30 minutes. Ethyl acetate and water were added to the reaction solution to separate the aqueous and organic layers. The organic layer was washed with saturated saline, dried over anhydrous sodium sulfate and then concentrated under reduced pressure. Ethyl acetate and n-hexane were added to the obtained residue, and the solid was collected by filtration to obtain the title compound (439 mg).

$^1$H-NMR (DMSO-d$_6$) δ: 4.47 (2H, d, J=5.5 Hz), 6.73 (1H, d, J=9.6 Hz), 6.75-6.79 (2H, m), 7.23-7.27 (1H, m), 7.33-7.37 (2H, m), 7.39-7.43 (2H, m), 7.61 (1H, t, J=5.5 Hz), 7.67 (1H, s), 7.73 (1H, d, J=9.6 Hz), 7.75-7.78 (2H, m), 9.54 (1H, s).

ESI-MS (m/z): 317 (M+H)$^+$.

Step 3 tert-Butyl (2S)-2-[2-[4-[6-(Benzylamino)imidazo[1,2-b]pyridazin-3-yl]phenoxy]ethyl]pyrrolidine-1-carboxylate Diisopropylethylamine (575 µl) was added to a solution of 2-[(2S)-1-tert-butoxycarbonylpyrrolidin-2-yl]acetic acid (688 mg) in tetrahydrofuran (15 ml, and the mixture was cooled to −20° C. Isobutyl chloroformate (428 µl) was added thereto, and the mixture was stirred at −20° C. for 45 minutes. The resulting solid was filtered off, and the solid was washed with tetrahydrofuran. Sodium borohydride (227 mg) was added to the filtrate, and the mixture was stirred at room temperature for 5 minutes. Then, methanol (5 ml) was added thereto, and the mixture was stirred at room temperature for 5 minutes. Ethyl acetate and water were added to the reaction solution to separate the aqueous and organic layers. The aqueous layer was subjected to extraction with ethyl acetate. The organic layers were combined, dried over anhydrous sodium sulfate and then concentrated under reduced pressure. The obtained residue was purified by silica gel column chromatography (n-hexane-ethyl acetate) to obtain tert-butyl (2S)-2-(2-hydroxyethyl)pyrrolidine-1-carboxylate (606 mg).

The compound (150 mg) obtained in the preceding step 2, tert-butyl (2S)-2-(2-hydroxyethyl)pyrrolidine-1-carboxylate (153 mg), and cyanomethylene tributylphosphorane (172 mg) were suspended in toluene (8 ml), and the suspension was heated to reflux for 45 minutes. Cyanomethylene tributylphosphorane (86 mg) was further added thereto, and the mixture was further heated to reflux for 1 hour. The solvent was distilled off under reduced pressure. The obtained residue was purified by silica gel column chromatography (dichloromethane-methanol) to obtain the title compound as a crude product, which was used directly in the next reaction.

ESI-MS (m/z): 514 (M+H)$^+$.

Step 4

N-Benzyl-3-[4-[2-[(2S)-pyrrolidin-2-yl]ethoxy]phenyl]imidazo[1,2-b]pyridazin-6-amine The crude product obtained in the preceding step 3 was dissolved in dichloromethane (5 ml). To the solution, a solution of 4 N hydrochloric acid in dioxane (5 ml) was added, and the mixture was stirred at room temperature for 1 hour. The solvent was distilled off under reduced pressure. A saturated aqueous solution of sodium bicarbonate and dichloromethane were added to the residue to separate the aqueous and organic layers. The organic layer was dried over anhydrous sodium sulfate and then concentrated under reduced pressure. The obtained residue was purified by silica gel column chromatography (basic silica gel, dichloromethane-methanol). Diethyl ether was added to the residue, and the solid was collected by filtration to obtain the title compound (110 mg).

$^1$H-NMR (CDCl$_3$) δ: 1.33-1.41 (1H, m), 1.71-1.83 (2H, m), 1.91-2.01 (3H, m), 2.86-2.91 (1H, m), 3.00-3.05 (1H, m), 3.21-3.27 (1H, m), 4.12 (2H, td, J=6.3, 1.7 Hz), 4.59 (2H, d, J=5.4 Hz), 4.74 (1H, t, J=5.4 Hz), 6.46 (1H, d, J=9.7 Hz), 6.92-6.96 (2H, m), 7.30-7.33 (1H, m), 7.36-7.42 (4H, m), 7.68 (1H, d, J=9.7 Hz), 7.71 (1H, s), 7.86-7.89 (2H, m).

ESI-MS (m/z): 414 (M+H)$^+$.

Example 7

2-[(2S)-2-[[3-[6-(Benzylamino)imidazo[1,2-b]pyridazin-3-yl]phenoxy]methyl]pyrrolidin-1-yl]ethanol

[Formula 49]

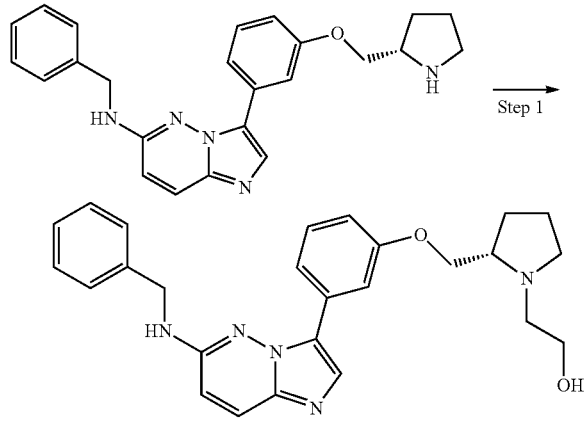

Step 1

2-[(2S)-2-[[3-[6-(Benzylamino)imidazo[1,2-b]pyridazin-3-yl]phenoxy]methyl]pyrrolidin-1-yl]ethanol To a solution of the compound (100 mg) obtained in Example 2 in dichloromethane (5 ml), triethylamine (0.07 ml) and 2-iodoethanol (0.024 ml) were added, and the mixture was stirred at room temperature for 4 hours and then heated to reflux for 7 hours. Triethylamine (0.07 ml) and 2-iodoethanol (0.024 ml) were further added to the reaction solution, and the mixture was further heated to reflux for 2 hours. After cooling, water was added to the reaction solution, followed by extraction with ethyl acetate. The extract was washed with saturated saline and then dried over anhydrous sodium sulfate. The solvent was distilled off under reduced pressure. The obtained residue was purified by silica gel column chromatography (basic silica gel, chloroform-methanol) to obtain the title compound (55 mg).

$^1$H-NMR (CDCl$_3$) δ: 1.62-1.81 (3H, m), 1.94-2.05 (1H, m), 2.34 (1H, q, J=8.3 Hz), 2.60 (1H, dt, J=12.7, 3.6 Hz), 2.80 (1H, br s), 2.97-3.18 (3H, m), 3.52-3.65 (2H, m), 3.86 (1H, dd, J=8.9, 6.2 Hz), 3.96 (1H, dd, J=8.7, 5.5 Hz), 4.61 (2H, d, J=5.5 Hz), 4.74 (1H, br s), 6.48 (1H, d, J=9.6 Hz), 6.87 (1H, d, J=9.2 Hz), 7.27-7.44 (5H, m), 7.56 (1H, d, J=7.8 Hz), 7.70 (1H, dd, J=9.4, 1.1 Hz), 7.80 (1H, br s), 7.82 (1H, s).

ESI-MS (m/z): 444 (M+H)$^+$.

Example 8

N-Benzyl-3-[3-[[(2S)-1-methylpyrrolidin-2-yl]methoxy]phenyl]imidazo[1,2-b]pyridazin-6-amine

[Formula 50]

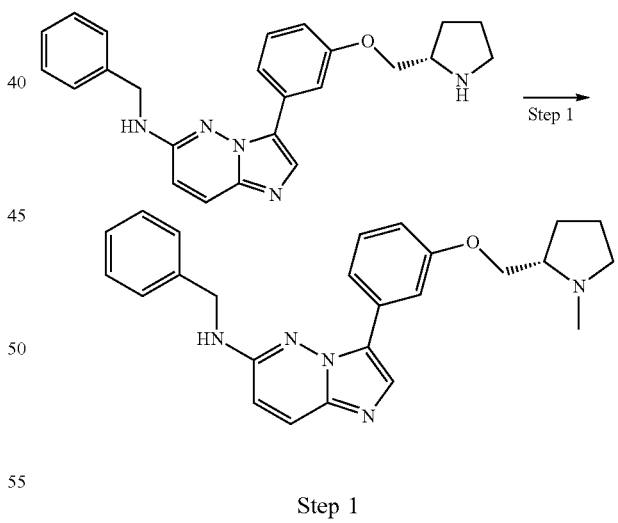

Step 1

N-Benzyl-3-[3-[[(2S)-1-methylpyrrolidin-2-yl]methoxy]phenyl]imidazo[1,2-b]pyridazin-6-amine To a solution of the compound (90 mg) obtained in Example 2 in tetrahydrofuran (10 ml), a 35% aqueous formaldehyde solution (1 ml) and sodium triacetoxyborohydride (72 mg) were added, and the mixture was stirred at room temperature for 2.5 hours. A saturated aqueous solution of sodium bicarbonate was added to the reaction solution, followed by extraction with ethyl acetate. The extract was washed with saturated saline and then dried over anhydrous sodium sulfate. The solvent was distilled off under reduced pressure. The obtained residue was purified by silica gel column chromatography (basic silica gel, chloroform-methanol) to obtain the title compound (65 mg).

$^1$H-NMR (CDCl$_3$) δ: 1.64-1.83 (3H, m), 1.95-2.05 (1H, m), 2.27 (1H, td, J=9.6, 7.3 Hz), 2.44 (3H, s), 2.60-2.67 (1H, m), 3.07 (1H, t, J=8.9 Hz), 3.94 (1H, dd, J=9.2, 5.7 Hz), 4.03 (1H, dd, J=9.2, 5.7 Hz), 4.61 (2H, d, J=5.2 Hz), 4.68 (1H, t, J=5.2 Hz), 6.47 (1H, d, J=9.7 Hz), 6.88 (1H, dd, J=8.0, 3.4 Hz), 7.29-7.33 (2H, m), 7.37 (2H, t, J=7.4 Hz), 7.42 (2H, d, J=7.4 Hz), 7.58 (1H, dd, J=6.9, 1.7 Hz), 7.69 (1H, d, J=9.2 Hz), 7.76 (1H, t, J=2.0 Hz), 7.81 (1H, s).

ESI-MS (m/z): 414 (M+H)$^+$.

Example 9

N-[(3-Fluorophenyl)methyl]-N-methyl-3-[4-[(3R)-pyrrolidin-3-yl]oxyphenyl]imidazo[1,2-b]pyridazin-6-amine Step 1

3-Bromo-N-[(3-fluorophenyl)methyl]-N-methylimidazo[1,2-b]pyridazin-6-amine

The title compound (4.04 g) was obtained by the same procedures as in step 1 of Example 1 using 1-(3-fluorophenyl)-N-methyl-methanamine instead of phenylmethanamine.

$^1$H-NMR (CDCl$_3$) δ: 3.20 (3H, s), 4.76 (2H, s), 6.72 (1H, d, J=9.7 Hz), 6.95-7.00 (1H, m), 7.03-7.06 (1H, m), 7.10-7.11 (1H, m), 7.28-7.34 (1H, m), 7.53 (1H, s), 7.66 (1H, d, J=9.7 Hz).

Step 2 tert-Butyl (3R)-3-[4-[6-[(3-fluorophenyl)methyl-methylamino]imidazo[1,2-b]pyridazin-3-yl]phenoxy]pyrrolidine-1-carboxylate The title compound (276 mg) was obtained by the same procedures as in step 2 of Example 1 using the compound (250 mg) obtained in the preceding step 1 and the compound (371 mg) obtained in Reference Example 3.

[Formula 51]

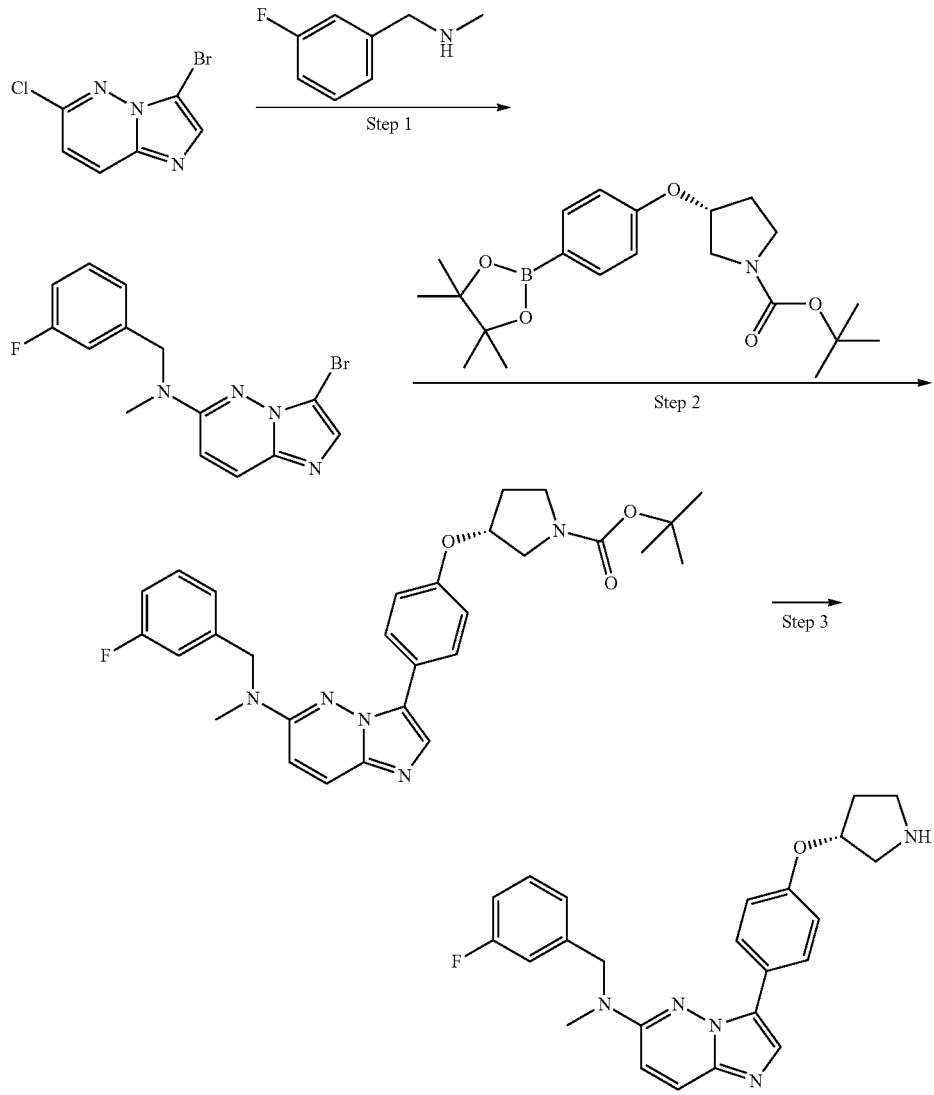

¹H-NMR (CDCl₃) δ: 1.47 (9H, s), 2.10-2.23 (2H, m), 3.49-3.67 (4H, m), 4.74 (2H, s), 4.93 (1H, br s), 6.75 (1H, d, J=9.7 Hz), 6.90 (2H, d, J=8.6 Hz), 6.95-7.01 (2H, m), 7.04-7.06 (1H, m), 7.29-7.34 (1H, m), 7.75 (2H, d, J=10.3 Hz), 7.87-7.91 (2H, m).

Step 3

N-[(3-Fluorophenyl)methyl]-N-methyl-3-[4-[(3R)-pyrrolidin-3-yl]oxyphenyl]imidazo[1,2-b]pyridazin-6-amine The title compound (241 mg) was obtained by the same procedures as in step 3 of Example 1 with the compound (276 mg) obtained in the preceding step 2 as the starting material.

¹H-NMR (CDCl₃) δ: 1.94-2.06 (1H, m), 2.09-2.16 (1H, m), 2.74-2.95 (2H, m), 3.02-3.22 (2H, m), 3.23 (3H, s), 4.74 (2H, s), 4.83-4.89 (1H, m), 6.72-6.75 (1H, m), 6.86-6.90 (2H, m), 6.95-6.99 (2H, m), 7.04-7.06 (1H, m), 7.27-7.33 (1H, m), 7.74-7.76 (2H, m), 7.88 (2H, d, J=9.2 Hz).

The following compound was obtained by the same procedures as in Example 9 with the compound obtained in step 1 of Example 9 as the starting material using the compound obtained in the Reference Example.

TABLE 10

| Example | Reference Example | Structure and name | Instrumental data |
|---|---|---|---|
| 10 | 1 | 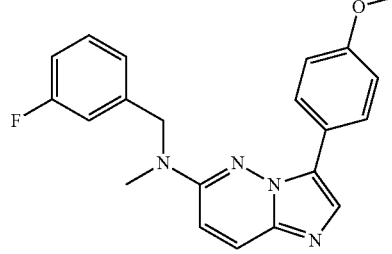<br>N-[(3-Fluorophenyl)methyl]-N-methyl-3-[4-[[(2S)-pyrrolidin-2-yl]methoxy]phenyl]imidazo[1,2-b]pyridazin-6-amine | ¹H-NMR (CDCl₃) δ: 1.54-1.61 (1H, m), 1.72-1.87 (2H, m), 1.93-1.99 (1H, m), 2.93-2.98 (1H, m), 3.02-3.07 (1H, m), 3.22 (3H, s), 3.50-3.56 (1H, m), 3.90 (1H, dd, J = 9.2, 6.9 Hz), 3.97 (1H, dd, J = 9.2, 5.2 Hz), 4.73 (2H, s), 6.73 (1H, d, J = 9.7 Hz), 6.92-6.98 (4H, m), 7.03-7.06 (1H, m), 7.28-7.34 (1H, m), 7.72-7.76 (2H, m), 7.89 (2H, d, J = 8.6 Hz). |

Example 11

6-[(3-Fluorophenyl)methoxy]-3-[4-[[(2R)-pyrrolidin-2-yl]methoxy]phenyl]imidazo[1,2-b]pyridazine

[Formula 52]

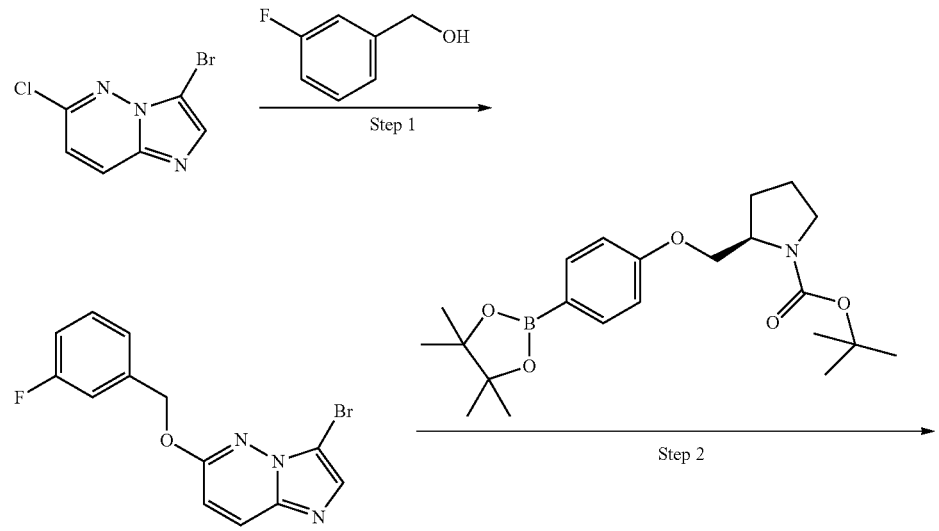

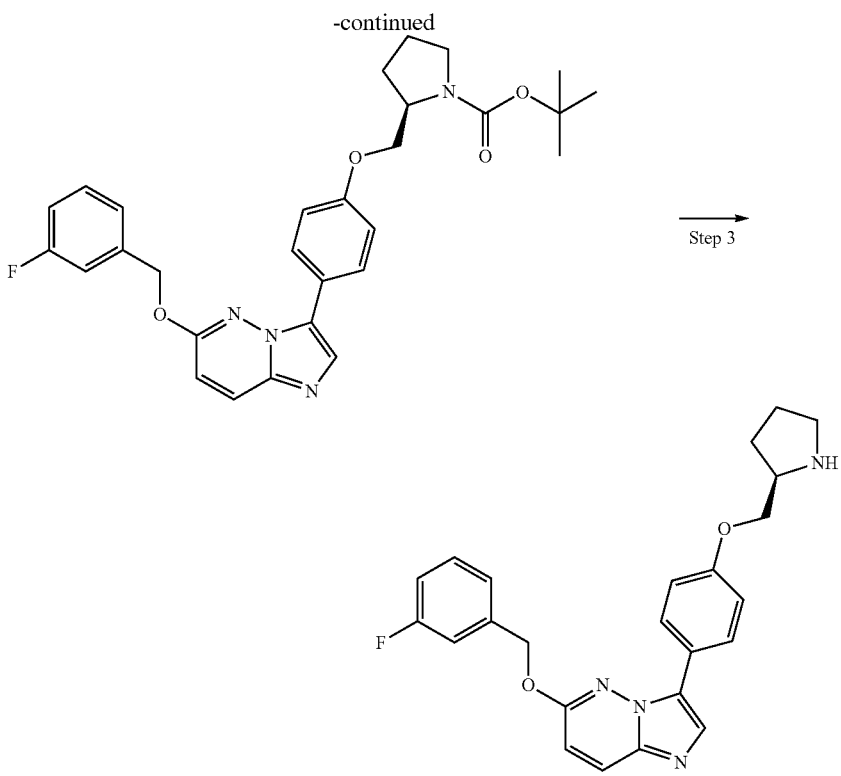

Step 1

3-Bromo-6-[(3-fluorophenyl)methoxy]imidazo[1,2-b]pyridazine

To a solution of 3-fluorobenzyl alcohol (0.59 g) in N,N-dimethylformamide (20 ml), sodium hydride (55% oil, 0.26 g) was added under ice cooling, and the mixture was stirred at the same temperature as above for 10 minutes. 3-Bromo-6-chloroimidazo[1,2-b]pyridazine (1 g) was added to the reaction solution, and the mixture was stirred at the same temperature as above for 1 hour. A saturated aqueous solution of ammonium chloride was added to the reaction solution, followed by extraction with ethyl acetate. The extract was washed with water and saturated saline in this order and then dried over anhydrous sodium sulfate. The solvent was distilled off under reduced pressure. The obtained residue was washed with n-hexane to obtain the title compound (1.2 g).

$^1$H-NMR (CDCl$_3$) δ: 5.45 (2H, s), 6.78 (1H, d, J=9.6 Hz), 7.02-7.08 (1H, m), 7.25-7.40 (3H, m), 7.61 (1H, s), 7.79 (1H, d, J=9.6 Hz).

Step 2 tert-Butyl (2R)-2-[[4-[6-[(3-fluorophenyl)methoxy]imidazo[1,2-b]pyridazin-3-yl]phenoxy]methyl]pyrrolidine-1-carboxylate 1,4-Dioxane (10 ml) and water (5 ml) were added to the compound (0.26 g) obtained in the preceding step 1, the compound (0.4 g) obtained in Reference Example 6, sodium carbonate (0.13 g), and a [1,1'-bis(diphenylphosphino)ferrocene]dichloropalladium(II)-dichloromethane adduct (68 mg), and the mixture was heated to reflux for 1.5 hours under a nitrogen atmosphere. After cooling, water was added to the reaction solution, and the mixture was subjected to extraction with ethyl acetate. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (0.35 g).

$^1$H-NMR (CDCl$_3$) δ: 1.49 (9H, s), 1.85-2.13 (4H, m), 3.32-3.49 (2H, br m), 3.83-4.03 (1H, br m), 4.14-4.29 (2H, m), 5.40 (2H, s), 6.77 (1H, d, J=9.6 Hz), 7.00-7.06 (3H, m), 7.19 (1H, d, J=9.6 Hz), 7.25 (1H, d, J=8.3 Hz), 7.34-7.41 (1H, m), 7.79-7.89 (4H, m).

Step 3

6-[(3-Fluorophenyl)methoxy]-3-[4-[[(2R)-pyrrolidin-2-yl]methoxy]phenyl]imidazo[1,2-b]pyridazine To a solution of the compound (0.35 g) obtained in the preceding step 2 in dichloromethane (10 ml), trifluoroacetic acid (3 ml) was added, and the mixture was stirred at room temperature for 5 hours. A saturated aqueous solution of sodium bicarbonate was added to the reaction solution, followed by extraction with chloroform. The extract was washed with saturated saline and then dried over anhydrous sodium sulfate. The solvent was distilled off under reduced pressure. Ethyl acetate was added to the obtained residue, and the deposits were collected by filtration to obtain the title compound (65 mg).

$^1$H-NMR (CDCl$_3$) δ: 1.83-2.21 (5H, m), 3.23-3.36 (2H, m), 3.84-3.92 (1H, m), 4.21-4.25 (2H, m), 5.35 (2H, s), 6.76 (1H, d, J=9.6 Hz), 7.00-7.06 (3H, m), 7.17 (1H, d, J=9.6 Hz), 7.23 (1H, d, J=7.8 Hz), 7.37 (1H, td, J=7.9, 5.8 Hz), 7.76 (1H, s), 7.81 (2H, d, J=9.5 Hz), 7.86 (1H, d, J=9.6 Hz).

The following compounds were obtained by the same procedures as in Example 11 with the compound obtained in step 1 of Example 11 as the starting material using the compounds obtained in the Reference Examples.

TABLE 11

| Example No. | Reference Example No. | Structure and name | Instrumental data |
|---|---|---|---|
| 12 | 1 | 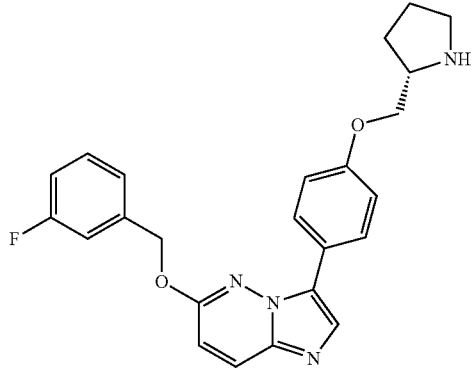 [SMILES: Fc1cccc(COc2ccc3ncc(-c4ccc(OC[C@@H]5CCCN5)cc4)n3n2)c1]<br>6-[(3-Fluorophenyl)methoxy]-3-[4-[[(2S)-pyrrolidin-2-yl]methoxy]phenyl]imidazo[1,2-b]pyridazine | $^{1}$H-NMR (CDCl$_3$) δ: 1.69-2.12 (5H, m), 3.06-3.21 (2H, m), 3.66-3.74 (1H, m), 4.03-4.13 (2H, m), 5.38 (2H, s), 6.77 (1H, d, J = 9.6 Hz), 7.00-7.06 (3H, m), 7.18 (1H, d, J = 9.6 Hz), 7.24 (1H, d, J = 7.8 Hz), 7.37 (1H, td, J = 7.9, 5.8 Hz), 7.79 (1H, s), 7.82 (2H, d, J = 9.5 Hz), 7.86 (1H, d, J = 9.6 Hz). |
| 13 | 3 | 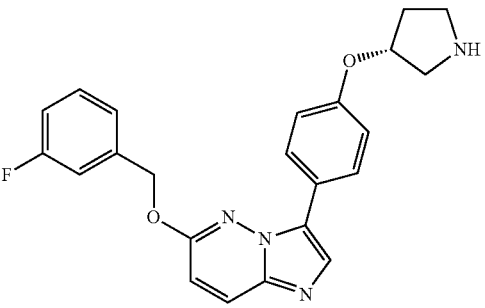 [SMILES: Fc1cccc(COc2ccc3ncc(-c4ccc(O[C@@H]5CCNC5)cc4)n3n2)c1]<br>6-[(3-Fluorophenyl)methoxy]-3-[4-[(3R)-pyrrolidin-3-yl]oxyphenyl]imidazo[1,2-b]pyridazine | $^{1}$H-NMR (CDCl$_3$) δ: 1.78 (1H, br s), 2.02-2.21 (2H, m), 2.96-3.03 (1H, m), 3.12 (1H, dd, J = 12.4, 4.6 Hz), 3.20-3.31 (2H, m), 4.93 (1H, t, J = 5.3 Hz), 5.40 (2H, s), 6.78 (1H, d, J = 9.6 Hz), 6.97 (2H, d, J = 9.2 Hz), 7.05 (1H, td, J = 8.5, 2.0 Hz), 7.19 (1H, d, J = 9.2 Hz), 7.24 (1H, d, J = 7.3 Hz), 7.37 (1H, td, J = 8.0, 6.0 Hz), 7.81 (1H, s), 7.83 (2H, d, J = 8.3 Hz), 7.87 (1H, d, J = 9.2 Hz). |
| 14 | 7 | 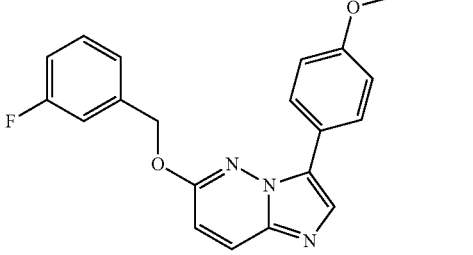<br>2-[4-[6-[(3-Fluorophenyl)methoxy]imidazo[1,2-b]pyridazin-3-yl]phenoxy]ethanamine | $^{1}$H-NMR (CDCl$_3$) δ: 1.60 (2H, br s), 3.14 (2H, t, J = 5.0 Hz), 4.08 (2H, t, J = 4.6 Hz), 5.40 (2H, s), 6.78 (1H, d, J = 9.6 Hz), 7.00-7.07 (3H, m), 7.19 (1H, d, J = 9.6 Hz), 7.24 (1H, d, J = 7.8 Hz), 7.38 (1H, td, J = 7.9, 5.8 Hz), 7.81 (1H, s), 7.84 (2H, d, J = 8.7 Hz), 7.87 (1H, d, J = 9.6 Hz). |

Example 15

6-[(1R)-1-(3-Fluorophenyl)ethoxy]-3-[4-(4-piperidyloxy)phenyl]imidazo[1,2-b]pyridazine

[Formula 53]

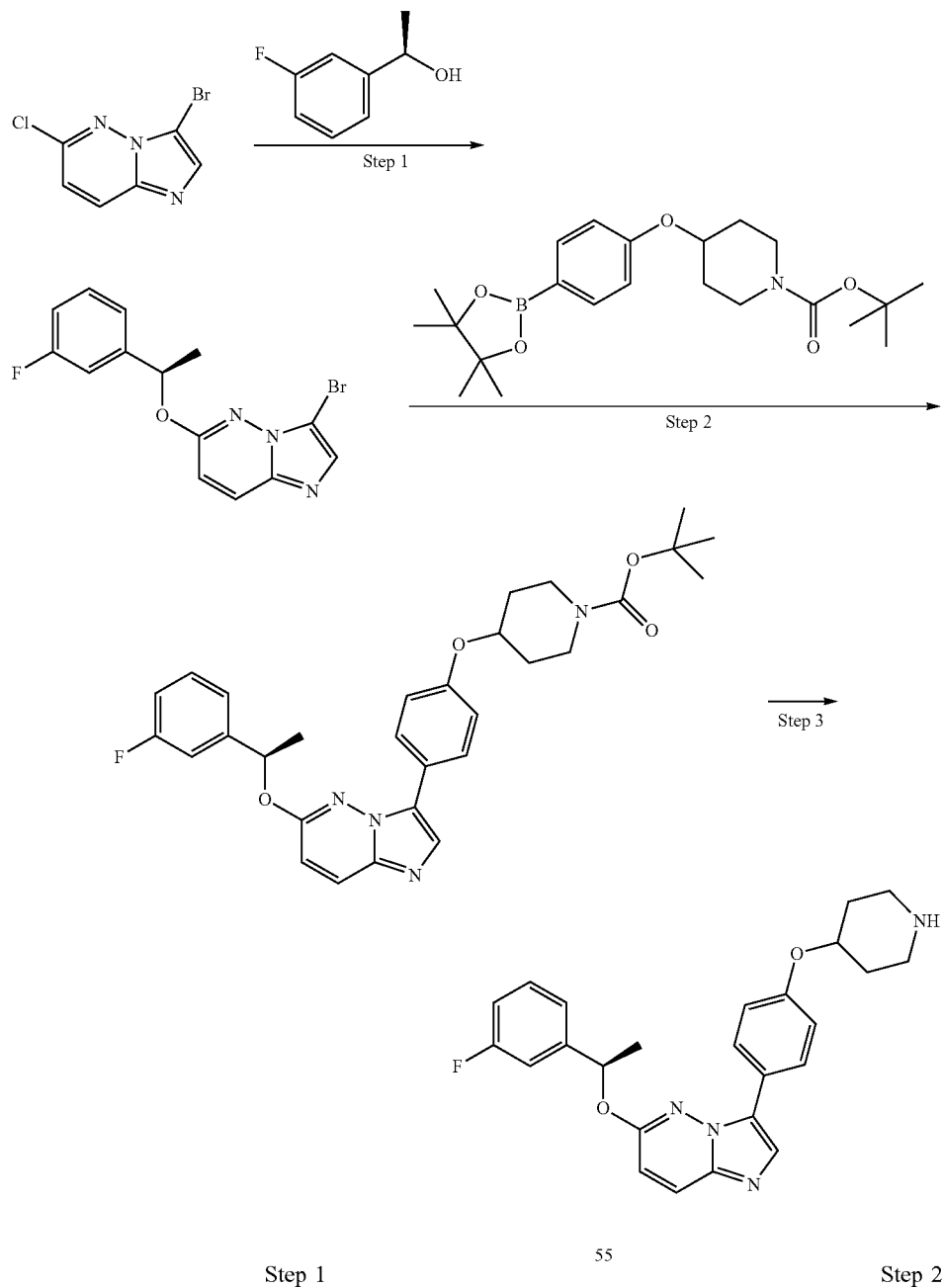

Step 1

3-Bromo-6-[(1R)-1-(3-fluorophenyl)ethoxy]imidazo[1,2-b]pyridazine

The title compound (3.3 g) was obtained by the same procedures as in step 1 of Example 11 using (1R)-1-(3-fluorophenyl)ethanol (1.54 g) instead of 3-fluorobenzyl alcohol.

$^1$H-NMR (CDCl$_3$) δ: 1.72 (3H, d, J=6.4 Hz), 6.12 (1H, q, J=6.4 Hz), 6.73 (1H, d, J=10.1 Hz), 6.93-7.01 (1H, m), 7.22-7.34 (3H, m), 7.55 (1H, s), 7.74 (1H, d, J=9.2 Hz).

Step 2 tert-Butyl 4-[4-[6-[(1R)-1-(3-fluorophenyl)ethoxy]imidazo[1,2-b]pyridazin-3-yl]phenoxy]piperidine-1-carboxylate 1,4-Dioxane (10 ml) and water (5 ml) were added to the compound (200 mg) obtained in the preceding step 1, the compound (290 mg) obtained in Reference Example 8, sodium carbonate (73 mg), and a [1,1'-bis(diphenylphosphino)ferrocene]dichloropalladium(II)-dichloromethane adduct (49 mg), and the mixture was heated to reflux for 1 hour under a nitrogen atmosphere. After cooling, water was added to the reaction solution, and the mixture was subjected to extraction with ethyl acetate. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (240 mg).

$^1$H-NMR (CDCl$_3$) δ: 1.49 (9H, s), 1.68 (3H, d, J=6.4 Hz), 1.76-1.88 (2H, br m), 1.94-2.04 (2H, m), 3.35-3.43 (2H, m), 3.72-3.80 (2H, m), 4.53-4.59 (1H, m), 5.92 (1H, q, J=6.6 Hz), 6.76 (1H, d, J=9.6 Hz), 6.95-7.02 (3H, m), 7.13 (1H, dt, J=9.6, 1.8 Hz), 7.20 (1H, d, J=7.8 Hz), 7.34 (1H, td, J=7.8, 6.0 Hz), 7.62 (2H, d, J=8.7 Hz), 7.74 (1H, s), 7.83 (1H, d, J=9.6 Hz).

Step 3
6-[(1R)-1-(3-Fluorophenyl)ethoxy]-3-[4-(4-piperidyloxy)phenyl]imidazo[1,2-b]pyridazine To a solution of the compound (240 mg) obtained in the preceding step 2 in dichloromethane (10 ml), trifluoroacetic acid (2 ml) was added, and the mixture was stirred at room temperature for 4 hours. A saturated aqueous solution of sodium bicarbonate was added to the reaction solution, followed by extraction with chloroform. The extract was washed with saturated saline and then dried over anhydrous sodium sulfate. The solvent was distilled off under reduced pressure. Ethyl acetate was added to the obtained residue, and the deposits were collected by filtration to obtain the title compound (20 mg).

$^1$H-NMR (CDCl$_3$) δ: 1.68 (3H, d, J=6.4 Hz), 1.85 (1H, br s), 2.08-2.18 (2H, br m), 2.25-2.35 (2H, br m), 3.19-3.28 (2H, m), 3.40 (2H, t, J=10.3 Hz), 4.70 (1H, br s), 5.91 (1H, q, J=6.9 Hz), 6.78 (1H, d, J=10.1 Hz), 6.94-7.02 (3H, m), 7.12 (1H, d, J=9.2 Hz), 7.21 (1H, d, J=7.8 Hz), 7.31-7.39 (1H, m), 7.63 (2H, d, J=8.3 Hz), 7.74 (1H, s), 7.84 (1H, d, J=9.6 Hz).

The following compounds were obtained by the same procedures as in Example 15 with the compound obtained in step 1 of Example 15 as the starting material using the compounds obtained in the Reference Examples.

TABLE 12

| Example | Reference Example | Structure and name | Instrumental data |
|---|---|---|---|
| 16 | 1 | 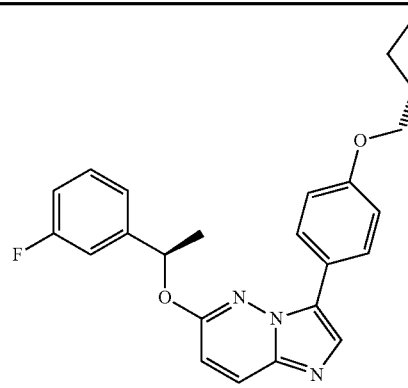<br>6-[(1R)-1-(3-Fluorophenyl)ethoxy]-3-[4-[[(2S)-pyrrolidin-2-yl]methoxy]phenyl]imidazo[1,2-b]pyridazine | $^1$H-NMR (CDCl$_3$) δ: 1.58-2.04 (5H, m), 1.67 (3H, d, J = 6.9 Hz), 2.96-3.12 (2H, m), 3.55-3.62 (1H, m), 3.95 (1H, dd, J = 9.2, 6.9 Hz), 4.02 (1H, dd, J = 9.2, 5.0 Hz), 5.93 (1H, q, J = 6.7 Hz), 6.76 (1H, d, J = 9.2 Hz), 6.95-7.01 (3H, m), 7.14 (1H, d, J = 9.6 Hz), 7.20 (1H, d, J = 7.8 Hz), 7.30-7.39 (1H, m), 7.62 (2H, d, J = 9.3 Hz), 7.73 (1H, s), 7.83 (1H, d, J = 9.6 Hz). |
| 17 | 25 | 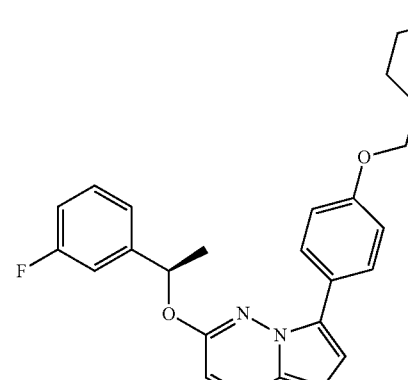<br>6-[(1R)-1-(3-Fluorophenyl)ethoxy]-3-[4-(4-piperidylmethoxy)phenyl]imidazo[1,2-b]pyridazine | $^1$H-NMR (CDCl$_3$) δ: 1.68 (3H, d, J = 6.3 Hz), 1.88 (2H, q, J = 11.8 Hz), 2.11-2.19 (3H, m), 2.98 (2H, dd, J = 12.9, 10.6 Hz), 3.61 (2H, d, J = 12.6 Hz), 3.95 (2H, d, J = 5.7 Hz), 5.92 (1H, q, J = 6.7 Hz), 6.77 (1H, d, J = 9.7 Hz), 6.93-7.01 (3H, m), 7.13 (1H, dt, J = 9.5, 1.7 Hz), 7.21 (1H, d, J = 7.4 Hz), 7.35 (1H, td, J = 8.0, 5.7 Hz), 7.61-7.63 (2H, m), 7.74 (1H, s), 7.84 (1H, d, J = 9.7 Hz). ESI-MS (m/z): 447 (M + H)$^+$. |

Example 18

3-[4-[[(2S)-Azetidin-2-yl]methoxy]phenyl]-6-[(1R)-1-(3-fluorophenyl)ethoxy]imidazo[1,2-b]pyridazine hydrochloride

[Formula 54]

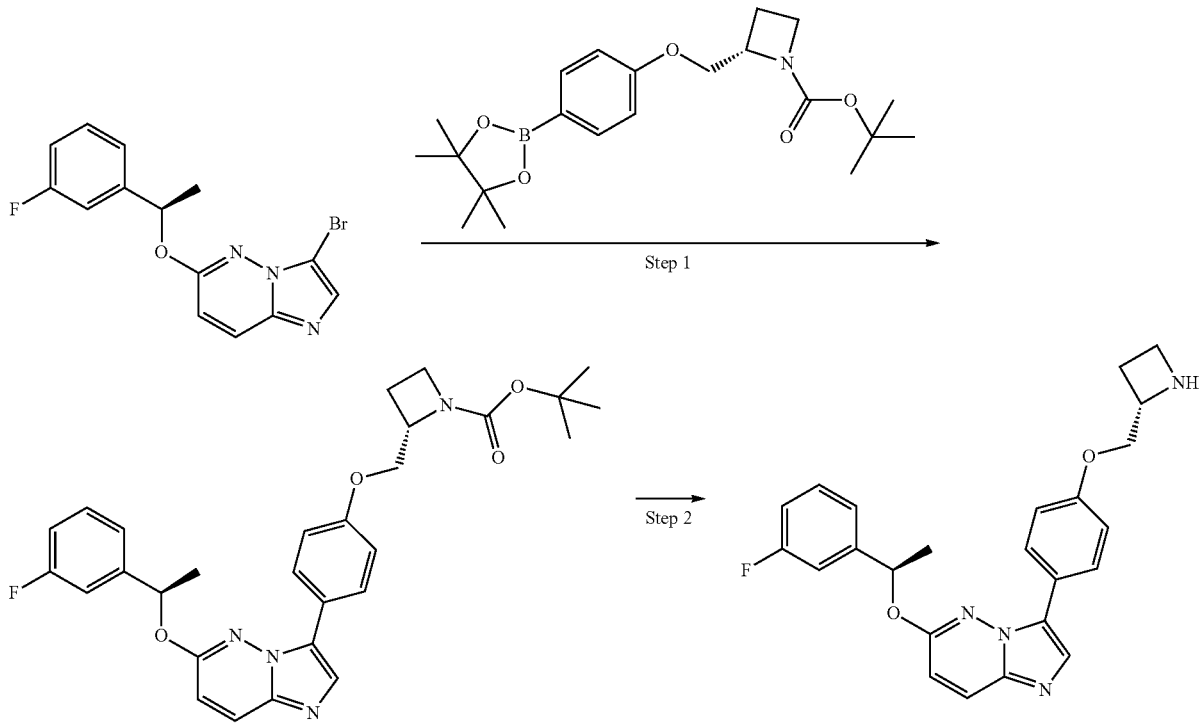

Step 1 tert-Butyl (2S)-2-[[4-[6-[(1R)-1-(3-fluorophenyl)ethoxy]imidazo[1,2-b]pyridazin-3-yl]phenoxy]methyl]azetidine-1-carboxylate

1,4-Dioxane (20 ml) and water (10 ml) were added to the compound (0.8 g) obtained in step 1 of Example 15, the compound (1.1 g) obtained in Reference Example 26, sodium carbonate (0.38 g), and a [1,1'-bis(diphenylphosphino)ferrocene]dichloropalladium(II)-dichloromethane adduct (0.19 g), and the mixture was heated to reflux for 40 minutes under a nitrogen atmosphere. After cooling, water was added to the reaction solution, and the mixture was subjected to extraction with ethyl acetate. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (0.85 g).

$^1$H-NMR (CDCl$_3$) δ: 1.45 (9H, s), 1.68 (3H, d, J=6.0 Hz), 3.89-3.99 (2H, m), 3.89-3.99 (2H, m), 4.20 (1H, dd, J=10.0, 2.7 Hz), 4.34 (1H, br s), 4.52-4.61 (1H, m), 5.94 (1H, q, J=6.7 Hz), 6.76 (1H, d, J=9.7 Hz), 6.95-7.03 (3H, m), 7.14 (1H, dt, J=9.7, 2.1 Hz), 7.21 (1H, d, J=7.3 Hz), 7.35 (1H, td, J=8.0, 5.8 Hz), 7.64 (2H, d, J=9.7 Hz), 7.75 (1H, s), 7.83 (1H, d, J=9.7 Hz).

Step 2

3-[4-[[(2S)-Azetidin-2-yl]methoxy]phenyl]-6-[(1R)-1-(3-fluorophenyl)ethoxy]imidazo[1,2-b]pyridazine hydrochloride

To a solution of the compound (0.85 g) obtained in the preceding step 1 in dichloromethane (10 ml), trifluoroacetic acid (3 ml) was added, and the mixture was stirred at room temperature for 2 hours. A saturated aqueous solution of sodium bicarbonate was added to the reaction solution, followed by extraction with chloroform. The extract was washed with saturated saline and then dried over anhydrous sodium sulfate. The solvent was distilled off under reduced pressure. A solution of 2 N hydrochloric acid in ethanol (5 ml) was added to the obtained residue, and the mixture was concentrated under reduced pressure. The obtained residue was dissolved in ethanol. To the solution, ethyl acetate was added, and the deposits were collected by filtration to obtain the title compound (0.61 g).

$^1$H-NMR (DMSO-d$_6$) δ: 1.68 (3H, d, J=6.7 Hz), 2.37-2.60 (2H, m), 3.88-4.01 (3H, m), 4.35 (1H, dd, J=10.9, 3.6 Hz), 4.45-4.54 (1H, m), 4.77 (1H, br s), 6.04 (1H, q, J=6.4 Hz), 7.11-7.17 (3H, m), 7.34 (2H, d, J=7.9 Hz), 7.40 (1H, d, J=9.7 Hz), 7.43-7.50 (1H, m), 7.85 (2H, d, J=8.5 Hz), 8.32 (1H, d, J=10.3 Hz), 8.38 (1H, s), 9.34 (1H, br s), 9.52 (1H, br s).

ESI-MS (m/z): 419 (M+H)$^+$.

Example 19

N-[(1R)-1-Phenylethyl]-3-[4-[[(2S)-pyrrolidin-2-yl]methoxy]phenyl]imidazo[1,2-b]pyridazin-6-amine

[Formula 55]

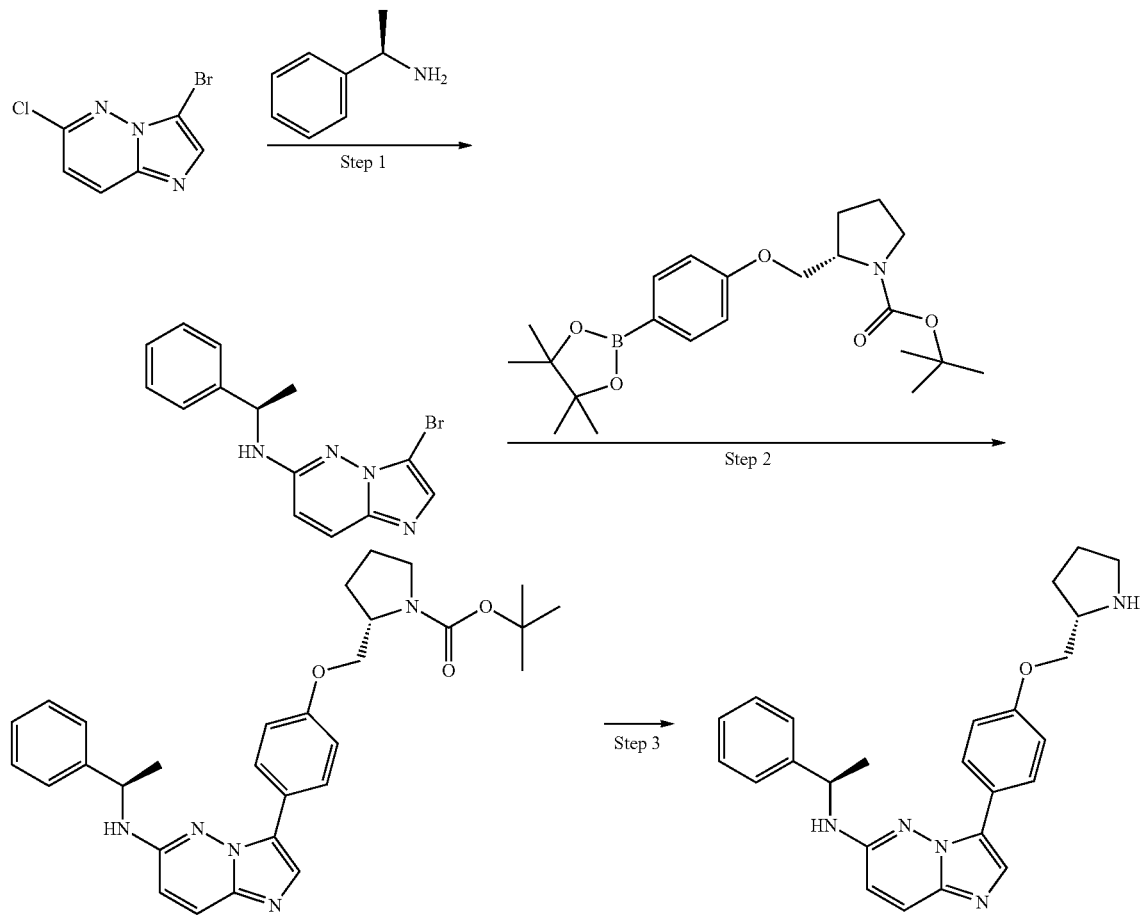

Step 1

3-Bromo-N-[(1R)-1-phenylethyl]imidazo[1,2-b]pyridazin-6-amine

The title compound (1.07 g) was obtained by the same procedures as in step 1 of Example 1 using (1R)-1-phenylethanamine (0.71 ml) instead of phenylmethanamine.

$^1$H-NMR (CDCl$_3$) δ: 1.62 (3H, s), 4.83 (1H, d, J=6.3 Hz), 5.01-5.07 (1H, m), 6.40 (1H, t, J=4.6 Hz), 7.27 (1H, tt, J=7.4, 1.6 Hz), 7.35 (2H, td, J=7.7, 3.2 Hz), 7.45 (3H, td, J=4.6, 2.1 Hz), 7.55 (1H, d, J=9.7 Hz).

Step 2 tert-Butyl (2S)-2-[[4-[6-[[(1R)-1-phenylethyl]amino]imidazo[1,2-b]pyridazin-3-yl]phenoxy]methyl]pyrrolidine-1-carboxylate 1,4-Dioxane (20 ml) and water (10 ml) were added to the compound (0.72 g) obtained in the preceding step 1, the compound (1.1 g) obtained in step 2 of Reference Example 1, sodium carbonate (0.36 g), and a [1,1'-bis(diphenylphosphino)ferrocene]dichloropalladium(II)-dichloromethane adduct (185 mg), and the mixture was heated to reflux for 2 hours under a nitrogen atmosphere. After cooling, water was added to the reaction solution, and the mixture was subjected to extraction with chloroform. The extract was washed with saturated saline and then dried over anhydrous sodium sulfate. The solvent was distilled off under reduced pressure. The obtained residue was purified by silica gel column chromatography (n-hexane-ethyl acetate) to obtain the title compound (0.85 g).

$^1$H-NMR (CDCl$_3$) δ: 1.50 (9H, s), 1.59 (3H, d, J=6.0 Hz), 1.87-2.12 (4H, m), 3.42-3.45 (2H, m), 3.78-4.27 (3H, m), 4.68 (1H, d, J=5.4 Hz), 4.96 (1H, q, J=6.3 Hz), 6.45 (1H, d, J=10.3 Hz), 6.89-6.98 (2H, m), 7.22-7.44 (5H, m), 7.62-7.71 (4H, m).

Step 3

N-[(1R)-1-Phenylethyl]-3-[4-[[(2S)-pyrrolidin-2-yl]methoxy]phenyl]imidazo[1,2-b]pyridazin-6-amine To a solution of the compound (0.85 g) obtained in the preceding step 2 in dichloromethane (10 ml), trifluoroacetic acid (3 ml) was added, and the mixture was stirred at room temperature for 1.5 hours. A saturated aqueous solution of sodium bicarbonate was added to the reaction solution, followed by extraction with chloroform. The extract was washed with saturated saline and then dried over anhydrous sodium sulfate. The solvent was distilled off under reduced pressure. Chloroform was added to the obtained residue, and the deposits were collected by filtration to obtain the title compound (0.3 g).

$^1$H-NMR (CDCl$_3$) δ: 1.49 (3H, d, J=6.7 Hz), 1.74-1.83 (1H, m), 1.88-2.05 (2H, m), 2.12-2.20 (1H, m), 3.17-3.35 (3H, m), 3.88-3.98 (1H, m), 4.18 (1H, br s), 4.32 (1H, dd, J=10.9, 3.6 Hz), 4.80-4.88 (1H, m), 6.78 (1H, d, J=9.1 Hz), 6.99 (2H, d, J=9.1 Hz), 7.21 (1H, t, J=7.9 Hz), 7.36 (2H, t, J=7.6 Hz), 7.43 (2H, d, J=6.7 Hz), 7.65 (1H, br s), 7.74 (2H, t, J=4.8 Hz), 7.83 (2H, d, J=9.1 Hz).

ESI-MS (m/z): 414 (M+H)$^+$.

The following compound was obtained by the same procedures as in Example 19 with the compound obtained in step 1 of Example 19 as the starting material using the compound obtained in the Reference Example.

TABLE 13

| Example | Reference Example | Structure and name | Instrumental data |
|---|---|---|---|
| 20 | 51 | 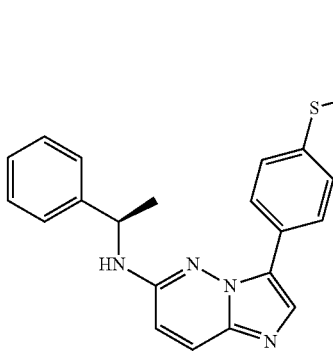<br>N-[(1R)-1-Phenylethyl]-3-[4-[[(2S)-pyrrolidin-2-yl]methylsulfanyl]phenyl]imidazo[1,2-b]pyridazin-6-amine | $^1$H-NMR (CDCl$_3$) δ: 1.47-1.57 (1H, m), 1.59 (3H, d, J = 6.7 Hz), 1.71-2.03 (4H, m), 2.89-2.96 (1H, m), 3.01-3.12 (3H, m), 3.31-3.38 (1H, m), 4.73 (1H, d, J = 5.4 Hz), 4.92-4.99 (1H, m), 6.48 (1H, d, J = 9.7 Hz), 7.26-7.44 (7H, m), 7.66 (1H, d, J = 9.1 Hz), 7.69 (2H, d, J = 8.5 Hz), 7.72 (1H, s).<br>ESI-MS (m/z): 431 (M + H)$^+$. |

Example 21

3-[4-[(2R)-2-Aminopropoxy]phenyl]-N-[(1R)-1-(3-fluorophenyl)ethyl]imidazo[1,2-b]pyridazin-6-amine

[Formula 56]

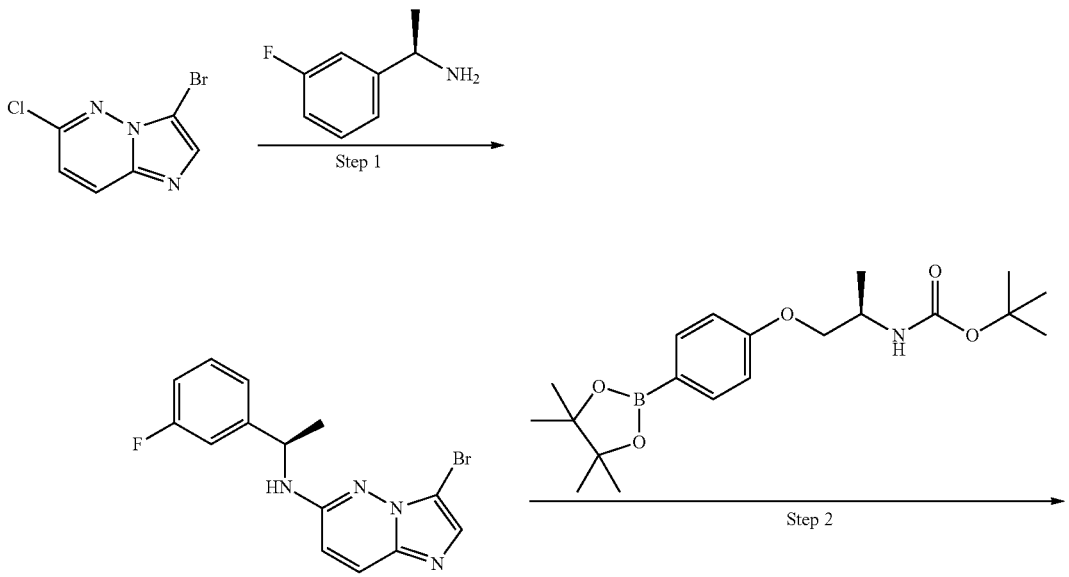

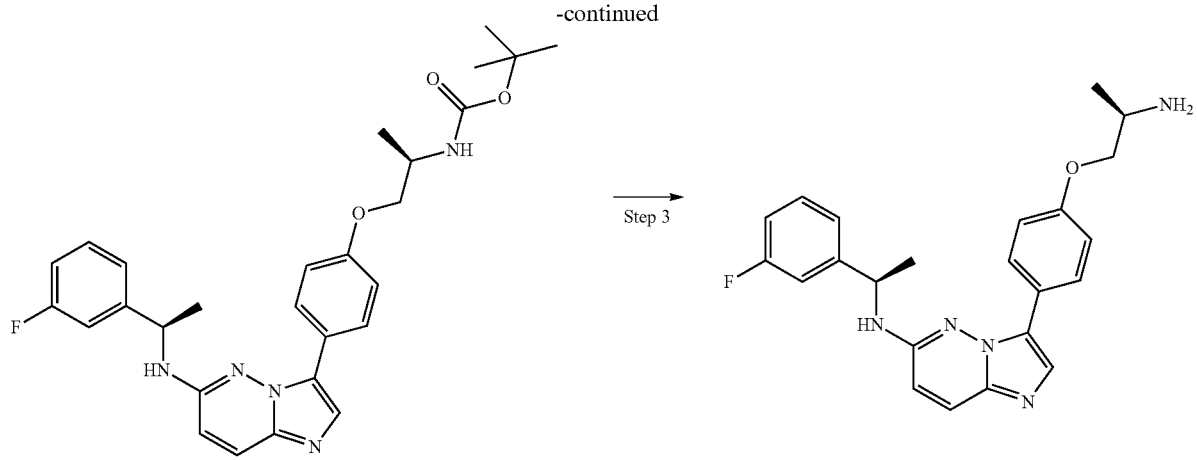

Step 1

3-Bromo-N-[(1R)-1-(3-fluorophenyl)ethyl]imidazo[1,2-b]pyridazin-6-amine

The title compound (0.59 g) was obtained by the same procedures as in step 1 of Example 1 using (1R)-1-(3-fluorophenyl)ethanamine (0.39 g) instead of phenylmethanamine.

$^1$H-NMR (CDCl$_3$) δ: 1.61 (3H, d, J=6.9 Hz), 4.83 (1H, d, J=6.3 Hz), 5.01-5.06 (1H, m), 6.42 (1H, d, J=9.7 Hz), 6.93-6.97 (1H, m), 7.17 (1H, dt, J=9.9, 2.1 Hz), 7.24 (1H, d, J=7.4 Hz), 7.30 (1H, td, J=7.9, 5.9 Hz), 7.46 (1H, s), 7.57 (1H, t, J=4.6 Hz).

Step 2 tert-Butyl N-[(1R)-2-[4-[6-[[(1R)-1-(3-fluorophenyl)ethyl]amino]imidazo[1,2-b]pyridazin-3-yl]phenoxy]-1-methylethyl]carbamate 1,4-Dioxane (25 ml) and water (5 ml) were added to the compound (0.34 g) obtained in the preceding step 1, the compound (0.39 g) obtained in Reference Example 15, potassium carbonate (0.55 g), and a [1,1'-bis(diphenylphosphino)ferrocene]dichloropalladium(II)-dichloromethane adduct (81 mg), and the mixture was heated to reflux for 1.5 hours under a nitrogen atmosphere. After cooling, water was added to the reaction solution, followed by extraction with ethyl acetate. The extract was washed with saturated saline and then dried over anhydrous magnesium sulfate. The solvent was distilled off under reduced pressure. The obtained residue was purified by silica gel column chromatography (ethyl acetate-methanol) to obtain the title compound (0.39 g).

$^1$H-NMR (CDCl$_3$) δ: 1.33 (3H, d, J=6.7 Hz), 1.48 (9H, s), 1.57 (3H, d, J=6.7 Hz), 3.99 (2H, d, J=3.6 Hz), 4.10-4.13 (1H, m), 4.68 (1H, d, J=4.8 Hz), 4.83 (1H, br s), 4.92 (1H, dq, J=4.8, 6.7 Hz), 6.47 (1H, d, J=9.7 Hz), 6.90 (2H, d, J=9.1 Hz), 6.97 (1H, td, J=8.5, 2.4 Hz), 7.11-7.14 (1H, m), 7.20 (1H, d, J=7.9 Hz), 7.36 (1H, td, J=7.9, 6.0 Hz), 7.61-7.62 (2H, m), 7.67 (2H, d, J=9.7 Hz).

Step 3

3-[4-[(2R)-2-Aminopropoxy]phenyl]-N-[(1R)-1-(3-fluorophenyl)ethyl]imidazo[1,2-b]pyridazin-6-amine To a solution of the compound (0.39 g) obtained in the preceding step 1 in methanol (3 ml), a solution of 4 N hydrochloric acid in 1,4-dioxane (8 ml) was added, and the mixture was stirred at room temperature for 40 minutes. The reaction solution was concentrated under reduced pressure. A 1 N aqueous sodium hydroxide solution was added to the obtained residue, followed by extraction with chloroform-methanol. The extract was washed with saturated saline and then dried over anhydrous sodium sulfate. The solvent was distilled off under reduced pressure. The obtained residue was purified by silica gel column chromatography (basic silica gel, chloroform-methanol) to obtain the title compound (0.09 g).

$^1$H-NMR (CDCl$_3$) δ: 1.21 (3H, d, J=6.7 Hz), 1.57 (3H, d, J=6.7 Hz), 3.37-3.41 (1H, m), 3.75 (1H, dd, J=9.1, 7.9 Hz), 3.93 (1H, dd, J=9.1, 4.2 Hz), 4.67 (1H, d, J 4.8 Hz), 4.92 (1H, dq, J=4.8, 6.7 Hz), 6.47 (1H, d, J 9.7 Hz), 6.89-6.92 (2H, m), 6.97 (1H, td, J=8.5, 3.2 Hz), 7.11-7.14 (1H, m), 7.20 (1H, d, J=7.3 Hz), 7.30-7.37 (1H, m), 7.60-7.63 (2H, m), 7.67 (2H, d, J=8.5 Hz).

$^1$H-NMR (DMSO-d$_6$) δ: 1.08 (3H, d, J=6.0 Hz), 1.48 (3H, d, J=7.3 Hz), 1.65 (2H, br s), 3.12-3.21 (1H, m), 4.19-4.19 (2H, m), 4.80-4.89 (1H, m), 6.77 (1H, d, J=9.7 Hz), 6.93 (2H, d, J=9.1 Hz), 7.03 (1H, td, J=8.5, 2.2 Hz), 7.22-7.29 (2H, m), 7.37-7.44 (1H, m), 7.62 (1H, d, J=6.0 Hz), 7.70-7.77 (4H, m).

ESI-MS (m/z): 406 (M+H)$^+$.

The following compounds were obtained by the same procedures as in Example 21 with the compound obtained in step 1 of Example 21 as the starting material using the compounds obtained in the Reference Examples.

TABLE 14-1

| Example | Reference Example | Structure and name | Instrumental data |
|---|---|---|---|
| 22 | 3 | N-[(1R)-1-(3-Fluorophenyl)ethyl]-3-[4-[(3R)-pyrrolidin-3-yl]oxyphenyl]imidazo[1,2-b]pyridazin-6-amine | $^1$H-NMR (CDCl$_3$) δ: 1.57 (3H, d, J = 6.9 Hz), 1.96-2.05 (1H, m), 2.10-2.19 (1H, m), 2.93-2.95 (1H, m), 3.07 (1H, dd, J = 12.6, 5.2 Hz), 3.19-3.26 (2H, m), 4.74 (1H, d, J = 5.2 Hz), 4.87-4.95 (2H, m), 6.48 (1H, d, J = 9.7 Hz), 6.86 (2H, d, J = 8.6 Hz), 6.97 (1H, td, J = 8.2, 2.1 Hz), 7.12 (1H, d, J = 9.7 Hz), 7.20 (1H, d, J = 8.0 Hz), 7.33 (1H, td, J = 7.9, 5.9 Hz), 7.59 (2H, dd, J = 9.5, 2.6 Hz), 7.65 (1H, s), 7.67 (1H, d, J = 9.7 Hz). |
| 23 | 5 | N-[(1R)-1-(3-Fluorophenyl)ethyl]-3-[4-[[(3R)-pyrrolidin-3-yl]methoxy]phenyl]imidazo[1,2-b]pyridazin-6-amine | $^1$H-NMR (CDCl$_3$) δ: 1.56 (3H, d, J = 6.9 Hz), 1.64-1.66 (1H, m), 2.05-2.07 (1H, m), 2.60-2.73 (1H, m), 2.89-2.91 (1H, m), 2.99-3.02 (1H, m), 3.09-3.11 (1H, m), 3.21 (1H, dd, J = 11.2, 7.7 Hz), 3.90-4.02 (2H, m), 4.75 (1H, d, J = 5.2 Hz), 4.89-4.94 (1H, m), 6.47 (1H, d, J = 9.2 Hz), 6.89 (2H, d, J = 8.6 Hz), 6.96 (1H, td, J = 8.2, 2.3 Hz), 7.12 (1H, d, J = 9.7 Hz), 7.20 (1H, d, J = 8.0 Hz), 7.34 (1H, td, J = 7.9, 5.9 Hz), 7.61 (2H, d, J = 8.6 Hz), 7.65 (1H, s), 7.67 (1H, d, J = 9.7 Hz). |
| 24 | 1 | N-[(1R)-1-(3-Fluorophenyl)ethyl]-3-[4-[[(2S)-pyrrolidin-2-yl]methoxy]phenyl]imidazo[1,2-b]pyridazin-6-amine | $^1$H-NMR (CDCl$_3$) δ: 1.56 (3H, d, J = 6.6 Hz), 1.58-1.63 (1H, m), 1.78-1.86 (2H, m), 1.93-2.01 (1H, m), 2.96 (1H, dt, J = 10.7, 7.1 Hz), 3.02-3.08 (1H, m), 3.53-3.56 (1H, m), 3.91 (1H, dd, J = 9.2, 6.8 Hz), 3.98 (1H, dd, J = 9.2, 5.1 Hz), 4.67 (1H, d, J = 5.1 Hz), 4.92 (1H, dq, J = 5.1, 6.6 Hz), 6.45 (1H, d, J = 9.8 Hz), 6.88-6.91 (2H, m), 6.93-6.98 (1H, m), 7.09-7.12 (1H, m), 7.19 (1H, d, J = 7.8 Hz), 7.33 (1H, td, J = 8.0, 5.9 Hz), 7.58-7.61 (2H, m), 7.66 (2H, d, J = 9.0 Hz). $^1$H-NMR (DMSO-d$_6$) δ: 1.42-1.52 (1H, m), 1.48 (3H, d, J = 6.7 Hz), 1.60-1.77 (2H, m), 1.83-1.91 (1H, m), 2.77-2.88 (2H, m), 3.36-3.44 (1H, m), 3.84 (2H, d, J = 6.0 Hz), 4.80-4.88 (1H, m), 6.76 (1H, d, J = 9.1 Hz), 6.92 (2H, d, J = 8.5 Hz), 7.03 (1H, td, J = 8.6, 2.2 Hz), 7.22-7.29 (2H, m), 7.36-7.43 (1H, m), 7.62 (1H, d, J = 6.0 Hz), 7.71-7.77 (4H, m). ESI-MS (m/z): 432 (M + H)$^+$. |

TABLE 14-2

| 25 | 27 | 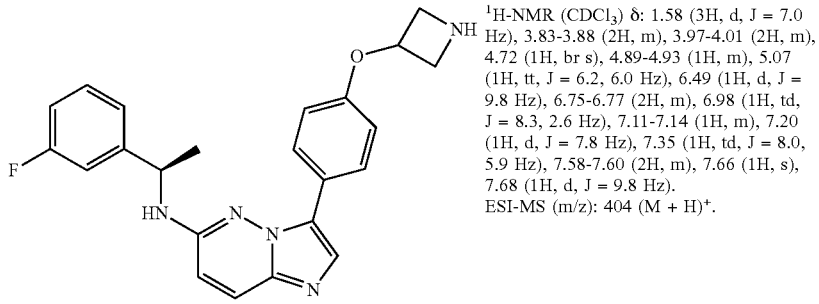<br>3-[4-(Azetidin-3-yloxy)phenyl]-N-[(1R)-1-(3-fluorophenyl)ethyl]imidazo[1,2-b]pyridazin-6-amine | $^1$H-NMR (CDCl$_3$) δ: 1.58 (3H, d, J = 7.0 Hz), 3.83-3.88 (2H, m), 3.97-4.01 (2H, m), 4.72 (1H, br s), 4.89-4.93 (1H, m), 5.07 (1H, tt, J = 6.2, 6.0 Hz), 6.49 (1H, d, J = 9.8 Hz), 6.75-6.77 (2H, m), 6.98 (1H, td, J = 8.3, 2.6 Hz), 7.11-7.14 (1H, m), 7.20 (1H, d, J = 7.8 Hz), 7.35 (1H, td, J = 8.0, 5.9 Hz), 7.58-7.60 (2H, m), 7.66 (1H, s), 7.68 (1H, d, J = 9.8 Hz).<br>ESI-MS (m/z): 404 (M + H)$^+$. |
|---|---|---|---|
| 26 | 7 | 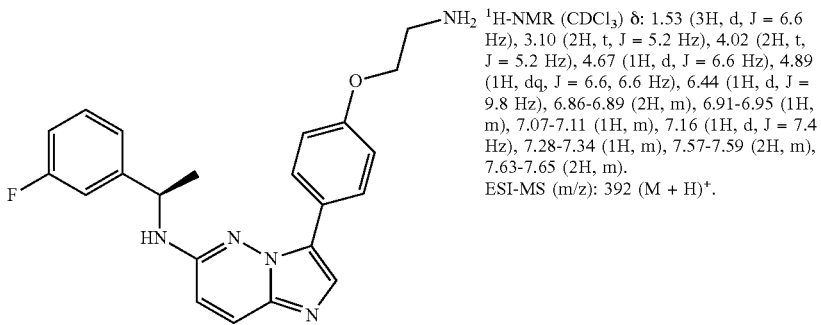<br>3-[4-(2-Aminoethoxy)phenyl]-N-[(1R)-1-(3-fluorophenyl)ethyl]imidazo[1,2-b]pyridazin-6-amine | $^1$H-NMR (CDCl$_3$) δ: 1.53 (3H, d, J = 6.6 Hz), 3.10 (2H, t, J = 5.2 Hz), 4.02 (2H, t, J = 5.2 Hz), 4.67 (1H, d, J = 6.6 Hz), 4.89 (1H, dq, J = 6.6, 6.6 Hz), 6.44 (1H, d, J = 9.8 Hz), 6.86-6.89 (2H, m), 6.91-6.95 (1H, m), 7.07-7.11 (1H, m), 7.16 (1H, d, J = 7.4 Hz), 7.28-7.34 (1H, m), 7.57-7.59 (2H, m), 7.63-7.65 (2H, m).<br>ESI-MS (m/z): 392 (M + H)$^+$. |
| 27 | 28 | 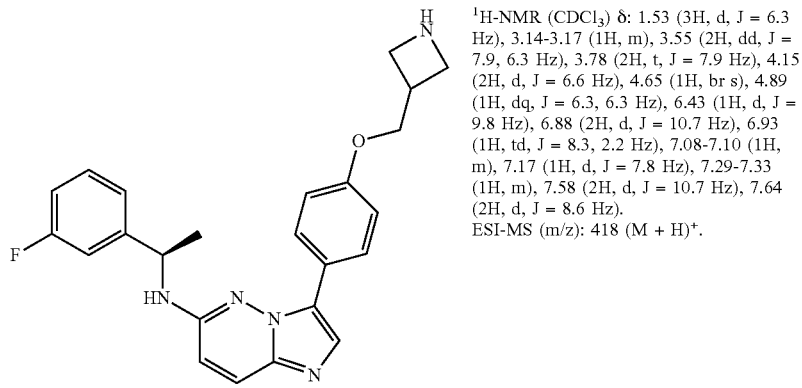<br>3-[4-(Azetidin-3-ylmethoxy)phenyl]-N-[(1R)-1-(3-fluorophenyl)ethyl]imidazo[1,2-b]pyridazin-6-amine | $^1$H-NMR (CDCl$_3$) δ: 1.53 (3H, d, J = 6.3 Hz), 3.14-3.17 (1H, m), 3.55 (2H, dd, J = 7.9, 6.3 Hz), 3.78 (2H, t, J = 7.9 Hz), 4.15 (2H, d, J = 6.6 Hz), 4.65 (1H, br s), 4.89 (1H, dq, J = 6.3, 6.3 Hz), 6.43 (1H, d, J = 9.8 Hz), 6.88 (2H, d, J = 10.7 Hz), 6.93 (1H, td, J = 8.3, 2.2 Hz), 7.08-7.10 (1H, m), 7.17 (1H, d, J = 7.8 Hz), 7.29-7.33 (1H, m), 7.58 (2H, d, J = 10.7 Hz), 7.64 (2H, d, J = 8.6 Hz).<br>ESI-MS (m/z): 418 (M + H)$^+$. |

TABLE 14-2-continued

| 28 | 9 | 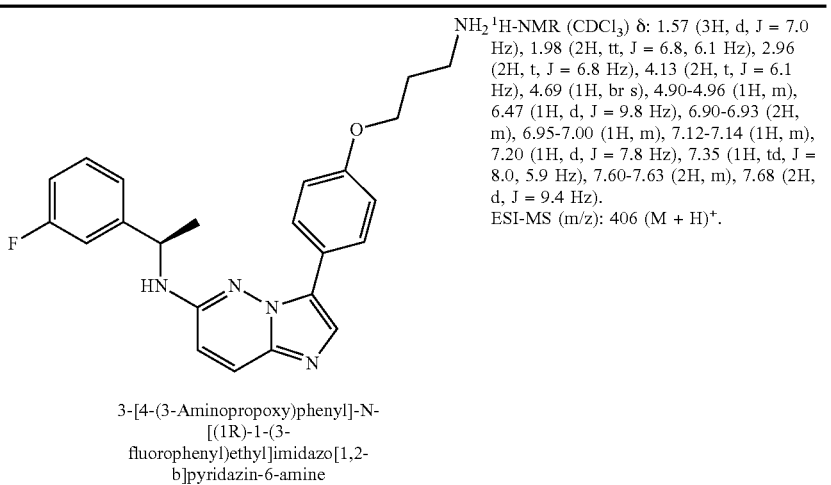<br>3-[4-(3-Aminopropoxy)phenyl]-N-[(1R)-1-(3-fluorophenyl)ethyl]imidazo[1,2-b]pyridazin-6-amine | $^1$H-NMR (CDCl$_3$) δ: 1.57 (3H, d, J = 7.0 Hz), 1.98 (2H, tt, J = 6.8, 6.1 Hz), 2.96 (2H, t, J = 6.8 Hz), 4.13 (2H, t, J = 6.1 Hz), 4.69 (1H, br s), 4.90-4.96 (1H, m), 6.47 (1H, d, J = 9.8 Hz), 6.90-6.93 (2H, m), 6.95-7.00 (1H, m), 7.12-7.14 (1H, m), 7.20 (1H, d, J = 7.8 Hz), 7.35 (1H, td, J = 8.0, 5.9 Hz), 7.60-7.63 (2H, m), 7.68 (2H, d, J = 9.4 Hz).<br>ESI-MS (m/z): 406 (M + H)$^+$. |

TABLE 14-3

| 29 | 10 | 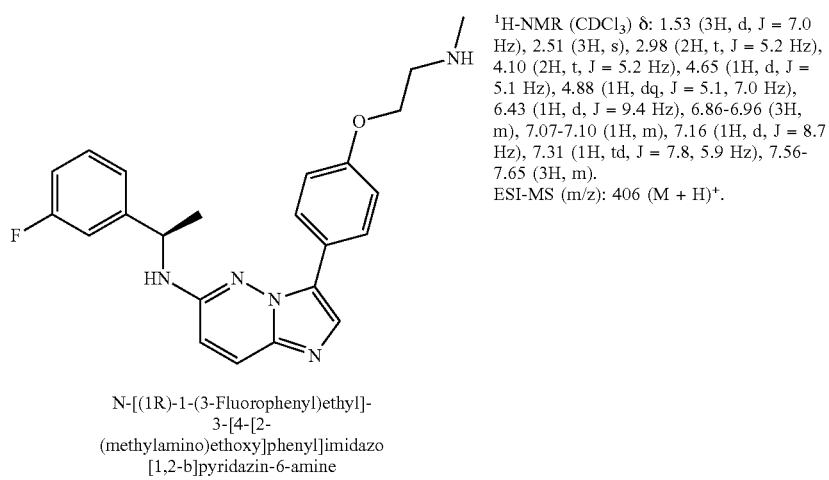<br>N-[(1R)-1-(3-Fluorophenyl)ethyl]-3-[4-[2-(methylamino)ethoxy]phenyl]imidazo[1,2-b]pyridazin-6-amine | $^1$H-NMR (CDCl$_3$) δ: 1.53 (3H, d, J = 7.0 Hz), 2.51 (3H, s), 2.98 (2H, t, J = 5.2 Hz), 4.10 (2H, t, J = 5.2 Hz), 4.65 (1H, d, J = 5.1 Hz), 4.88 (1H, dq, J = 5.1, 7.0 Hz), 6.43 (1H, d, J = 9.4 Hz), 6.86-6.96 (3H, m), 7.07-7.10 (1H, m), 7.16 (1H, d, J = 8.7 Hz), 7.31 (1H, td, J = 7.8, 5.9 Hz), 7.56-7.65 (3H, m).<br>ESI-MS (m/z): 406 (M + H)$^+$. |
| 30 | 26 | 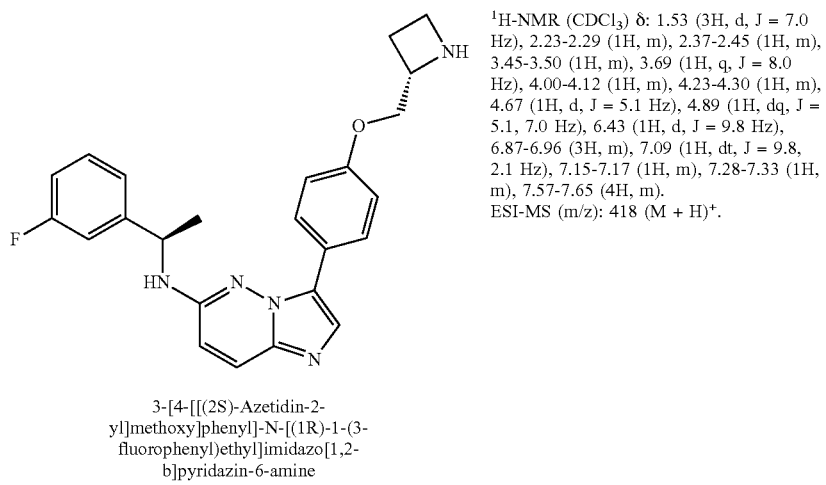<br>3-[4-[[(2S)-Azetidin-2-yl]methoxy]phenyl]-N-[(1R)-1-(3-fluorophenyl)ethyl]imidazo[1,2-b]pyridazin-6-amine | $^1$H-NMR (CDCl$_3$) δ: 1.53 (3H, d, J = 7.0 Hz), 2.23-2.29 (1H, m), 2.37-2.45 (1H, m), 3.45-3.50 (1H, m), 3.69 (1H, q, J = 8.0 Hz), 4.00-4.12 (1H, m), 4.23-4.30 (1H, m), 4.67 (1H, d, J = 5.1 Hz), 4.89 (1H, dq, J = 5.1, 7.0 Hz), 6.43 (1H, d, J = 9.8 Hz), 6.87-6.96 (3H, m), 7.09 (1H, dt, J = 9.8, 2.1 Hz), 7.15-7.17 (1H, m), 7.28-7.33 (1H, m), 7.57-7.65 (4H, m).<br>ESI-MS (m/z): 418 (M + H)$^+$. |

TABLE 14-3-continued

| 31 | 11 | 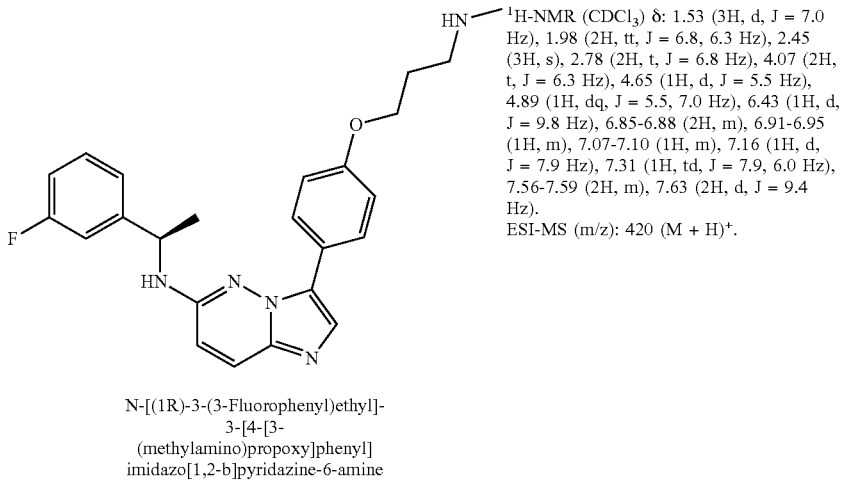<br>N-[(1R)-3-(3-Fluorophenyl)ethyl]-3-[4-[3-(methylamino)propoxy]phenyl]imidazo[1,2-b]pyridazine-6-amine | $^1$H-NMR (CDCl$_3$) δ: 1.53 (3H, d, J = 7.0 Hz), 1.98 (2H, tt, J = 6.8, 6.3 Hz), 2.45 (3H, s), 2.78 (2H, t, J = 6.8 Hz), 4.07 (2H, t, J = 6.3 Hz), 4.65 (1H, d, J = 5.5 Hz), 4.89 (1H, dq, J = 5.5, 7.0 Hz), 6.43 (1H, d, J = 9.8 Hz), 6.85-6.88 (2H, m), 6.91-6.95 (1H, m), 7.07-7.10 (1H, m), 7.16 (1H, d, J = 7.9 Hz), 7.31 (1H, td, J = 7.9, 6.0 Hz), 7.56-7.59 (2H, m), 7.63 (2H, d, J = 9.4 Hz).<br>ESI-MS (m/z): 420 (M + H)$^+$. |
| 32 | 34 | 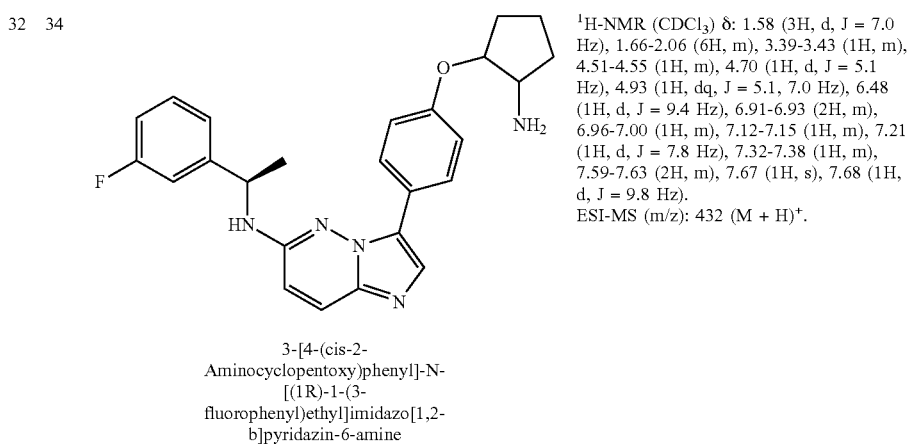<br>3-[4-(cis-2-Aminocyclopentoxy)phenyl]-N-[(1R)-1-(3-fluorophenyl)ethyl]imidazo[1,2-b]pyridazin-6-amine | $^1$H-NMR (CDCl$_3$) δ: 1.58 (3H, d, J = 7.0 Hz), 1.66-2.06 (6H, m), 3.39-3.43 (1H, m), 4.51-4.55 (1H, m), 4.70 (1H, d, J = 5.1 Hz), 4.93 (1H, dq, J = 5.1, 7.0 Hz), 6.48 (1H, d, J = 9.4 Hz), 6.91-6.93 (2H, m), 6.96-7.00 (1H, m), 7.12-7.15 (1H, m), 7.21 (1H, d, J = 7.8 Hz), 7.32-7.38 (1H, m), 7.59-7.63 (2H, m), 7.67 (1H, s), 7.68 (1H, d, J = 9.8 Hz).<br>ESI-MS (m/z): 432 (M + H)$^+$. |

TABLE 14-4

| 33 | 36 | 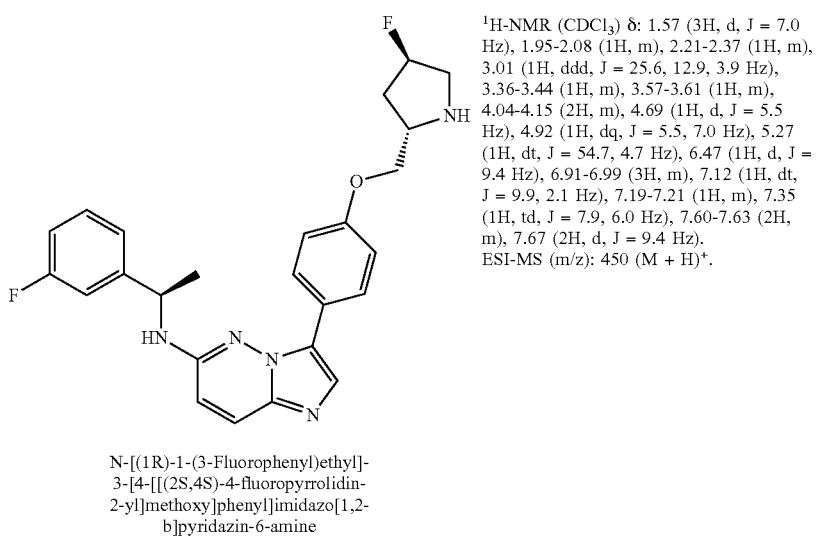<br>N-[(1R)-1-(3-Fluorophenyl)ethyl]-3-[4-[[(2S,4S)-4-fluoropyrrolidin-2-yl]methoxy]phenyl]imidazo[1,2-b]pyridazin-6-amine | $^1$H-NMR (CDCl$_3$) δ: 1.57 (3H, d, J = 7.0 Hz), 1.95-2.08 (1H, m), 2.21-2.37 (1H, m), 3.01 (1H, ddd, J = 25.6, 12.9, 3.9 Hz), 3.36-3.44 (1H, m), 3.57-3.61 (1H, m), 4.04-4.15 (2H, m), 4.69 (1H, d, J = 5.5 Hz), 4.92 (1H, dq, J = 5.5, 7.0 Hz), 5.27 (1H, dt, J = 54.7, 4.7 Hz), 6.47 (1H, d, J = 9.4 Hz), 6.91-6.99 (3H, m), 7.12 (1H, dt, J = 9.9, 2.1 Hz), 7.19-7.21 (1H, m), 7.35 (1H, td, J = 7.9, 6.0 Hz), 7.60-7.63 (2H, m), 7.67 (2H, d, J = 9.4 Hz).<br>ESI-MS (m/z): 450 (M + H)$^+$. |

TABLE 14-4-continued

| 34 | 35 | 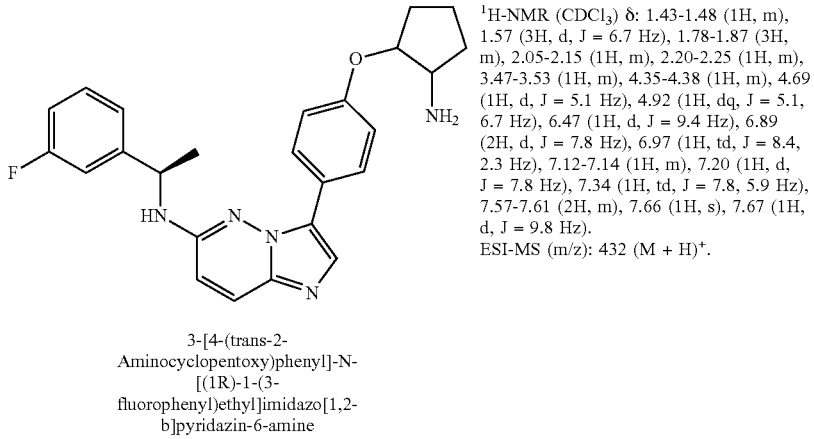<br>3-[4-(trans-2-Aminocyclopentoxy)phenyl]-N-[(1R)-1-(3-fluorophenyl)ethyl]imidazo[1,2-b]pyridazin-6-amine | $^1$H-NMR (CDCl$_3$) δ: 1.43-1.48 (1H, m), 1.57 (3H, d, J = 6.7 Hz), 1.78-1.87 (3H, m), 2.05-2.15 (1H, m), 2.20-2.25 (1H, m), 3.47-3.53 (1H, m), 4.35-4.38 (1H, m), 4.69 (1H, d, J = 5.1 Hz), 4.92 (1H, dq, J = 5.1, 6.7 Hz), 6.47 (1H, d, J = 9.4 Hz), 6.89 (2H, d, J = 7.8 Hz), 6.97 (1H, td, J = 8.4, 2.3 Hz), 7.12-7.14 (1H, m), 7.20 (1H, d, J = 7.8 Hz), 7.34 (1H, td, J = 7.8, 5.9 Hz), 7.57-7.61 (2H, m), 7.66 (1H, s), 7.67 (1H, d, J = 9.8 Hz).<br>ESI-MS (m/z): 432 (M + H)$^+$. |
|---|---|---|---|
| 35 | 12 | 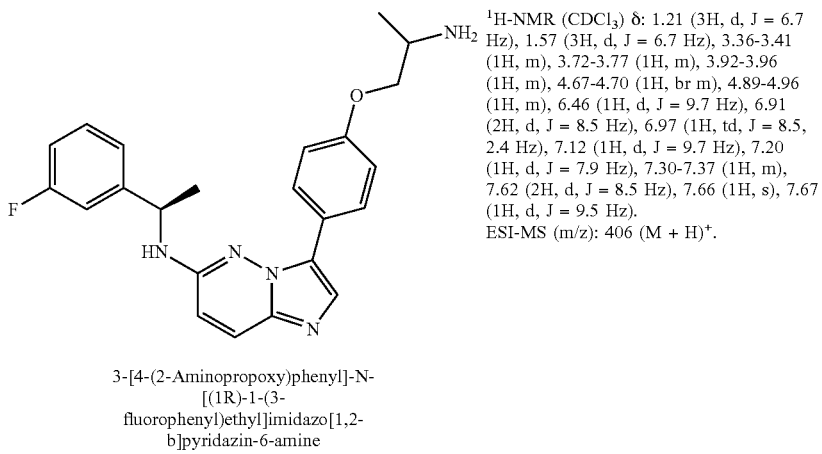<br>3-[4-(2-Aminopropoxy)phenyl]-N-[(1R)-1-(3-fluorophenyl)ethyl]imidazo[1,2-b]pyridazin-6-amine | $^1$H-NMR (CDCl$_3$) δ: 1.21 (3H, d, J = 6.7 Hz), 1.57 (3H, d, J = 6.7 Hz), 3.36-3.41 (1H, m), 3.72-3.77 (1H, m), 3.92-3.96 (1H, m), 4.67-4.70 (1H, br m), 4.89-4.96 (1H, m), 6.46 (1H, d, J = 9.7 Hz), 6.91 (2H, d, J = 8.5 Hz), 6.97 (1H, td, J = 8.5, 2.4 Hz), 7.12 (1H, d, J = 9.7 Hz), 7.20 (1H, d, J = 7.9 Hz), 7.30-7.37 (1H, m), 7.62 (2H, d, J = 8.5 Hz), 7.66 (1H, s), 7.67 (1H, d, J = 9.5 Hz).<br>ESI-MS (m/z): 406 (M + H)$^+$. |
| 36 | 13 | 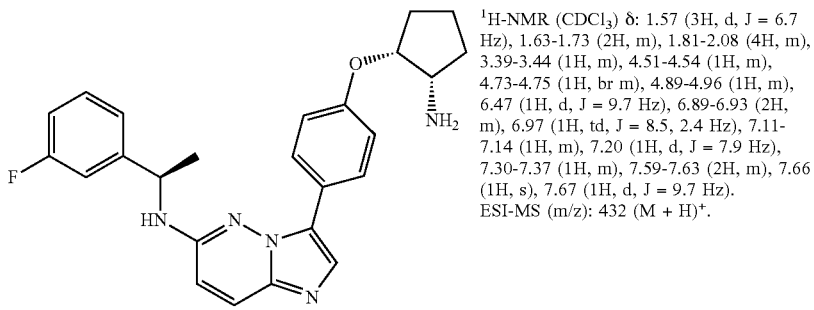<br>3-[4-[(1R,2S)-2-Aminocyclopentoxy]phenyl]-N-[(1R)-1-(3-fluorophenyl)ethyl]imidazo[1,2-b]pyridazin-6-amine | $^1$H-NMR (CDCl$_3$) δ: 1.57 (3H, d, J = 6.7 Hz), 1.63-1.73 (2H, m), 1.81-2.08 (4H, m), 3.39-3.44 (1H, m), 4.51-4.54 (1H, m), 4.73-4.75 (1H, br m), 4.89-4.96 (1H, m), 6.47 (1H, d, J = 9.7 Hz), 6.89-6.93 (2H, m), 6.97 (1H, td, J = 8.5, 2.4 Hz), 7.11-7.14 (1H, m), 7.20 (1H, d, J = 7.9 Hz), 7.30-7.37 (1H, m), 7.59-7.63 (2H, m), 7.66 (1H, s), 7.67 (1H, d, J = 9.7 Hz).<br>ESI-MS (m/z): 432 (M + H)$^+$. |

TABLE 14-5

| 37 | 37 | 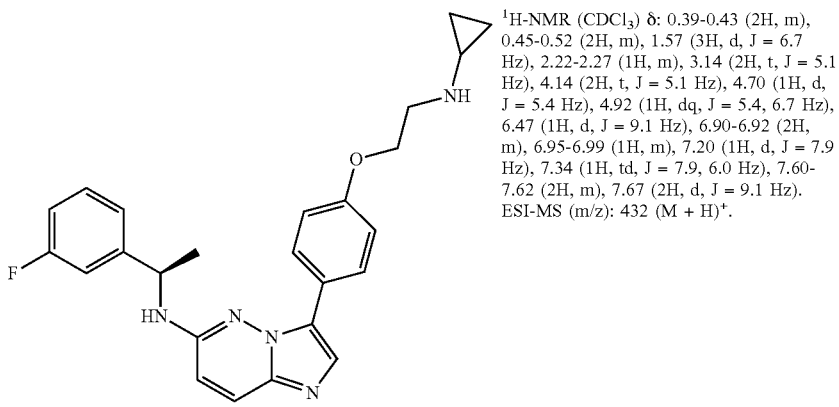

3-[4-[2-(Cyclopropylamino)ethoxy]phenyl]-N-[(1R)-1-(3-fluorophenyl)ethyl]imidazo[1,2-b]pyridazin-6-amine | $^1$H-NMR (CDCl$_3$) δ: 0.39-0.43 (2H, m), 0.45-0.52 (2H, m), 1.57 (3H, d, J = 6.7 Hz), 2.22-2.27 (1H, m), 3.14 (2H, t, J = 5.1 Hz), 4.14 (2H, t, J = 5.1 Hz), 4.70 (1H, d, J = 5.4 Hz), 4.92 (1H, dq, J = 5.4, 6.7 Hz), 6.47 (1H, d, J = 9.1 Hz), 6.90-6.92 (2H, m), 6.95-6.99 (1H, m), 7.20 (1H, d, J = 7.9 Hz), 7.34 (1H, td, J = 7.9, 6.0 Hz), 7.60-7.62 (2H, m), 7.67 (2H, d, J = 9.1 Hz). ESI-MS (m/z): 432 (M + H)$^+$. |
|---|---|---|---|
| 38 | 38 | 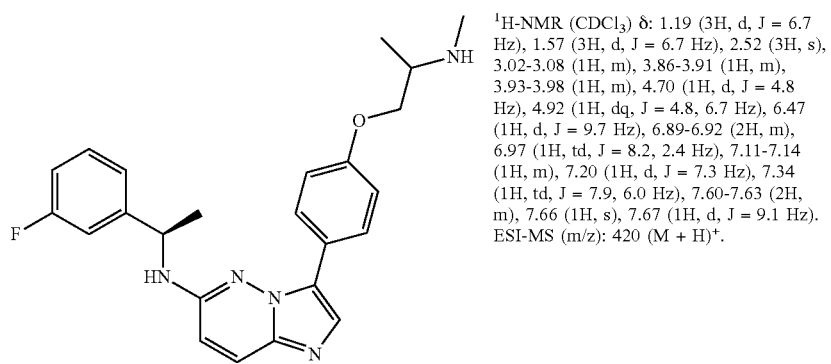

N-[(1R)-1-(3-Fluorophenyl)ethyl]-3-[4-[2-(methylamino)propoxy]phenyl]imidazo[1,2-b]pyridazin-6-amine | $^1$H-NMR (CDCl$_3$) δ: 1.19 (3H, d, J = 6.7 Hz), 1.57 (3H, d, J = 6.7 Hz), 2.52 (3H, s), 3.02-3.08 (1H, m), 3.86-3.91 (1H, m), 3.93-3.98 (1H, m), 4.70 (1H, d, J = 4.8 Hz), 4.92 (1H, dq, J = 4.8, 6.7 Hz), 6.47 (1H, d, J = 9.7 Hz), 6.89-6.92 (2H, m), 6.97 (1H, td, J = 8.2, 2.4 Hz), 7.11-7.14 (1H, m), 7.20 (1H, d, J = 7.3 Hz), 7.34 (1H, td, J = 7.9, 6.0 Hz), 7.60-7.63 (2H, m), 7.66 (1H, s), 7.67 (1H, d, J = 9.1 Hz). ESI-MS (m/z): 420 (M + H)$^+$. |
| 39 | 39 | 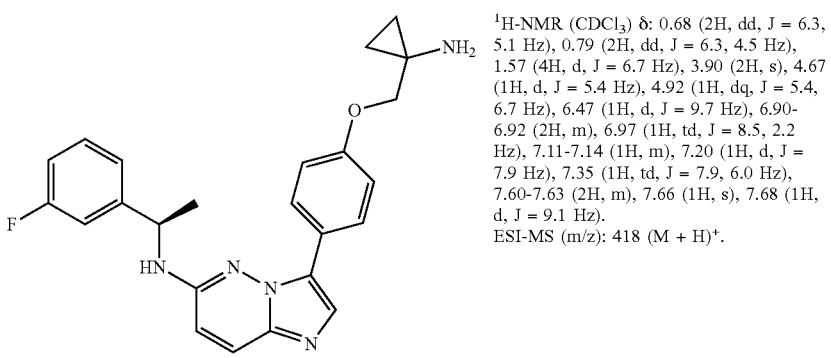

3-[4-[(1-Aminocyclopropyl)methoxy]phenyl]-N-[(1R)-1-(3-fluorophenyl)ethyl]imidazo[1,2-b]pyridazin-6-amine | $^1$H-NMR (CDCl$_3$) δ: 0.68 (2H, dd, J = 6.3, 5.1 Hz), 0.79 (2H, dd, J = 6.3, 4.5 Hz), 1.57 (4H, d, J = 6.7 Hz), 3.90 (2H, s), 4.67 (1H, d, J = 5.4 Hz), 4.92 (1H, dq, J = 5.4, 6.7 Hz), 6.47 (1H, d, J = 9.7 Hz), 6.90-6.92 (2H, m), 6.97 (1H, td, J = 8.5, 2.2 Hz), 7.11-7.14 (1H, m), 7.20 (1H, d, J = 7.9 Hz), 7.35 (1H, td, J = 7.9, 6.0 Hz), 7.60-7.63 (2H, m), 7.66 (1H, s), 7.68 (1H, d, J = 9.1 Hz). ESI-MS (m/z): 418 (M + H)$^+$. |

TABLE 14-5-continued

| 40 | 14 | 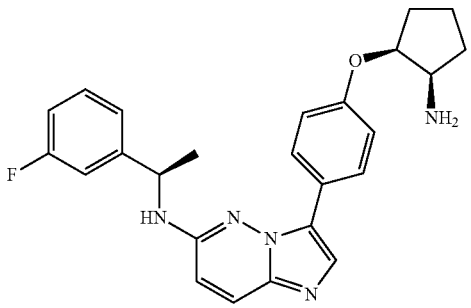 [SMILES: C[C@@H](Nc1ccc2ncc(-c3ccc(O[C@H]4CCC[C@H]4N)cc3)n2n1)c1cccc(F)c1]<br>3-[4-[(1S,2R)-2-Aminocyclopentoxy]phenyl]-N-[(1R)-1-(3-fluorophenyl)ethyl]imidazo[1,2-b]pyridazin-6-amine | $^1$H-NMR (CDCl$_3$) δ: 1.57 (3H, d, J = 7.0 Hz), 1.62-1.73 (2H, m), 1.81-2.10 (4H, m), 3.38-3.43 (1H, m), 4.51-4.54 (1H, m), 4.69 (1H, br s), 4.89-4.96 (1H, m), 6.47 (1H, d, J = 9.7 Hz), 6.90-6.92 (2H, m), 6.97 (1H, td, J = 8.3, 2.6 Hz), 7.11-7.15 (1H, m), 7.20 (1H, d, J = 7.9 Hz), 7.34 (1H, td, J = 7.9, 6.0 Hz), 7.59-7.61 (2H, m), 7.67 (2H, d, J = 9.1 Hz).<br>ESI-MS (m/z): 432 (M + H)$^+$. |

20

TABLE 14-6

| 41 | 16 | 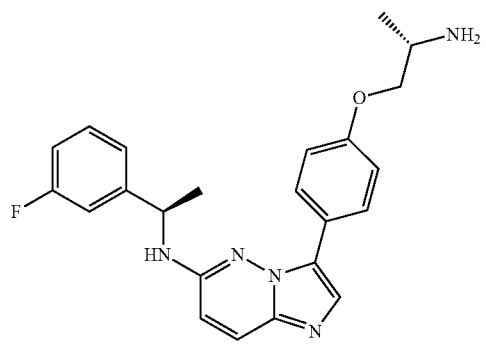 [SMILES: C[C@H](N)COc1ccc(-c2cnc3ccc(N[C@H](C)c4cccc(F)c4)nn23)cc1]<br>3-[4-[(2S)-2-Aminopropoxy]phenyl]-N-[(1R)-1-(3-fluorophenyl)ethyl]imidazo[1,2-b]pyridazin-6-amine | $^1$H-NMR (CDCl$_3$) δ: 1.21 (3H, d, J = 6.7 Hz), 1.57 (3H, d, J = 6.7 Hz), 3.35-3.43 (1H, m), 3.74 (1H, dd, J = 9.1, 7.9 Hz), 3.94 (1H, dd, J = 9.1, 4.2 Hz), 4.70 (1H, br s), 4.89-4.96 (1H, m), 6.47 (1H, d, J = 9.4 Hz), 6.89-6.92 (2H, m), 6.93-6.99 (1H, m), 7.12 (1H, dt, J = 9.9, 2.0 Hz), 7.20 (1H, d, J = 7.9 Hz), 7.30-7.37 (1H, m), 7.60-7.63 (2H, m), 7.66-7.69 (2H, m).<br>ESI-MS (m/z): 406 (M + H)$^+$. |
| 42 | 17 | 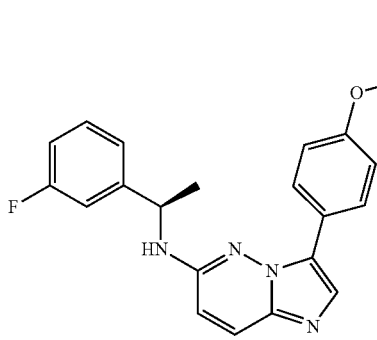<br>2-[2-[4-[6-[[(1R)-1-(3-Fluorophenyl)ethyl]amino]imidazo[1,2-b]pyridazin-3-yl]phenoxy]ethyl amino]ethanol | $^1$H-NMR (CDCl$_3$) δ: 1.56 (3H, d, J = 6.8 Hz), 1.73 (1H, br s), 2.90 (2H, t, J = 5.1 Hz), 3.08 (2H, t, J = 4.8 Hz), 3.70 (2H, t, J = 5.1 Hz), 4.14 (2H, t, J = 4.8 Hz), 4.70 (1H, d, J = 4.8 Hz), 4.92 (1H, dq, J = 4.8, 6.8 Hz), 6.47 (1H, d, J = 9.7 Hz), 6.90 (2H, d, J = 9.1 Hz), 6.94-6.99 (1H, m), 7.11-7.13 (1H, m), 7.20 (1H, d, J = 7.3 Hz), 7.30-7.37 (1H, m), 7.61 (2H, d, J = 8.5 Hz), 7.67 (2H, d, J = 9.1 Hz).<br>ESI-MS (m/z): 436 (M + H)$^+$. |

TABLE 14-6-continued

| 43 | 29 | 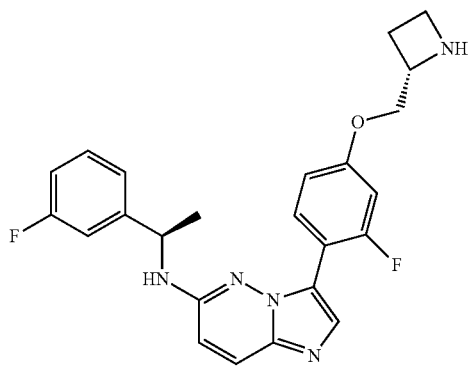 [SMILES: C[C@@H](Nc1ccc2ncc(-c3ccc(OC[C@@H]4CCN4)cc3F)n2n1)c1cccc(F)c1]<br>3-[4-[[(2S)-Azetidin-2-yl]methoxy]-2-fluoro-phenyl]-N-[(1R)-1-(3-fluorophenyl)ethyl]imidazo[1,2-b]pyridazin-6-amine | $^1$H-NMR (CDCl$_3$) δ: 1.56 (3H, d, J = 6.7 Hz), 2.27-2.32 (1H, m), 2.39-2.45 (1H, m), 3.47-3.52 (1H, m), 3.73 (1H, q, J = 7.9 Hz), 3.99-4.08 (2H, m), 4.28-4.33 (1H, m), 4.67 (1H, d, J = 5.4 Hz), 4.89 (1H, dq, J = 5.4, 6.7 Hz), 6.49 (1H, d, J = 9.7 Hz), 6.67-6.76 (2H, m), 6.90-6.98 (1H, m), 7.06-7.09 (1H, m), 7.15-7.17 (1H, m), 7.30-7.35 (1H, m), 7.61-7.70 (2H, m), 7.77 (1H, d, J = 3.6 Hz).<br>ESI-MS (m/z): 436 (M + H)$^+$. |
| 44 | 30 | 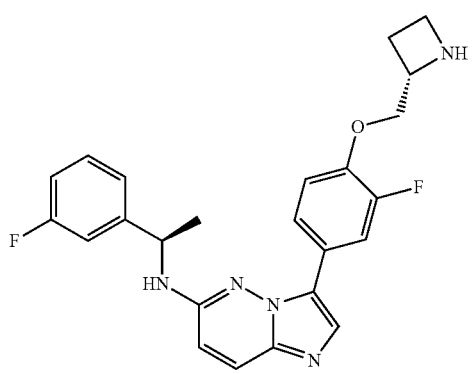 [SMILES: C[C@@H](Nc1ccc2ncc(-c3ccc(OC[C@@H]4CCN4)c(F)c3)n2n1)c1cccc(F)c1]<br>3-[4-[[(2S)-Azetidin-2-yl]methoxy]-3-fluoro-phenyl]-N-[(1R)-1-(3-fluorophenyl)ethyl]imidazo[1,2-b]pyridazin-6-amine | $^1$H-NMR (CDCl$_3$) δ: 1.58 (3H, d, J = 7.0 Hz), 2.25-2.33 (1H, m), 2.40-2.48 (1H, m), 3.48-3.53 (1H, m), 3.72 (1H, q, J = 7.9 Hz), 4.10-4.16 (2H, m), 4.30-4.37 (1H, m), 4.72 (1H, d, J = 5.4 Hz), 4.97 (1H, dq, J = 5.4, 7.0 Hz), 6.49 (1H, d, J = 9.1 Hz), 6.92-7.01 (2H, m), 7.11 (1H, dt, J = 10.1, 2.0 Hz), 7.21-7.23 (1H, m), 7.30-7.37 (1H, m), 7.40-7.42 (1H, m), 7.65-7.69 (3H, m).<br>ESI-MS (m/z): 436 (M + H)$^+$. |

TABLE 14-7

| 45 | 18 | 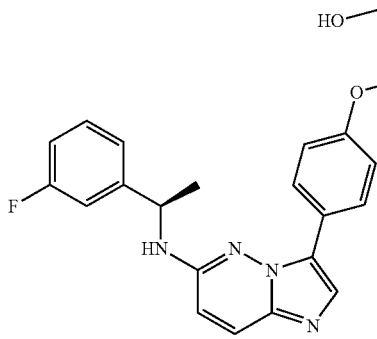<br>2-Amino-3-[4-[6-[[(1R)-1-(3-fluorophenyl)ethyl]amino]imidazo[1,2-b]pyridazin-3-yl]phenoxy]propan-1-ol | $^1$H-NMR (CDCl$_3$) δ: 1.57 (3H, d, J = 6.7 Hz), 3.34-3.37 (1H, m), 3.66 (1H, dd, J = 10.8, 6.0 Hz), 3.78 (1H, dd, J = 10.8, 4.5 Hz), 3.96-4.00 (1H, m), 4.04-4.08 (1H, m), 4.69 (1H, d, J = 5.4 Hz), 4.92 (1H, dq, J = 5.4, 6.7 Hz), 6.47 (1H, d, J = 9.7 Hz), 6.88-6.93 (2H, m), 6.97 (1H, td, J = 8.3, 2.6 Hz), 7.10-7.14 (1H, m), 7.20 (1H, t, J = 7.3 Hz), 7.30-7.37 (1H, m), 7.60-7.63 (2H, m), 7.67 (2H, d, J = 10.9 Hz).<br>ESI-MS (m/z): 422 (M + H)$^+$. |

TABLE 14-7-continued

| 46 | 19 | 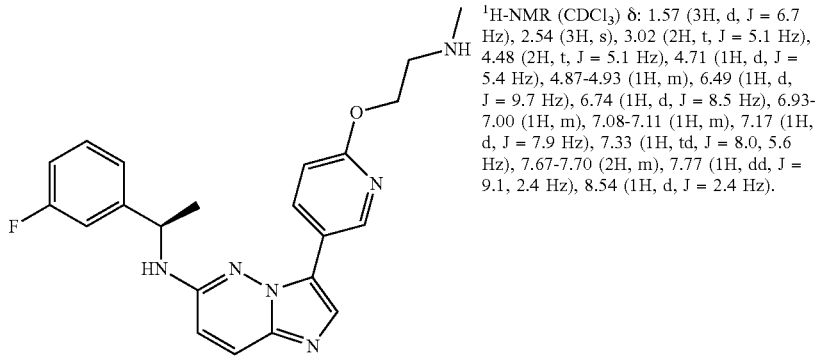<br>N-[(1R)-1-(3-Fluorophenyl)ethyl]-3-[6-[2-(methylamino)ethoxy]-3-pyridyl]imidazo[1,2-b]pyridazin-6-amine | $^1$H-NMR (CDCl$_3$) δ: 1.57 (3H, d, J = 6.7 Hz), 2.54 (3H, s), 3.02 (2H, t, J = 5.1 Hz), 4.48 (2H, t, J = 5.1 Hz), 4.71 (1H, d, J = 5.4 Hz), 4.87-4.93 (1H, m), 6.49 (1H, d, J = 9.7 Hz), 6.74 (1H, d, J = 8.5 Hz), 6.93-7.00 (1H, m), 7.08-7.11 (1H, m), 7.17 (1H, d, J = 7.9 Hz), 7.33 (1H, td, J = 8.0, 5.6 Hz), 7.67-7.70 (2H, m), 7.77 (1H, dd, J = 9.1, 2.4 Hz), 8.54 (1H, d, J = 2.4 Hz). |
| --- | --- | --- | --- |
| 47 | 40 | 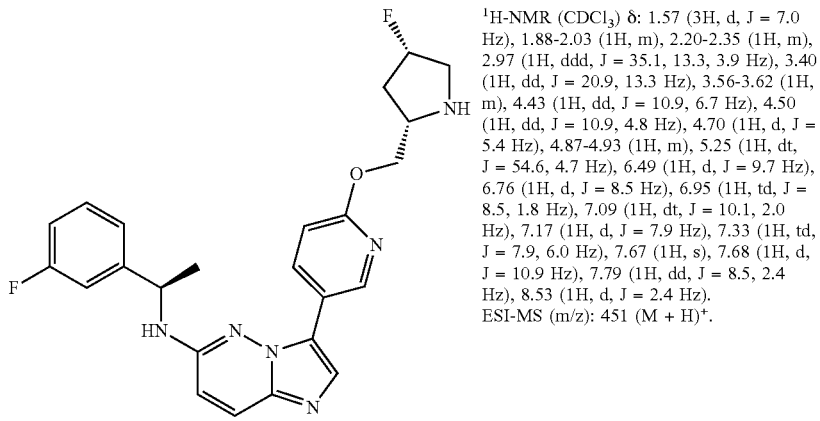<br>N-[(1R)-1-(3-Fluorophenyl)ethyl]-3-[6-[[(2S,4S)-4-fluoropyrrolidin-2-yl]methoxy]-3-pyridyl]imidazo[1,2-b]pyridazin-6-amine | $^1$H-NMR (CDCl$_3$) δ: 1.57 (3H, d, J = 7.0 Hz), 1.88-2.03 (1H, m), 2.20-2.35 (1H, m), 2.97 (1H, ddd, J = 35.1, 13.3, 3.9 Hz), 3.40 (1H, dd, J = 20.9, 13.3 Hz), 3.56-3.62 (1H, m), 4.43 (1H, dd, J = 10.9, 6.7 Hz), 4.50 (1H, dd, J = 10.9, 4.8 Hz), 4.70 (1H, d, J = 5.4 Hz), 4.87-4.93 (1H, m), 5.25 (1H, dt, J = 54.6, 4.7 Hz), 6.49 (1H, d, J = 9.7 Hz), 6.76 (1H, d, J = 8.5 Hz), 6.95 (1H, td, J = 8.5, 1.8 Hz), 7.09 (1H, dt, J = 10.1, 2.0 Hz), 7.17 (1H, d, J = 7.9 Hz), 7.33 (1H, td, J = 7.9, 6.0 Hz), 7.67 (1H, s), 7.68 (1H, d, J = 10.9 Hz), 7.79 (1H, dd, J = 8.5, 2.4 Hz), 8.53 (1H, d, J = 2.4 Hz).<br>ESI-MS (m/z): 451 (M + H)$^+$. |
| 48 | 20 | 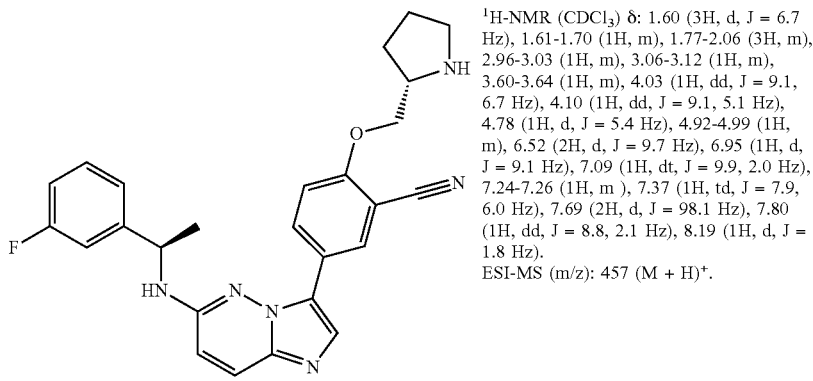<br>5-[6-[[(1R)-1-(3-Fluorophenyl)ethyl]amino]imidazo[1,2-b]pyridazin-3-yl]-2-[[(2S)-pyrrolidin-2-yl]methoxy]benzonitrile | $^1$H-NMR (CDCl$_3$) δ: 1.60 (3H, d, J = 6.7 Hz), 1.61-1.70 (1H, m), 1.77-2.06 (3H, m), 2.96-3.03 (1H, m), 3.06-3.12 (1H, m), 3.60-3.64 (1H, m), 4.03 (1H, dd, J = 9.1, 6.7 Hz), 4.10 (1H, dd, J = 9.1, 5.1 Hz), 4.78 (1H, d, J = 5.4 Hz), 4.92-4.99 (1H, m), 6.52 (2H, d, J = 9.7 Hz), 6.95 (1H, d, J = 9.1 Hz), 7.09 (1H, dt, J = 9.9, 2.0 Hz), 7.24-7.26 (1H, m), 7.37 (1H, td, J = 7.9, 6.0 Hz), 7.69 (2H, d, J = 98.1 Hz), 7.80 (1H, dd, J = 8.8, 2.1 Hz), 8.19 (1H, d, J = 1.8 Hz).<br>ESI-MS (m/z): 457 (M + H)$^+$. |

TABLE 14-8

| 49 | 21 | 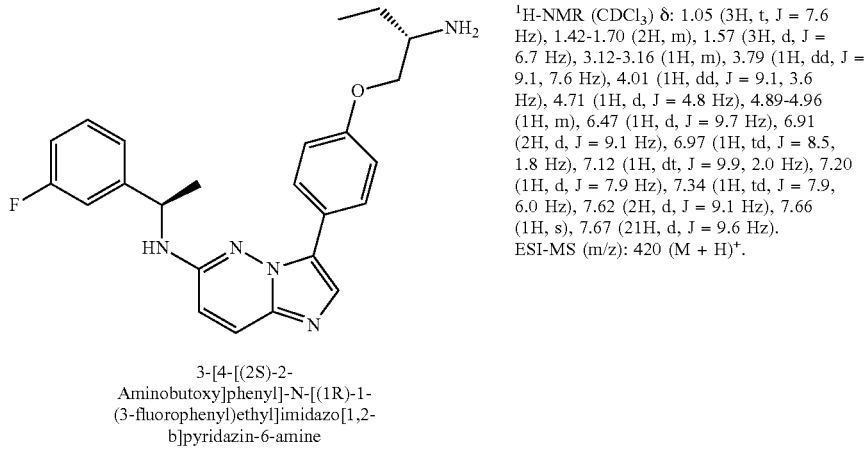<br>3-[4-[(2S)-2-Aminobutoxy]phenyl]-N-[(1R)-1-(3-fluorophenyl)ethyl]imidazo[1,2-b]pyridazin-6-amine | $^1$H-NMR (CDCl$_3$) δ: 1.05 (3H, t, J = 7.6 Hz), 1.42-1.70 (2H, m), 1.57 (3H, d, J = 6.7 Hz), 3.12-3.16 (1H, m), 3.79 (1H, dd, J = 9.1, 7.6 Hz), 4.01 (1H, dd, J = 9.1, 3.6 Hz), 4.71 (1H, d, J = 4.8 Hz), 4.89-4.96 (1H, m), 6.47 (1H, d, J = 9.7 Hz), 6.91 (2H, d, J = 9.1 Hz), 6.97 (1H, td, J = 8.5, 1.8 Hz), 7.12 (1H, dt, J = 9.9, 2.0 Hz), 7.20 (1H, d, J = 7.9 Hz), 7.34 (1H, td, J = 7.9, 6.0 Hz), 7.62 (2H, d, J = 9.1 Hz), 7.66 (1H, s), 7.67 (21H, d, J = 9.6 Hz).<br>ESI-MS (m/z): 420 (M + H)$^+$. |
|---|---|---|---|
| 50 | 2 | 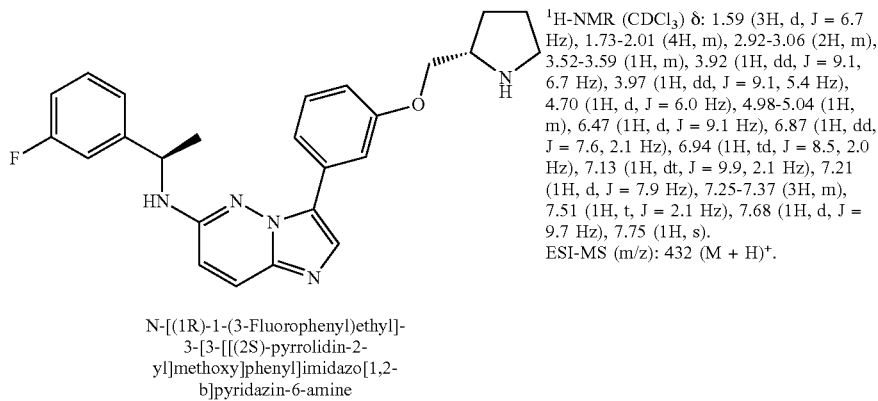<br>N-[(1R)-1-(3-Fluorophenyl)ethyl]-3-[3-[[(2S)-pyrrolidin-2-yl]methoxy]phenyl]imidazo[1,2-b]pyridazin-6-amine | $^1$H-NMR (CDCl$_3$) δ: 1.59 (3H, d, J = 6.7 Hz), 1.73-2.01 (4H, m), 2.92-3.06 (2H, m), 3.52-3.59 (1H, m), 3.92 (1H, dd, J = 9.1, 6.7 Hz), 3.97 (1H, dd, J = 9.1, 5.4 Hz), 4.70 (1H, d, J = 6.0 Hz), 4.98-5.04 (1H, m), 6.47 (1H, d, J = 9.1 Hz), 6.87 (1H, dd, J = 7.6, 2.1 Hz), 6.94 (1H, td, J = 8.5, 2.0 Hz), 7.13 (1H, dt, J = 9.9, 2.1 Hz), 7.21 (1H, d, J = 7.9 Hz), 7.25-7.37 (3H, m), 7.51 (1H, t, J = 2.1 Hz), 7.68 (1H, d, J = 9.7 Hz), 7.75 (1H, s).<br>ESI-MS (m/z): 432 (M + H)$^+$. |
| 51 | 22 | 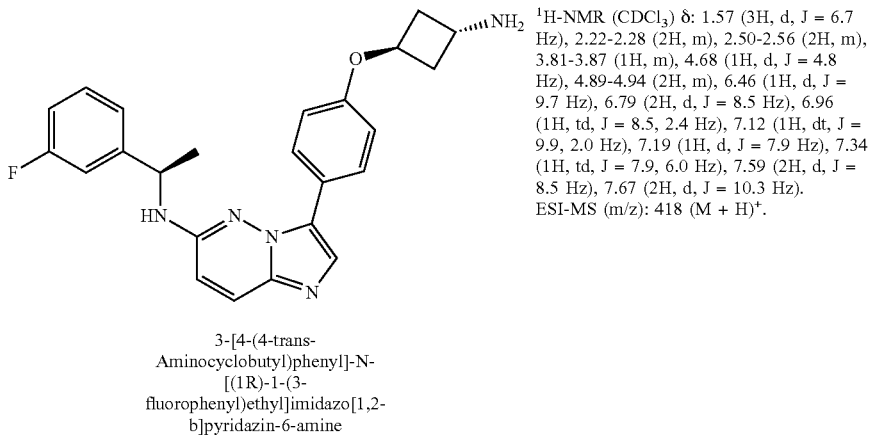<br>3-[4-(4-trans-Aminocyclobutyl)phenyl]-N-[(1R)-1-(3-fluorophenyl)ethyl]imidazo[1,2-b]pyridazin-6-amine | $^1$H-NMR (CDCl$_3$) δ: 1.57 (3H, d, J = 6.7 Hz), 2.22-2.28 (2H, m), 2.50-2.56 (2H, m), 3.81-3.87 (1H, m), 4.68 (1H, d, J = 4.8 Hz), 4.89-4.94 (2H, m), 6.46 (1H, d, J = 9.7 Hz), 6.79 (2H, d, J = 8.5 Hz), 6.96 (1H, td, J = 8.5, 2.4 Hz), 7.12 (1H, dt, J = 9.9, 2.0 Hz), 7.19 (1H, d, J = 7.9 Hz), 7.34 (1H, td, J = 7.9, 6.0 Hz), 7.59 (2H, d, J = 8.5 Hz), 7.67 (2H, d, J = 10.3 Hz).<br>ESI-MS (m/z): 418 (M + H)$^+$. |

TABLE 14-8-continued

| 52 | 23 | 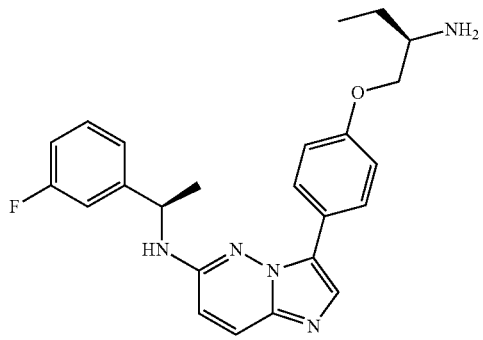 [SMILES: CC[C@@H](N)COc1ccc(-c2cnc3ccc(N[C@H](C)c4cccc(F)c4)nn23)cc1]<br>3-[4-[(2R)-2-Aminobutoxy]phenyl]-N-[(1R)-1-(3-fluorophenyl)ethyl]imidazo[1,2-b]pyridazin-6-amine | $^1$H-NMR (CDCl$_3$) δ: 1.04 (3H, t, J = 7.6 Hz), 1.45-1.67 (2H, m), 1.57 (3H, d, J = 6.7 Hz), 3.11-3.17 (1H, m), 3.80 (1H, dd, J = 9.1, 7.9 Hz), 4.00 (1H, dd, J = 9.1, 4.2 Hz), 4.68 (1H, d, J = 5.4 Hz), 4.89-4.96 (1H, m), 6.46 (1H, d, J = 9.1 Hz), 6.91 (2H, d, J = 8.5 Hz), 6.97 (1H, td, J = 8.5, 2.4 Hz), 7.12 (1H, dt, J = 10.1, 2.1 Hz), 7.20 (1H, d, J = 7.9 Hz), 7.34 (1H, td, J = 7.9, 6.0 Hz), 7.62 (2H, d, J = 8.5 Hz), 7.66 (1H, s), 7.67 (1H, d, J = 9.6 Hz).<br>ESI-MS (m/z): 420 (M + H)$^+$. |

TABLE 14-9

| 53 | 41 | 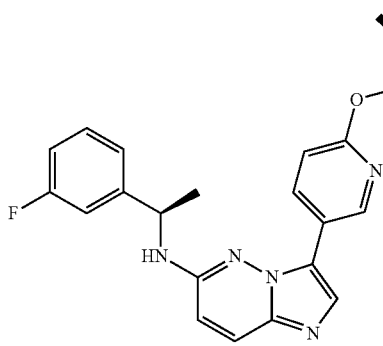<br>3-[6-[(2R)-2-Aminopropoxy]-3-pyridyl]-N-[(1R)-1-(3-fluorophenyl)ethyl]imidazo[1,2-b]pyridazin-6-amine | $^1$H-NMR (CDCl$_3$) δ: 1.21 (3H, d, J = 6.7 Hz), 1.57 (3H, d, J = 6.7 Hz), 3.37-3.41 (1H, m), 4.07 (1H, dd, J = 10.3, 7.9 Hz), 4.31 (1H, dd, J = 10.3, 4.2 Hz), 4.75 (1H, d, J = 5.4 Hz), 4.87-4.94 (1H, m), 6.49 (1H, d, J = 9.7 Hz), 6.75 (1H, d, J = 8.5 Hz), 6.96 (1H, td, J = 8.2, 4.2 Hz), 7.10 (1H, d, J = 9.7 Hz), 7.17 (1H, d, J = 7.9 Hz), 7.33 (1H, td, J = 7.9, 6.0 Hz), 7.68 (2H, d, J = 9.7 Hz), 7.79 (1H, dd, J = 8.5, 2.4 Hz), 8.54 (1H, d, J = 2.4 Hz).<br>ESI-MS (m/z): 407 (M + H)$^+$. |
| 54 | 43 | 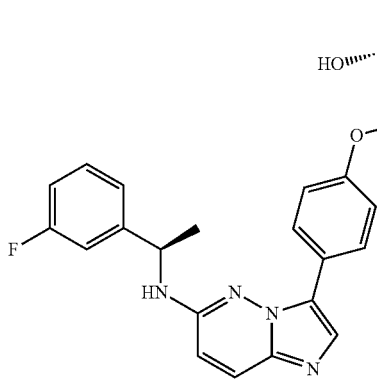<br>(2R,3R)-3-Amino-4-[4-[6-[[(1R)-1-(3-fluorophenyl)ethyl]amino]imidazo[1,2-b]pyridazin-3-yl]phenoxy]butan-2-ol | $^1$H-NMR (CDCl$_3$) δ: 1.29 (3H, d, J = 6.0 Hz), 1.57 (3H, d, J = 6.7 Hz), 3.00-3.02 (1H, m), 3.10 (1H, br s), 3.79-3.85 (1H, m), 3.96 (1H, dd, J = 9.7, 6.7 Hz), 4.11 (1H, dd, J = 9.7, 4.2 Hz), 4.67 (1H, d, J = 4.8 Hz), 4.89-4.95 (1H, m), 6.47 (1H, d, J = 9.7 Hz), 6.90 (2H, d, J = 8.5 Hz), 6.97 (1H, td, J = 8.3, 2.8 Hz), 7.12 (1H, dt, J = 9.9, 2.0 Hz), 7.20 (1H, d, J = 7.9 Hz), 7.34 (1H, td, J = 7.9, 6.0 Hz), 7.62 (2H, d, J = 9.1 Hz), 7.67 (2H, d, J = 9.1 Hz).<br>ESI-MS (m/z): 436 (M + H)$^+$. |

TABLE 14-9-continued

| 55 | 44 | 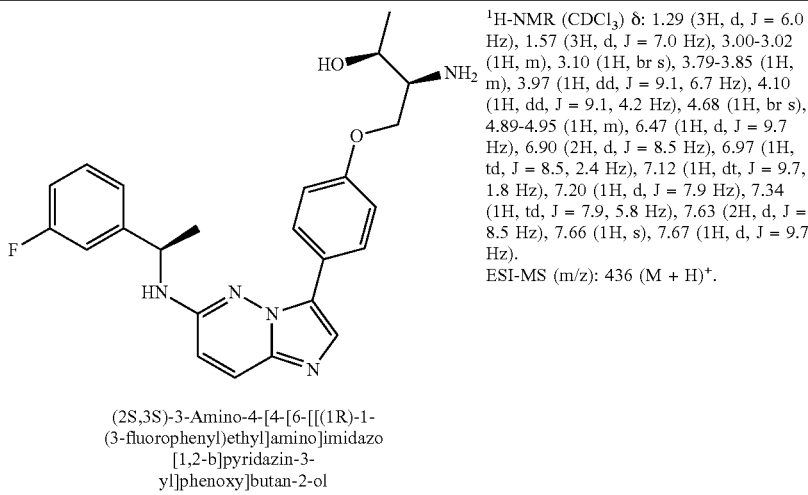 (2S,3S)-3-Amino-4-[4-[6-[[(1R)-1-(3-fluorophenyl)ethyl]amino]imidazo[1,2-b]pyridazin-3-yl]phenoxy]butan-2-ol | $^1$H-NMR (CDCl$_3$) δ: 1.29 (3H, d, J = 6.0 Hz), 1.57 (3H, d, J = 7.0 Hz), 3.00-3.02 (1H, m), 3.10 (1H, br s), 3.79-3.85 (1H, m), 3.97 (1H, dd, J = 9.1, 6.7 Hz), 4.10 (1H, dd, J = 9.1, 4.2 Hz), 4.68 (1H, br s), 4.89-4.95 (1H, m), 6.47 (1H, d, J = 9.7 Hz), 6.90 (2H, d, J = 8.5 Hz), 6.97 (1H, td, J = 8.5, 2.4 Hz), 7.12 (1H, dt, J = 9.7, 1.8 Hz), 7.20 (1H, d, J = 7.9 Hz), 7.34 (1H, td, J = 7.9, 5.8 Hz), 7.63 (2H, d, J = 8.5 Hz), 7.66 (1H, s), 7.67 (1H, d, J = 9.7 Hz). ESI-MS (m/z): 436 (M + H)$^+$. |
|---|---|---|---|
| 56 | 45 | 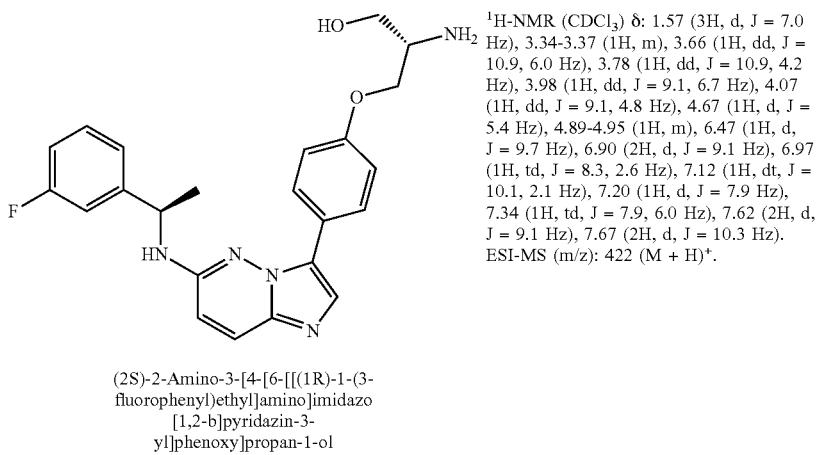 (2S)-2-Amino-3-[4-[6-[[(1R)-1-(3-fluorophenyl)ethyl]amino]imidazo[1,2-b]pyridazin-3-yl]phenoxy]propan-1-ol | $^1$H-NMR (CDCl$_3$) δ: 1.57 (3H, d, J = 7.0 Hz), 3.34-3.37 (1H, m), 3.66 (1H, dd, J = 10.9, 6.0 Hz), 3.78 (1H, dd, J = 10.9, 4.2 Hz), 3.98 (1H, dd, J = 9.1, 6.7 Hz), 4.07 (1H, dd, J = 9.1, 4.8 Hz), 4.67 (1H, d, J = 5.4 Hz), 4.89-4.95 (1H, m), 6.47 (1H, d, J = 9.7 Hz), 6.90 (2H, d, J = 9.1 Hz), 6.97 (1H, td, J = 8.3, 2.6 Hz), 7.12 (1H, dt, J = 10.1, 2.1 Hz), 7.20 (1H, d, J = 7.9 Hz), 7.34 (1H, td, J = 7.9, 6.0 Hz), 7.62 (2H, d, J = 9.1 Hz), 7.67 (2H, d, J = 10.3 Hz). ESI-MS (m/z): 422 (M + H)$^+$. |

TABLE 14-10

| 57 | 31 | 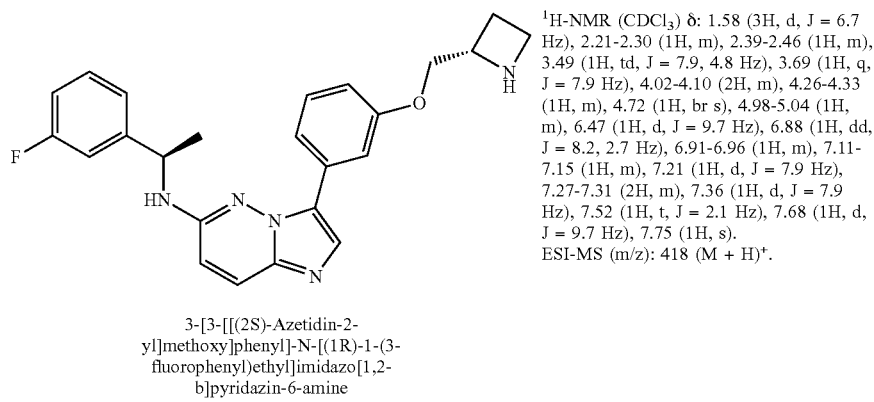 3-[3-[[(2S)-Azetidin-2-yl]methoxy]phenyl]-N-[(1R)-1-(3-fluorophenyl)ethyl]imidazo[1,2-b]pyridazin-6-amine | $^1$H-NMR (CDCl$_3$) δ: 1.58 (3H, d, J = 6.7 Hz), 2.21-2.30 (1H, m), 2.39-2.46 (1H, m), 3.49 (1H, td, J = 7.9, 4.8 Hz), 3.69 (1H, q, J = 7.9 Hz), 4.02-4.10 (2H, m), 4.26-4.33 (1H, m), 4.72 (1H, br s), 4.98-5.04 (1H, m), 6.47 (1H, d, J = 9.7 Hz), 6.88 (1H, dd, J = 8.2, 2.7 Hz), 6.91-6.96 (1H, m), 7.11-7.15 (1H, m), 7.21 (1H, d, J = 7.9 Hz), 7.27-7.31 (2H, m), 7.36 (1H, d, J = 7.9 Hz), 7.52 (1H, t, J = 2.1 Hz), 7.68 (1H, d, J = 9.7 Hz), 7.75 (1H, s). ESI-MS (m/z): 418 (M + H)$^+$. |

TABLE 14-10-continued

| 58 | 46 | 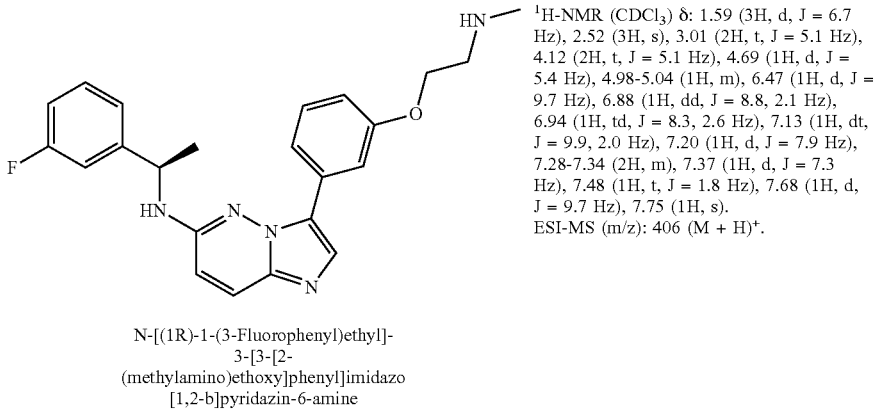<br>N-[(1R)-1-(3-Fluorophenyl)ethyl]-3-[3-[2-(methylamino)ethoxy]phenyl]imidazo[1,2-b]pyridazin-6-amine | $^1$H-NMR (CDCl$_3$) δ: 1.59 (3H, d, J = 6.7 Hz), 2.52 (3H, s), 3.01 (2H, t, J = 5.1 Hz), 4.12 (2H, t, J = 5.1 Hz), 4.69 (1H, d, J = 5.4 Hz), 4.98-5.04 (1H, m), 6.47 (1H, d, J = 9.7 Hz), 6.88 (1H, dd, J = 8.8, 2.1 Hz), 6.94 (1H, td, J = 8.3, 2.6 Hz), 7.13 (1H, dt, J = 9.9, 2.0 Hz), 7.20 (1H, d, J = 7.9 Hz), 7.28-7.34 (2H, m), 7.37 (1H, d, J = 7.3 Hz), 7.48 (1H, t, J = 1.8 Hz), 7.68 (1H, d, J = 9.7 Hz), 7.75 (1H, s).<br>ESI-MS (m/z): 406 (M + H)$^+$. |
|---|---|---|---|
| 59 | 52 | 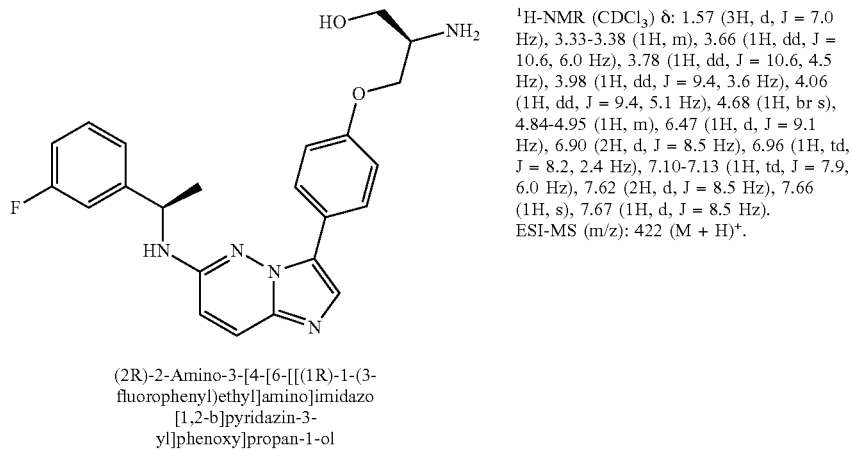<br>(2R)-2-Amino-3-[4-[6-[[(1R)-1-(3-fluorophenyl)ethyl]amino]imidazo[1,2-b]pyridazin-3-yl]phenoxy]propan-1-ol | $^1$H-NMR (CDCl$_3$) δ: 1.57 (3H, d, J = 7.0 Hz), 3.33-3.38 (1H, m), 3.66 (1H, dd, J = 10.6, 6.0 Hz), 3.78 (1H, dd, J = 10.6, 4.5 Hz), 3.98 (1H, dd, J = 9.4, 3.6 Hz), 4.06 (1H, dd, J = 9.4, 5.1 Hz), 4.68 (1H, br s), 4.84-4.95 (1H, m), 6.47 (1H, d, J = 9.1 Hz), 6.90 (2H, d, J = 8.5 Hz), 6.96 (1H, td, J = 8.2, 2.4 Hz), 7.10-7.13 (1H, td, J = 7.9, 6.0 Hz), 7.62 (2H, d, J = 8.5 Hz), 7.66 (1H, s), 7.67 (1H, d, J = 8.5 Hz).<br>ESI-MS (m/z): 422 (M + H)$^+$. |
| 60 | 47 | 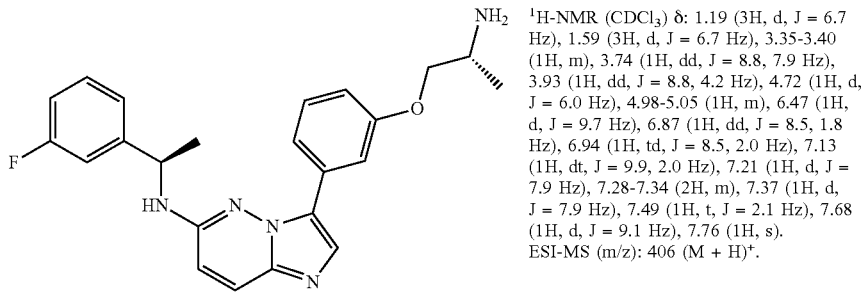<br>3-[3-[(2R)-2-Aminopropoxy]phenyl]-N-[(1R)-1-(3-fluorophenyl)ethyl]imidazo[1,2-b]pyridazin-6-amine | $^1$H-NMR (CDCl$_3$) δ: 1.19 (3H, d, J = 6.7 Hz), 1.59 (3H, d, J = 6.7 Hz), 3.35-3.40 (1H, m), 3.74 (1H, dd, J = 8.8, 7.9 Hz), 3.93 (1H, dd, J = 8.8, 4.2 Hz), 4.72 (1H, d, J = 6.0 Hz), 4.98-5.05 (1H, m), 6.47 (1H, d, J = 9.7 Hz), 6.87 (1H, dd, J = 8.5, 1.8 Hz), 6.94 (1H, td, J = 8.5, 2.0 Hz), 7.13 (1H, dt, J = 9.9, 2.0 Hz), 7.21 (1H, d, J = 7.9 Hz), 7.28-7.34 (2H, m), 7.37 (1H, d, J = 7.9 Hz), 7.49 (1H, t, J = 2.1 Hz), 7.68 (1H, d, J = 9.1 Hz), 7.76 (1H, s).<br>ESI-MS (m/z): 406 (M + H)$^+$. |

TABLE 14-11

| 61 | 53 | 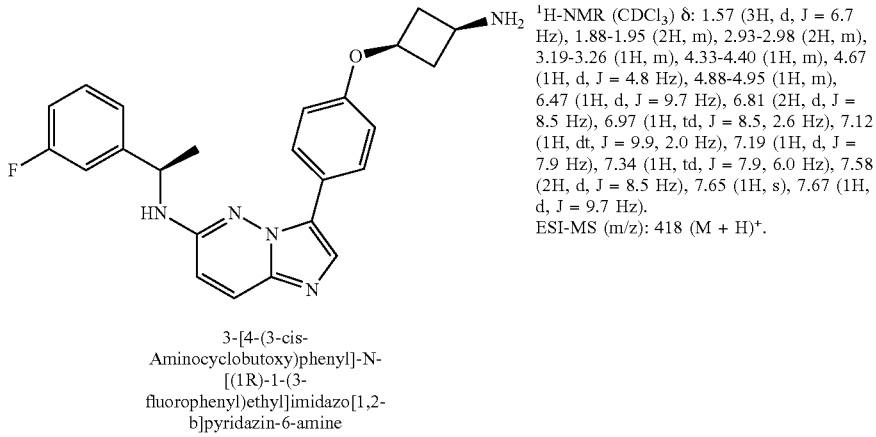<br>3-[4-(3-cis-Aminocyclobutoxy)phenyl]-N-[(1R)-1-(3-fluorophenyl)ethyl]imidazo[1,2-b]pyridazin-6-amine | $^1$H-NMR (CDCl$_3$) δ: 1.57 (3H, d, J = 6.7 Hz), 1.88-1.95 (2H, m), 2.93-2.98 (2H, m), 3.19-3.26 (1H, m), 4.33-4.40 (1H, m), 4.67 (1H, d, J = 4.8 Hz), 4.88-4.95 (1H, m), 6.47 (1H, d, J = 9.7 Hz), 6.81 (2H, d, J = 8.5 Hz), 6.97 (1H, td, J = 8.5, 2.6 Hz), 7.12 (1H, dt, J = 9.9, 2.0 Hz), 7.19 (1H, d, J = 7.9 Hz), 7.34 (1H, td, J = 7.9, 6.0 Hz), 7.58 (2H, d, J = 8.5 Hz), 7.65 (1H, s), 7.67 (1H, d, J = 9.7 Hz).<br>ESI-MS (m/z): 418 (M + H)$^+$. |
| 62 | 32 | 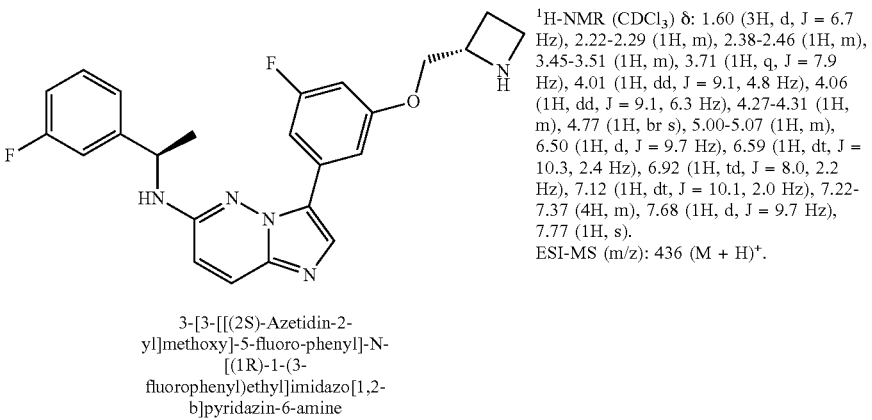<br>3-[3-[[(2S)-Azetidin-2-yl]methoxy]-5-fluoro-phenyl]-N-[(1R)-1-(3-fluorophenyl)ethyl]imidazo[1,2-b]pyridazin-6-amine | $^1$H-NMR (CDCl$_3$) δ: 1.60 (3H, d, J = 6.7 Hz), 2.22-2.29 (1H, m), 2.38-2.46 (1H, m), 3.45-3.51 (1H, m), 3.71 (1H, q, J = 7.9 Hz), 4.01 (1H, dd, J = 9.1, 4.8 Hz), 4.06 (1H, dd, J = 9.1, 6.3 Hz), 4.27-4.31 (1H, m), 4.77 (1H, br s), 5.00-5.07 (1H, m), 6.50 (1H, d, J = 9.7 Hz), 6.59 (1H, dt, J = 10.3, 2.4 Hz), 6.92 (1H, td, J = 8.0, 2.2 Hz), 7.12 (1H, dt, J = 10.1, 2.0 Hz), 7.22-7.37 (4H, m), 7.68 (1H, d, J = 9.7 Hz), 7.77 (1H, s).<br>ESI-MS (m/z): 436 (M + H)$^+$. |
| 63 | 42 | 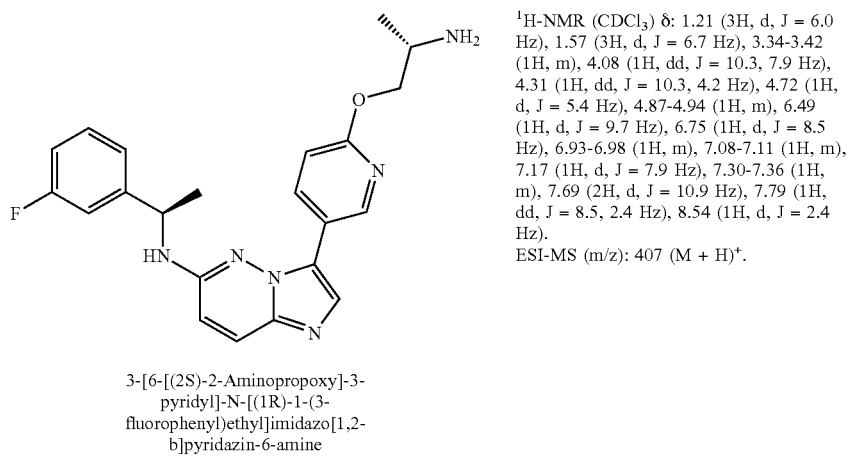<br>3-[6-[(2S)-2-Aminopropoxy]-3-pyridyl]-N-[(1R)-1-(3-fluorophenyl)ethyl]imidazo[1,2-b]pyridazin-6-amine | $^1$H-NMR (CDCl$_3$) δ: 1.21 (3H, d, J = 6.0 Hz), 1.57 (3H, d, J = 6.7 Hz), 3.34-3.42 (1H, m), 4.08 (1H, dd, J = 10.3, 7.9 Hz), 4.31 (1H, dd, J = 10.3, 4.2 Hz), 4.72 (1H, d, J = 5.4 Hz), 4.87-4.94 (1H, m), 6.49 (1H, d, J = 9.7 Hz), 6.75 (1H, d, J = 8.5 Hz), 6.93-6.98 (1H, m), 7.08-7.11 (1H, m), 7.17 (1H, d, J = 7.9 Hz), 7.30-7.36 (1H, m), 7.69 (2H, d, J = 10.9 Hz), 7.79 (1H, dd, J = 8.5, 2.4 Hz), 8.54 (1H, d, J = 2.4 Hz).<br>ESI-MS (m/z): 407 (M + H)$^+$. |

TABLE 14-11-continued

| | | | |
|---|---|---|---|
| 64 | 33 | 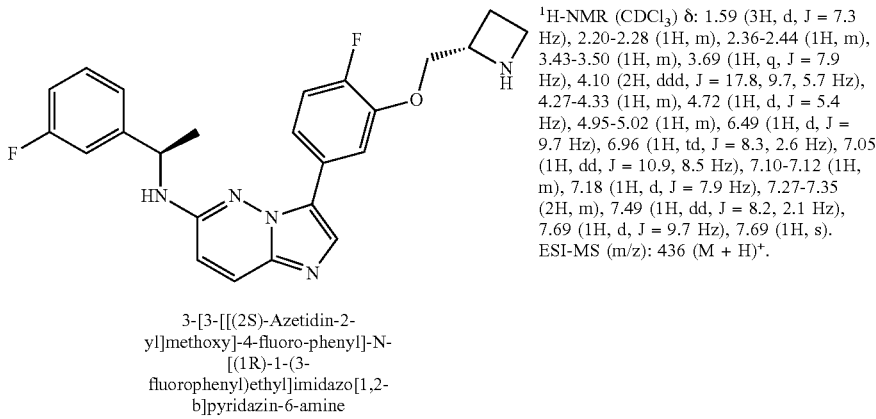<br>3-[3-[[(2S)-Azetidin-2-yl]methoxy]-4-fluoro-phenyl]-N-[(1R)-1-(3-fluorophenyl)ethyl]imidazo[1,2-b]pyridazin-6-amine | $^1$H-NMR (CDCl$_3$) δ: 1.59 (3H, d, J = 7.3 Hz), 2.20-2.28 (1H, m), 2.36-2.44 (1H, m), 3.43-3.50 (1H, m), 3.69 (1H, q, J = 7.9 Hz), 4.10 (2H, ddd, J = 17.8, 9.7, 5.7 Hz), 4.27-4.33 (1H, m), 4.72 (1H, d, J = 5.4 Hz), 4.95-5.02 (1H, m), 6.49 (1H, d, J = 9.7 Hz), 6.96 (1H, td, J = 8.3, 2.6 Hz), 7.05 (1H, dd, J = 10.9, 8.5 Hz), 7.10-7.12 (1H, m), 7.18 (1H, d, J = 7.9 Hz), 7.27-7.35 (2H, m), 7.49 (1H, dd, J = 8.2, 2.1 Hz), 7.69 (1H, d, J = 9.7 Hz), 7.69 (1H, s).<br>ESI-MS (m/z): 436 (M + H)$^+$. |

TABLE 14-12

| | | | |
|---|---|---|---|
| 65 | 24 | 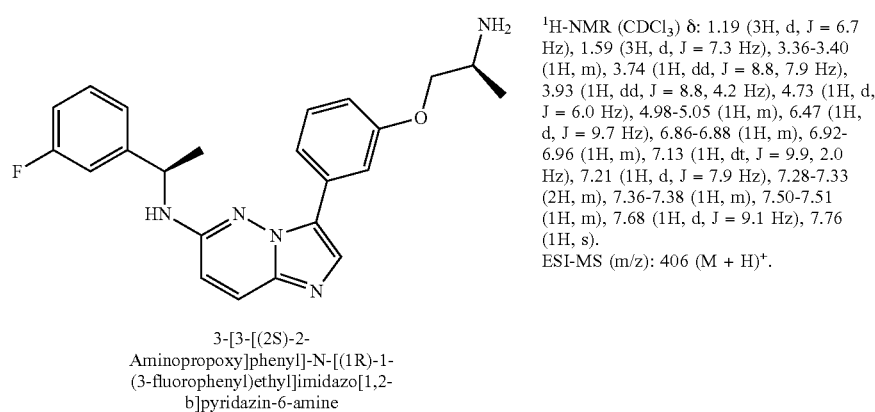<br>3-[3-[(2S)-2-Aminopropoxy]phenyl]-N-[(1R)-1-(3-fluorophenyl)ethyl]imidazo[1,2-b]pyridazin-6-amine | $^1$H-NMR (CDCl$_3$) δ: 1.19 (3H, d, J = 6.7 Hz), 1.59 (3H, d, J = 7.3 Hz), 3.36-3.40 (1H, m), 3.74 (1H, dd, J = 8.8, 7.9 Hz), 3.93 (1H, dd, J = 8.8, 4.2 Hz), 4.73 (1H, d, J = 6.0 Hz), 4.98-5.05 (1H, m), 6.47 (1H, d, J = 9.7 Hz), 6.86-6.88 (1H, m), 6.92-6.96 (1H, m), 7.13 (1H, dt, J = 9.9, 2.0 Hz), 7.21 (1H, d, J = 7.9 Hz), 7.28-7.33 (2H, m), 7.36-7.38 (1H, m), 7.50-7.51 (1H, m), 7.68 (1H, d, J = 9.1 Hz), 7.76 (1H, s).<br>ESI-MS (m/z): 406 (M + H)$^+$. |
| 66 | 48 | 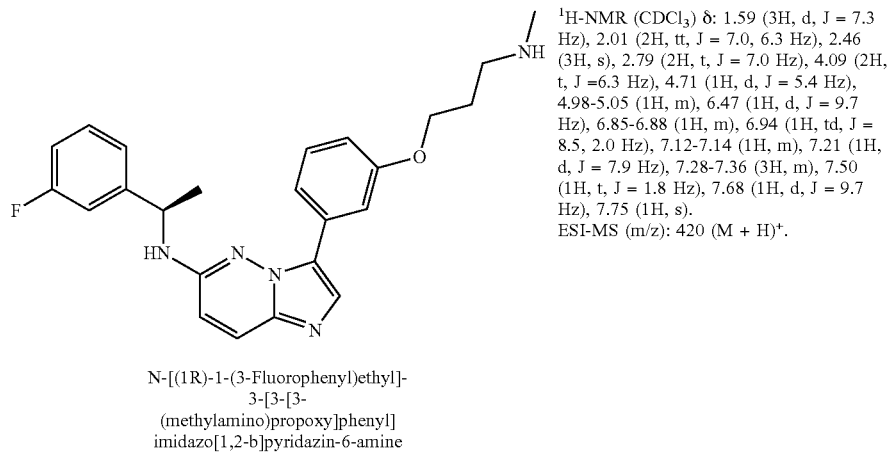<br>N-[(1R)-1-(3-Fluorophenyl)ethyl]-3-[3-[3-(methylamino)propoxy]phenyl]imidazo[1,2-b]pyridazin-6-amine | $^1$H-NMR (CDCl$_3$) δ: 1.59 (3H, d, J = 7.3 Hz), 2.01 (2H, tt, J = 7.0, 6.3 Hz), 2.46 (3H, s), 2.79 (2H, t, J = 7.0 Hz), 4.09 (2H, t, J =6.3 Hz), 4.71 (1H, d, J = 5.4 Hz), 4.98-5.05 (1H, m), 6.47 (1H, d, J = 9.7 Hz), 6.85-6.88 (1H, m), 6.94 (1H, td, J = 8.5, 2.0 Hz), 7.12-7.14 (1H, m), 7.21 (1H, d, J = 7.9 Hz), 7.28-7.36 (3H, m), 7.50 (1H, t, J = 1.8 Hz), 7.68 (1H, d, J = 9.7 Hz), 7.75 (1H, s).<br>ESI-MS (m/z): 420 (M + H)$^+$. |

TABLE 14-12-continued

| 67 | 49 | 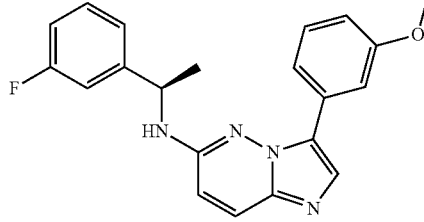 3-[3-(2-Aminoethoxy)phenyl]-N-[(1R)-1-(3-fluorophenyl)ethyl]imidazo[1,2-b]pyridazin-6-amine | $^1$H-NMR (CDCl$_3$) δ: 1.59 (3H, d, J = 6.7 Hz), 3.12 (2H, t, J = 5.1 Hz), 4.04 (2H, t, J = 5.1 Hz), 4.73 (1H, br s), 4.98-5.04 (1H, m), 6.48 (1H, d, J = 9.7 Hz), 6.88 (1H, d, J = 7.9, 2.4 Hz), 6.94 (1H, td, J = 8.3, 2.6 Hz), 7.12-7.14 (1H, m), 7.21 (1H, d, J = 7.9 Hz), 7.29-7.37 (3H, m), 7.49 (1H, t, J = 1.8 Hz), 7.68 (1H, d, J = 9.7 Hz), 7.75 (1H, s). ESI-MS (m/z): 392 (M + H)$^+$. |
|---|---|---|---|
| 68 | 50 | 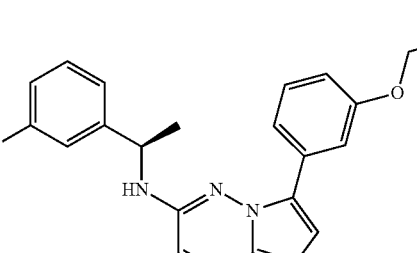 3-[3-(3-Aminopropoxy)phenyl]-N-[(1R)-1-(3-fluorophenyl)ethyl]imidazo[1,2-b]pyridazin-6-amine | $^1$H-NMR (CDCl$_3$) δ: 1.58 (3H, d, J = 6.7 Hz), 1.93-2.00 (2H, m), 2.94 (2H, t, J = 6.7 Hz), 4.10 (2H, t, J = 6.0 Hz), 4.75 (1H, br s), 4.98-5.04 (1H, m), 6.47 (1H, d, J = 9.7 Hz), 6.86-6.87 (1H, m), 6.92-6.96 (1H, m), 7.13 (1H, dt, J = 9.9, 2.1 Hz), 7.21 (1H, d, J = 7.9 Hz), 7.28-7.36 (3H, m), 7.49 (1H, t, J = 2.1 Hz), 7.68 (1H, d, J = 9.7 Hz), 7.75 (1H, s). ESI-MS (m/z): 406 (M + H)$^+$. |

Example 69

3-[4-(2-Dimethylaminoethoxy)phenyl]-N-[(1R)-1-(3-fluorophenyl)ethyl]imidazo[1,2-b]pyridazin-6-amine

[Formula 57]

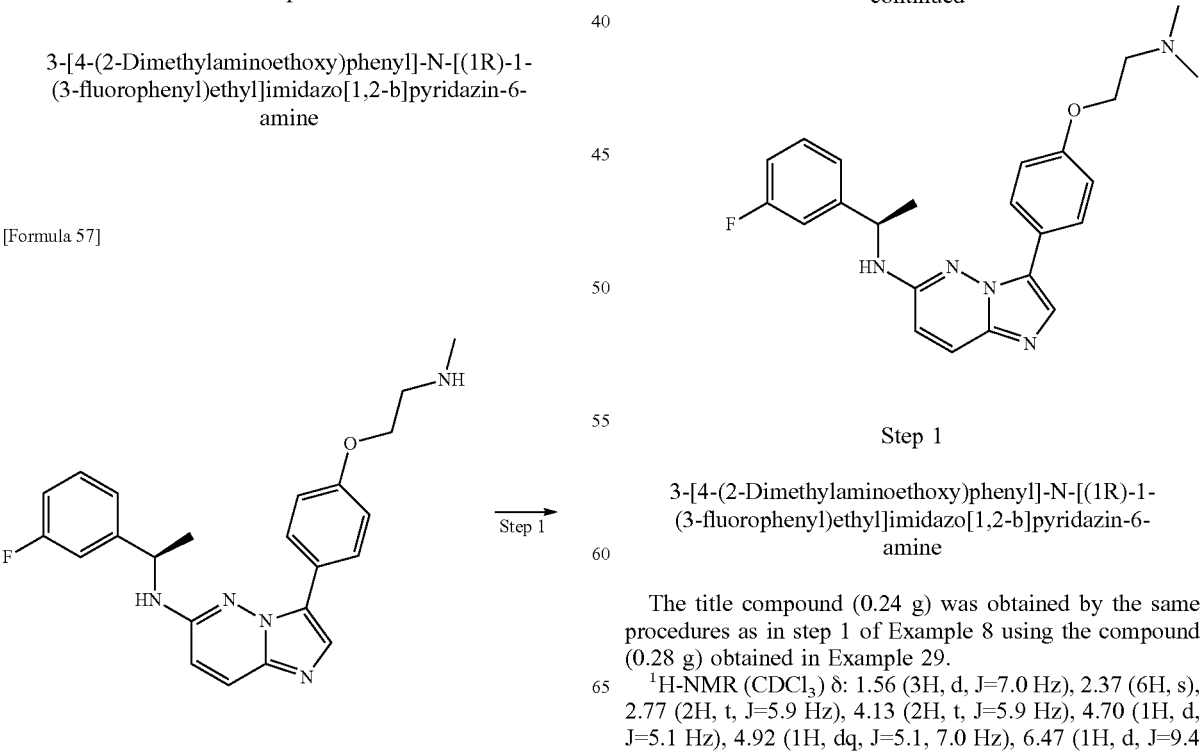

Step 1

3-[4-(2-Dimethylaminoethoxy)phenyl]-N-[(1R)-1-(3-fluorophenyl)ethyl]imidazo[1,2-b]pyridazin-6-amine The title compound (0.24 g) was obtained by the same procedures as in step 1 of Example 8 using the compound (0.28 g) obtained in Example 29.

$^1$H-NMR (CDCl$_3$) δ: 1.56 (3H, d, J=7.0 Hz), 2.37 (6H, s), 2.77 (2H, t, J=5.9 Hz), 4.13 (2H, t, J=5.9 Hz), 4.70 (1H, d, J=5.1 Hz), 4.92 (1H, dq, J=5.1, 7.0 Hz), 6.47 (1H, d, J=9.4

Hz), 6.91-6.98 (3H, m), 7.12 (1H, dt, J=9.5, 2.1 Hz), 7.19 (1H, d, J=7.4 Hz), 7.34 (1H, td, J=8.0, 5.9 Hz), 7.61 (2H, dt, J=9.5, 2.5 Hz), 7.66-7.68 (2H, m).

ESI-MS (m/z): 420 (M+H)+.

Example 70

3-[4-[3-(Dimethylamino)propoxy]phenyl]-N-[(1R)-1-(3-fluorophenyl)ethyl]imidazo[1,2-b]pyridazin-6-amine

[Formula 58]

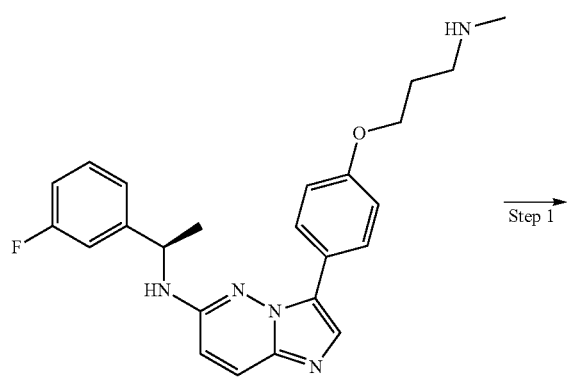

Step 1

3-[4-[3-(Dimethylamino)propoxy]phenyl]-N-[(1R)-1-(3-fluorophenyl)ethyl]imidazo[1,2-b]pyridazin-6-amine The title compound (0.26 g) was obtained by the same procedures as in step 1 of Example 8 using the compound (0.28 g) obtained in Example 31.

$^1$H-NMR (CDCl$_3$) δ: 1.57 (3H, d, J=6.7 Hz), 1.98-2.02 (2H, m), 2.29 (6H, s), 2.49 (2H, t, J=7.2 Hz), 4.08 (2H, t, J=6.3 Hz), 4.67 (1H, d, J=5.1 Hz), 4.90-4.96 (1H, m), 6.46 (1H, d, J=9.8 Hz), 6.90 (2H, d, J=9.0 Hz), 6.94-6.99 (1H, m), 7.12 (1H, dt, J=9.9, 2.1 Hz), 7.20 (1H, d, J=7.8 Hz), 7.34 (1H, td, J=8.0, 5.9 Hz), 7.62 (2H, d, J=9.0 Hz), 7.67 (2H, d, J=9.0 Hz).

ESI-MS (m/z): 434 (M+H)+.

Example 71

3-[6-(2-Dimethylaminoethoxy)-3-pyridyl]-N-[(1R)-1-(3-fluorophenyl)ethyl]imidazo[1,2-b]pyridazin-6-amine

[Formula 59]

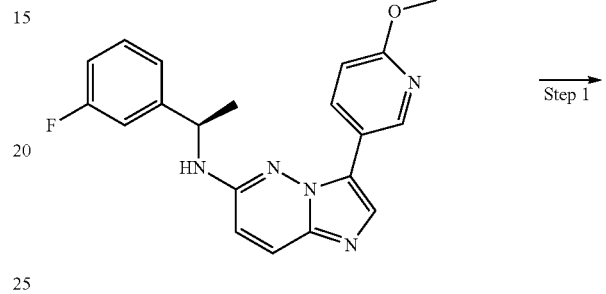

Step 1

3-[6-(2-Dimethylaminoethoxy)-3-pyridyl]-N-[(1R)-1-(3-fluorophenyl)ethyl]imidazo[1,2-b]pyridazin-6-amine The title compound (0.10 g) was obtained by the same procedures as in step 1 of Example 8 using the compound obtained in Example 46.

$^1$H-NMR (CDCl$_3$) δ: 1.57 (3H, d, J=7.0 Hz), 2.37 (6H, s), 2.76 (2H, t, J=5.7 Hz), 4.48 (2H, t, J=5.7 Hz), 4.70 (1H, d, J=4.8 Hz), 4.87-4.93 (1H, m), 6.49 (1H, d, J=9.7 Hz), 6.78 (1H, d, J=9.1 Hz), 6.95 (1H, td, J=8.3, 2.6 Hz), 7.07-7.11 (1H, m), 7.17 (1H, d, J=7.3 Hz), 7.33 (1H, td, J=8.0, 5.6 Hz), 7.68 (2H, d, J=10.9 Hz), 7.77 (1H, dd, J=8.5, 2.4 Hz), 8.53 (1H, d, J=2.4 Hz).

Example 72

4-Amino-1-[4-[6-(benzylamino)imidazo[1,2-b]pyridazin-3-yl]phenyl]pyrrolidin-2-one

[Formula 60]

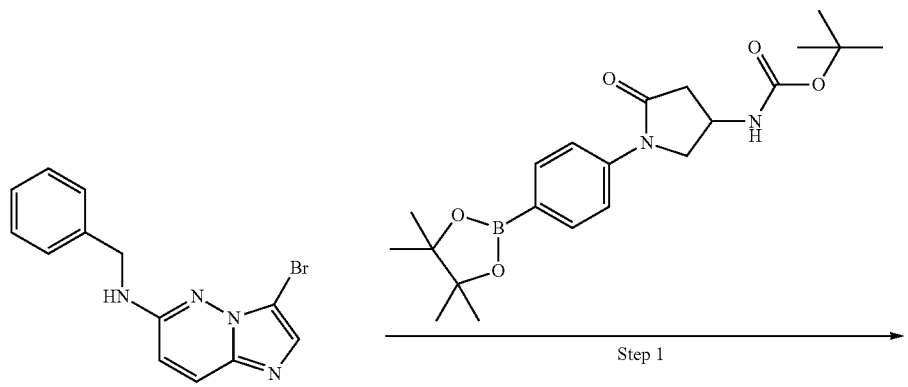

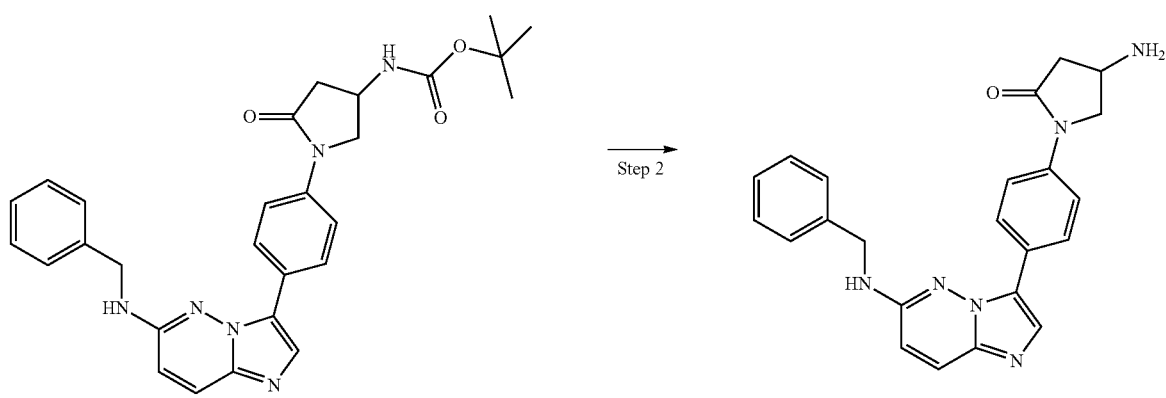

Step 1 tert-Butyl N-[1-[4-[6-(benzylamino)imidazo[1,2-b]pyridazin-3-yl]phenyl]-5-oxopyrrolidin-3-yl]carbamate 1,4-Dioxane (10 ml) and water (5 ml) were added to the compound (100 mg) obtained in step 1 of Example 1, the compound (160 mg) obtained in step 3 of Reference Example 61, sodium carbonate (52 mg), and a [1,1'-bis(diphenylphosphino)ferrocene]dichloropalladium(II)-dichloromethane adduct (27 mg), and the mixture was heated to reflux for 40 minutes under a nitrogen atmosphere. After cooling, water was added to the reaction solution, and the mixture was subjected to extraction with ethyl acetate. The extract was washed with saturated saline and then dried over anhydrous sodium sulfate. The solvent was distilled off under reduced pressure. The obtained residue was washed with an ethyl acetate-diethyl ether mixed solution to obtain the title compound (125 mg).

$^1$H-NMR (CDCl$_3$) δ: 1.46 (9H, s), 2.51 (1H, dd, J=17.2, 4.4 Hz), 3.00 (1H, dd, J=17.4, 7.8 Hz), 3.77 (1H, d, J=7.8 Hz), 4.16-4.25 (1H, m), 4.44 (1H, br s), 4.59 (2H, d, J=6.0 Hz), 4.76 (1H, t, J=5.0 Hz), 4.90 (1H, br s), 6.49 (1H, d, J=9.2 Hz), 7.29-7.43 (5H, m), 7.64 (2H, d, J=8.7 Hz), 7.69 (1H, d, J=9.6 Hz), 7.78 (1H, s), 8.00 (2H, d, J=8.7 Hz).

Step 2

4-Amino-1-[4-[6-(benzylamino)imidazo[1,2-b]pyridazin-3-yl]phenyl]pyrrolidin-2-one To a solution of the compound (125 mg) obtained in the preceding step 1 in dichloromethane (10 ml), trifluoroacetic acid (2 ml) was added, and the mixture was stirred at room temperature for 3 hours. A saturated aqueous solution of sodium bicarbonate was added to the reaction solution, followed by extraction with chloroform. The extract was washed with saturated saline and then dried over anhydrous sodium sulfate. The solvent was distilled off under reduced pressure. The obtained residue was purified by silica gel column chromatography (basic silica gel, chloroform) to obtain the title compound (20 mg).

$^1$H-NMR (CDCl$_3$) δ: 2.43 (1H, dd, J=17.0, 5.0 Hz), 2.93 (1H, dd, J=17.0, 7.3 Hz), 3.59 (1H, dd, J=10.1, 4.1 Hz), 3.81-3.89 (1H, m), 4.11 (1H, dd, J=9.9, 6.6 Hz), 4.59 (2H, d, J=5.5 Hz), 4.75 (1H, s), 6.49 (1H, d, J=9.6 Hz), 7.28-7.44 (5H, m), 7.66 (2H, d, J=8.7 Hz), 7.69 (1H, d, J=9.2 Hz), 7.78 (1H, s), 7.99 (2H, d, J=8.7 Hz).

Example 73

4-Amino-1-[4-[6-[(3-fluorophenyl)methoxy]imidazo[1,2-b]pyridazin-3-yl]phenyl]pyrrolidin-2-one

[Formula 61]

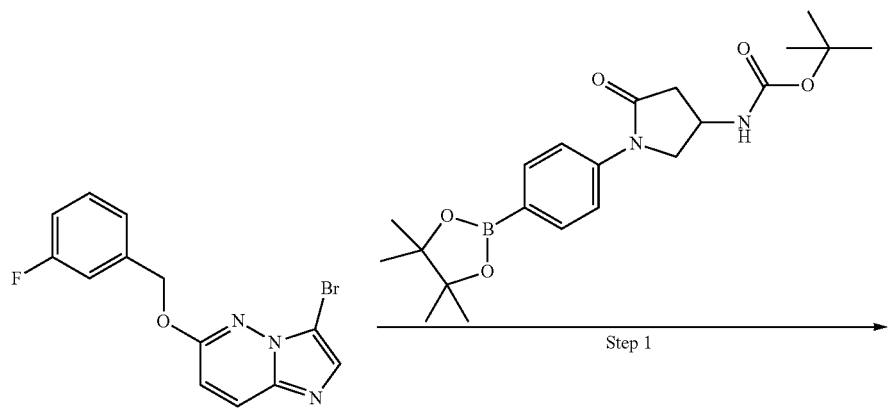

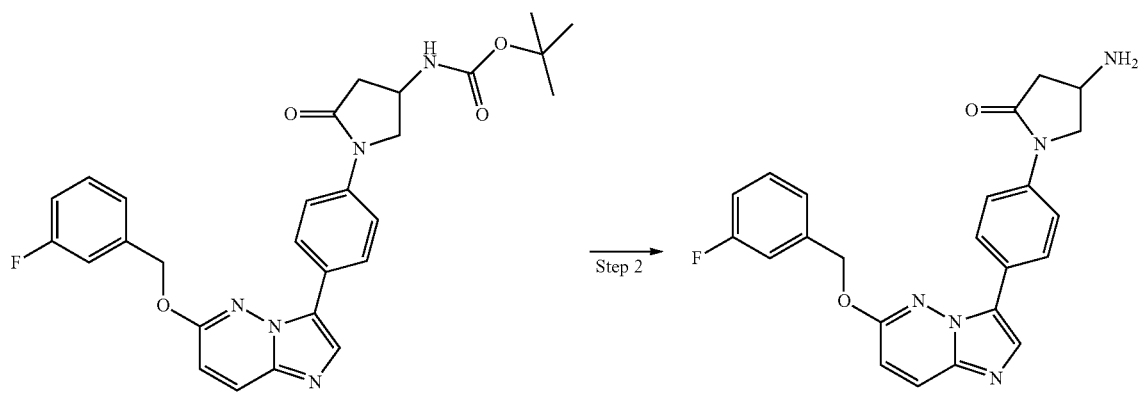

Step 1 tert-Butyl N-[1-[4-[6-[(3-fluorophenyl)methoxy]imidazo[1,2-b]pyridazin-3-yl]phenyl]-5-oxopyrrolidin-3-yl]carbamate The title compound (100 mg) was obtained by the same procedures as in step 1 of Example 72 using the compound (100 mg) obtained in step 1 of Example 11 and the compound (140 mg) obtained in step 3 of Reference Example 61.

$^1$H-NMR (CDCl$_3$) δ: 1.47 (9H, s), 2.53 (1H, dd, J=17.2, 4.6 Hz), 3.02 (1H, dd, J=17.8, 8.0 Hz), 3.80 (1H, dd, J=9.7, 2.9 Hz), 4.20-4.27 (1H, m), 4.46 (1H, br s), 4.88 (1H, br s), 5.40 (2H, s), 6.81 (1H, d, J=9.7 Hz), 7.05 (1H, td, J=8.3, 3.1 Hz), 7.20 (1H, d, J=9.2 Hz), 7.25 (1H, d, J=8.0 Hz), 7.39 (1H, td, J=8.0, 5.7 Hz), 7.73 (2H, d, J=8.6 Hz), 7.88 (1H, s), 7.89 (1H, d, J=9.2 Hz), 7.96 (2H, d, J=8.6 Hz).

Step 2

4-Amino-1-[4-[6-[(3-fluorophenyl)methoxy]imidazo[1,2-b]pyridazin-3-yl]phenyl]pyrrolidin-2-one The title compound (35 mg) was obtained by the same procedures as in step 2 of Example 72 with the compound (100 mg) obtained in the preceding step 1 as the starting material.

$^1$H-NMR (CDCl$_3$) δ: 2.44 (1H, dd, J=16.7, 3.4 Hz), 2.95 (1H, dd, J=17.0, 6.9 Hz), 3.62 (1H, dd, J=9.9, 2.5 Hz), 3.84-3.92 (1H, m), 4.10-4.16 (1H, m), 5.40 (2H, s), 6.80 (1H, d, J=9.6 Hz), 7.05 (1H, t, J=8.3 Hz), 7.17-7.28 (2H, m), 7.35-7.42 (1H, m), 7.74 (2H, d, J=8.7 Hz), 7.87-7.90 (2H, m), 7.95 (2H, d, J=9.2 Hz).

The following compounds were obtained by the same procedures as in Example 73 with the compound obtained in step 1 of Example 11 as the starting material using the compounds obtained in the Reference Examples.

TABLE 15-1

| Example | Reference Example | Structure and name | Instrumenta data |
|---|---|---|---|
| 74 | 63 | 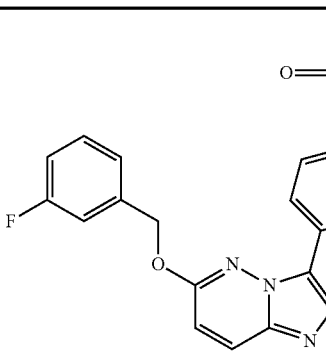<br>4-(Aminomethyl)-1-[4-[6-[(3-fluorophenyl)methoxy]imidazo[1,2-b]pyridazin-3-yl]phenyl]pyrrolidin-2-one | $^1$H-NMR (CDCl$_3$) δ: 1.63 (2H, br s), 2.42-2.52 (1H, m), 2.78-2.90 (2H, m), 3.23-3.39 (2H, m), 3.73-3.79 (1H, m), 4.06-4.13 (2H, m), 3.40 (2H, s), 6.79 (1H, d, J = 10.1 Hz), 7.05 (1H, t, J = 8.3 Hz), 7.20 (1H, d, J = 9.2 Hz), 7.23-7.27 (1H, m), 7.35-7.42 (1H, m), 7.78 (2H, d, J = 8.9 Hz), 7.86-7.89 (2H, m), 7.95 (2H, d, J = 8.9 Hz). |
| 75 | 64 | 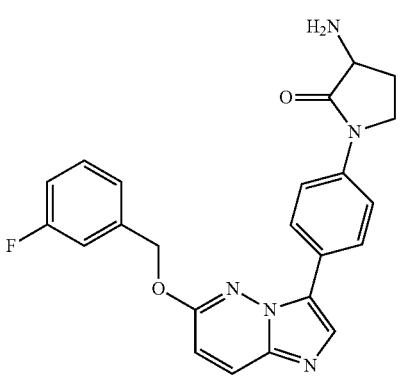 [SMILES: NC1CCN(c2ccc(-c3cnc4ccc(OCc5cccc(F)c5)nn34)cc2)C1=O]<br>3-Amino-1-[4-[6-[(3-fluorophenyl)methoxy]imidazo[1,2-b]pyridazin-3-yl]phenyl]pyrrolidin-2-one | $^1$H-NMR (CDCl$_3$) δ: 1.65 (2H, br s), 1.86-1.98 (1H, m), 2.58-2.67 (1H, m), 3.74 (1H, dd, J = 10.1, 7.8 Hz), 3.81-3.87 (2H, m), 5.41 (2H, s), 6.81 (1H, d, J = 9.6 Hz), 7.05 (1H, td, J = 8.3, 2.8 Hz), 7.20 (1H, d, J = 10.5 Hz), 7.25 (1H, d, J = 7.8 Hz), 7.36-7.42 (1H, m), 7.79 (2H, d, J = 8.7 Hz), 7.88 (1H, s), 7.89 (1H, d, J = 9.6 Hz), 7.97 (2H, d, J = 8.7 Hz). |

TABLE 15-2

| | | | |
|---|---|---|---|
| 76 | 65 | 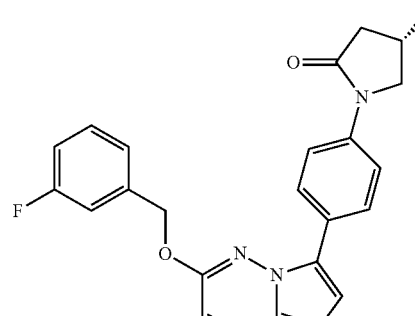<br>(4S)-4-Amino-1-[4-[6-[(3-fluorophenyl)methoxy]imidazo[1,2-b]pyridazin-3-yl]phenyl]pyrrolidin-2-one | $^1$H-NMR (CDCl$_3$) δ: 1.55 (2H, br s), 2.41 (1H, dd, J = 16.8, 5.1 Hz), 2.91 (1H, dd, J = 16.8, 7.0 Hz), 3.59 (1H, dd, J = 9.4, 4.3 Hz), 3.81-3.87 (1H, m), 4.10 (1H, dd, J = 9.4, 6.6 Hz), 5.36 (2H, s), 6.76 (1H, d, J = 9.8 Hz), 7.02 (1H, td, J = 8.6, 2.7 Hz), 7.16 (1H, d, J = 9.4 Hz), 7.22 (1H, d, J = 7.4 Hz), 7.35 (1H, td, J = 7.8, 5.9 Hz), 7.70 (2H, d, J = 9.0 Hz), 7.84 (1H, s), 7.85 (1H, d, J = 9.8 Hz), 7.92 (2H, d, J = 8.6 Hz). |

| 77 | 73 | 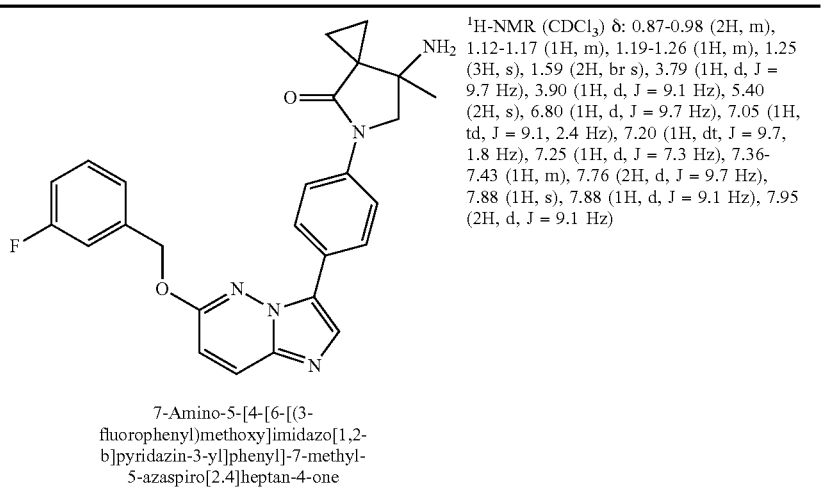<br>7-Amino-5-[4-[6-[(3-fluorophenyl)methoxy]imidazo[1,2-b]pyridazin-3-yl]phenyl]-7-methyl-5-azaspiro[2.4]heptan-4-one | $^1$H-NMR (CDCl$_3$) δ: 0.87-0.98 (2H, m), 1.12-1.17 (1H, m), 1.19-1.26 (1H, m), 1.25 (3H, s), 1.59 (2H, br s), 3.79 (1H, d, J = 9.7 Hz), 3.90 (1H, d, J = 9.1 Hz), 5.40 (2H, s), 6.80 (1H, d, J = 9.7 Hz), 7.05 (1H, td, J = 9.1, 2.4 Hz), 7.20 (1H, dt, J = 9.7, 1.8 Hz), 7.25 (1H, d, J = 7.3 Hz), 7.36-7.43 (1H, m), 7.76 (2H, d, J = 9.7 Hz), 7.88 (1H, s), 7.88 (1H, d, J = 9.1 Hz), 7.95 (2H, d, J = 9.1 Hz) |

Example 78

(4R)-4-Amino-1-[4-[6-[(1R)-1-(3-fluorophenyl)ethoxy]imidazo[1,2-b]pyridazin-3-yl]phenyl]pyrrolidin-2-one

[Formula 62]

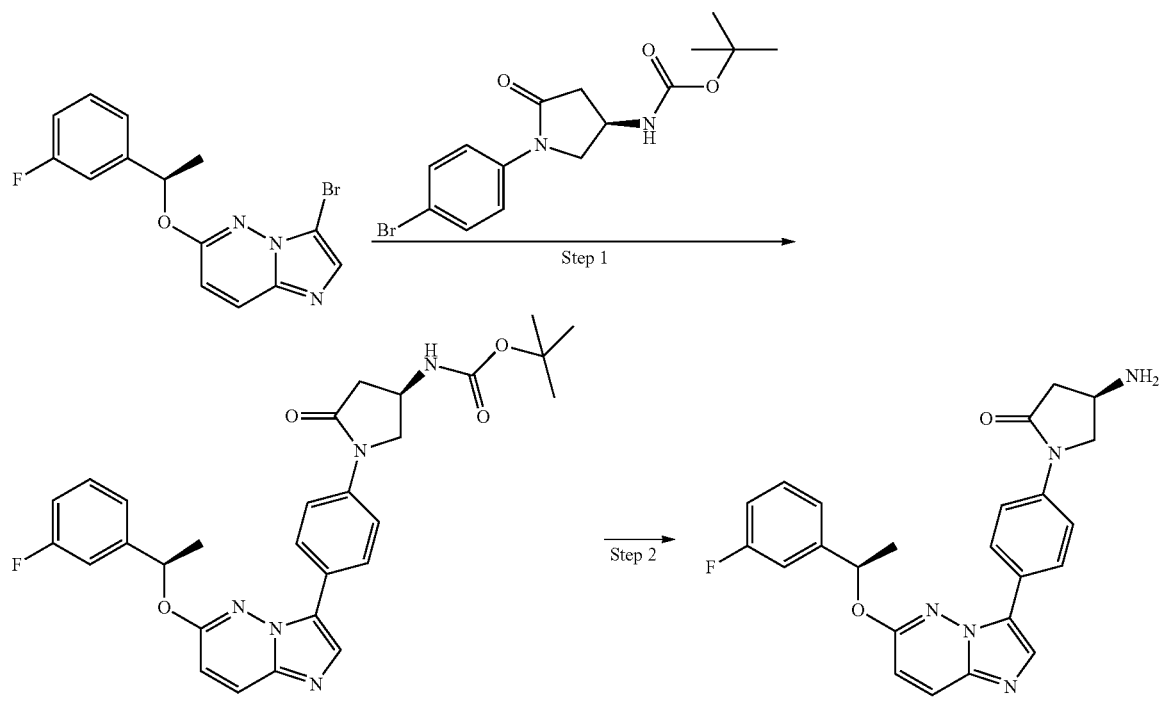

Step 1 tert-Butyl N-[(3R)-1-[4-[6-[(1R)-1-(3-fluorophenyl)ethoxy]imidazo[1,2-b]pyridazin-3-yl]phenyl]-5-oxopyrrolidin-3-yl]carbamate 1,4-Dioxane was added to the compound (91 mg) obtained in step 1 of Reference Example 62, a [1,1'-bis(diphenylphosphino)ferrocene]dichloropalladium(II)-dichloromethane adduct (10 mg), bis(pinacolato)diborane (65 mg), and potassium acetate (50 mg), and the mixture was stirred at 90° C. for 1 hour under an argon atmosphere and then heated to reflux for 1 hour.

The reaction solution was temporarily brought back to room temperature. The compound (86 mg) obtained in step 1 of Example 15, a [1,1'-bis(diphenylphosphino)ferrocene]

dichloropalladium(II)-dichloromethane adduct (10 mg), tripotassium phosphate (109 mg), and water (0.5 ml) were added thereto, and the mixture was heated to reflux for 1 hour under an argon atmosphere. Ethyl acetate and water were added to the reaction solution to separate the aqueous and organic layers. The organic layer was dried over anhydrous sodium sulfate and then concentrated under reduced pressure. The obtained residue was purified by silica gel column chromatography (basic silica gel, n-hexane-ethyl acetate→dichloromethane-methanol) to obtain the title compound (31 mg).

$^1$H-NMR (CDCl$_3$) δ: 1.48 (9H, s), 1.68 (3H, d, J=6.9 Hz), 2.55 (1H, dd, J=17.2, 4.6 Hz), 3.03 (1H, dd, J=17.2, 8.0 Hz), 3.80 (1H, dd, J=10.0, 3.4 Hz), 4.24 (1H, dd, J=10.0, 6.3 Hz), 4.45-4.51 (1H, m), 5.03-5.07 (1H, m), 5.93 (1H, q, J=6.9 Hz), 6.79 (1H, d, J=9.7 Hz), 6.96-7.01 (1H, m), 7.12-7.15 (1H, m), 7.21 (1H, d, J=7.4 Hz), 7.33-7.38 (1H, m), 7.66-7.69 (2H, m), 7.72-7.75 (2H, m), 7.79 (1H, s), 7.85 (1H, d, J=9.7 Hz).

ESI-MS (m/z): 532 (M+H)$^+$.

Step 2

(4R)-4-Amino-1-[4-[6-[(1R)-1-(3-fluorophenyl)ethoxy]imidazo[1,2-b]pyridazin-3-yl]phenyl]pyrrolidin-2-one The compound (31 mg) obtained in the preceding step 1 was dissolved in dichloromethane (3 ml). To the solution, a solution of 4 N hydrochloric acid in dioxane (3 ml) was added, and the mixture was stirred at room temperature for 1 hour. The solvent was distilled off under reduced pressure. Dichloromethane and a saturated aqueous solution of sodium bicarbonate were added to the residue to separate the aqueous and organic layers. The organic layer was dried over anhydrous sodium sulfate and then concentrated under reduced pressure. The obtained residue was purified by silica gel column chromatography (basic silica gel, dichloromethane-methanol) to obtain the title compound (23 mg).

$^1$H-NMR (CDCl$_3$) δ: 1.69 (3H, d, J=6.4 Hz), 2.46 (1H, dd, J=17.2, 5.2 Hz), 2.96 (1H, dd, J=17.2, 7.4 Hz), 3.63 (1H, dd, J=10.0, 4.0 Hz), 3.87-3.92 (1H, m), 4.15 (1H, dd, J=10.0, 6.6 Hz), 5.93 (1H, q, J=6.4 Hz), 6.79 (1H, d, J=9.7 Hz), 6.99 (1H, td, J=8.4, 2.3 Hz), 7.13-7.16 (1H, m), 7.22 (1H, d, J=7.4 Hz), 7.34-7.38 (1H, m), 7.69-7.75 (4H, m), 7.80 (1H, s), 7.85 (1H, d, J=9.7 Hz).

ESI-MS (m/z): 432 (M+H)$^+$.

Example 79

(4S)-4-Amino-1-[4-[6-[(1R)-1-(3-fluorophenyl)ethoxy]imidazo[1,2-b]pyridazin-3-yl]phenyl]pyrrolidin-2-one

[Formula 63]

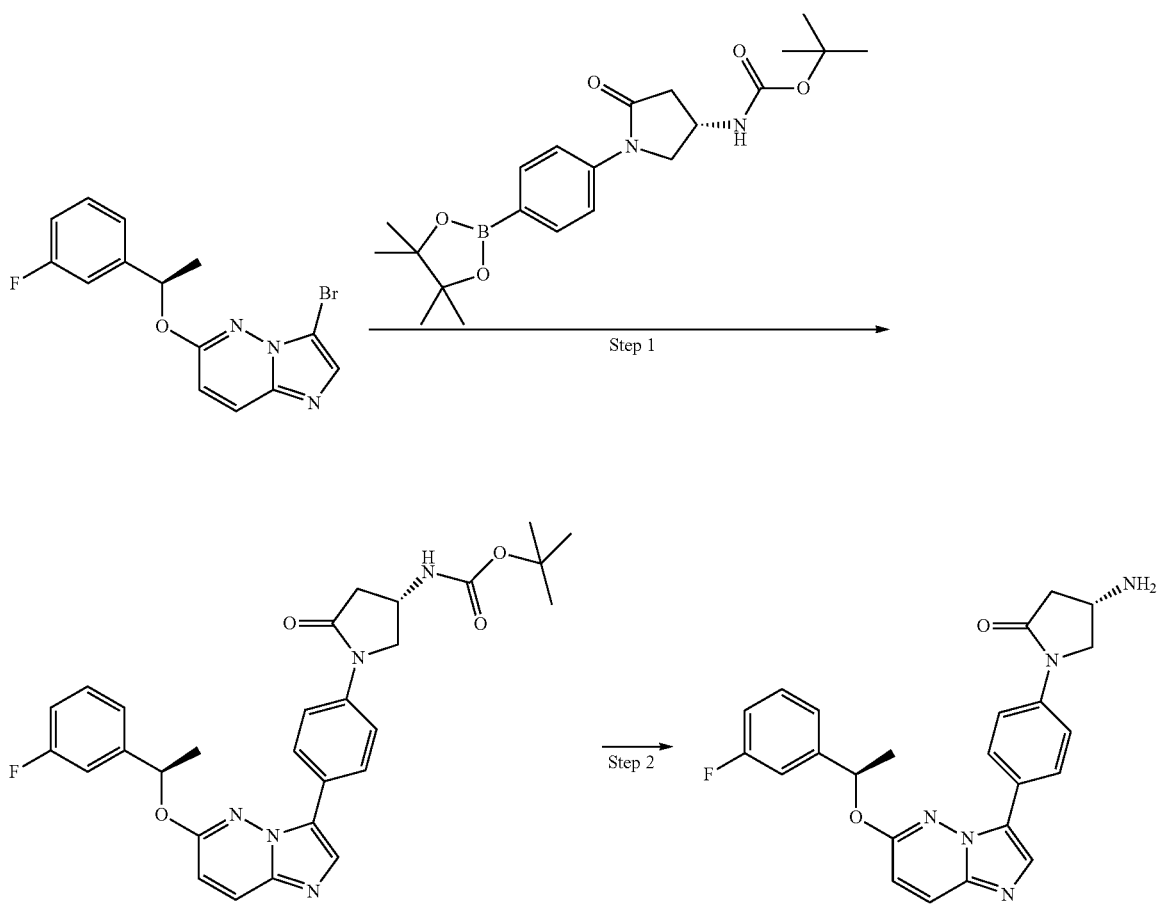

Step 1 tert-Butyl N-[(3S)-1-[4-[6-[(1R)-1-(3-fluorophenyl) ethoxy]imidazo[1,2-b]pyridazin-3-yl]phenyl]-5-oxopyrrolidin-3-yl]carbamate A mixed solvent of 1,4-dioxane (8 ml) and water (0.8 ml) was added to the compound (501 mg) obtained in step 1 of Example 15, the compound (600 mg) obtained in step 3 of Reference Example 65, a [1,1'-bis(diphenylphosphino)ferrocene]dichloropalladium(II)-dichloromethane adduct (122 mg), and tripotassium phosphate (633 mg), and the mixture was heated to reflux for 1.5 hours under an argon atmosphere. Then, a [1,1'-bis(diphenylphosphino)ferrocene]dichloropalladium(II)-dichloromethane adduct (122 mg) was further added thereto, and the mixture was further heated to reflux for 1 hour. After standing to cool, ethyl acetate and water were added to the reaction solution to separate the aqueous and organic layers. The organic layer was dried over anhydrous sodium sulfate and then concentrated under reduced pressure. The obtained residue was purified by silica gel column chromatography (basic silica gel, dichloromethane-methanol) to obtain the title compound (607 mg).

$^1$H-NMR (CDCl$_3$) δ: 1.48 (9H, s), 1.67 (3H, d, J=6.3 Hz), 2.58 (1H, dd, J=17.8, 4.0 Hz), 3.02 (1H, dd, J=17.8, 8.6 Hz), 3.80 (1H, dd, J=10.3, 3.4 Hz), 4.20-4.25 (1H, m), 4.43-4.50 (1H, m), 5.41 (1H, d, J=6.9 Hz), 5.90 (1H, q, J=6.3 Hz), 6.78 (1H, d, J=9.7 Hz), 6.97 (1H, td, J=8.0, 2.9 Hz), 7.13 (1H, dt, J=9.7, 2.3 Hz), 7.20 (1H, d, J=8.0 Hz), 7.35 (1H, td, J=7.9, 5.9 Hz), 7.64-7.67 (2H, m), 7.70-7.72 (2H, m), 7.77 (1H, s), 7.84 (1H, d, J=9.7 Hz).

ESI-MS (m/z): 532 (M+H)$^+$.

Step 2

(4S)-4-Amino-1-[4-[6-[(1R)-1-(3-fluorophenyl) ethoxy]imidazo[1,2-b]pyridazin-3-yl]phenyl]pyrrolidin-2-one The compound (13.90 g) obtained in the preceding step 1 was dissolved in dichloromethane (200 ml). To the solution, a solution of 4 N hydrochloric acid in 1,4-dioxane (133 ml) was added under ice cooling, and the mixture was stirred at 0° C. for 2 hours. The solvent was distilled off under reduced pressure. Dichloromethane and a saturated aqueous solution of sodium bicarbonate were added to the residue to separate the aqueous and organic layers. The aqueous layer was subjected to extraction with dichloromethane. The organic layers were combined, dried over anhydrous sodium sulfate and then concentrated under reduced pressure.

The same procedures as above were carried out using the compound (12.42 g) obtained in the preceding step 1. The obtained crude products were combined and purified by silica gel column chromatography (basic silica gel, dichloromethane-methanol; and subsequently silica gel, dichloromethane-methanol) to obtain the title compound (20.30 g).

$^1$H-NMR (CDCl$_3$) δ: 1.69 (3H, d, J=6.7 Hz), 2.46 (1H, dd, J=17.0, 4.8 Hz), 2.96 (1H, dd, J=17.0, 7.6 Hz), 3.64 (1H, dd, J=9.7, 4.2 Hz), 3.86-3.92 (1H, m), 4.15 (1H, dd, J=9.7, 6.0 Hz), 5.93 (1H, q, J=6.7 Hz), 6.78 (1H, d, J=9.7 Hz), 6.99 (1H, td, J=8.5, 2.4 Hz), 7.12-7.17 (1H, m), 7.22 (1H, d, J=8.0 Hz), 7.37 (1H, td, J=8.0, 5.8 Hz), 7.68-7.75 (4H, m), 7.80 (1H, s), 7.85 (1H, d, J=9.7 Hz).

$^1$H-NMR (DMSO-d$_6$) δ: 1.66 (3H, d, J=6.0 Hz), 1.93 (2H, br s), 2.25 (1H, dd, J=16.9, 4.2 Hz), 2.76 (1H, dd, J=16.6, 7.0 Hz), 3.51 (1H, dd, J=9.7, 3.0 Hz), 3.65-3.71 (1H, m), 4.02 (1H, dd, J=9.7, 6.7 Hz), 6.04 (1H, q, J=6.4 Hz), 7.01 (1H, d, J=9.7 Hz), 7.10 (1H, td, J=8.5, 2.4 Hz), 7.31-7.36 (2H, m), 7.39-7.45 (1H, m), 7.75 (2H, d, J=9.1 Hz), 7.90 (2H, d, J=9.1 Hz), 8.03 (1H, s), 8.09 (1H, d, J=9.7 Hz).

The following compound was obtained by the same procedures as in Example 79 with the compound obtained in step 1 of Example 15 as the starting material using the compound obtained in the Reference Example.

TABLE 16

| Example No. | Reference Example No. | Structure and name | Instrumental data |
|---|---|---|---|
| 80 | 71 | 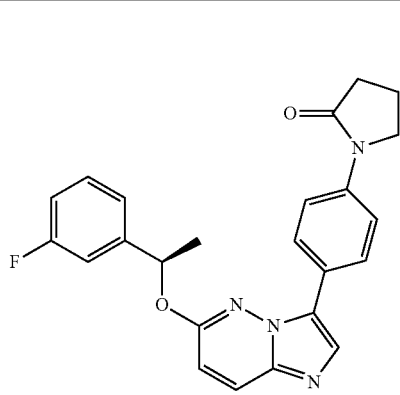<br>(4S)-1-[4-[6-[(1R)-1-(3-Fluorophenyl)ethoxy]imidazo[1,2-b]pyridazin-3-yl]phenyl]-4-(methylamino)pyrrolidin-2-one | $^1$H-NMR (CDCl$_3$) δ: 1.69 (3H, d, J = 6.6 Hz), 2.52 (3H, s), 2.54 (1H, dd, J = 17.2, 4.8 Hz), 2.92 (1H, dd, J = 17.2, 7.6 Hz), 3.54-3.59 (1H, m), 3.73 (1H, dd, J = 9.76, 4.2 Hz), 4.11 (1H, dd, J = 9.7, 6.7 Hz), 5.93 (1H, q, J = 6.6 Hz), 6.78 (1H, d, J = 9.7 Hz), 6.99 (1H, td, J = 8.5, 2.4 Hz), 7.13-7.17 (1H, m), 7.22 (1H, d, J = 7.9 Hz), 7.33-7.39 (1H, m), 7.68-7.75 (4H, m), 7.80 (1H, s), 7.85 (1H, d, J = 9.76 Hz). ESI-MS (m/z): 446 (M + H)$^+$. |

Example 81

(4S)-4-Amino-1-[4-[6-[(3-fluorophenyl)methyl-methylamino]imidazo[1,2-b]pyridazin-3-yl]phenyl]pyrrolidin-2-one

[Formula 64]

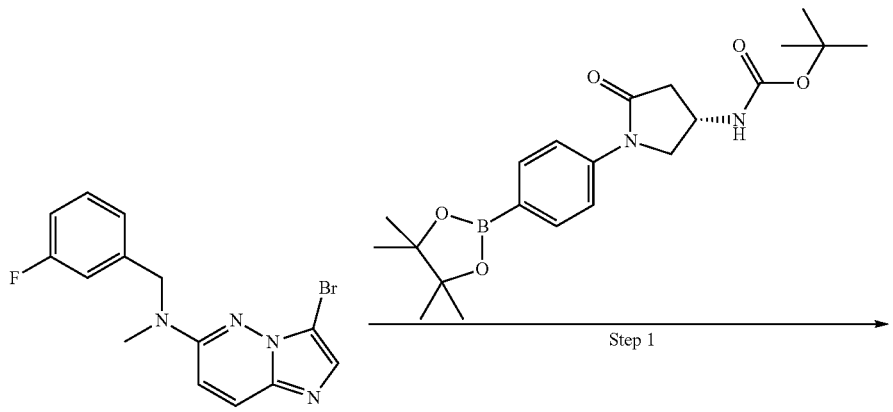

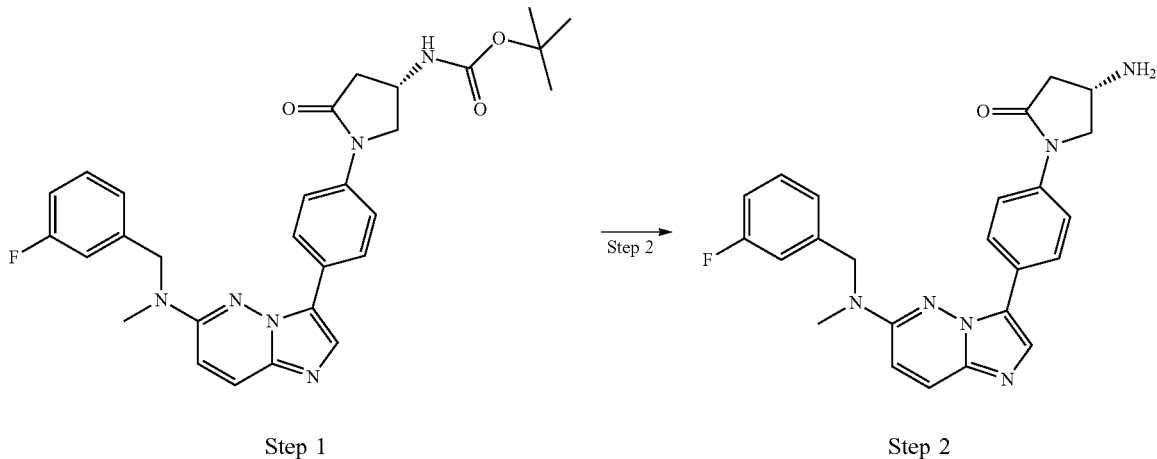

Step 1 tert-Butyl N-[(3S)-1-[4-[6-[(3-fluorophenyl)methyl-methylamino]imidazo[1,2-b]pyridazin-3-yl]phenyl]-5-oxopyrrolidin-3-yl]carbamate The title compound (0.22 g) was obtained by the same procedures as in step 1 of Example 72 with the compound (0.25 g) obtained in step 1 of Example 9 and the compound (0.36 g) obtained in step 3 of Reference Example 65 as starting materials.

$^1$H-NMR (CDCl$_3$) δ: 1.48 (9H, s), 2.53 (1H, dd, J=17.4, 4.5 Hz), 3.02 (1H, dd, J=17.2, 8.2 Hz), 3.25 (3H, s), 3.76-3.81 (1H, m), 4.23 (1H, dd, J=9.8, 6.7 Hz), 4.47 (1H, br s), 4.77 (2H, s), 4.89 (1H, br s), 6.78 (1H, d, J=10.2 Hz), 6.97-7.03 (2H, m), 7.07 (1H, d, J=7.8 Hz), 7.31-7.37 (1H, m), 7.67 (2H, d, J=9.0 Hz), 7.78 (1H, d, J=9.8 Hz), 7.85 (1H, s), 8.04 (2H, d, J=9.0 Hz).

Step 2

(4S)-4-Amino-1-[4-[6-[(3-fluorophenyl)methyl-methylamino]imidazo[1,2-b]pyridazin-3-yl]phenyl]pyrrolidin-2-one The title compound (0.15 g) was obtained by the same procedures as in step 2 of Example 72 with the compound (0.22 g) obtained in the preceding step 1 as the starting material.

$^1$H-NMR (CDCl$_3$) δ: 2.45 (1H, dd, J=17.0, 4.9 Hz), 2.95 (1H, dd, J=16.8, 7.4 Hz), 3.25 (3H, s), 3.61 (1H, dd, J=9.8, 3.9 Hz), 3.85-3.91 (1H, m), 4.13 (1H, dd, J=9.8, 6.3 Hz), 4.77 (2H, s), 6.78 (1H, d, J=9.8 Hz), 6.98-7.01 (2H, m), 7.08 (1H, d, J=7.4 Hz), 7.31-7.37 (1H, m), 7.68 (2H, d, J=9.0 Hz), 7.78 (1H, d, J=9.8 Hz), 7.85 (1H, s), 8.04 (2H, d, J=9.0 Hz).

$^1$H-NMR (DMSO-d$_6$) δ: 1.89 (2H, br s), 2.22 (1H, dd, J=16.3, 4.2 Hz), 2.74 (1H, dd, J=16.9, 7.3 Hz), 3.24 (3H, s), 3.47 (1H, dd, J=9.7, 3.6 Hz), 3.62-3.68 (1H, m), 3.98 (1H, dd, J=9.7, 6.0 Hz), 4.83 (2H, s), 7.05-7.14 (4H, m), 7.35-7.42 (1H, m), 7.69 (2H, d, J=9.4 Hz), 7.90 (1H, d, J=9.7 Hz), 7.94 (1H, s), 8.07 (2H, d, J 9.1 Hz).

The following compounds were obtained by the same procedures as in Example 81 with the compound obtained in step 1 of Example 9 as the starting material using the compounds obtained in the Reference Examples.

TABLE 17-1

| Example | Reference Example | Structure and name | Instrumental data |
|---|---|---|---|
| 82 | 61 | 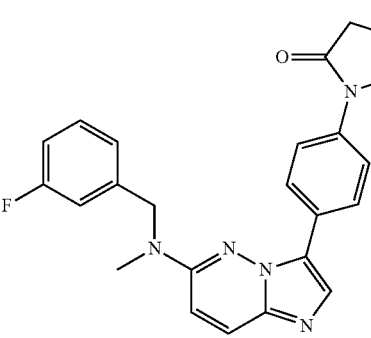<br>4-Amino-1-[4-[6-[(3-fluorophenyl)methyl-methylamino]imidazo[1,2-b]pyridazin-3-yl]phenyl]pyrrolidin-2-one | $^1$H-NMR (CDCl$_3$) δ: 2.45 (1H, dd, J = 17.0, 4.9 Hz), 2.95 (1H, dd, J = 16.8, 7.4 Hz), 3.25 (3H, s), 3.61 (1H, dd, J = 9.8, 3.9 Hz), 3.85-3.91 (1H, m), 4.13 (1H, dd, J = 9.8, 6.3 Hz), 4.77 (2H, s), 6.78 (1H, d, J = 9.8 Hz), 6.98-7.01 (2H, m), 7.08 (1H, d, J = 7.4 Hz), 7.31-7.37 (1H, m), 7.68 (2H, d, J = 9.0 Hz), 7.78 (1H, d, J = 9.8 Hz), 7.85 (1H, s), 8.03 (2H, d, J = 9.0 Hz). |
| 83 | 67 | 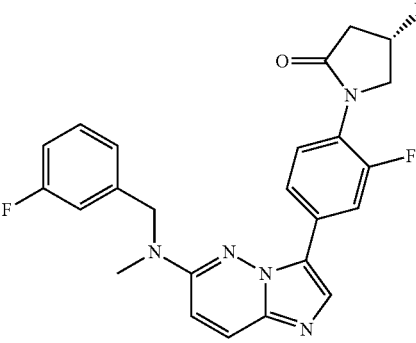<br>(4S)-4-Amino-1-[2-fluoro-4-[6-[(3-fluorophenyl)methyl-methylamino]imidazo[1,2-b]pyridazin-3-yl]phenyl]pyrrolidin-2-one | $^1$H-NMR (CDCl$_3$) δ: 2.37 (1H, dd, J = 16.9, 4.8 Hz), 2.88 (1H, dd, J = 9.7, 4.2 Hz), 3.85-3.91 (1H, m), 4.06-4.15 (1H, m), 4.76 (2H, s), 6.79 (1H, d, J = 9.7 Hz), 6.94-7.00 (2H, m), 7.05 (1H, d, J = 7.9 Hz), 7.29-7.34 (1H, m), 7.48 (1H, t, J = 8.5 Hz), 7.77 (2H, d, J = 10.3 Hz), 7.86 (1H, s), 7.95-7.99 (1H, m). |
| 84 | 75 | 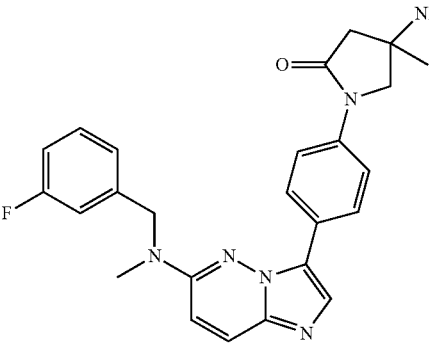<br>4-Amino-1-[4-[6-[(3-fluorophenyl)methyl-methylamino]imidazo[1,2-b]pyridazin-3-yl]phenyl]-4-methylpyrrolidin-2-one | $^1$H-NMR (CDCl$_3$) δ: 1.46 (3H, s), 2.57 (1H, d, J = 16.9 Hz), 2.68 (1H, d, J = 16.3 Hz), 3.22 (3H, s), 3.69 (1H, d, J = 9.7 Hz), 3.79 (1H, d, J = 9.7 Hz), 4.74 (2H, s), 6.75 (1H, d, J = 9.7 Hz), 7.00-6.95 (2H, m), 7.05 (1H, d, J = 7.9 Hz), 7.35-7.29 (1H, m), 7.65 (2H, d, J = 9.1 Hz), 7.75 (1H, d, J = 9.7 Hz), 7.82 (1H, s), 8.01 (2H, d, J = 8.5 Hz). |

TABLE 17-1-continued

| Example | Reference Example | Structure and name | Instrumental data |
|---|---|---|---|
| 85 | 69 | 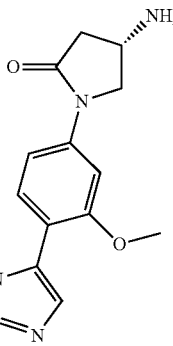<br>(4S)-4-Amino-1-[4-[6-[(3-fluorophenyl)methyl-methylamino]imidazo[1,2-b]pyridazin-3-yl]-3-methoxyphenyl]pyrrolidin-2-one | $^1$H-NMR (DMSO-$d_6$) δ: 1.85-1.96 (2H, br m), 2.23 (1H, dd, J = 16.6, 3.9 Hz), 2.75 (1H, dd, J = 16.6, 7.3 Hz), 3.16 (3H, s), 3.50 (1H, dd, J = 9.7, 3.9 Hz), 3.63-3.68 (1H, m), 3.81 (3H, s), 4.01 (1H, dd, J = 10.0, 6.3 Hz), 4.76 (2H, s), 7.04-7.13 (5H, m), 7.34-7.39 (1H, m), 7.62-7.64 (1H, m), 7.80 (1H, s), 7.88 (1H, d, J = 9.7 Hz), 8.00 (1H, d, J = 8.5 Hz).<br>ESI-MS (m/z): 461 (M + H)$^+$. |

TABLE 17-2

| 86 | 78 | 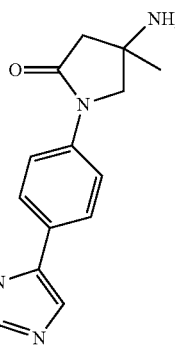<br>4-Amino-1-[4-[6-[(3-fluorophenyl)methyl-methylamino]imidazo[1,2-b]pyridazin-3-yl]phenyl]-4-methylpyrrolidin-2-one | $^1$H-NMR (CDCl$_3$) δ: 1.46 (3H, s), 2.57 (1H, d, J = 16.9 Hz), 2.68 (1H, d, J = 16.9 Hz), 3.22 (3H, s), 3.69 (1H, d, J = 9.7 Hz), 3.79 (1H, d, J = 9.7 Hz), 4.74 (2H, s), 6.75 (1H, d, J = 9.7 Hz), 6.95-6.99 (m, 2H), 7.04-7.07 (1H, m), 7.29-7.35 (1H, m), 7.65 (2H, d, J = 9.1 Hz), 7.75 (1H, d, J = 9.7 Hz), 7.83 (1H, s), 8.01 (2H, d, J = 9.1 Hz). |
| 87 | 79 | 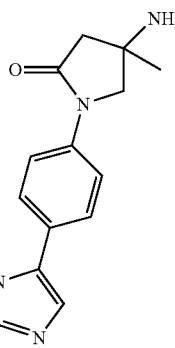<br>4-Amino-1-[4-[6-[(3-fluorophenyl)methyl-methylamino]imidazo[1,2-b]pyridazin-3-yl]phenyl]-4-methyl pyrrolidin-2-one | $^1$H-NMR (CDCl$_3$) δ: 1.46 (3H, s), 2.57 (1H, d, J = 16.9 Hz), 2.68 (1H, d, J = 16.9 Hz), 3.22 (3H, s), 3.69 (1H, d, J = 9.7 Hz), 3.79 (1H, d, J = 9.7 Hz), 4.74 (2H, s), 6.75 (1H, d, J = 9.7 Hz), 6.95-6.99 (2H, m), 7.04-7.07 (1H, m), 7.29-7.35 (1H, m), 7.65 (2H, d, J = 9.1 Hz), 7.75 (1H, d, J = 9.7 Hz), 7.83 (1H, s), 8.01 (2H, d, J = 9.1 Hz). |

Example 88

(4S)-4-Amino-1-[4-[6-[[(1R)-1-phenylethyl]amino]imidazo[1,2-b]pyridazin-3-yl]phenyl]pyrrolidin-2-one

[Formula 65]

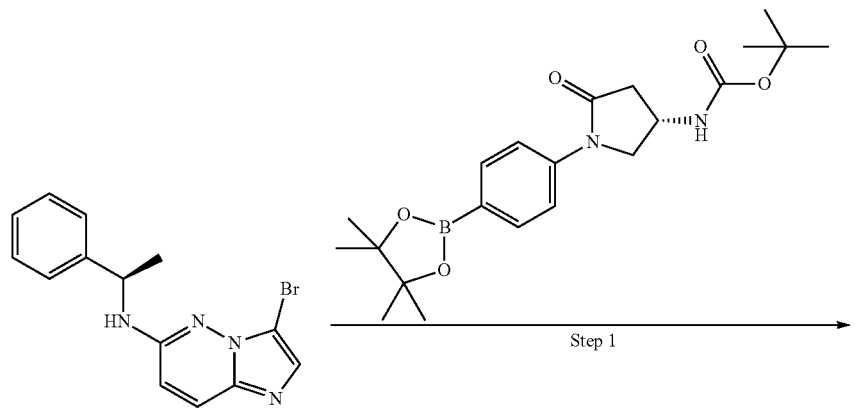

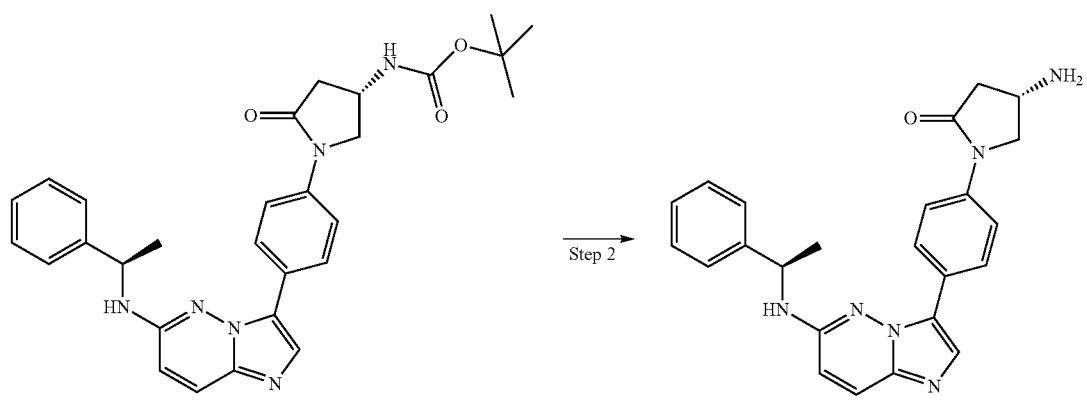

Step 1 tert-Butyl N-[(3S)-5-oxo-1-[4-[6-[[(1R)-1-phenylethyl]amino]imidazo[1,2-b]pyridazin-3-yl]phenyl]pyrrolidin-3-yl]carbamate The title compound (0.42 g) was obtained by the same procedures as in step 1 of Example 72 with the compound (0.31 g) obtained in step 1 of Example 19 as the starting material using the compound (0.47 g) obtained in step 3 of Reference Example 65.

$^1$H-NMR (CDCl$_3$) δ: 1.44 (9H, s), 1.56 (3H, d, J=6.6 Hz), 2.49 (1H, dd, J=17.4, 4.5 Hz), 2.99 (1H, dd, J=17.6, 7.8 Hz), 3.74 (1H, dd, J=10.6, 3.9 Hz), 4.14-4.23 (1H, m), 4.44 (1H, br s), 4.66 (1H, d, J=5.9 Hz), 4.85 (1H, br s), 4.88-4.97 (1H, m), 6.44 (1H, d, J=9.4 Hz), 7.22-7.40 (5H, m), 7.57 (2H, d, J=9.4 Hz), 7.63 (1H, d, J=9.0 Hz), 7.69 (1H, s), 7.75 (2H, d, J=9.0 Hz).

(4S)-4-Amino-1-[4-[6-[[(1R)-1-phenylethyl]amino]imidazo[1,2-b]pyridazin-3-yl]phenyl]pyrrolidin-2-one The title compound (0.17 g) was obtained by the same procedures as in step 2 of Example 72 with the compound (0.42 g) obtained in the preceding step 1 as the starting material.

$^1$H-NMR (CDCl$_3$) δ: 1.53 (2H, br s), 1.56 (3H, d, J=6.6 Hz), 2.41 (1H, dd, J=17.0, 4.9 Hz), 2.91 (1H, dd, J=17.0, 7.2 Hz), 3.57 (1H, dd, J=9.8, 3.9 Hz), 3.81-3.86 (1H, m), 4.09 (1H, dd, J=10.2, 6.3 Hz), 4.67 (1H, d, J=5.9 Hz), 4.89-4.96 (1H, m), 6.44 (1H, d, J=9.8 Hz), 7.24-7.41 (5H, m), 7.58 (2H, d, J=8.6 Hz), 7.63 (1H, d, J=9.8 Hz), 7.69 (1H, s), 7.75 (2H, d, J 9.0 Hz).

The following compound was obtained by the same procedures as in Example 88 with the compound obtained in step 1 of Example 19 as the starting material using the compound obtained in the Reference Example.

TABLE 18
| Example | Reference Example | Structure and name | Instrumental data |
|---|---|---|---|
| 89 | 72 | 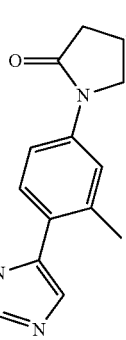<br>(4S)-4-Amino-1-[3-methyl-1-[6-[[(1R)-1-phenylethyl]amino]imidazo[1,2-b]yl]phenyl]pyrrolidin-2-one | $^1$H-NMR (CDCl$_3$) δ: 1.49 (3H, d, J = 7.3 Hz), 1.65 (2H, br s), 2.08 (3H, s), 2.61 (1H, dd, J = 16.9, 6.0 Hz), 2.90 (1H, dd, J = 16.9, 8.5 Hz), 4.05-4.17 (2H, m), 4.29-4.39 (1H, m), 4.70 (1H, d, J = 6.7 Hz), 4.74-4.83 (1H, m), 6.44 (1H, d, J = 9.7Hz), 7.22-7.35 (6H, m), 7.43-7.50 (2H,m), 7.55-7.59 (m, 1H), 7.64 (1H, d, J =9.1 Hz). |
Example 90
(4S)-4-Amino-1-[4-[6-[[(1R)-1-(3-fluorophenyl)ethyl]amino]imidazo[1,2-b]pyridazin-3-yl]phenyl]pyrrolidin-2-one
[Formula 66]
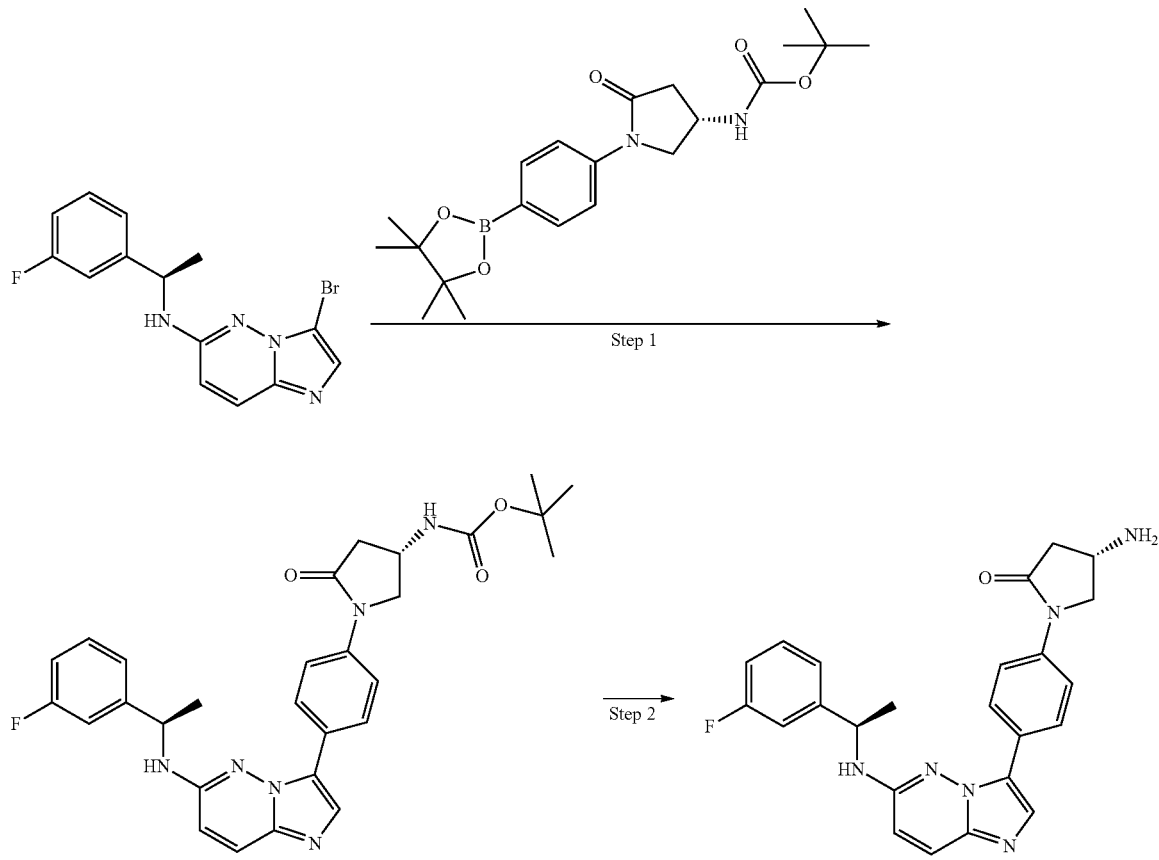

Step 1 tert-Butyl N-[(3S)-1-[4-[6-[[(1R)-1-(3-fluorophenyl)ethyl]amino]imidazo[1,2-b]pyridazin-3-yl]phenyl]-5-oxopyrrolidin-3-yl]carbamate 1,4-Dioxane (10 ml) and water (3 ml) were added to the compound (0.31 g) obtained in step 1 of Example 21, the compound (0.31 g) obtained in step 3 of Reference Example 65, potassium carbonate (0.43 g), and a [1,1'-bis(diphenylphosphino)ferrocene]dichloropalladium(II)-dichloromethane adduct (89 mg), and the mixture was heated to reflux for 1 hour under a nitrogen atmosphere. After cooling, water was added to the reaction solution, followed by extraction with ethyl acetate. The extract was washed with saturated saline and then dried over anhydrous magnesium sulfate. The solvent was distilled off under reduced pressure. The obtained residue was purified by silica gel column chromatography (ethyl acetate-methanol) to obtain the title compound (0.31 g).

$^1$H-NMR (CDCl$_3$) δ: 1.48 (9H, s), 1.58 (3H, d, J=6.6 Hz), 2.53 (1H, dd, J=17.3, 4.3 Hz), 3.02 (1H, dd, J=17.3, 8.0 Hz), 3.78 (1H, dd, J=10.6, 3.5 Hz), 4.20-4.25 (1H, m), 4.47 (1H, br s), 4.71 (1H, br s), 4.89-4.94 (1H, m), 6.50 (1H, d, J=9.4 Hz), 6.97 (1H, td, J=8.6, 2.7 Hz), 7.11-7.14 (1H, m), 7.21 (1H, d, J=7.8 Hz), 7.34-7.40 (1H, m), 7.60 (2H, d, J=9.0 Hz), 7.68-7.74 (4H, m).

(4S)-4-Amino-1-[4-[6-[[(1R)-1-(3-fluorophenyl)ethyl]amino]imidazo[1,2-b]pyridazin-3-yl]phenyl]pyrrolidin-2-one To a solution of the compound (0.31 g) obtained in the preceding step 1 in methanol (3 ml), a solution of 4 N hydrochloric acid in 1,4-dioxane (5 ml) was added, and the mixture was stirred at room temperature for 1 hour. The reaction solution was concentrated under reduced pressure. A 1 N aqueous sodium hydroxide solution was added to the obtained residue, followed by extraction with chloroform-methanol. The extract was washed with saturated saline and then dried over anhydrous sodium sulfate. The solvent was distilled off under reduced pressure. The obtained residue was purified by silica gel column chromatography (basic silica gel, chloroform-methanol) to obtain the title compound (0.16 g).

$^1$H-NMR (DMSO-d$_6$) δ: 1.49 (3H, d, J=7.0 Hz), 2.23 (1H, dd, J=16.8, 4.3 Hz), 2.75 (1H, dd, J=16.8, 7.2 Hz), 3.17 (1H, d, J=5.1 Hz), 3.49 (1H, dd, J=9.6, 3.9 Hz), 3.66-3.68 (1H, m), 4.00 (1H, dd, J=9.6, 6.1 Hz), 4.87 (1H, dq, J=5.1, 7.0 Hz), 6.79 (1H, d, J=9.4 Hz), 7.01-7.06 (1H, m), 7.23-7.29 (2H, m), 7.36-7.42 (1H, m), 7.65 (2H, dd, J=5.5, 3.5 Hz), 7.77 (1H, d, J=9.4 Hz), 7.81-7.86 (3H, m).

The following compounds were obtained by the same procedures as in Example 90 with the compound obtained in step 1 of Example 21 as the starting material using the compounds obtained in the Reference Examples.

TABLE 19

| Example | Reference Example | Structure and name | Instrumental data |
|---|---|---|---|
| 91 | 66 | 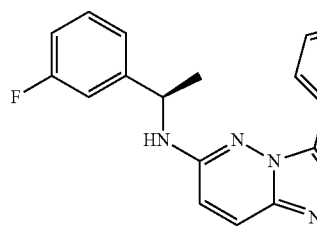<br>(4S)-4-Amino-1-[3-[6-[[(1R)-1-(3-fluorophenyl)ethyl]amino]imidazo[1,2-b]pyridazin-3-yl]phenyl]pyrrolidin-2-one | $^1$H-NMR (CDCl$_3$) δ: 1.58 (3H, d, J = 6.6 Hz), 2.42 (1H, dd, J = 17.2, 4.9 Hz), 2.92 (1H, dd, J = 17.2, 7.4 Hz), 3.58 (1H, dd, J = 9.0, 4.6 Hz), 3.81-3.87 (1H, m), 4.10 (1H, dd, J = 9.0, 7.0 Hz), 4.72 (1H, d, J = 5.9 Hz), 4.99-5.06 (1H, m), 6.49 (1H, d, J = 9.8 Hz), 6.92-6.97 (1H, m), 7.11-7.14 (1H, m), 7.19 (1H, d, J = 7.8 Hz), 7.28-7.38 (2H, m), 7.53-7.56 (2H, m), 7.68 (1H, d, J = 9.4 Hz), 7.76 (1H, s), 8.09 (1H, t, J = 2.0 Hz). |
| 92 | 67 | 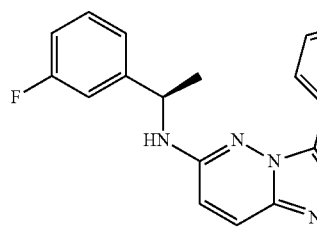<br>(4S)-4-Amino-1-[2-fluoro-4-[6-[[(1R)-1-(3-fluorophenyl)ethyl]amino]imidazo[1,2-b]pyridazin-3-yl]phenyl]pyrrolidin-2-one | $^1$H-NMR (CDCl$_3$) δ: 1.59 (3H, d, J = 7.0 Hz), 2.40 (1H, dd, J = 16.8, 4.7 Hz), 2.90 (1H, dd, J = 16.8, 7.2 Hz), 3.57 (1H, dd, J = 9.8, 4.3 Hz), 3.88-3.93 (1H, m), 4.08-4.12 (1H, m), 4.87 (1H, br s), 4.93-5.00 (1H, m), 6.52 (1H, d, J = 9.8 Hz), 6.91-6.96 (1H, m), 7.11 (1H, dt, J = 9.8, 2.2 Hz), 7.22 (1H, d, J = 7.8 Hz), 7.33 (1H, td, J = 7.8, 5.9 Hz), 7.42 (1H, t, J = 8.2 Hz), 7.51 (1H, dd, J = 8.4, 1.8 Hz), 7.67-7.69 (1H, m), 7.74-7.77 (2H, m). |

TABLE 19-continued

| Example | Reference Example | Structure and name | Instrumental data |
|---|---|---|---|
| 93 | 68 | 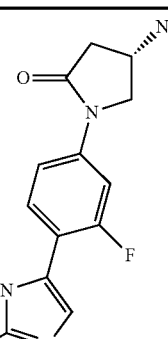<br>(4S)-4-Amino-1-[3-fluoro-4-[6-[[(1R)-1-(3-fluorophenyl)ethyl]amino]imidazo[1,2-b]pyridazin-3-yl]phenyl]pyrrolidin-2-one | $^1$H-NMR (CDCl$_3$) δ: 1.57 (3H, d, J = 6.6 Hz), 2.45 (1H, dd, J = 17.0, 4.9 Hz), 2.95 (1H, dd, J = 17.0, 7.2 Hz), 3.61 (1H, dd, J = 10.0, 4.1 Hz), 3.87-3.91 (1H, m), 4.10 (1H, dd, J = 10.0, 6.5 Hz), 4.71 (1H, d, J = 5.1 Hz), 4.85-4.91 (1H, m), 6.52 (1H, d, J = 9.4 Hz), 6.95-6.99 (1H, m), 7.09 (1H, dt, J = 9.8, 2.0 Hz), 7.19 (1H, d, J = 7.8 Hz), 7.25-7.28 (1H, m), 7.35 (1H, td, J = 8.0, 6.0 Hz), 7.66-7.72 (2H, m), 7.77 (1H, t, J = 8.6 Hz), 7.85 (1H, d, J = 3.9 Hz). |

Example 94

(4S)-4-Amino-1-[4-[6-[benzyl(methyl)amino]imidazo[1,2-b]pyridazin-3-yl]phenyl]pyrrolidin-2-one

[Formula 67]

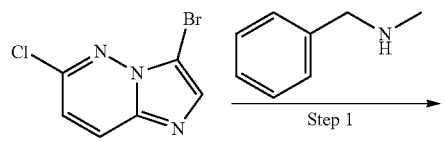

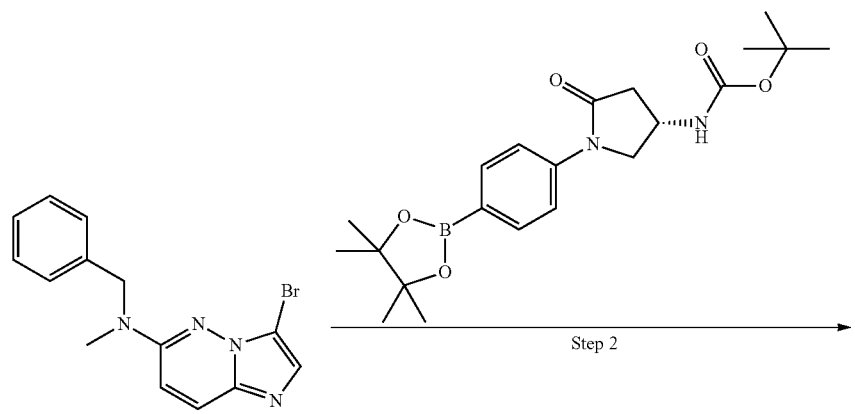

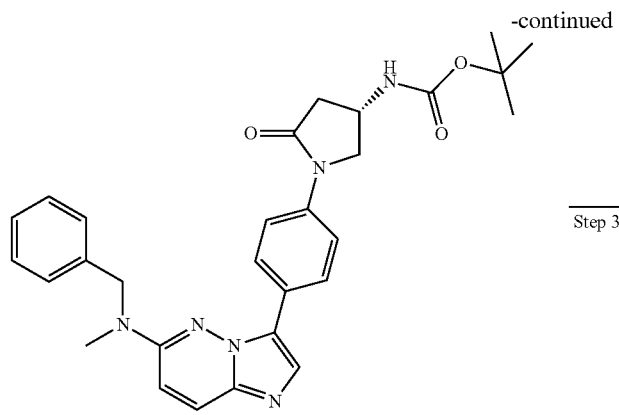
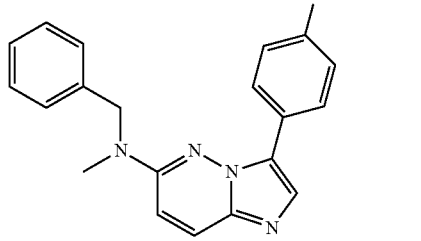

Step 1

N-Benzyl-3-bromo-N-methylimidazo[1,2-b]pyridazin-6-amine

The title compound (0.43 g) was obtained by the same procedures as in step 1 of Example 1 using N-methyl-1-phenyl-methanamine instead of phenylmethanamine.

$^1$H-NMR (CDCl$_3$) δ: 3.20 (3H, s), 4.76 (2H, s), 6.73 (1H, d, J=9.7 Hz), 7.27-7.36 (5H, m), 7.51 (1H, s), 7.63 (1H, d, J=9.7 Hz).

Step 2 tert-Butyl N-[(3S)-1-[4-[6-[benzyl(methyl)amino]imidazo[1,2-b]pyridazin-3-yl]phenyl]-5-oxopyrrolidin-3-yl]carbamate The title compound (0.36 g) was obtained by the same procedures as in step 1 of Example 72 with the compound (0.22 g) obtained in the preceding step 1 and the compound (0.33 g) obtained in step 3 of Reference Example 65 as starting materials.

$^1$H-NMR (CDCl$_3$) δ: 1.46 (9H, s), 2.51 (1H, dd, J=17.2, 4.5 Hz), 3.00 (1H, dd, J=17.5, 7.9 Hz), 3.22 (3H, s), 3.76 (1H, dd, J=10.3, 3.0 Hz), 4.13-4.23 (1H, m), 4.44 (1H, br s), 4.76 (2H, s), 4.88 (1H, br s), 6.77 (1H, d, J=10.3 Hz), 7.22-7.30 (3H, m), 7.32-7.38 (2H, m), 7.65 (2H, d, J=9.1 Hz), 7.73 (1H, d, J=9.7 Hz), 7.83 (1H, s), 8.05-8.09 (2H, m).

Step 3

(4S)-4-Amino-1-[4-[6-[benzyl(methyl)amino]imidazo[1,2-b]pyridazin-3-yl]phenyl]pyrrolidin-2-one The title compound (0.18 g) was obtained by the same procedures as in step 2 of Example 72 with the compound (0.36 g) obtained in the preceding step 2 as the starting material.

$^1$H-NMR (CDCl$_3$) δ: 2.43 (1H, dd, J=16.9, 4.8 Hz), 2.93 (1H, dd, J=17.2, 7.6 Hz), 3.22 (3H, s), 3.59 (1H, dd, J=9.7, 4.2 Hz), 3.82-3.88 (1H, m), 4.10 (1H, dd, J=10.0, 6.3 Hz), 4.76 (2H, s), 6.77 (1H, d, J=10.3 Hz), 7.25-7.31 (3H, m), 7.34-7.37 (2H, m), 7.67 (2H, d, J=9.1 Hz), 7.73 (1H, d, J=9.7 Hz), 7.83 (1H, s), 8.07 (2H, d, J=8.5 Hz).

The following compound was obtained by the same procedures as in Example 94.

TABLE 20

| Example | Reference Example | Structure and name | Instrumental data |
|---|---|---|---|
| 95 | 65 | (4S)-4-Amino-1-[4-[6-[benzo(ethyl)amino]imidazo[1,2-b]pyridazin-3-yl]phenyl]pyrrolidin-2-one | $^1$H-NMR (CDCl$_3$) δ: 1.29 (3H, t, J = 7.3 Hz), 2.42 (1H, dd, J = 17.2, 5.1 Hz), 2.93 (1H, dd, J = 16.9, 7.3 Hz), 3.59 (1H, dd, J = 9.7, 4.2 Hz), 3.66 (2H, q, J = 7.1 Hz), 3.82-3.88 (1H, m), 4.08-4.12 (1H, m), 4.74 (2H, s), 6.71 (1H, d, J = 9.7 Hz), 7.26-7.31 (3H, m), 7.32-7.37 (2H, m), 7.63 (2H, d, J = 8.5 Hz), 7.71 (1H, d, J = 9.7 Hz), 7.80 (1H, s), 8.00 (2H, d, J = 8.5 Hz). |

Example 96

4-Amino-1-[4-[6-[(3-chlorophenyl)methyl-methylamino]imidazo[1,2-b]pyridazin-3-yl]phenyl]pyrrolidin-2-one

[Formula 68]

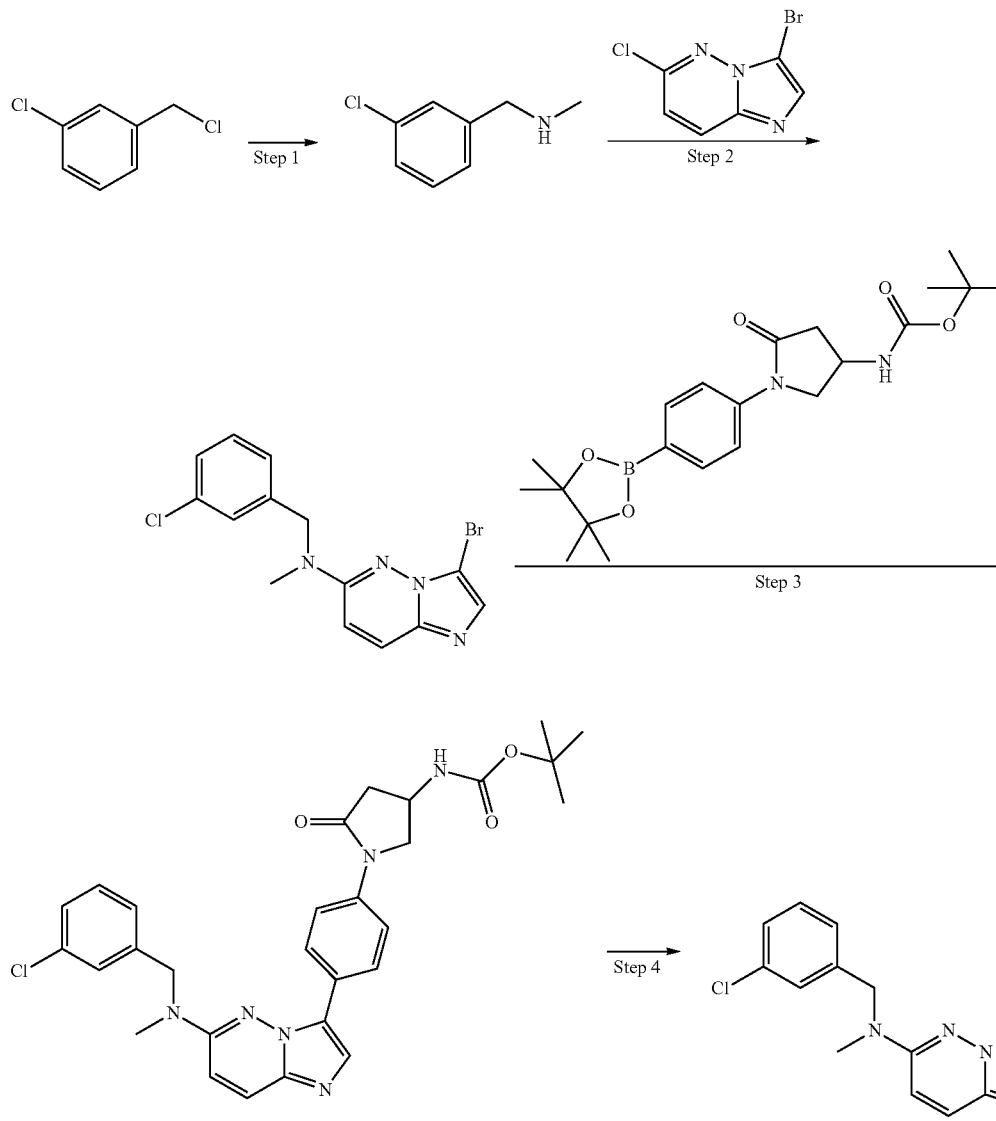

Step 1

1-(3-Chlorophenyl)-N-methylmethanamine

To a solution of methylamine (2.0 M solution in tetrahydrofuran, 30 ml) in N,N-dimethylformamide (30 ml), 3-chlorobenzyl chloride (2.5 ml) was added, and the mixture was stirred at room temperature for 4.5 hours. Water was added to the reaction solution, followed by extraction with ethyl acetate. The extract was washed with water and saturated saline in this order and then dried over anhydrous sodium sulfate. The solvent was distilled off under reduced pressure to obtain a crude product of the title compound, which was used in the next reaction without being purified.

$^1$H-NMR (CDCl$_3$) δ: 2.42 (3H, s), 3.69 (2H, s), 7.14-7.36 (4H, m).

Step 2

3-Bromo-N-[(3-chlorophenyl)methyl]-N-methylimidazo[1,2-b]pyridazin-6-amine

The title compound (1.7 g) was obtained by the same procedures as in step 1 of Example 1 using the compound obtained in the preceding step 1 instead of phenylmethanamine.

$^1$H-NMR (CDCl$_3$) δ: 3.17 (3H, s), 4.71 (2H, s), 6.69 (1H, d, J=9.8 Hz), 7.16-7.32 (4H, m), 7.49 (1H, s), 7.63 (1H, d, J=9.8 Hz).

Step 3 tert-Butyl N-[1-[4-[6-[(3-chlorophenyl)methyl-methylamino]imidazo[1,2-b]pyridazin-3-yl]phenyl]-5-oxopyrrolidin-3-yl]carbamate The title compound (0.26 g) was obtained by the same procedures as in step 1 of Example 72 with the compound (0.20 g) obtained in the preceding step 2 and the compound (0.30 g) obtained in step 3 of Reference Example 61 as starting materials.

$^1$H-NMR (CDCl$_3$) δ: 1.47 (9H, s), 2.52 (1H, dd, J=17.4, 4.5 Hz), 3.01 (1H, dd, J=17.4, 8.0 Hz), 3.23 (3H, s), 3.75-3.81 (1H, m), 4.18-4.25 (1H, m), 4.45 (1H, br s), 4.73 (2H, s), 4.95 (1H, br s), 6.76 (1H, d, J=9.8 Hz), 7.13-7.17 (1H, m), 7.26-7.33 (3H, m), 7.65 (2H, d, J=8.6 Hz), 7.77 (1H, d, J=9.8 Hz), 7.83 (1H, s), 8.00 (2H, d, J=9.0 Hz).

Step 4

4-Amino-1-[4-[6-[(3-chlorophenyl)methyl-methylamino]imidazo[1,2-b]pyridazin-3-yl]phenyl]pyrrolidin-2-one The title compound (0.16 g) was obtained by the same procedures as in step 2 of Example 72 with the compound (0.26 g) obtained in the preceding step 3 as the starting material.

$^1$H-NMR (CDCl$_3$) δ: 2.39 (1H, dd, J=17.2, 5.1 Hz), 2.89 (1H, dd, J=17.2, 7.4 Hz), 3.20 (3H, s), 3.56 (1H, dd, J=9.8, 4.3 Hz), 3.79-3.85 (1H, m), 4.05-4.09 (1H, m), 4.69 (2H, s), 6.72 (1H, d, J=10.2 Hz), 7.11-7.13 (1H, m), 7.20-7.27 (3H, m), 7.63 (2H, d, J=9.0 Hz), 7.73 (1H, d, J=9.8 Hz), 7.79 (1H, s), 7.96 (2H, d, J=9.0 Hz).

The following compounds were obtained by the same procedures as in Example 96

TABLE 21

| Example | Reference Example | Structure and name | Instrumental data |
|---|---|---|---|
| 97 | 65 | 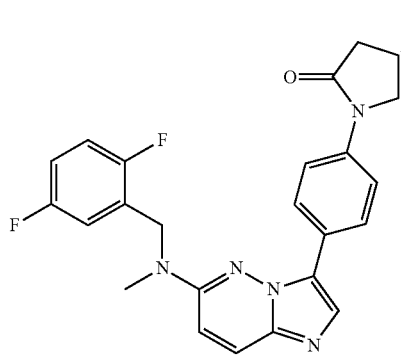<br>(4S)-4-Amino-1-[4-[6-[(2,5-difluorophenyl)methyl-methylamino]imidazo[1,2-b]pyridazin-3-yl]phenyl]pyrrolidin-2-one | $^1$H-NMR (CDCl$_3$) δ: 2.42 (1H, dd, J = 17.2, 5.1 Hz), 2.93 (1H, dd, J = 16.9, 7.3 Hz), 3.25 (3H, s), 3.59 (1H, dd, J = 9.7, 4.2 Hz), 3.82-3.88 (1H, m), 4.08-4.13 (1H, m), 4.77 (2H, s), 6.76 (1H, d, J = 9.7 Hz), 6.89-6.97 (2H, m), 7.05-7.11 (1H, m), 7.66 (2H, d, J = 9.1 Hz), 7.78 (1H, dd, J = 10.3 Hz), 7.83 (s, 1H), 8.01 (2H, d, J = 9.1 Hz). |
| 98 | 65 | 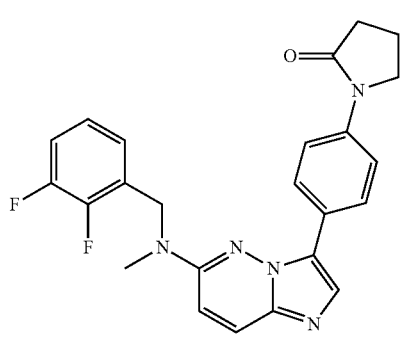<br>(4S)-4-Amino-1-[4-[6-[(2,3-difluorophenyl)methyl-methylamino]imidazo[1,2-b]pyridazin-3-yl]phenyl]pyrrolidin-2-one | $^1$H-NMR (CDCl$_3$) δ: 2.22 (1H, dd, J = 16.9, 4.2 Hz), 2.74 (1H, dd, J = 16.3, 7.3 Hz), 3.25 (3H, s), 3.44-3.48 (1H, m), 3.63-3.68 (1H, m), 3.98 (1H, dd, J = 9.7, 6.0 Hz), 4.91 (2H, s), 7.03-7.07 (1H, m), 7.11-7.16 (2H, m), 7.30-7.37 (1H, m), 7.67 (2H, d, J = 9.1 Hz), 7.91-7.95 (2H, m), 8.02 (2H, d, J = 9.1 Hz). |

TABLE 21-continued

| Example | Reference Example | Structure and name | Instrumental data |
|---|---|---|---|
| 99 | 65 | 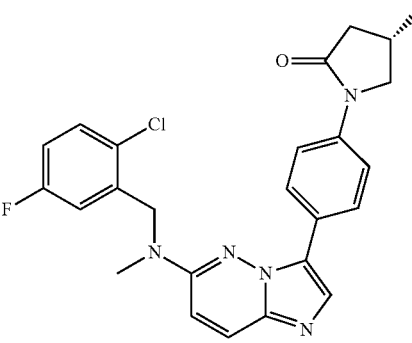<br>(4S)-4-Amino-1-[4-[6-[(2-chloro-5-fluorophenyl)methyl-methylamino]imidazo[1,2-b]pyridazin-3-yl]phenyl]pyrrolidin-2-one | $^1$H-NMR (CDCl$_3$) δ: 2.43 (1H, dd, J = 16.9, 4.8 Hz), 2.93 (1H, dd, J = 17.2, 7.6 Hz), 3.30 (3H, s), 3.59 (1H, dd, J = 10.0, 3.9 Hz), 3.84-3.89 (1H, m), 4.10 (1H, dd, J = 9.7, 6.7 Hz), 4.78 (2H, s), 6.71 (1H, d, J = 10.3 Hz), 6.87-6.97 (2H, m), 7.42 (1H, dd, J = 8.5, 4.8 Hz), 7.64 (2H, d, J = 8.5 Hz), 7.78 (1H, d, J = 9.7 Hz), 7.85 (1H, s), 7.98 (2H, d, J = 9.1 Hz). |
| 100 | 65 | 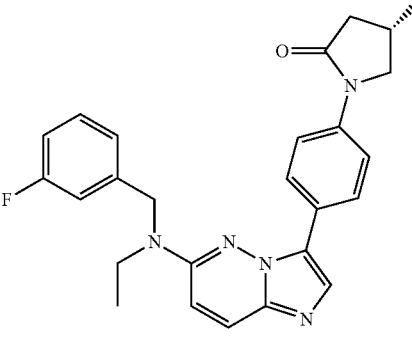<br>(4S)-4-Amino-1-[4-[6-[ethyl[(3-fluorophenyl)methyl]amino]imidazo[1,2-b][yridazin-3-yl]phenyl]pyrrolidin-2-one | $^1$H-NMR (CDCl$_3$) δ: 1.26 (3H, t, J = 7.0 Hz), 2.39 (1H, dd, J = 17.0, 4.9 Hz), 2.89 (1H, dd, J = 16.8, 7.4 Hz), 3.55 (1H, dd, J = 9.8, 3.9 Hz), 3.62 (2H, q, J = 7.0 Hz), 3.79-3.85 (1H, m), 4.06 (1H, dd, J = 9.8, 6.3 Hz), 4.68 (2H, s), 6.68 (1H, d, J = 10.2 Hz), 6.90-6.99 (2H, m), 7.03-7.05 (1H, m), 7.26-7.32 (1H, m), 7.59 (2H, d, J = 9.0 Hz), 7.70 (1H, dd, J = 9.8 Hz), 7.77 (1H, s), 7.89 (2H, d, J = 9.0 Hz). |

Example 101

3-[[3-[4-[(4S)-4-Amino-2-oxopyrrolidin-1-yl]phenyl]imidazo[1,2-b]pyridazin-6-yl]oxymethyl]benzonitrile

[Formula 69]

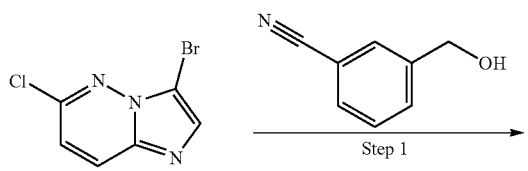
Step 1

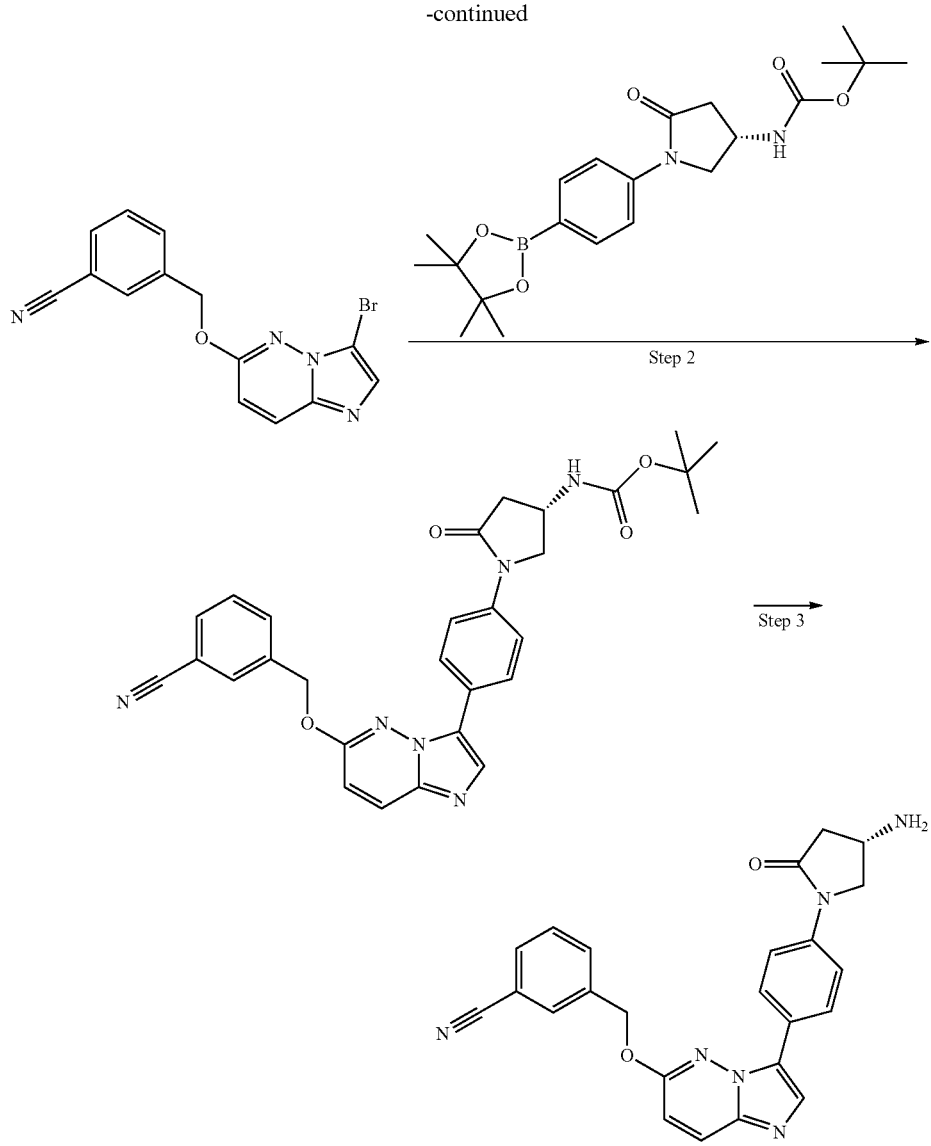

Step 1

3-[(3-Bromoimidazo[1,2-b]pyridazin-6-yl)oxymethyl]benzonitrile

The title compound (1.75 g) was obtained by the same procedures as in step 1 of Example 11 using 3-(hydroxymethyl)benzonitrile (1.50 g) instead of 3-fluorobenzyl alcohol.
$^1$H-NMR (CDCl$_3$) δ: 5.45 (2H, s), 6.75 (1H, d, J=9.8 Hz), 7.49 (1H, t, J=7.8 Hz), 7.59 (1H, s), 7.62 (1H, dt, J=7.8, 1.4 Hz), 7.75-7.79 (2H, m), 7.87 (1H, t, J=1.4 Hz).
ESI-MS (m/z): 329, 331 (M+H)$^+$.

Step 2 tert-Butyl N-[(3S)-1-[4-[6-[(3-cyanophenyl)methoxy]imidazo[1,2-b]pyridazin-3-yl]phenyl]-5-oxopyrrolidin-3-yl]carbamate The title compound (286 mg) was obtained by the same procedures as in step 1 of Example 72 using the compound (250 mg) obtained in the preceding step 1 and the compound (306 mg) obtained in step 3 of Reference Example 65.
$^1$H-NMR (CDCl$_3$) δ: 1.47 (9H, s), 2.55 (1H, dd, J=17.6, 4.3 Hz), 3.02 (1H, dd, J=17.6, 7.8 Hz), 3.82 (1H, dd, J=10.4, 3.3 Hz), 4.26 (1H, dd, J=10.4, 6.8 Hz), 4.44-4.49 (1H, m), 4.98-5.02 (1H, m), 5.43 (2H, s), 6.81 (1H, d, J=9.4 Hz), 7.52 (1H, t, J=7.8 Hz), 7.61-7.64 (1H, m), 7.70-7.72 (1H, m), 7.75-7.78 (3H, m), 7.87 (1H, s), 7.88-7.93 (3H, m).
ESI-MS (m/z): 525 (M+H)$^+$.

Step 3

3-[[3-[4-[(4S)-4-Amino-2-oxopyrrolidin-1-yl]phenyl]imidazo[1,2-b]pyridazin-6-yl]oxymethyl]benzonitrile The title compound (194 mg) was obtained by the same procedures as in step 2 of Example 79 using the compound (286 mg) obtained in the preceding step 2.
$^1$H-NMR (CDCl$_3$) δ: 1.48-1.63 (2H, m), 2.45 (1H, dd, J=16.8, 4.7 Hz), 2.95 (1H, dd, J=16.8, 7.4 Hz), 3.65 (1H, dd, J=9.8, 3.9 Hz), 3.85-3.91 (1H, m), 4.16 (1H, dd, J=9.8, 6.7 Hz), 5.43 (2H, s), 6.80 (1H, d, J=9.8 Hz), 7.53 (1H, t, J=7.8 Hz), 7.64 (1H, dt, J=7.8, 1.4 Hz), 7.72 (1H, dt, J=7.8, 1.4 Hz), 7.75-7.79 (3H, m), 7.86-7.91 (4H, m).
ESI-MS (m/z): 425 (M+H)$^+$.

The following compounds were obtained by the same procedures as in Example 101.

TABLE 22

| Example | Reference Example | Structure and name | Instrumental data |
|---|---|---|---|
| 102 | 65 | 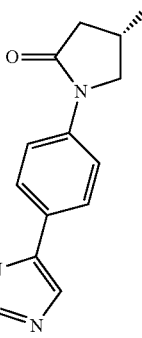<br>(4S)-4-Amino-1-[4-[6-[1-(2,3-difluorophenyl)ethoxy]imidazo[1,2-b]pyridazin-3-yl]phenyl]pyrrolidin-2-one | $^1$H-NMR (CDCl$_3$) δ: 1.72 (3H, d, J = 6.7 Hz), 2.45 (1H, dd, J = 17.2, 5.1 Hz), 2.95 (1H, dd, J = 17.2, 7.6 Hz), 3.61-3.67 (1H, m), 3.85-3.91 (1H, m), 4.13-4.18 (1H, m), 6.26 (1H, q, J = 6.7 Hz), 6.79 (1H, d, J = 9.7 Hz), 7.02-7.11 (2H, m), 7.18 (1H, t, J = 6.3 Hz), 7.70 (2H, d, J = 8.5 Hz), 7.76 (2H, d, J = 8.5 Hz), 7.84 (1H, s), 7.86 (1H, d, J = 9.7 Hz).<br>ESI-MS (m/z): 450 (M + H)$^+$. |
| 103 | 65 | 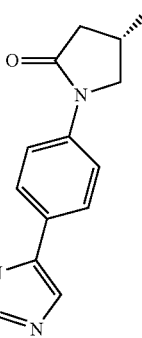<br>(4S)-4-Amino-1-[4-[6-[(5-fluoro-2-methylphenyl)methoxy]imidazo[1,2-b]pyriazin-3-yl]phenyl]pyrrolidin-2-one | $^1$H-NMR (CDCl$_3$) δ: 1.54 (2H, br s), 2.36 (3H, s), 2.44 (1H, dd, J = 16.9, 4.8 Hz), 2.95 (1H, dd, J = 16.9, 7.3 Hz), 3.62 (1H, dd, J = 10.0, 4.2 Hz), 3.85-3.91 (1H, m), 4.13 (1H, dd, J = 10.0, 6.7 Hz), 5.38 (2H, s), 6.79 (1H, d, J = 9.7 Hz), 6.97 (1H, td, J = 8.5, 3.0 Hz), 7.16 (1H, dd, J = 9.7, 3.0 Hz), 7.22 (1H, dd, J = 8.5, 5.4 Hz), 7.72-7.75 (2H, m), 7.89 (2H, t, J = 4.8 Hz), 7.95-7.99 (2H, m).<br>ESI-MS (m/z): 432 (M + H)$^+$. |
| 104 | 65 | 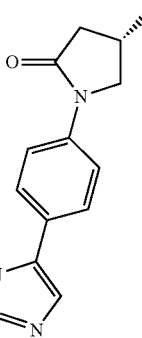<br>(4S)-4-Amino-1-[4-[6-[1-(2,5-difluorophenyl)ethoxy]imidazo[1,2-b]pyridazin-3-yl]phenyl]pyrrolidin-2-one | $^1$H-NMR (CDCl$_3$) δ: 1.70 (3H, d, J = 6.7 Hz), 2.45 (1H, dd, J = 16.9, 4.8 Hz), 2.95 (1H, dd, J = 17.2, 7.6 Hz), 3.62 (1H, dd, J = 10.0, 3.9 Hz), 3.85-3.92 (1H, m), 4.11-4.16 (1H, m), 6.25 (1H, q, J = 6.4 Hz), 6.80 (1H, d, J = 9.1 Hz), 6.90-6.96 (1H, m), 7.08-7.14 (2H, m), 7.68 (2H, d, J = 9.1 Hz), 7.79-7.88 (4H, m). |

TABLE 22-continued
| Example | Reference Example | Structure and name | Instrumental data |
|---|---|---|---|
| 105 | 65 | 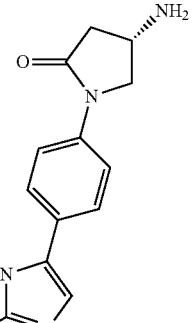(4S)-4-Amino-1-[4-[6-(1-thiazol-2-ylethoxy)imidazo[1,2-b]pyridazin-3-yl]phenyl]pyrrolidin-2-one | $^1$H-NMR (DMSO-$d_6$) δ: 1.81 (3H, d, J = 6.7 Hz), 1.95-2.10 (2H, br m), 2.20-2.27 (1H, m), 2.72-2.79 (1H, m), 3.47-3.53 (1H, m), 3.63-3.69 (1H, m), 3.99-4.05 (1H, m), 6.42 (1H, q, J = 6.7 Hz), 7.03 (1H, d, J = 9.7 Hz), 7.72 (1H, d, J = 3.6 Hz), 7.74-7.78 (2H, m), 7.82-7.84 (1H, m), 8.00-8.04 (2H, m), 8.10 (1H, s), 8.13 (1H, d, J = 9.7 Hz). ESI-MS (m/z): 421 (M + H)$^+$. |
Example 106
(4S)-4-Amino-1-[4-[6-[(1-(2,5-difluoro-3-pyridyl)ethoxy]imidazo[1,2-b]pyridazin-3-yl]phenyl]pyrrolidin-2-one
[Formula 70]
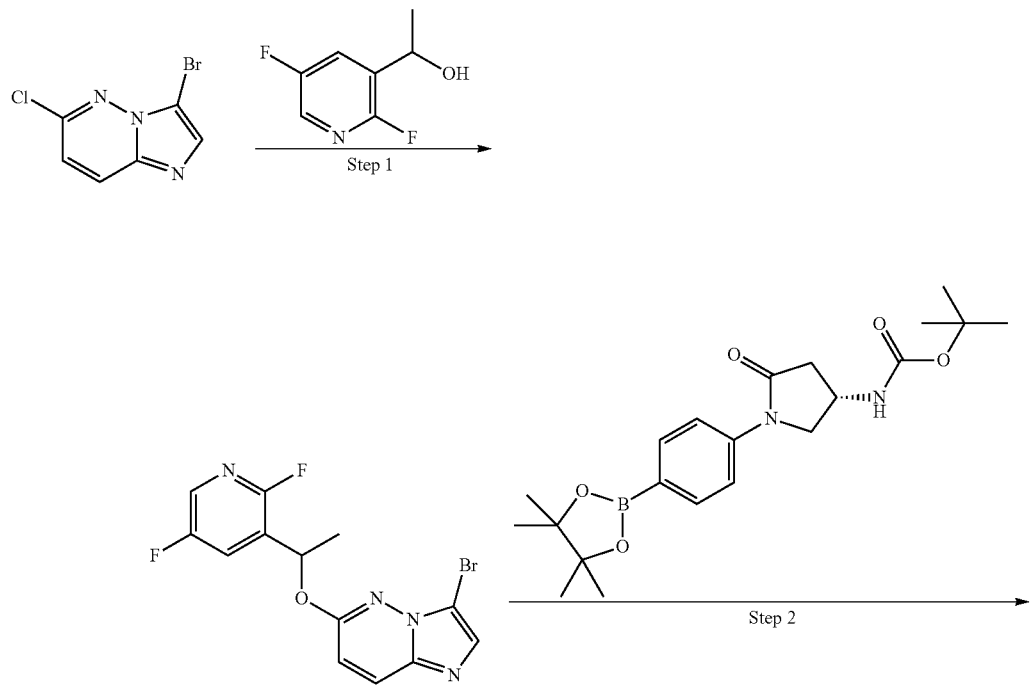

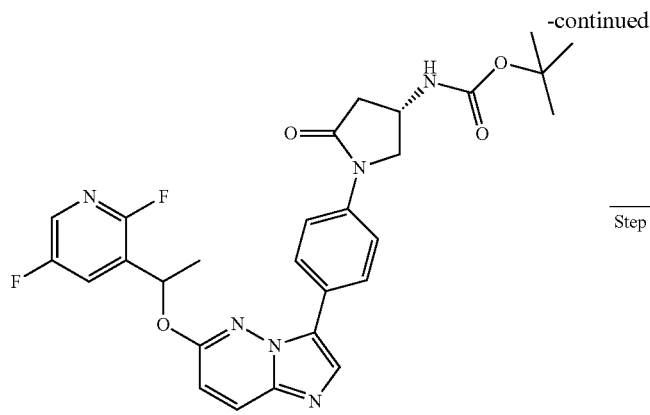
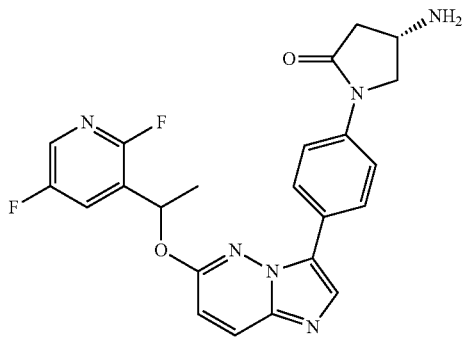

Step 1

3-Bromo-6-[1-(2,5-difluoro-3-pyridyl)ethoxy]imidazo[1,2-b]pyridazine

The title compound (0.74 g) was obtained by the same procedures as in step 1 of Example 11 using the compound (0.35 g) obtained in step 5 of Reference Example 54 instead of 3-fluorobenzyl alcohol.

$^1$H-NMR (CDCl$_3$) δ: 1.76 (3H, d, J=6.7 Hz), 6.23 (1H, q, J=6.7 Hz), 6.78 (1H, d, J=9.7 Hz), 7.58 (1H, s), 7.65 (1H, td, J=7.9, 3.0 Hz), 7.80 (1H, d, J=9.7 Hz), 7.96-7.98 (1H, m).

Step 2 tert-Butyl N-[(3S)-1-[4-[6-[1-(2,5-difluoro-3-pyridyl)ethoxy]imidazo[1,2-b]pyridazin-3-yl]phenyl]-5-oxopyrrolidin-3-yl]carbamate The title compound (154 mg) was obtained by the same procedures as in step 1 of Example 72 with the compound (290 mg) obtained in the preceding step 1 as the starting material using the compound (329 mg) obtained in step 3 of Reference Example 65.

$^1$H-NMR (CDCl$_3$) δ: 1.48 (9H, s), 1.72 (3H, d, J=6.7 Hz), 2.58 (1H, dd, J=17.5, 4.8 Hz), 3.01 (1H, dd, J=17.5, 8.5 Hz), 3.81 (1H, dd, J=10.3, 4.2 Hz), 4.19-4.28 (1H, m), 4.43-4.53 (1H, m), 5.41 (1H, d, J=7.3 Hz), 6.13 (1H, q, J=6.7 Hz), 6.80 (1H, d, J=9.7 Hz), 7.58 (1H, td, J=7.3, 3.0 Hz), 7.65-7.73 (4H, m), 7.84 (1H, s), 7.89 (1H, d, J=9.7 Hz), 7.93-7.95 (1H, m).

ESI-MS (m/z): 551 (M+H)$^+$.

Step 3

(4S)-4-Amino-1-[4-[6-[1-(2,5-difluoro-3-pyridyl)ethoxy]imidazo[1,2-b]pyridazin-3-yl]phenyl]pyrrolidin-2-one The title compound (81 mg) was obtained by the same procedures as in step 2 of Example 79 using the compound (154 mg) obtained in the preceding step 2.

$^1$H-NMR (CDCl$_3$) δ: 1.73 (3H, d, J=6.7 Hz), 2.45 (1H, dd, J=16.9, 5.1 Hz), 2.95 (1H, dd, J=16.9, 7.3 Hz), 3.65 (1H, dd, J=10.0, 3.9 Hz), 3.85-3.91 (1H, m), 4.16 (1H, dd, J=10.0, 6.3 Hz), 6.16 (1H, q, J=6.7 Hz), 6.81 (1H, d, J=9.7 Hz), 7.58 (1H, td, J=7.3, 3.0 Hz), 7.69-7.75 (4H, m), 7.86 (1H, s), 7.90 (1H, d, J=9.7 Hz), 7.95-7.96 (1H, m).

ESI-MS (m/z): 451 (M+H)$^+$.

The following compounds were obtained by the same procedures as in Example 106.

TABLE 23-1

| Example No. | Reference Example No. | Structure and name | Instrumental data |
|---|---|---|---|
| 107 | 56, 65 | (4S)-4-Amino-1-[4-[6-[(1-(5-fluoro-3-pyridyl)ethoxy]imidazo[1,2-b]pyridazin-3-yl]phenyl]pyrrolidin-2-one | $^1$H-NMR (CDCl$_3$) δ: 1.48 (9H, s), 1.74 (3H, d, J = 6.6 Hz), 2.55 (1H, dd, J = 17.2, 4.3 Hz), 3.03 (1H, dd, J = 17.4, 8.0 Hz), 3.82 (1H, dd, J = 10.0, 3.3 Hz), 4.23-4.28 (1H, m), 4.44-4.51 (1H, m), 4.92 (1H, br s), 6.03 (1H, q, J = 6.6 Hz), 6.79 (1H, d, J = 9.4 Hz), 7.46-7.50 (1H, m), 7.71-7.75 (4H, m), 7.83 (1H, s), 7.88 (1H, d, J = 9.4 Hz), 8.41 (1H, d, J = 2.7 Hz), 8.53 (1H, t, J = 1.6 Hz). ESI-MS (m/z): 533 (M + H)$^+$. |

TABLE 23-1-continued

| Example No. | Reference Example No. | Structure and name | Instrumental data |
|---|---|---|---|
| 108 | 56, 71 | 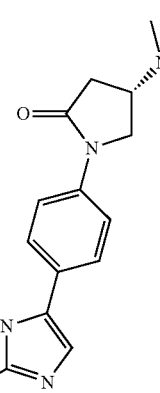(4S)-1-[4-[6-[(1R)-1-(5-Fluoro-3-pyridyl)ethoxy]imidazo[1,2-b]pyridazin-3-yl]phenyl]-4-(methylamino)pyrrolidin-2-one | ¹H-NMR (CDCl₃) δ: 1.74 (3H, d, J = 6.7 Hz), 2.50-2.56 (1H, m), 2.52 (3H, s), 2.91 (1H, dd, J = 17.2, 7.6 Hz), 3.53-3.59 (1H, m), 3.74 (1H, dd, J = 9.7, 4.2 Hz), 4.11 (1H, dd, J = 9.7, 6.7 Hz), 6.03 (1H, q, J = 6.7 Hz), 6.78 (1H, d, J = 9.7 Hz), 7.48 (1H, dt, J = 9.1, 2.1 Hz), 7.70-7.75 (4H, m), 7.82 (1H, s), 7.87 (1H, d, J = 9.7 Hz), 8.41 (1H, d, J = 2.4 Hz), 8.53 (1H, s).<br>ESI-MS (m/z): 447 (M + H)⁺. |

TABLE 23-2

| Example No. | Reference Example No. | Structure and name | Instrumental data |
|---|---|---|---|
| 109 | 56, 67 | 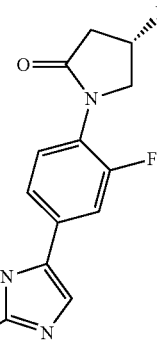(4S)-4-Amino-1-[2-fluoro-4-[6-[(1R)-1-(5-fluoro-3-pyridyl)ethoxy]imidazo[1,2-b]pyridazin-3-yl]phenyl]pyrrolidin-2-one | ¹H-NMR (CDCl₃) δ: 1.75 (3H, d, J = 6.7 Hz), 2.40 (1H, dd, J = 17.0, 5.4 Hz), 2.90 (1H, dd, J = 17.0, 7.6 Hz), 3.61 (1H, dd, J = 10.3, 4.2 Hz), 3.88-3.94 (1H, m), 4.10-4.14 (1H, m), 6.07 (1H, q, J = 6.7 Hz), 6.84 (1H, d, J = 9.7 Hz), 7.47-7.59 (3H, m), 7.70 (1H, dd, J = 12.7, 1.8 Hz), 7.86 (1H, s), 7.90 (1H, d, J = 9.7 Hz), 8.41 (1H, d, J = 2.4 Hz), 8.55-8.56 (1H, m).<br>ESI-MS (m/z): 451 (M + H)⁺. |
| 110 | 56, 68 | 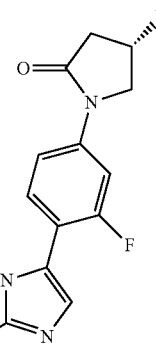(4S)-4-Amino-1-[3-fluoro-4-[6-[(1R)-1-(5-fluoro-3-pyridyl)ethoxy]imidazo[1,2-b]pyridazin-3-yl]phenyl]pyrrolidin-2-one | ¹H-NMR (CDCl₃) δ: 1.71 (3H, d, J = 6.7 Hz), 2.46 (1H, dd, J = 16.9, 4.8 Hz), 2.96 (1H, dd, J = 16.9, 6.7 Hz), 3.64 (1H, dd, J = 10.0, 3.9 Hz), 3.88-3.92 (1H, m), 4.13 (1H, dd, J = 10.0, 7.0 Hz), 5.96 (1H, q, J = 6.7 Hz), 6.80 (1H, d, J = 9.7 Hz), 7.40-7.44 (2H, m), 7.66 (1H, t, J = 8.2 Hz), 7.77 (1H, dd, J = 12.7, 1.8 Hz), 7.87-7.90 (2H, m), 8.40 (1H, d, J = 3.0 Hz), 8.47 (1H, s).<br>ESI-MS (m/z): 451 (M + H)⁺. |

TABLE 23-2-continued

| 111 | 56 74 | 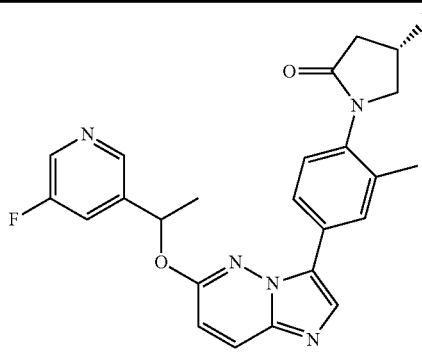<br>(4S)-4-Amino-1-[4-[6-[(1-(5-fluoro-3-pyridyl)ethoxy]imidazo[1,2-b]pyridazin-3-yl]-2-methylphenyl]pyrrolidin-2-one | $^1$H-NMR (CDCl$_3$) δ: 1.73 (3H, d, J = 6.7 Hz), 2.34 (3H, s), 2.40 (1H, dd, J = 16.9, 4.8 Hz), 2.91 (1H, dd, J = 16.9, 7.3 Hz), 3.48 (1H, dd, J = 9.7, 3.6 Hz), 3.91-3.97 (1H, m), 4.02 (1H, dd, J = 9.7, 6.7 Hz), 6.05 (1H, q, J = 6.7 Hz), 6.80 (1H, d, J = 9.7 Hz), 7.25-7.28 (1H, m), 7.46-7.53 (2H, m), 7.67 (1H, br s), 7.81 (1H, s), 7.88 (1H, d, J = 9.7 Hz), 8.42 (1H, d, J = 2.4 Hz), 8.53 (1H, br s).<br>ESI-MS (m/z): 447 (M + H)$^+$. |
|---|---|---|---|
| 112 | 57 65 | 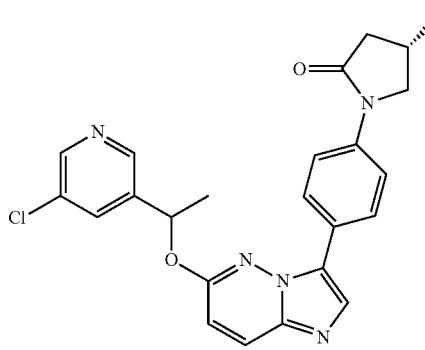<br>(4S)-4-Amino-1-[4-[6-[(1-(5-chloro-3-pyridyl)ethoxy]imidazo[1,2-b]pyridazin-3-yl]phenyl]pyrrolidin-2-one | $^1$H-NMR (CDCl$_3$) δ: 1.73 (3H, d, J = 6.7 Hz), 2.46 (1H, dd, J = 16.9, 4.8 Hz), 2.95 (1H, dd, J = 16.9, 7.3 Hz), 3.65 (1H, dd, J = 10.0, 4.2 Hz), 3.86-3.92 (1H, m), 4.15 (1H, dd, J = 10.0, 6.3 Hz), 5.98 (1H, q, J = 6.7 Hz), 6.78 (1H, d, J = 9.7 Hz), 7.70-7.77 (5H, m), 7.82 (1H, s), 7.87 (1H, d, J = 9.7 Hz), 8.51 (1H, d, J = 2.0 Hz), 8.58 (1H, d, J = 2.0 Hz).<br>ESI-MS (m/z): 449, 451 (M + H)$^+$. |

40

TABLE 23-3

| 113 | 55 65 | 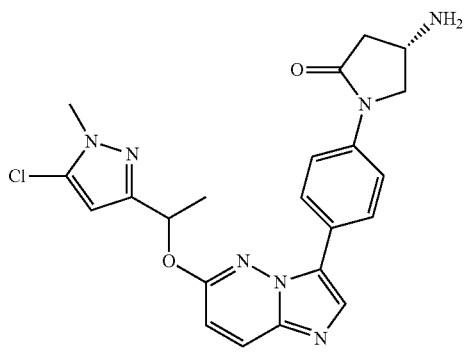<br>(4S)-4-Amino-1-[4-[6-[1-(5-chloro-1-methylpyrazol-3-yl)ethoxy]imidazo[1,2-b]pyridazin-3-yl]phenyl]pyrrolidin-2-one | $^1$H-NMR (CDCl$_3$) δ: 1.47 (9H, s), 1.74 (3H, d, J = 6.7 Hz), 2.53 (1H, dd, J = 17.5, 4.8 Hz), 3.02 (1H, dd, J = 17.5, 7.9 Hz), 3.79-3.84 (1H, m), 3.83 (3H, s), 4.24 (1H, dd, J = 10.3, 6.7 Hz), 4.46 (1H, br s), 4.88 (1H, br s), 6.11 (1H, q, J = 6.7 Hz), 6.25 (1H, s), 6.74 (1H, d, J = 9.7 Hz), 7.72-7.76 (2H, m), 7.83 (1H, d, J = 9.7 Hz), 7.89 (1H, s), 8.05-8.09 (2H, m).<br>ESI-MS (m/z): 552 (M + H)$^+$. |
|---|---|---|---|

TABLE 23-3-continued

| 114 | 58 65 | 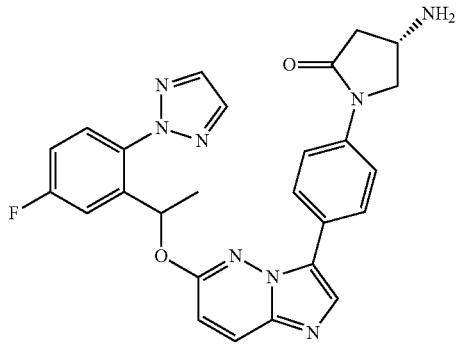 [SMILES: CC(Oc1ccc2ncc(-c3ccc(N4C[C@@H](N)CC4=O)cc3)n2n1)c1cc(F)ccc1-n1nccn1]<br><br>(4S)-4-Amino-1-[4-[6-[1-[5-fluoro-2-(triazol-2-yl)phenyl]ethoxy]imidazo[1,2-b]pyridazin-3-yl]phenyl]pyrrolidin-2-one | $^1$H-NMR (CDCl$_3$) δ: 1.62 (3H, d, J = 6.1 Hz), 2.46 (1H, dd, J = 17.1, 4.9 Hz), 2.96 (1H, ddd, J = 17.1, 7.5, 1.7 Hz), 3.59 (1H, dd, J = 9.8, 3.7 Hz), 3.85-3.92 (1H, m), 4.08-4.13 (1H, m), 6.76-6.81 (2H, m), 7.08-7.13 (1H, m), 7.45 (1H, dd, J = 9.8, 3.1 Hz), 7.60-7.64 (2H, m), 7.77 (1H, dd, J = 9.2, 5.2 Hz), 7.85-7.89 (4H, m), 7.96-7.97 (2H, m).<br>ESI-MS (m/z): 499 (M + H)$^+$. |
| 115 | 59 65 | 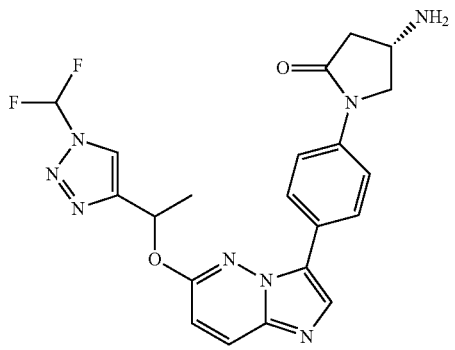 [SMILES: CC(Oc1ccc2ncc(-c3ccc(N4C[C@@H](N)CC4=O)cc3)n2n1)c1cn(C(F)F)nn1]<br><br>(4S)-4-Amino-1-[4-[6-[1-[1-(difluoromethyl)triazol-4-yl]ethoxy]imidazo[1,2-b]pyridazin-3-yl]phenyl]pyrrolidin-2-one | $^1$H-NMR (DMSO-d$_6$) δ: 1.81 (3H, d, J = 6.5 Hz), 1.90-2.02 (2H, br m), 2.24 (1H, dd, J = 16.6, 4.1 Hz), 2.76 (1H, dd, J = 16.6, 7.0 Hz), 3.47-3.52 (1H, m), 3.64-3.70 (1H, m), 3.98-4.04 (1H, m), 6.36 (1H, q, J = 6.5 Hz), 6.95 (1H, d, J = 9.8 Hz), 7.76-7.81 (2H, m), 8.05-8.12 (4H, m), 8.23 (1H, t, J = 58.3 Hz), 8.83 (1H, s).<br>ESI-MS (m/z): 455 (M + H)$^+$. |
| 116 | 60 65 | 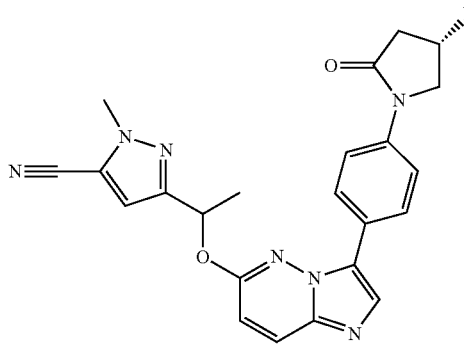<br><br>5-[1-[3-[4-[(4S)-4-Amino-2-oxopyrrolidin-1-yl]phenyl]imidazo[1,2-b]pyridazin-6-yl]oxyethyl]-2-methyl pyrazole-3-carbonitrile | $^1$H-NMR (DMSO-d$_6$) δ: 1.71 (3H, d, J = 6.5 Hz), 1.89-1.97 (2H, br m), 2.24 (1H, dd, J = 16.6, 4.1 Hz), 2.76 (1H, dd, J = 16.6, 7.0 Hz), 3.49-3.53 (1H, m), 3.64-3.69 (1H, m), 4.00 (3H, s), 4.01-4.05 (1H, m), 6.17 (1H, q, J = 6.5 Hz), 6.92 (1H, d, J = 9.8 Hz), 7.24 (1H, s), 7.78-7.82 (2H, m), 8.07-8.14 (4H, m).<br>ESI-MS (m/z): 443 (M + H)$^+$. |

Example 117

(4S)-4-Amino-1-[4-[6-[methyl(3-pyridylmethyl)amino]imidazo[1,2-b]pyridazin-3-yl]phenyl]pyrrolidin-2-one

[Formula 71]

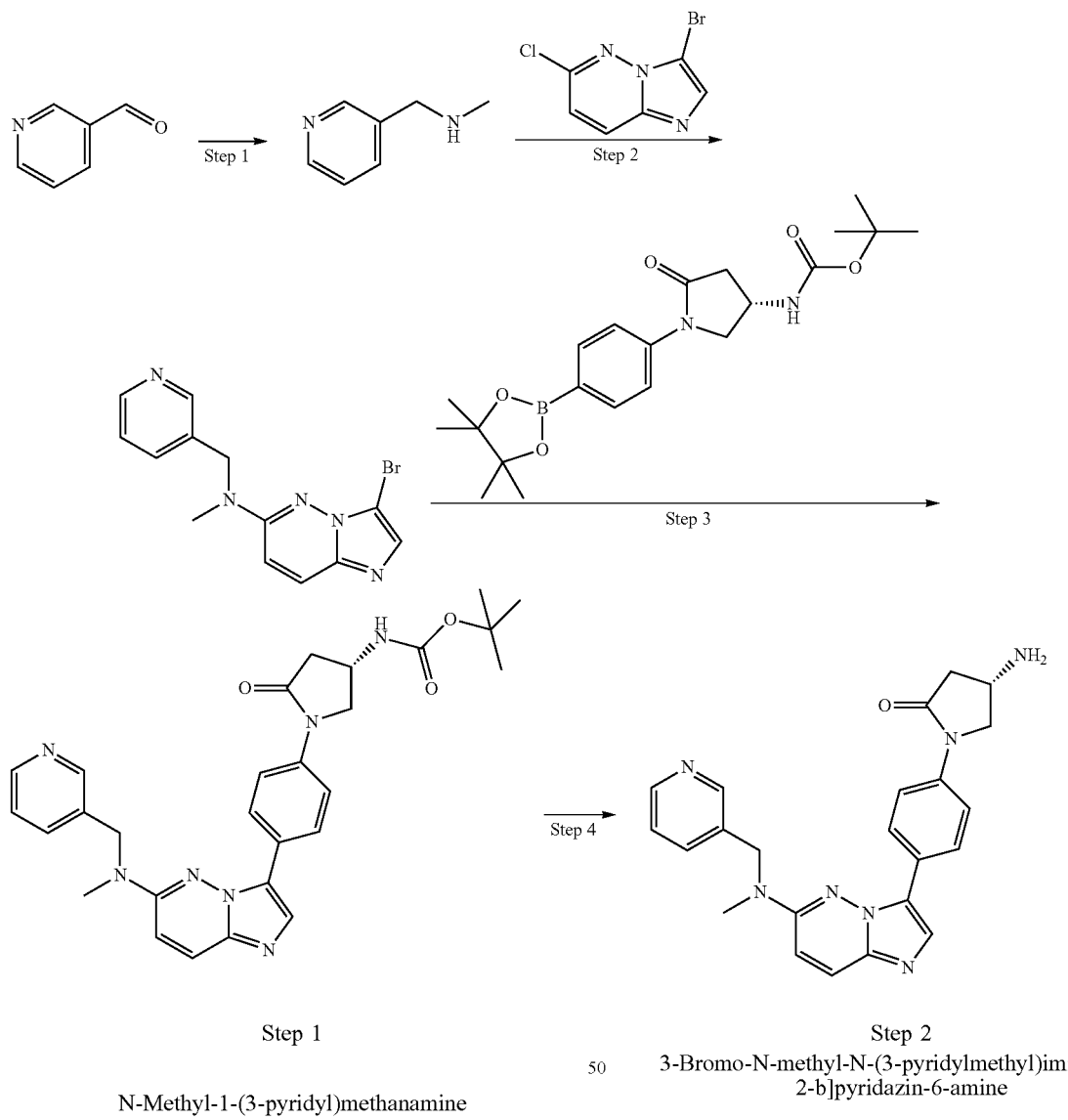

Step 1

N-Methyl-1-(3-pyridyl)methanamine

To a solution of 3-pyridine-carboxaldehyde (0.24 g) in methanol, methylamine (2.0 M solution in tetrahydrofuran, 6 ml) was added, and the mixture was stirred at room temperature for 23 hours. Then, sodium borohydride (0.22 g) was added thereto, and the mixture was stirred for 1 hour. The reaction solution was concentrated under reduced pressure. The residue was partially purified on a reverse-phase silica gel column. A crude product was obtained by decantation and directly used in the next reaction.

$^1$H-NMR (CD$_3$OD) δ: 3.75 (3H, s), 4.87 (2H, s), 7.33-7.46 (1H, m), 7.78-7.89 (1H, m), 8.44-8.59 (2H, m).

Step 2

3-Bromo-N-methyl-N-(3-pyridylmethyl)imidazo[1,2-b]pyridazin-6-amine

The title compound (0.07 g) was obtained by the same procedures as in step 1 of Example 1 using the compound obtained in the preceding step 1 instead of phenylmethanamine.

ESI-MS (m/z): 318 (M+H)$^+$.

Step 3 tert-Butyl N-[(3S)-1-[4-[6-[methyl(3-pyridylmethyl)amino]imidazo[1,2-b]pyridazin-3-yl]phenyl]-5-oxopyrrolidin-3-yl]carbamate The title compound (0.06 g) was obtained by the same procedures as in step 1 of Example 72 with the compound (0.07 g) obtained in the preceding step 2 and the compound (0.11 g) obtained in step 3 of Reference Example 65 as starting materials.

ESI-MS (m/z): 514 (M+H)$^+$.

Step 4

(4S)-4-Amino-1-[4-[6-[methyl(3-pyridylmethyl)amino]imidazo[1,2-b]pyridazin-3-yl]phenyl]pyrrolidin-2-one The title compound (0.037 g) was obtained by the same procedures as in step 2 of Example 72 with the compound (0.06 g) obtained in the preceding step 3 as the starting material.

¹H-NMR (CDCl₃) δ: 2.42 (1H, dd, J=16.9, 4.8 Hz), 2.92 (1H, dd, J=16.9, 7.3 Hz), 3.22 (3H, s), 3.59 (1H, dd, J=9.7, 4.2 Hz), 3.82-3.88 (1H, m), 4.10 (1H, dd, J=9.7, 6.7 Hz), 4.79 (2H, s), 6.79 (1H, d, J=9.7 Hz), 7.27-7.30 (1H, m), 7.59-7.62 (1H, m), 7.65 (2H, d, J=9.1 Hz), 7.78 (1H, d, J=10.3 Hz), 7.83 (1H, s), 7.98 (2H, d, J=9.1 Hz), 8.53-8.59 (2H, m).

The following compounds were obtained by the same procedures as in Example 117.

TABLE 24-1

| Example | Reference Example | Structure and name | Instrumental data |
|---|---|---|---|
| 118 | 65 | 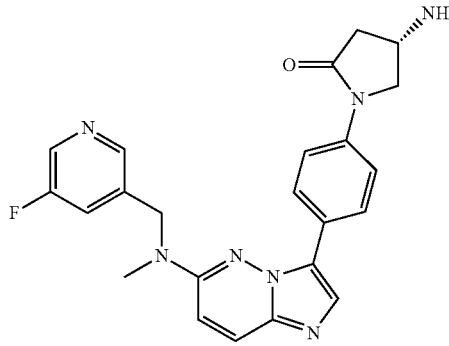<br>(4S)-4-Amino-1-[4-[6-[(5-fluoro-3-pyridyl)methyl-methylamino]imidazo[1,2-b]pyridazin-3-yl]phenyl]pyrrolidin-2-one | ¹H-NMR (CDCl₃) δ: 2.42 (1H, dd, J = 16.9, 4.8 Hz), 2.93 (1H, dd, J = 16.9, 7.3 Hz), 3.24 (3H, s), 3.59 (1H, dd, J = 9.7, 4.2 Hz), 3.83-3.89 (1H, m), 4.08-4.15 (1H, m), 4.80 (2H, s), 6.79 (1H, d, J = 10.3 Hz), 7.31-7.36 (1H, m), 7.66 (2H, d J = 9.1 Hz), 7.78-7.86 (2H, m), 7.93 (2H, d, J = 9.1 Hz), 8.39-8.42 (2H, m). |
| 119 | 75 | 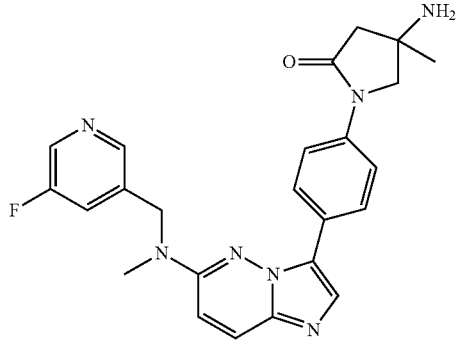 [SMILES: CN(Cc1cncc(F)c1)c1ccc2ncc(-c3ccc(N4CC(C)(N)CC4=O)cc3)n2n1]<br>4-Amino-1-[4-[6-[(5-fluoro-3-pyridyl)methyl-methylamino]imidazo[1,2-b]pyridazin-3-yl]phenyl]-4-methylpyrrolidin-2-one | ¹H-NMR (CDCl₃) δ: 1.46 (3H, s), 2.57 (1H, d, J = 16.3 Hz), 2.68 (1H, d, J = 16.9 Hz), 3.23 (3H, s), 3.69 (1H, d, J = 9.7 Hz), 3.79 (1H, d, J = 9.7 Hz), 4.80 (2H, s), 6.78 (1H, d, J = 10.3 Hz), 7.31-7.36 (1H, m), 7.65 (2H, d, J = 9.1 Hz), 7.79-7.84 (2H, m), 7.93 (2H, d, J = 8.5 Hz), 8.40-8.41 (2H, m). |

TABLE 24-1-continued

| Example | Reference Example | Structure and name | Instrumental data |
|---|---|---|---|
| 120 | 65 | 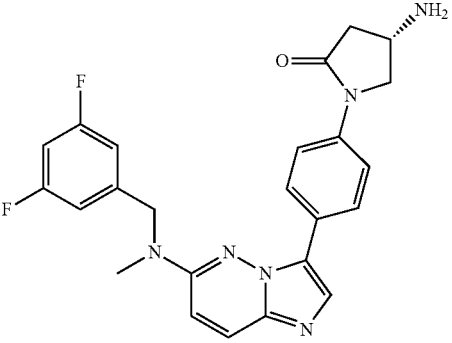 [SMILES: CN(Cc1cc(F)cc(F)c1)c1ccc2ncc(-c3ccc(N4C[C@@H](N)CC4=O)cc3)n2n1]<br>(4S)-4-Amino-1-[4-[6-[(3,5-difluorophenyl)methyl-methylamino]imidazo[1,2-b]pyridazin-3-yl]phenyl]pyrrolidin-2-one | $^1$H-NMR (DMSO-$d_6$) δ: 1.93 (2H, br s), 2.22 (1H, dd, J = 16.3, 4.2 Hz), 2.74 (1H, dd, J = 16.3, 7.3 Hz), 3.26 (3H, s), 3.47 (1H, dd, J = 9.7, 3.6 Hz), 3.62-3.69 (1H, m), 3.98 (1H, dd, J = 9.7, 6.0 Hz), 4.82 (2H, s), 6.99-7.15 (3H, m), 7.09 (1H, d, J = 10.3 Hz), 7.66-7.71 (2H, m), 7.92 (1H, d, J = 10.3 Hz), 7.95 (1H, s), 8.02-8.07 (2H, m).<br>ESI-MS (m/z): 449 (M + H)$^+$. |
| 121 | 65 | 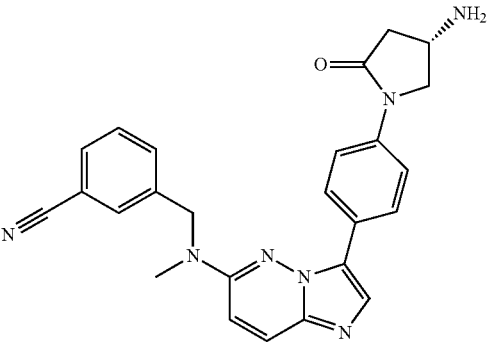 [SMILES: CN(Cc1cccc(C#N)c1)c1ccc2ncc(-c3ccc(N4C[C@@H](N)CC4=O)cc3)n2n1]<br>3-[[[3-[4-[(4S)-4-Amino-2-oxopyrrolidin-1-yl]phenyl]imidazo[1,2-b]pyridazin-6-yl]-methylamino]methyl]benzonitrile | $^1$H-NMR (DMSO-$d_6$) δ: 1.92-2.10 (2H, br m), 2.22 (1H, dd, J = 16.6, 4.2 Hz), 2.74 (1H, dd, J = 16.6, 7.3 Hz), 3.26 (3H, s), 3.48 (1H, dd, J = 9.7, 3.6 Hz), 3.62-3.68 (1H, m), 3.99 (1H, dd, J = 9.7, 6.0 Hz), 4.86 (2H, s), 7.11 (1H, d, J = 9.7 Hz), 7.55 (1H, t, J = 7.9 Hz), 7.61-7.80 (5H, m), 7.91 (1H, d, J = 9.7 Hz), 7.93 (1H, s), 8.01-8.05 (2H, m).<br>ESI-MS (m/z): 438 (M + H)$^+$. |

TABLE 24-2

| 122 | 65 | 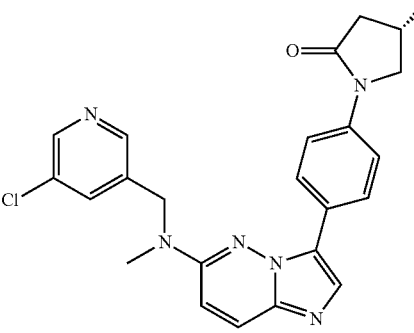<br>(4S)-4-Amino-1-[4-[6-[(5-chloro-3-pyridyl)methyl-methylamino]imidazo[1,2-b]pyridazin-3-yl]phenyl]pyrrolidin-2-one | $^1$H-NMR (CDCl$_3$) δ: 2.42 (1H, dd, J = 16.9, 4.8 Hz), 2.93 (1H, dd, J = 17.2, 7.6 Hz), 3.24 (3H, s), 3.59 (1H, dd, J = 9.7, 4.2 Hz), 3.83-3.89 (1H, m), 4.11 (1H, dd, J = 10.0, 6.3 Hz), 4.77 (2H, s), 6.79 (1H, d, J = 9.7 Hz), 7.60-7.62 (1H, m), 7.67 (2H, d, J = 9.1 Hz), 7.80-7.83 (2H, m), 7.92 (2H, d, J = 8.5 Hz), 8.46-8.51 (2H, m). |

TABLE 24-2-continued

| 123 | 75 | 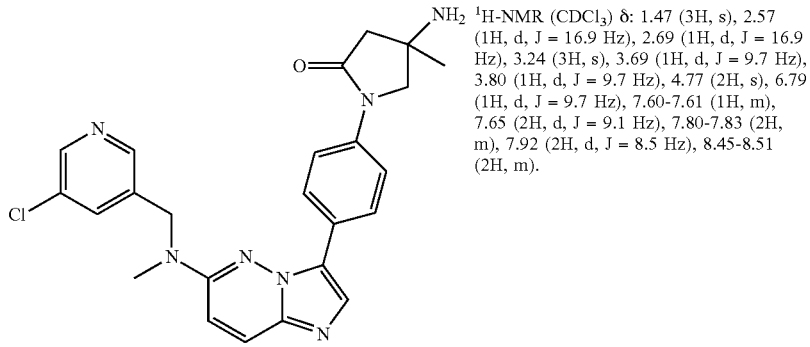

4-Amino-1-[4-[6-[(5-chloro-3-pyridyl)methyl-methylamino]imidazo[1,2-b]pyridazin-3-yl]phenyl]-4-methylpyrrolidin-2-one | $^1$H-NMR (CDCl$_3$) δ: 1.47 (3H, s), 2.57 (1H, d, J = 16.9 Hz), 2.69 (1H, d, J = 16.9 Hz), 3.24 (3H, s), 3.69 (1H, d, J = 9.7 Hz), 3.80 (1H, d, J = 9.7 Hz), 4.77 (2H, s), 6.79 (1H, d, J = 9.7 Hz), 7.60-7.61 (1H, m), 7.65 (2H, d, J = 9.1 Hz), 7.80-7.83 (2H, m), 7.92 (2H, d, J = 8.5 Hz), 8.45-8.51 (2H, m). |
|---|---|---|---|
| 124 | 78 | 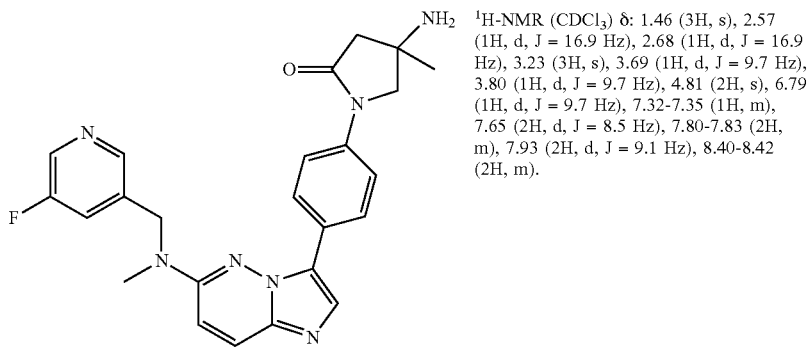

4-Amino-1-[4-[6-[(5-fluoro-3-pyridyl)methyl-methylamino]imidazo[1,2-b]pyridazin-3-yl]phenyl]-4-methylpyrrolidin-2-one | $^1$H-NMR (CDCl$_3$) δ: 1.46 (3H, s), 2.57 (1H, d, J = 16.9 Hz), 2.68 (1H, d, J = 16.9 Hz), 3.23 (3H, s), 3.69 (1H, d, J = 9.7 Hz), 3.80 (1H, d, J = 9.7 Hz), 4.81 (2H, s), 6.79 (1H, d, J = 9.7 Hz), 7.32-7.35 (1H, m), 7.65 (2H, d, J = 8.5 Hz), 7.80-7.83 (2H, m), 7.93 (2H, d, J = 9.1 Hz), 8.40-8.42 (2H, m). |
| 125 | 79 | 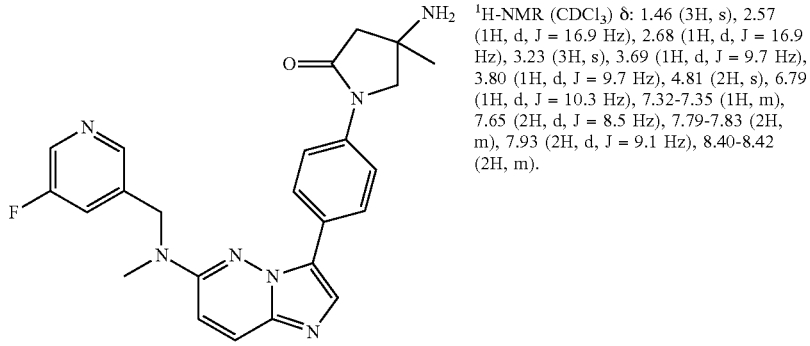

4-Amino-1-[4-[6-[(5-fluoro-3-pyridyl)methyl-methylamino]imidazo[1,2-b]pyridazin-3-yl]phenyl]-4-methylpyrrolidin-2-one | $^1$H-NMR (CDCl$_3$) δ: 1.46 (3H, s), 2.57 (1H, d, J = 16.9 Hz), 2.68 (1H, d, J = 16.9 Hz), 3.23 (3H, s), 3.69 (1H, d, J = 9.7 Hz), 3.80 (1H, d, J = 9.7 Hz), 4.81 (2H, s), 6.79 (1H, d, J = 10.3 Hz), 7.32-7.35 (1H, m), 7.65 (2H, d, J = 8.5 Hz), 7.79-7.83 (2H, m), 7.93 (2H, d, J = 9.1 Hz), 8.40-8.42 (2H, m). |

Example 126

(4S)-4-Amino-1-[4-[6-[(4-chloro-5-fluoro-3-pyridyl)methyl-methylamino]imidazo[1,2-b]pyridazin-3-yl]phenyl]pyrrolidin-2-one

[Formula 72]

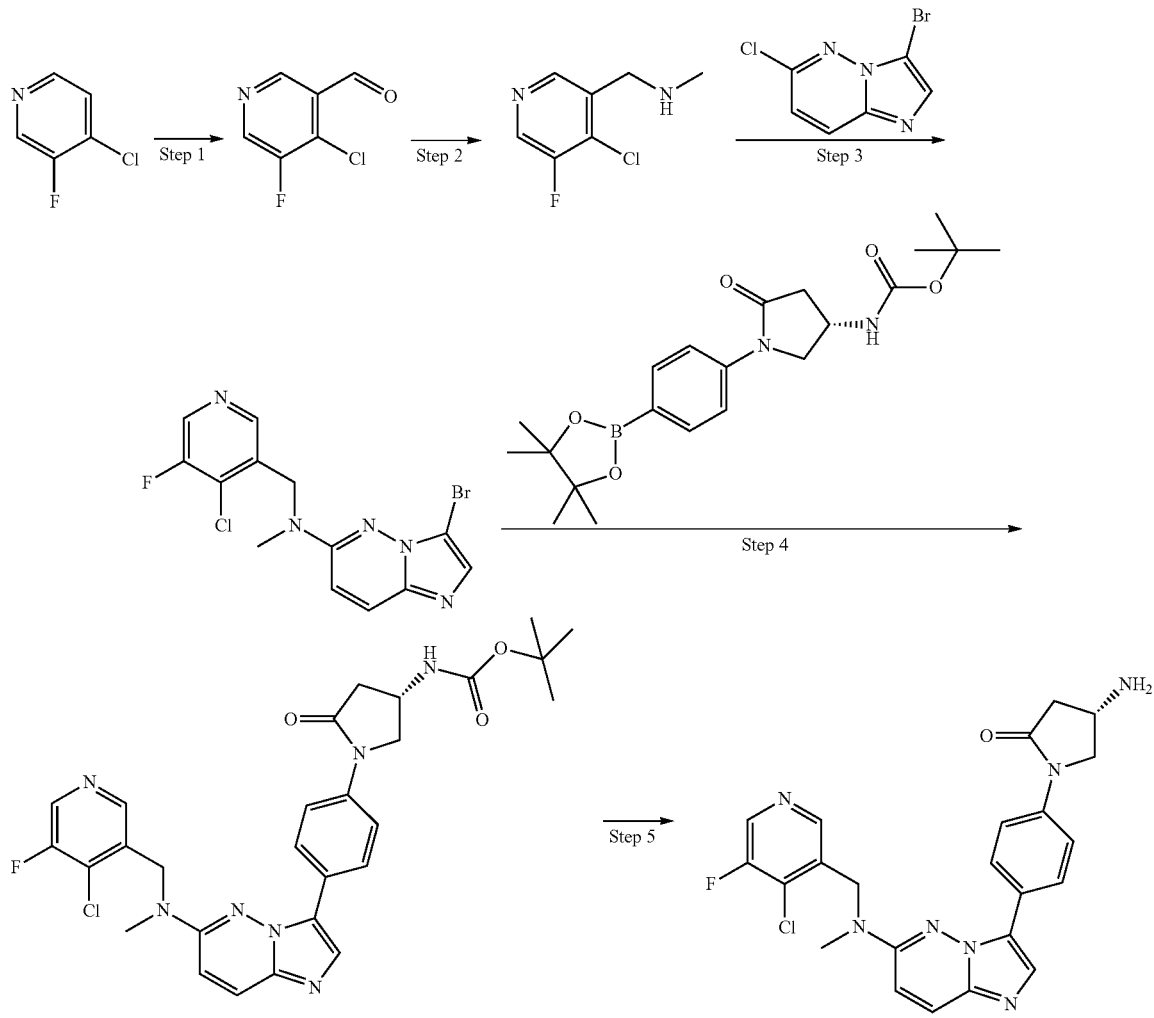

Step 1

4-Chloro-5-fluoropyridine-3-carboxaldehyde

4-Chloro-3-fluoropyridine (1 g) was dissolved in tetrahydrofuran (15 ml), and the solution was then cooled to −78° C. Lithium diisopropylamide (1.1 M solution in tetrahydrofuran and n-hexane, 7.6 ml) was added dropwise thereto, and the mixture was stirred at the same temperature as above for 5 hours. Then, N,N-dimethylformamide (1 ml) was added thereto, and the mixture was further stirred for 30 minutes while being heated to room temperature. Saturated saline was added to the reaction solution, followed by extraction with ethyl acetate. The extract was washed with water and saturated saline in this order and then dried over anhydrous sodium sulfate. The solvent was distilled off under reduced pressure. The obtained residue was purified by silica gel chromatography (n-hexane-ethyl acetate) to obtain the title compound (521 mg).

$^1$H-NMR (CDCl$_3$) δ: 8.70 (1H, s), 8.88 (1H, s), 10.47 (1H, s).

Step 2

1-(4-Chloro-5-fluoro-3-pyridyl)-N-methyl-methanamine

The title compound (258 mg) was obtained by the same procedures as in step 1 of Example 117 using the compound (521 mg) obtained in the preceding step 1 instead of 3-pyridine-carboxaldehyde.

ESI-MS (m/z): 175 (M+H)$^+$.

Step 3

3-Bromo-N-[(4-chloro-5-fluoro-3-pyridyl)methyl]-N-methylimidazo[1,2-b]pyridazin-6-amine The title compound (140 mg) was obtained by the same procedures as in step 1 of Example 1 using the compound (258 mg) obtained in the preceding step 2 instead of phenylmethanamine.

$^1$H-NMR (CDCl$_3$) δ: 3.30 (3H, s), 4.90 (2H, s), 6.76 (1H, d, J=9.7 Hz), 7.54 (1H, s), 7.73 (1H, d, J=9.7 Hz), 8.44 (1H, s), 8.52 (1H, s).

Step 4 tert-Butyl N-[(3S)-1-[4-[6-[(4-chloro-5-fluoro-3-pyridyl)methyl-methylamino]imidazo[1,2-b]pyridazin-3-yl]phenyl]-5-oxopyrrolidin-3-yl]carbamate The title compound (187 mg) was obtained by the same procedures as in step 1 of Example 72 with the compound (140 mg) obtained in the preceding step 3 as the starting material using the compound (210 mg) obtained in step 3 of Reference Example 65.

$^1$H-NMR (CDCl$_3$) δ: 1.47 (9H, s), 2.51 (1H, dd, J=17.2, 4.5 Hz), 3.01 (1H, dd, J=17.5, 7.9 Hz), 3.30 (3H, s), 3.74-3.79 (1H, m), 4.18-4.23 (1H, m), 4.44 (1H, br s), 4.83-4.90 (3H, m), 6.79 (1H, d, J=10.3 Hz), 7.62 (2H, d, J=8.5 Hz), 7.81-7.84 (2H, m), 7.90 (2H, d, J=9.1 Hz), 8.25 (1H, s), 8.44 (1H, s).

Step 5

(4S)-4-Amino-1-[4-[6-[(4-chloro-5-fluoro-3-pyridyl)methyl-methylamino]imidazo[1,2-b]pyridazin-3-yl]phenyl]pyrrolidin-2-one The title compound (73 mg) was obtained by the same procedures as in step 2 of Example 72 with the compound (185 mg) obtained in the preceding step 4 as the starting material.

$^1$H-NMR (DMSO-d$_6$): 2.22 (1H, dd, J=16.6, 4.5 Hz), 2.73 (1H, dd, J=16.6, 7.0 Hz), 3.32 (3H, s), 3.45 (1H, dd, J=9.7, 3.6 Hz), 3.63-3.68 (1H, m), 3.96 (1H, dd, J=9.7, 6.0 Hz), 4.93 (2H, s), 7.16 (1H, d, J=9.7 Hz), 7.62 (2H, d, J=9.1 Hz), 7.89-7.97 (4H, m), 8.26 (1H, s), 8.64 (1H, s).

Example 127

(4S)-4-Amino-1-[5-[6-[(1R)-1-(3-fluorophenyl)ethoxy]imidazo[1,2-b]pyridazin-3-yl]-2-pyridyl]pyrrolidin-2-one

[Formula 73]

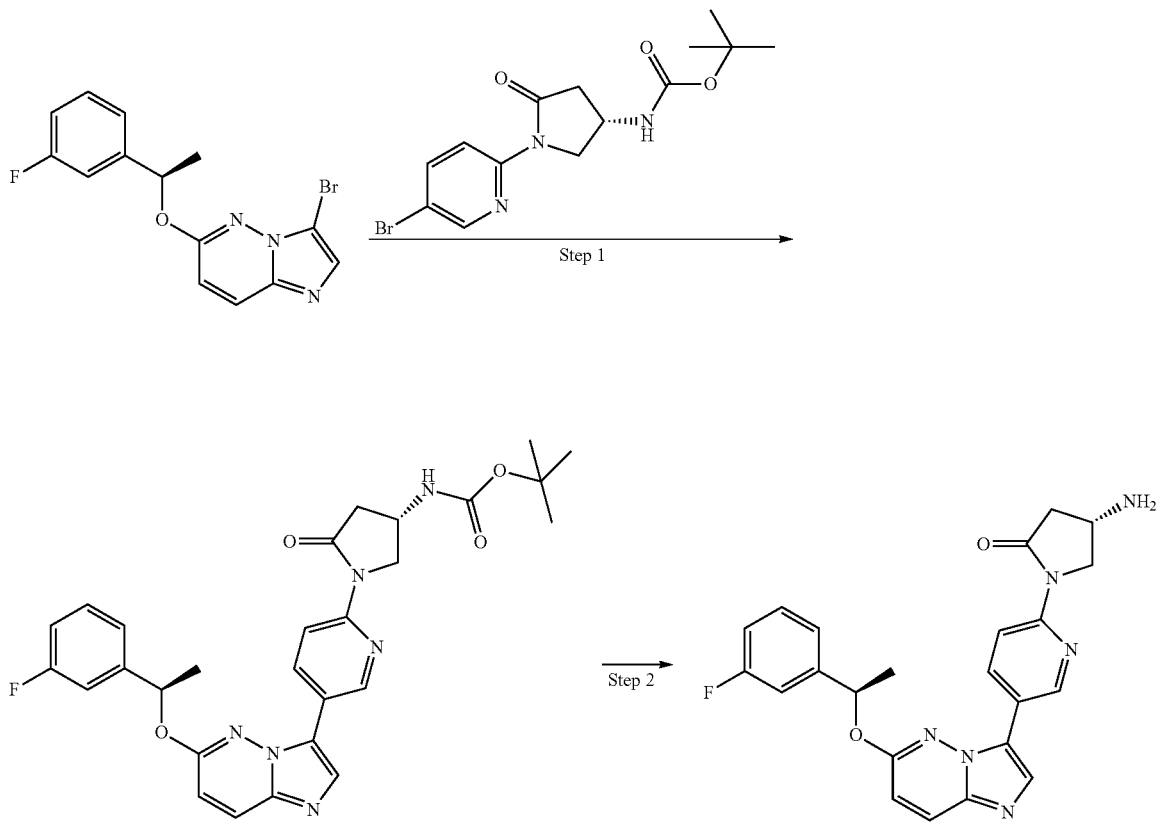

Step 1 tert-Butyl N-[(3S)-1-[5-[6-[(1R)-1-(3-fluorophenyl)ethoxy]imidazo[1,2-b]pyridazin-3-yl]-2-pyridyl]-5-oxopyrrolidin-3-yl]carbamate 1,4-Dioxane (15 ml) was added to the compound (1.12 g) obtained in step 2 of Reference Example 70, bis(pinacolato)diborane (0.838 g), a [1,1'-bis(diphenylphosphino)ferrocene]dichloropalladium(II)-dichloromethane adduct (0.257 g), and potassium acetate (0.617 g), and the mixture was stirred at 90° C. for 1 hour and then at 100° C. for 1.5 hours under a nitrogen atmosphere.

The reaction solution was brought back to room temperature. The compound (1.06 g) obtained in step 1 of Example 15, tripotassium phosphate (1.33 g), a [1,1'-bis(diphenylphosphino)ferrocene]dichloropalladium(II)-dichloromethane adduct (0.257 g), and water (1.5 ml) were added thereto, and the mixture was heated at 100° C. for 1.5 hours under a nitrogen atmosphere and then heated to reflux for 1 hour. The reaction solution was diluted with ethyl acetate and water to separate the aqueous and organic layers. The aqueous layer was subjected to extraction with ethyl acetate. The organic layers were combined, washed with saturated saline, dried over anhydrous sodium sulfate and then concentrated under reduced pressure. The obtained residue was purified by silica gel column chromatography (basic silica gel, n-hexane-ethyl acetate) to obtain the title compound (0.839 g).

$^1$H-NMR (CDCl$_3$) δ: 1.47 (9H, br s), 1.69 (3H, d, J=6.0 Hz), 2.64 (1H, dd, J=17.5, 3.6 Hz), 3.08 (1H, dd, J=17.5, 7.9 Hz), 4.08-4.12 (1H, m), 4.40-4.48 (2H, m), 4.90 (1H, br s), 5.92 (1H, q, J=6.4 Hz), 6.82 (1H, d, J=9.7 Hz), 6.98 (1H, td, J=8.5, 2.4 Hz), 7.13 (1H, d, J 9.7 Hz), 7.20 (1H, d, J=7.9 Hz), 7.33-7.39 (1H, m), 7.83 (1H, s), 7.87 (1H, d, J=9.7 Hz), 8.02 (1H, dd, J 8.5, 2.4 Hz), 8.45 (1H, d, J=8.5 Hz), 8.75 (1H, d, J=2.4 Hz).

ESI-MS (m/z): 533 (M+H)$^+$.

Step 2

(4S)-4-Amino-1-[5-[6-[(1R)-1-(3-fluorophenyl)ethoxy]imidazo[1,2-b]pyridazin-3-yl]-2-pyridyl]pyrrolidin-2-one The title compound (430 mg) was obtained by the same procedures as in step 2 of Example 79 using the compound (804 mg) obtained in the preceding step 1.

$^1$H-NMR (CDCl$_3$) δ: 1.69 (3H, d, J=6.7 Hz), 2.50 (1H, dd, J=17.0, 4.2 Hz), 3.00 (1H, dd, J=17.0, 7.0 Hz), 3.85-3.90 (1H, m), 3.93 (1H, dd, J=11.5, 4.2 Hz), 4.35 (1H, dd, J=11.5, 6.0 Hz), 5.93 (1H, q, J=6.7 Hz), 6.81 (1H, d, J=9.7 Hz), 6.98 (1H, td, J=8.3, 2.6 Hz), 7.12-7.16 (1H, m), 7.20 (1H, d, J=7.9 Hz), 7.36 (1H, td, J=8.0, 5.6 Hz), 7.83 (1H, s), 7.86 (1H, d, J=9.7 Hz), 8.03 (1H, dd, J=9.1, 2.4 Hz), 8.49 (1H, d, J=9.1 Hz), 8.74 (1H, d, J=2.4 Hz).

ESI-MS (m/z): 433 (M+H)$^+$.

The following compounds were obtained by the same procedures as in Example 127.

TABLE 25-1

| Example No. | Reference Example No. | Structure and name | Instrumental data |
|---|---|---|---|
| 128 | 70 | 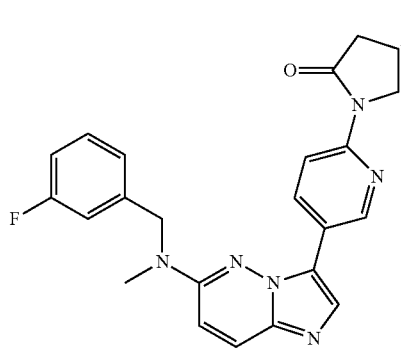<br>(4S)-4-Amino-1-[5-[6-[(3-fluorophenyl)methyl-methylamino]imidazo[1,2-b]pyridazin-3-yl]-2-pyridyl]pyrrolidin-2-one | $^1$H-NMR (CDCl$_3$) δ: 2.47 (1H, dd, J = 16.9, 4.2 Hz), 2.97 (1H, dd, J = 17.2, 7.0 Hz), 3.23 (3H, s), 3.82-3.96 (2H, m), 4.31 (1H, dd, J = 11.5, 6.0 Hz), 4.74 (2H, s), 6.78 (1H, d, J = 10.3 Hz), 6.91-7.09 (3H, m), 7.29-7.36 (1H, m), 7.77 (1H, d, J = 10.3 Hz), 7.85 (1H, s), 8.28-8.37 (1H, m), 8.44 (1H, d, J = 9.7 Hz), 8.91-8.99 (1H, m). |

TABLE 25-1-continued

| Example No. | Reference Example No. | Structure and name | Instrumental data |
|---|---|---|---|
| 129 | 70 | 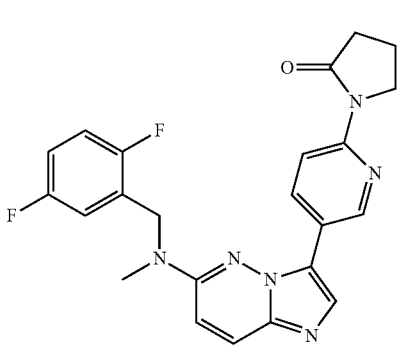<br>(4S)-4-Amino-1-[5-[6-[(2,5-difluorophenyl)methyl-methylamino]imidazo[1,2-b]pyridazin-3-yl]-2-pyridyl]pyrrolidin-2-one | $^1$H-NMR (CDCl$_3$) δ: 2.47 (1H, dd, J = 16.9, 4.2 Hz), 2.97 (1H, dd, J = 16.9, 7.3 Hz), 3.25 (3H, s), 3.82-3.92 (2H, m), 4.31 (1H, dd, J = 11.5, 6.0 Hz), 4.76 (2H, s), 6.79 (1H, d, J = 10.3 Hz), 6.87-6.97 (2H, m), 7.06-7.11 (1H, m), 7.79 (1H, d, J = 10.3 Hz), 7.85 (1H, s), 8.30-8.33 (1H, m), 8.44 (1H, d, J = 9.7 Hz), 8.92-8.94 (1H, m). |
| 130 | 76 | 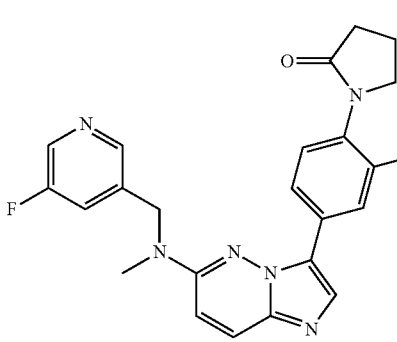<br>2-[(4S)-4-Amino-2-oxopyrrolidin-1-yl]-5-[6-[(5-fluoro-3-pyridyl)methyl]-methylamino]imidazo[1,2-b]pyridazin-3-yl]benzonitrile | $^1$H-NMR (CDCl$_3$) δ: 2.42 (1H, dd, J = 17.2, 4.5 Hz), 2.92 (1H, dd, J = 16.9, 7.3 Hz), 3.27 (3H, s), 3.65 (1H, dd, J = 9.7, 4.2 Hz), 3.90-3.96 (1H, m), 4.19 (1H, dd, J = 9.7, 6.0 Hz), 4.83 (2H, s), 6.86 (1H, d, J = 10.3 Hz), 7.31-78.34 (1H, m), 7.49 (1H, d, J = 8.5 Hz), 7.84 (1H, d, J = 10.3 Hz), 7.90 (1H, s), 8.11 (1H, dd, J = 8.8, 2.1 Hz), 8.39-8.42 (2H, m), 8.47-8.48 (1H, m). |

TABLE 25-2

| 131 | 76 | 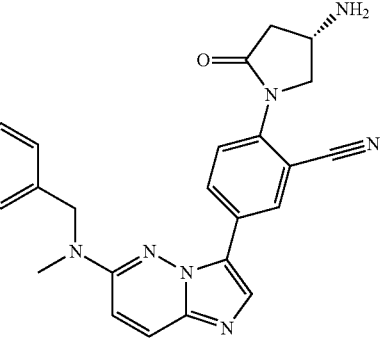<br>2-[(4S)-4-Amino-2-oxopyrrolidin-1-yl]-5-[6-[(3-fluorophenyl)methyl-methylamino]imidazo[1,2-b]pyridazin-3-yl]benzonitrile | $^1$H-NMR (CDCl$_3$) δ: 2.42 (1H, dd, J = 16.9, 4.8 Hz), 2.93 (1H, dd, J = 16.9, 7.3 Hz), 3.26 (3H, s), 3.65 (1H, dd, J = 9.7, 3.6 Hz), 3.90-3.96 (1H, m), 4.20 (1H, dd, J = 9.7, 6.0 Hz), 4.77 (2H, s), 6.82 (1H, d, J = 9.7 Hz), 6.93-6.99 (2H, m), 7.05 (1H, d, J = 7.9 Hz), 7.31-7.37 (1H, m), 7.49 (1H, d, J = 8.5 Hz), 7.79 (1H, d, J = 9.7 Hz), 7.89 (1H, s), 8.18 (1H, dd, J = 8.5, 2.4 Hz), 8.54-8.55 (1H, m). |

| 132 | 70 | 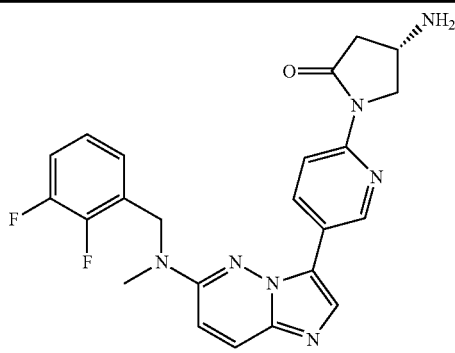<br>(4S)-4-Amino-1-[5-[6-[(2,3-difluorophenyl)methyl-methylamino]imidazo[1,2-b]pyridazin-3-yl]-2-pyridyl]pyrrolidin-2-one | ¹H-NMR (CDCl₃) δ: 2.47 (1H, dd, J = 16.9, 4.2 Hz), 2.97 (1H, dd, J = 17.2, 7.0 Hz), 3.23 (3H, s), 3.82-3.92 (2H, m), 4.32 (1H, dd, J = 11.2, 6.3 Hz), 4.81 (2H, s), 6.80 (1H, d, J = 9.7 Hz), 6.93-7.04 (2H, m), 7.06-7.14 (1H, m), 7.78 (1H, d, J = 9.7 Hz), 7.84 (1H, s), 8.34 (1H, dd, J = 9.1, 2.4 Hz), 8.47 (1H, d, J = 9.1 Hz), 8.94 (1H, d, J = 1.8 Hz). |

Example 133

(4S)-4-Amino-1-[4-[6-[(1R)-1-(3-fluorophenyl)ethoxy]imidazo[1,2-b]pyridazin-3-yl]phenyl]pyrrolidin-2-one hydrochloride The compound (15.65 g) obtained in step 2 of Example 79 was dissolved in a mixed solvent of ethanol (400 ml) and methanol (10 ml). To the solution, a solution of 1 N hydrochloric acid in ethanol (74.4 ml) was added, and the mixture was stirred at room temperature for 10 minutes. Then, the solvent was distilled off under reduced pressure. Diethyl ether was added to the residue, and the solid was collected by filtration to obtain the title compound (17.16 g).

¹H-NMR (DMSO-d₆) δ: 1.68 (3H, d, J=6.7 Hz), 2.67 (1H, dd, J=17.5, 3.0 Hz), 3.08 (1H, dd, J=17.5, 8.5 Hz), 3.94 (1H, dd, J=11.5, 2.4 Hz), 4.07-4.14 (1H, m), 4.30 (1H, dd, J=11.5, 7.0 Hz), 6.07 (1H, q, J=6.7 Hz), 7.12 (1H, td, J=8.3, 2.0 Hz), 7.31 (1H, d, J=9.7 Hz), 7.33-7.37 (2H, m), 7.43 (1H, td, J=8.3, 6.0 Hz), 7.78-7.82 (2H, m), 7.93-7.97 (2H, m), 8.27 (1H, d, J=9.7 Hz), 8.34 (1H, s), 8.58-8.68 (3H, m).

ESI-MS (m/z): 432 (M+H)⁺.

Example 134

(4S)-4-Amino-1-[4-[6-[(1-(2,5-difluoro-3-pyridyl)ethoxy]imidazo[1,2-b]pyridazin-3-yl]phenyl]pyrrolidin-2-one hydrochloride The compound (567 mg) obtained in step 3 of Example 106 was dissolved in dichloromethane. To the solution, a solution of 1 N hydrochloric acid in ethanol (2.77 ml) was added. The solvent was distilled off under reduced pressure. Diethyl ether was added to the residue, and the solid was collected by filtration to obtain the title compound (643 mg).

¹H-NMR (DMSO-d₆) δ: 1.72 (3H, d, J=6.7 Hz), 2.64 (1H, dd, J=17.5, 3.0 Hz), 3.08 (1H, dd, J=17.5, 8.5 Hz), 3.91 (1H, dd, J=10.9, 2.4 Hz), 4.06-4.13 (1H, m), 4.30 (1H, dd, J=10.9, 7.0 Hz), 6.16 (1H, q, J=6.7 Hz), 7.29 (1H, d, J=9.7 Hz), 7.75-7.79 (2H, m), 7.89-7.92 (2H, m), 8.08 (1H, td, J=7.6, 3.0 Hz), 8.20-8.22 (1H, m), 8.28 (1H, d, J=9.7 Hz), 8.32 (1H, s), 8.52 (3H, br s). ESI-MS (m/z): 451 (M+H)⁺.

Example 135

(4S)-4-(Dimethylamino)-1-[4-[6-[(1R)-1-(3-fluorophenyl)ethoxy]imidazo[1,2-b]pyridazin-3-yl]phenyl]pyrrolidin-2-one

[Formula 74]

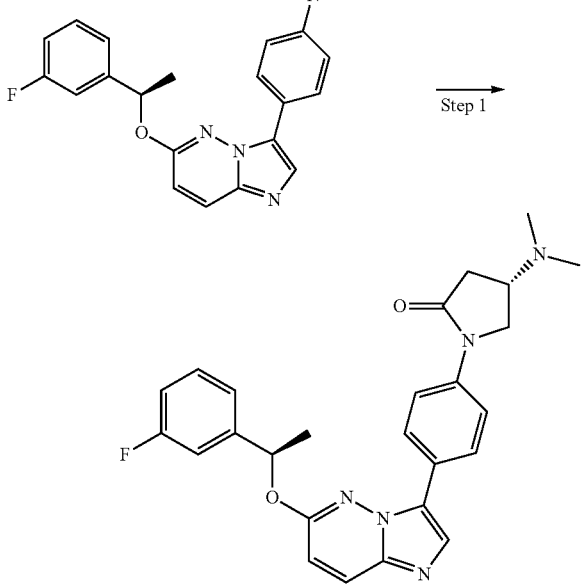

Step 1

(4S)-4-(Dimethylamino)-1-[4-[6-[(1R)-1-(3-fluorophenyl)ethoxy]imidazo[1,2-b]pyridazin-3-yl]phenyl]pyrrolidin-2-one The compound (127 mg) obtained in Example 131 was suspended in dichloromethane (5 ml). To the suspension, a 35% aqueous formaldehyde solution (47 μl), triethylamine (82 μl), and sodium triacetoxyborohydride (149 mg) were added, and the mixture was stirred at room temperature for 1.5 hours. Dichloromethane and water were added thereto to separate the aqueous and organic layers. The aqueous layer was subjected to extraction with dichloromethane. The organic layers were combined, dried over anhydrous sodium sulfate and then concentrated under reduced pressure. The obtained residue was purified by silica gel column chromatography (basic silica gel, ethyl acetate). After addition of n-hexane, the solid was collected by filtration to obtain the title compound (86 mg).

$^1$H-NMR (CDCl$_3$) δ: 1.69 (3H, d, J=6.6 Hz), 2.33 (6H, s), 2.67 (1H, dd, J=16.8, 8.6 Hz), 2.79 (1H, dd, J=16.8, 7.8 Hz), 3.12-3.19 (1H, m), 3.81 (1H, dd, J=9.5, 6.8 Hz), 3.99 (1H, dd, J=9.5, 7.4 Hz), 5.93 (1H, q, J 6.5 Hz), 6.79 (1H, d, J=9.4 Hz), 6.96-7.01 (1H, m), 7.15 (1H, dt, J=9.8, 2.2 Hz), 7.22 (1H, d, J=8.0 Hz), 7.36 (1H, td, J=8.0, 5.9 Hz), 7.68-7.75 (4H, m), 7.81 (1H, s), 7.85 (1H, d, J=9.4 Hz).

ESI-MS (m/z): 460 (M+H)$^+$.

Example 136

N-[(1R)-1-(3-Fluorophenyl)ethyl]-3-[4-[[(2S)-pyrrolidin-2-yl]methoxy]phenyl]imidazo[1,2-b]pyridazin-6-amine monomaleate

[Formula 75]

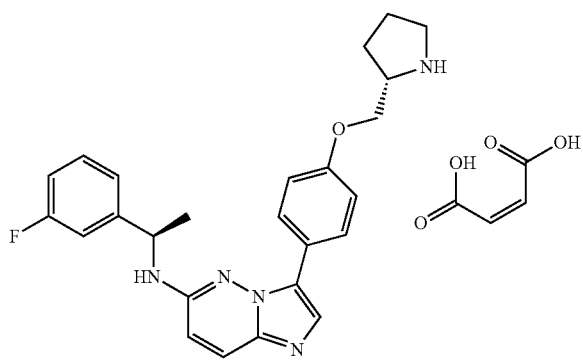

To N-[(1R)-1-(3-fluorophenyl)ethyl]-3-[4-[[(2S)-pyrrolidin-2-yl]methoxy]phenyl]imidazo[1,2-b]pyridazin-6-amine (105 mg) obtained in Example 24, water (1.8 ml) and a 1 mol/l aqueous maleic acid solution (242 μl) were added at room temperature. Then, the mixture was stirred at 40° C. for 20 hours and further stirred at room temperature for 0.5 hours. Then, the deposited solid was collected by filtration to obtain the title compound (112 mg).

$^1$H-NMR (DMSO-d$_6$) δ: 1.49 (3H, d, J=6.7 Hz), 1.71-1.81 (1H, m), 1.87-2.04 (2H, m), 2.10-2.21 (1H, m), 3.19-3.28 (2H, m), 3.89-3.98 (1H, m), 4.12 (1H, t, J=9.7 Hz), 4.30 (1H, dd, J=10.6, 3.3 Hz), 4.80-4.89 (1H, m), 6.02 (2H, s), 6.78 (1H, d, J=9.7 Hz), 6.98 (2H, d, J=9.7 Hz), 7.04 (1H, td, J=8.5, 2.4 Hz), 7.22-7.29 (2H, m), 7.36-7.43 (1H, m), 7.66 (1H, d, J=6.0 Hz), 7.75-7.84 (4H, m), 8.84 (1H, br s).

Anal. Calcd for C$_{25}$H$_{26}$FN$_5$O.C$_4$H$_4$O$_4$: C, 63.61; H, 5.52; F, 3.47; N, 12.79. Found: C, 62.26; H, 5.45; F, 4.25; N, 12.54.

Example 137

N-[(1R)-1-(3-Fluorophenyl)ethyl]-3-[4-[[(2S)-pyrrolidin-2-yl]methoxy]phenyl]imidazo[1,2-b]pyridazin-6-amine monoadipate monohydrate

[Formula 76]

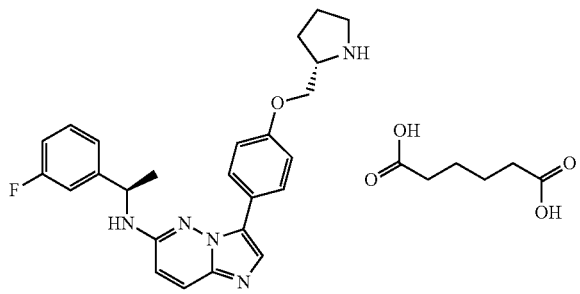

To the compound (104 mg) obtained in Example 24, adipic acid (38 mg) and water (2 ml) were added at room temperature. Then, the mixture was stirred at 40° C. for 20 hours and further stirred at room temperature for 0.5 hours. Then, the deposited solid was collected by filtration to obtain the title compound (125 mg).

$^1$H-NMR (DMSO-d$_6$) δ: 1.46-1.55 (5H, m), 1.48 (3H, d, J=7.3 Hz), 1.63-1.81 (2H, m), 1.86-1.95 (1H, m), 2.16-2.21 (4H, m), 2.82-2.93 (2H, m), 3.43-3.51 (1H, m), 3.89 (2H, d, J=6.7 Hz), 4.80-4.88 (1H, m), 6.77 (1H, d, J=9.7 Hz), 6.92 (2H, d, J=8.5 Hz), 7.03 (1H, td, J=8.3, 2.4 Hz), 7.22-7.29 (2H, m), 7.36-7.43 (1H, m), 7.63 (1H, d, J=6.0 Hz), 7.71-7.77 (4H, m).

Anal. Calcd for C$_{25}$H$_{26}$FN$_5$O.C$_6$H$_{10}$O$_4$.H$_2$O: C, 62.51; H, 6.43; F, 5.32; N, 11.76. Found: C, 61.01; H, 6.16; F, 5.32; N, 11.45.

Example 138

(4S)-4-Amino-1-[4-[6-[(3-fluorophenyl)methylmethylamino]imidazo[1,2-b]pyridazin-3-yl]phenyl]pyrrolidin-2-one monobenzenesulfonate

[Formula 77]

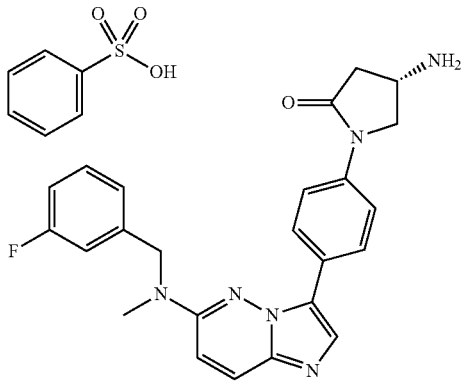

To the compound (102 mg) obtained in step 2 of Example 81, acetone (1.8 ml), water (146 μl), and a 4 mol/l aqueous benzenesulfonic acid solution (59 μl) were added at room temperature. Then, the mixture was stirred at room temperature for 3 hours. Then, the deposited solid was collected by filtration to obtain the title compound (121 mg).

$^1$H-NMR (DMSO-$d_6$) δ: 2.54 (1H, dd, J=17.5, 3.0 Hz), 3.06 (1H, dd, J=17.5, 8.5 Hz), 3.24 (3H, s), 3.79 (1H, dd, J=11.2, 2.1 Hz), 4.04-4.10 (1H, m), 4.26 (1H, dd, J=10.9, 7.3 Hz), 4.84 (2H, s), 7.05-7.15 (4H, m), 7.27-7.41 (4H, m), 7.58-7.61 (2H, m), 7.70 (2H, d, J=9.1 Hz), 7.92 (1H, d, J=9.7 Hz), 7.97 (1H, s), 8.11 (3H, br s), 8.12 (2H, d, J=9.1 Hz).

Anal. Calcd for $C_{24}H_{23}FN_6O\cdot C_6H_6O_3S$: C, 61.21; H, 4.97; F, 3.23; N, 14.28, S; 5.45. Found: C, 60.84; H, 5.04; F, 3.40; N, 14.13, S; 5.40.

Example 139

(4S)-4-Amino-1-[4-[6-[(3-fluorophenyl)methyl-methylamino]imidazo[1,2-b]pyridazin-3-yl]phenyl]pyrrolidin-2-one monoadipate

[Formula 78]

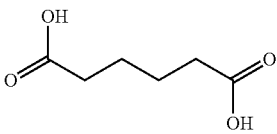

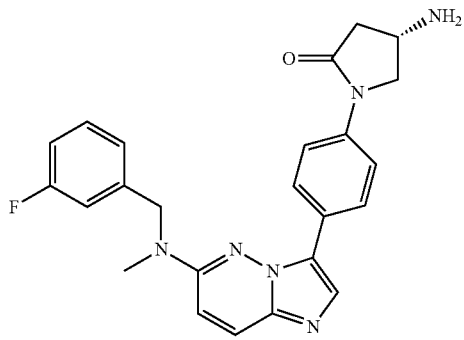

To the compound (105 mg) obtained in step 2 of Example 81, adipic acid (39 mg) and acetone (1 ml) were added at room temperature. The mixture was stirred at 40° C. for 20 hours. Then, ethyl acetate (3.2 ml) was added thereto, and the mixture was further stirred at room temperature for 0.5 hours. The deposited solid was collected by filtration to obtain the title compound (124 mg).

$^1$H-NMR (DMSO-$d_6$) δ: 1.46-1.53 (4H, m), 2.17-2.26 (5H, m), 2.75 (1H, dd, J=16.6, 7.0 Hz), 3.24 (3H, s), 3.48 (1H, dd, J=9.7, 3.6 Hz), 3.63-3.70 (1H, m), 3.99 (1H, dd, J=9.7, 6.7 Hz), 4.83 (2H, s), 7.05-7.15 (4H, m), 7.35-7.42 (1H, m), 7.69 (2H, d, J=9.1 Hz), 7.90 (1H, d, J=9.7 Hz), 7.94 (1H, s), 8.08 (2H, d, J=9.1 Hz).

Anal. Calcd for $C_{24}H_{23}FN_6O\cdot C_6H_{10}O_4$: C, 62.49; H, 5.77; F, 3.29; N, 14.57. Found: C, 62.08; H, 5.70; F, 3.76; N, 14.32.

Example 140

(4S)-4-Amino-1-[4-[6-[(3-fluorophenyl)methyl-methylamino]imidazo[1,2-b]pyridazin-3-yl]phenyl]pyrrolidin-2-one monocamphorate monohydrate

[Formula 79]

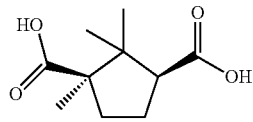

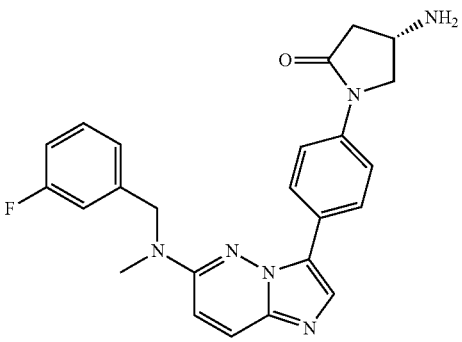

To the compound (100 mg) obtained in step 2 of Example 81, camphoric acid (39 mg), acetone (1.8 ml), and water (200 μl) were added at room temperature. The mixture was stirred at 40° C. for 20 hours and further stirred at room temperature for 0.5 hours. The deposited solid was collected by filtration to obtain the title compound (93 mg).

$^1$H-NMR (DMSO-$d_6$) δ: 0.77 (3H, s), 1.12 (3H, s), 1.18 (3H, s), 1.33-1.40 (1H, m), 1.66-1.77 (1H, m), 1.93-2.02 (1H, m), 2.24 (1H, dd, J=16.3, 4.2 Hz), 2.29-2.39 (1H, m), 2.69-2.79 (2H, m), 3.24 (3H, s), 3.49 (1H, dd, J=9.7, 3.6 Hz), 3.64-3.70 (1H, m), 4.00 (1H, dd, J=9.7, 6.0 Hz), 4.83 (2H, s), 7.05-7.15 (4H, m), 7.35-7.42 (1H, m), 7.69 (2H, d, J=8.5 Hz), 7.90 (1H, d, J=9.7 Hz), 7.95 (1H, s), 8.07 (2H, d, J=8.5 Hz).

Anal. Calcd for $C_{24}H_{23}FN_6O\cdot C_{10}H_{16}O_4\cdot H_2O$: C, 62.95; H, 6.37; F, 2.93; N, 12.95.

Found: C, 62.44; H, 6.25; F, 3.37; N, 13.01.

Example 141

(4S)-4-Amino-1-[4-[6-[(1R)-1-(3-fluorophenyl)ethoxy]imidazo[1,2-b]pyridazin-3-yl]phenyl]pyrrolidin-2-one monobenzenesulfonate monohydrate

[Formula 80]

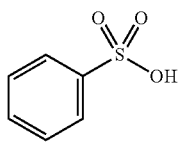

233

-continued

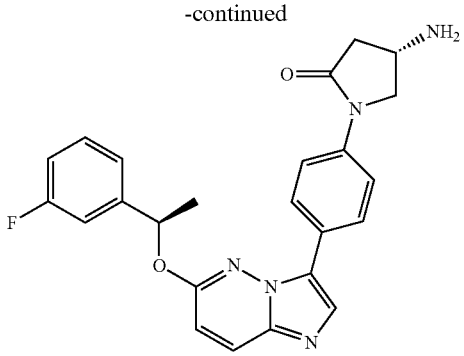

To the compound (101 mg) obtained in step 2 of Example 79, acetone (202 μl), water (574 μl), and a 1 mol/l aqueous benzenesulfonic acid solution (233 μl) were added at room temperature. The mixture was stirred at 40° C. for 20 hours and further stirred at room temperature for 0.5 hours. The deposited solid was collected by filtration to obtain the title compound (131 mg).

$^1$H-NMR (DMSO-$d_6$) δ: 1.67 (3H, d, J=6.7 Hz), 2.57 (1H, dd, J=17.8, 2.7 Hz), 3.09 (1H, dd, J=18.1, 8.5 Hz), 3.83 (1H, dd, J=11.2, 2.1 Hz), 4.07-4.14 (1H, m), 4.30 (1H, dd, J=11.2, 7.0 Hz), 6.05 (1H, q, J=6.4 Hz), 7.03 (1H, d, J=9.7 Hz), 7.10 (1H, td, J=8.5, 1.8 Hz), 7.29-7.44 (6H, m), 7.58-7.61 (2H, m), 7.77 (2H, d, J=9.4 Hz), 7.96 (2H, d, J=9.1 Hz), 8.07 (1H, s), 8.11 (1H, d, J=10.9 Hz), 8.16 (3H, br s).

Anal. Calcd for $C_{24}H_{22}FN_5O_2 \cdot C_6H_7O_3S \cdot H_2O$: C, 59.30; H, 4.98; F, 3.13; N, 11.53; S, 5.28. Found: C, 59.10; H, 5.01; F, 3.25; N, 11.37; S, 5.15.

Example 142

(4S)-4-Amino-1-[4-[6-[(1R)-1-(3-fluorophenyl)ethoxy]imidazo[1,2-b]pyridazin-3-yl]phenyl]pyrrolidin-2-one monoadipate

[Formula 81]

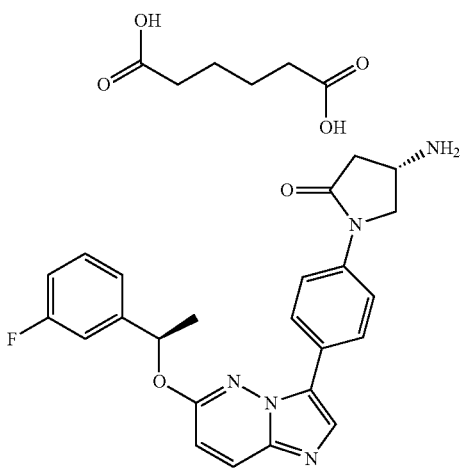

To the compound (101 mg) obtained in step 2 of Example 79, adipic acid (37 mg) and 1,2-methoxyethane (1 ml) were added at room temperature. The mixture was stirred at 40° C. for 3 hours. Then, ethyl acetate (1 ml) was added thereto, and the mixture was stirred at room temperature for 3 hours. The deposited solid was collected by filtration to obtain the title compound (126 mg).

234

$^1$H-NMR (DMSO-$d_6$) δ: 1.46-1.52 (4H, m), 1.66 (3H, d, J=6.7 Hz), 2.17-2.22 (4H, m), 2.26 (1H, dd, J=16.9, 3.0 Hz), 2.77 (1H, dd, J=16.6, 7.0 Hz), 3.53 (1H, dd, J=9.7, 3.6 Hz), 3.66-3.73 (1H, m), 4.03 (1H, dd, J=9.7, 6.0 Hz), 6.04 (1H, q, J=6.4 Hz), 7.02 (1H, d, J=9.7 Hz), 7.11 (1H, td, J=8.5, 3.0 Hz), 7.31-7.36 (2H, m), 7.39-7.46 (1H, m), 7.75 (2H, d, J=9.1 Hz), 7.90 (2H, d, J=9.1 Hz), 8.03 (1H, s), 8.09 (1H, d, J=9.7 Hz).

Anal. Calcd for $C_{24}H_{22}FN_5O_2 \cdot C_6H_{10}O_4$: C, 62.38; H, 5.58; F, 3.29; N, 12.12. Found: C, 62.25; H, 5.57; F, 3.38; N, 12.05.

Example 143

(4S)-4-Amino-1-[4-[6-[(1R)-1-(3-fluorophenyl)ethoxy]imidazo[1,2-b]pyridazin-3-yl]phenyl]pyrrolidin-2-one monolactate monohydrate

[Formula 82]

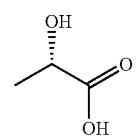

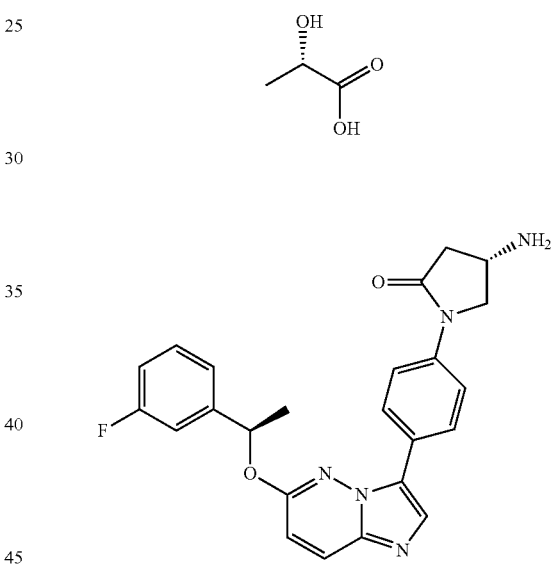

To the compound (103 mg) obtained in step 2 of Example 79, acetone (924 μl), water (43 μl), and a 4 mol/l aqueous lactic acid solution (59 μl) were added at room temperature. The mixture was stirred at 40° C. for 20 hours and further stirred at room temperature for 0.5 hours. The deposited solid was collected by filtration to obtain the title compound (95 mg).

$^1$H-NMR (DMSO-$d_6$) δ: 1.19 (3H, d, J=6.7 Hz), 1.67 (3H, d, J=6.7 Hz), 2.34 (1H, dd, J=16.9, 4.2 Hz), 2.84 (1H, dd, J=16.9, 7.3 Hz), 3.61 (1H, dd, J=10.0, 3.3 Hz), 3.76-3.82 (1H, m), 3.91 (1H, q, J=6.9 Hz), 4.09 (1H, dd, J=10.0, 6.3 Hz), 6.04 (1H, q, J=6.4 Hz), 7.02 (1H, d, J=9.7 Hz), 7.10 (1H, td, J=8.3, 2.2 Hz), 7.31-7.36 (2H, m), 7.39-7.45 (1H, m), 7.75 (2H, d, J=9.1 Hz), 7.91 (2H, d, J=9.1 Hz), 8.04 (1H, s), 8.10 (1H, d, J 9.7 Hz).

Anal. Calcd for $C_{24}H_{22}FN_5O_2 \cdot C_3H_6O_3 \cdot H_2O$: C, 60.10; H, 5.60; F, 3.52; N, 12.98.

Found: C, 59.71; H, 5.57; F, 3.81; N, 12.85.

Example 144

(4S)-4-Amino-1-[4-[6-[(1R)-1-(3-fluorophenyl)ethoxy]imidazo[1,2-b]pyridazin-3-yl]phenyl]pyrrolidin-2-one monobenzoate monohydrate

[Formula 83]

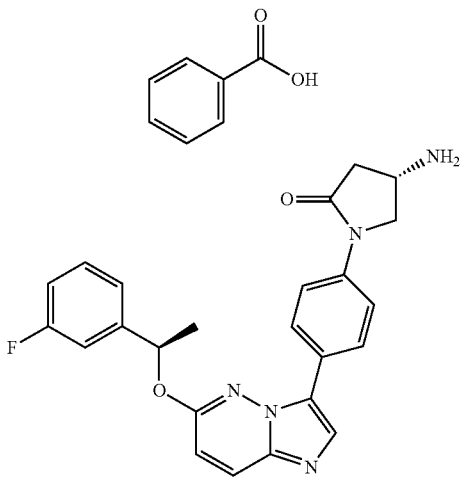

To the compound (101.01 mg) obtained in step 2 of Example 79, benzoic acid (31 mg), acetone (916 μl), and water (102 μl) were added at room temperature. The mixture was stirred at 40° C. for 24 hours and further stirred at room temperature for 0.5 hours. The deposited solid was collected by filtration to obtain the title compound (119 mg).

$^1$H-NMR (DMSO-d$_6$) δ: 1.66 (3H, d, J=6.7 Hz), 2.30 (1H, dd, J=16.6, 3.9 Hz), 2.81 (1H, dd, J=16.9, 7.3 Hz), 3.57 (1H, dd, J=9.7, 3.6 Hz), 3.71-3.77 (1H, m), 4.06 (1H, dd, J=9.7, 6.0 Hz), 6.04 (1H, q, J=6.4 Hz), 7.02 (1H, d, J=9.7 Hz), 7.10 (1H, td, J=8.5, 2.3 Hz), 7.31-7.36 (2H, m), 7.39-7.45 (1H, m), 7.47 (2H, t, J=7.9 Hz), 7.58 (1H, tt, J=7.3, 1.6 Hz), 7.75 (2H, d, J=9.1 Hz), 7.91 (2H, d, J=9.1 Hz), 7.93 (2H, d, J=8.5 Hz), 8.04 (1H, s), 8.09 (1H, d, J=9.7 Hz).

Anal. Calcd for C$_{24}$H$_{22}$FN$_5$O$_2$·C$_7$H$_6$O$_2$·H$_2$O: C, 65.14; H, 5.29; F, 3.32; N, 12.25.

Found: C, 64.91; H, 5.29; F, 3.62; N, 12.16.

Example 145

3-[4-[(2R)-2-Aminopropoxy]phenyl]-N-[(1R)-1-(3-fluorophenyl)ethyl]imidazo[1,2-b]pyridazin-6-amine dimethanesulfonate

[Formula 84]

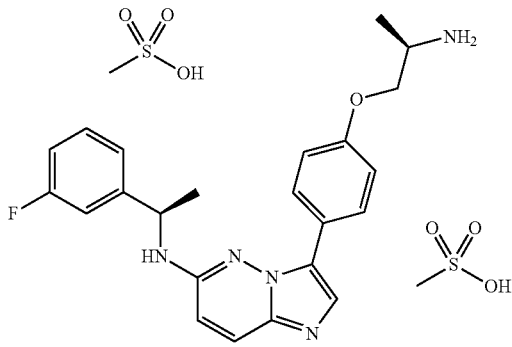

To the compound (503 mg) obtained in step 3 of Example 21, methanesulfonic acid (169 μl) and 1-propanol (5 ml) were added at room temperature. The mixture was stirred at 40° C. for 24 hours and further stirred at room temperature for 0.5 hours. The deposited solid was collected by filtration to obtain the title compound (642 mg).

$^1$H-NMR (DMSO-d6) δ: 1.32 (3H, d, J=6.7 Hz), 1.51 (3H, d, J=6.7 Hz), 2.32 (6H, s), 3.63-3.74 (1H, m), 4.05 (1H, dd, J=10.3, 7.3 Hz), 4.21 (1H, dd, J=10.0, 3.9 Hz), 4.81-4.89 (1H, m), 7.04-7.10 (3H, m), 7.22-7.29 (3H, m), 7.38-7.44 (1H, m), 7.78 (2H, d, J=9.1 Hz), 8.03 (3H, br s), 8.06 (1H, d, J=10.3 Hz), 8.29 (1H, s), 8.33 (1H, d, J=6.0 Hz).

Anal. Calcd for C$_{23}$H$_{24}$FN$_5$O·2CH$_4$O$_3$S: C, 50.24; H, 5.40; N, 11.72. Found: C, 49.68; H, 5.30; N, 11.55.

Example 146

3-[4-[(2R)-2-Aminopropoxy]phenyl]-N-[(1R)-1-(3-fluorophenyl)ethyl]imidazo[1,2-b]pyridazin-6-amine monoadipate

[Formula 85]

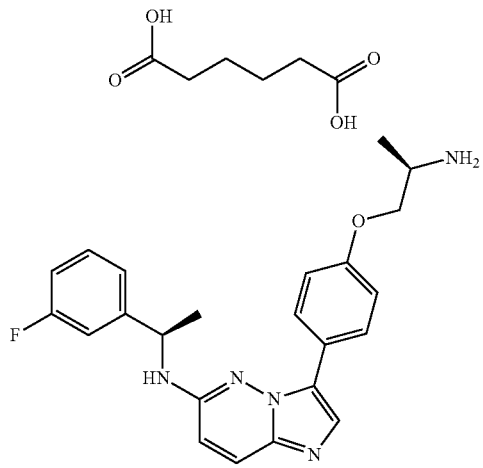

To the compound (500 mg) obtained in step 3 of Example 21, adipic acid (181 mg) and 1-propanol (5 ml) were added at room temperature. The mixture was stirred at 40° C. for 24 hours and further stirred at room temperature for 0.5 hours. The deposited solid was collected by filtration to obtain the title compound (622 mg).

$^1$H-NMR (DMSO-d$_6$) δ: 1.11 (3H, d, J=6.0 Hz), 1.46-1.51 (4H, m), 1.48 (3H, d, J=7.3 Hz), 2.15-2.21 (4H, m), 3.18-3.27 (1H, m), 3.77-3.86 (2H, m), 4.80-4.88 (1H, m), 6.77 (1H, d, J=9.7 Hz), 6.93 (2H, d, J=9.1 Hz), 7.03 (1H, td, J=8.5, 2.4 Hz), 7.22-7.29 (2H, m), 7.36-7.43 (1H, m), 7.61 (1H, d, J=6.0 Hz), 7.70-7.77 (4H, m).

Anal. Calcd for C$_{23}$H$_{24}$FN$_5$O·C$_6$H$_{10}$O$_4$: C, 63.14; H, 6.21; N, 12.70. Found: C, 62.97; H, 6.29; N, 12.59.

Test Example 1

ROS1 Kinase Inhibitory Activity Evaluation

A hundred mM HEPES (pH 7.4), 0.003% Brij-35, 0.004% Tween-20, 1 mM DTT, ROS1 (Carna Biosciences #08-163, final concentration: 25 pg/μL), and MgCl (final concentration: 10 mM) were mixed to prepare a ROS1 kinase solution.

Next, a substrate reaction solution was prepared. The composition is as follows: 100 mM HEPES (pH 7.4), 0.003% Brij-35, 0.004% Tween-20, 1 mM DTT, FL-Peptide 22 (Caliper Life Sciences #760366, final concentration: 1.5 µM), and ATP (final concentration: Km=55 µM or 1 mM). A reaction stop solution is prepared. The composition is as follows: 100 mM HEPES (pH 7.4), 0.015% Brij-35, 40 mM EDTA, and 0.1% Coating Reagent 3 (Caliper Life Sciences #760050).

The ROS1 kinase solution was added at a concentration of 19 µL/well to a 96-well plate. Each compound for evaluation dissolved in DMSO to achieve each final concentration was added to the plate, mixed using a plate mixer, and then preincubated at room temperature for 20 minutes. The substrate reaction solution was further added thereto at a concentration of 5 µL/well to cause enzymatic reaction (28° C. for 90 minutes under the condition of ATP=Km or 45 minutes under the condition of 1 mM ATP). Then, the reaction stop solution was added thereto at a concentration of 40 µL/well. Substrate phosphorylation intensity was measured using EZ Reader II (Caliper Life Sciences). $IC_{50}$ values were calculated by curve fitting using Microsoft Excel 2010 on the basis of data obtained from three separate measurements.

The compounds of Examples 16, 18, 21 to 24, 26, 28 to 30, 32 to 50, 52 to 56, 59, 62 to 63, 69 to 70, 72, 76 to 77, 79 to 82, 88, 90, 92 to 93, 104, 106 to 107, 114, 120, 127 to 128, and 133 exhibited ROS1 kinase inhibitory activity at $IC_{50}$ of lower than 1 nM. The compounds of Examples 1 to 15, 17, 19 to 20, 25, 27, 31, 51, 57 to 58, 60 to 61, 64 to 68, 71, 73 to 75, 78, 83 to 87, 91, 94 to 103, 108, 110 to 113, 117 to 119, 121 to 122, 124 to 126, 129, 131 to 132, and 134 to 135 exhibited ROS1 kinase inhibitory activity at $IC_{50}$ of 1 nM or higher and lower than 10 nM. The compounds of Examples 89, 105, 109, 115 to 116, 123, and 130 exhibited ROS1 kinase inhibitory activity at $IC_{50}$ of 10 nM or higher and lower than 60 nM. This suggested that the compounds of the present invention can suppress the growth of cells with the activated ROS1 pathway by inhibiting the ROS1 pathway.

Test Example 2

ROS1 Autophosphorylation Inhibitory Activity Evaluation

Fifty mM HEPES (pH 7.5), 10 mM MgCl2, 0.01% Brij-58, and 2.5 mM DTT were mixed to prepare an enzymatic reaction solution. Each compound for evaluation dissolved in DMSO to achieve each final concentration was added to the enzymatic reaction solution containing 200 nM inactive ROS1, and the mixture was added at a concentration of 2.5 µL/well to a 384-well plate (small volume black, Grainer #784900). ATP (final concentration: 1 mM) was further added thereto at a concentration of 2.5 µL/well. The resulting plate was left standing at 25° C. for 1.5 hours to cause enzymatic reaction. After the completion of enzymatic reaction, ADP-Glo Reagent-1 (Promega, V9103) was added thereto at a concentration of 2.5 µL/well, and the plate was left standing at room temperature for 60 minutes. Then, ADP-Glo Reagent-2 (Promega) was added thereto at a concentration of 5 µL/well, and the plate was left standing at room temperature for 60 minutes. The amount of ADP generated by the autophosphorylation of ROS1 was measured using EnVision (PerkinElmer Japan). The amount of ADP generated in four separate measurements was defined as the autophosphorylation intensity of ROS1. $IC_{50}$ values were calculated by curve fitting using GraphPad Prism version 4 (GraphPad software).

The compounds of Examples 19, 21 to 36, 38 to 56, 58 to 61, 63, 65 to 73, 76, 78 to 82, 85 to 86, 88, 90 to 93, 98, 100, 102, 104, 106 to 107, 110, 112 to 114, 118 to 120, 124, 127 to 128, 131, and 133 to 134 exhibited ROS1 autophosphorylation inhibitory activity at $IC_{50}$ of lower than 20 nM. The compounds of Examples 1 to 3, 5 to 6, 8, 10 to 12, 14 to 15, 17 to 18, 20, 37, 57, 62, 75, 77, 83 to 84, 87, 89, 94 to 97, 99, 101, 103, 105, 108, 111, 117, 121 to 122, 125 to 126, 129 to 130, 132, and 135 exhibited ROS1 autophosphorylation inhibitory activity at $IC_{50}$ of 20 nM or higher and lower than 100 nM. The compounds of Examples 4, 7, 9, 13, 64, 74, 109, 115 to 116, and 123 exhibited ROS1 autophosphorylation inhibitory activity at $IC_{50}$ of 100 nM or higher and lower than 150 nM. This suggested that the compounds of the present invention can suppress the growth of cells with the activated ROS1 pathway by inhibiting the ROS1 pathway.

Test Example 3

NTRK Kinase Enzyme Inhibitory Activity Evaluation

NTRK1, NTRK2, and NTRK3 kinase solutions were each prepared. The composition is as follows: 100 mM HEPES (pH 7.4), 0.003% Brij-35, 0.004% Tween-20, 1 mM DTT, NTRK (for NTRK1, Carna Biosciences #08-186, final concentration: 140 ng/mL; for NTRK2, Carna Biosciences #08-187, final concentration: 100 ng/mL; and for NTRK3, Carna Biosciences #08-197, final concentration: 50 ng/mL), and MgCl (final concentration: 10 mM).

Next, a substrate reaction solution was prepared. The composition is as follows: 100 mM HEPES (pH 7.4), 0.003% Brij-35, 0.004% Tween-20, 1 mM DTT, FL-Peptide 27 (Caliper Life Sciences #760424, final concentration: 1.5 µM), and ATP (for NTRK1, final concentration: Km=33 µM; for NTRK2, final concentration: Km=63 µM; and for NTRK3, final concentration: Km=32 µM).

Subsequently, a reaction stop solution was prepared. The composition is as follows: 100 mM HEPES (pH 7.4), 0.015% Brij-35, 40 mM EDTA, and 0.1% Coating Reagent 3 (Caliper Life Sciences #760050).

The NTRK1, NTRK2, and NTRK3 kinase solutions were each added at a concentration of 19 µL/well to a 96-well plate. Each compound for evaluation dissolved in DMSO to achieve each final concentration was added to the plate, mixed using a plate mixer, and then preincubated at room temperature for 20 minutes. The substrate reaction solution was further added thereto at a concentration of 5 µL/well to cause enzymatic reaction (28° C. for 90 minutes under the condition of ATP=Km or 45 minutes under the condition of 1 mM ATP). Then, the reaction stop solution was added thereto at a concentration of 40 µL/well. Substrate phosphorylation intensity was measured using EZ Reader II (Caliper Life Sciences). $IC_{50}$ values were calculated by curve fitting using Microsoft Excel 2010 on the basis of data obtained from three separate measurements.

The compounds of Examples 21, 24, 29, 30, 41, 79, 81, 85, and 90 exhibited NTRK1 inhibitory activity at $IC_{50}$ of lower than 5 nM. The compound of Example 127 exhibited NTRK1 inhibitory activity at $IC_{50}$ of 10 nM or higher and lower than 15 nM. The compounds of Examples 21, 24, 29, 30, 41, 79, 81, 85, and 90 exhibited NTRK2 inhibitory activity at $IC_{50}$ of lower than 10 nM. The compound of Example 127 exhibited NTRK2 inhibitory activity at $IC_{50}$ of 20 nM or higher and lower than 25 nM. The compounds of Examples 21, 24, 29, 30, 41, 79, 81, 85, and 90 exhibited NTRK3 inhibitory activity at IC$_{50}$ of lower than 5 nM. The compound of Example 127 exhibited NTRK3 inhibitory activity at IC$_{50}$ of 5 nM or higher and lower than 10 nM. This suggested that the compounds of the present invention can suppress the growth of cells with activated NTRK by inhibiting NTRK.

Test Example 4

HCC78 Cell Growth Assay

Each compound of the present invention was assayed for its cell growth inhibitory effect using HCC78 cells having ROS1 fusion gene.

HCC78 cells (ATCC) were suspended in RPMI 1640 (Invitrogen, Cat No 11875-093) containing 2% FBS (Hy-Clone, Cat No ANC18297) (hereinafter, referred to as a medium) to adjust their concentration to 3×10$^4$ cells/mL. The suspension was dispensed at a concentration of 100 μL/well to a 96-well culture plate for cell culture (SUMITOMO BAKELITE, Cat No MS-0096S) (hereinafter, referred to as an assay plate). A medium containing each compound for evaluation at a final concentration of 0, 0.15, 0.61, 2.4, 10, 39, 156, 625, or 2,500 nM was dispensed at a concentration of 25 μL/well to the assay plate. In this context, the final concentration of DMSO was set to 0.4%. Then, the cells were cultured for 72 hours in a CO$_2$ incubator.

CellTiter-Glo Luminescent Cell Viability Assay reagent (Promega, Cat No G7571) was dispensed at a concentration of 100 μL/well to the assay plate. The contents in each well were reacted at room temperature for 10 minutes while stirred using a plate mixer. A 100 μL aliquot of each reaction solution was dispensed to each well of a 96-well assay plate, black (CORNING, Cat No 3650). The luminescence intensity of each well was measured using EnVision. The luminescence intensity of each well obtained in four separate measurements was defined as the number of cells. IC$_{50}$ values were calculated by curve fitting using GraphPad Prism version 4.

The compounds of Examples 21, 26, 29 to 30, 35, 38, 40 to 49, 53 to 56, 59, 63, 69, 71 to 72, 79, 81, 88, 90, 92 to 93, 97, 106 to 107, 113, 118 to 120, 124 to 125, and 133 to 134 exhibited a growth inhibitory effect on HCC78 cells having ROS1 fusion gene at IC$_{50}$ of lower than 20 nM. The compounds of Examples 1, 3, 5 to 8, 16, 18, 22, 24 to 25, 28, 31 to 33, 37, 39, 50 to 52, 57 to 58, 60 to 62, 65 to 68, 70, 73, 76 to 78, 80, 82 to 87, 91, 98 to 100, 103 to 104, 108 to 112, 114, 117, 121 to 123, 126 to 129, and 131 to 132 exhibited a growth inhibitory effect on HCC78 cells having ROS1 fusion gene at IC$_{50}$ of 20 nM or higher and lower than 100 nM. The compounds of Examples 2, 4, 9 to 15, 17, 19 to 20, 23, 27, 34, 36, 64, 74 to 75, 89, 94 to 96, 101 to 102, 105, 115 to 116, 130, and 135 exhibited a growth inhibitory effect on HCC78 cells having ROS1 fusion gene at IC$_{50}$ of 100 nM or higher and lower than 600 nM. This suggested that the compounds of the present invention are effective for a tumor having ROS1 fusion gene.

INDUSTRIAL APPLICABILITY

The compound represented by the general formula (I) of the present invention or a pharmacologically acceptable salt thereof has an excellent ROS1 kinase inhibitory effect and NTRK kinase enzyme inhibitory effect and as such, is useful as a therapeutic drug for a tumor with the activated ROS1 pathway and tumor with the activated NTRK pathway.

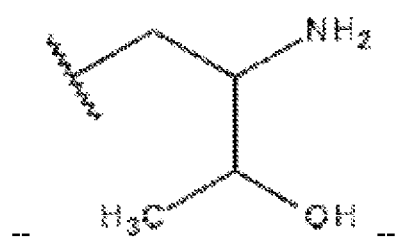

The invention claimed is:

1. A compound represented by the general formula (I) or a pharmacologically acceptable salt thereof:

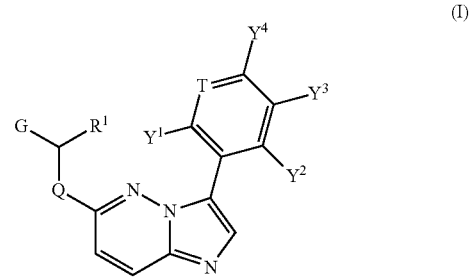

(I)

wherein
R$^1$ represents a hydrogen atom, a C$_1$-C$_6$ alkyl group, a fluoro-C$_1$-C$_6$ alkyl group, or a hydroxy-C$_1$-C$_6$ alkyl group;
Q represents an oxygen atom or R$^a$N, wherein
R$^a$ represents a hydrogen atom or a C$_1$-C$_6$ alkyl group;
G is represented by the following formula (IV):

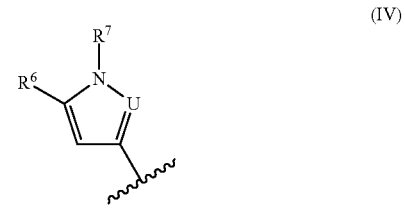

(IV)

wherein
U represents a nitrogen atom or CH;
R$^7$ represents a hydrogen atom or a C1-C6 alkyl group; and
R$^8$ represents a hydrogen atom, a C1-C6 alkyl group, or a halogen atom, or
is represented by G$^a$ to G$^e$:

G$^a$

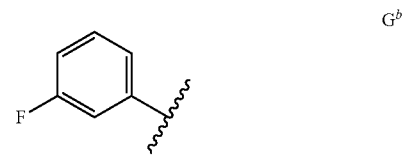

G$^b$

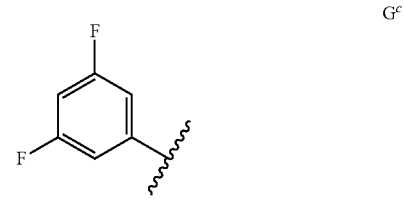

G$^c$

-continued

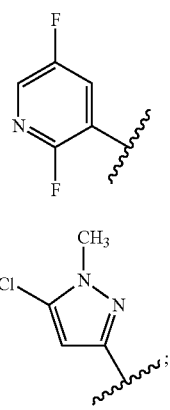
G$^d$

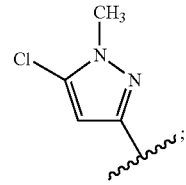
G$^e$;

T represents a nitrogen atom or CR$^b$, wherein
R$^b$ represents a hydrogen atom, a halogen atom, a C$_1$-C$_6$ alkyl group, a C$_1$-C$_6$ alkoxy group, or a cyano group;
Y$^1$ and Y$^2$ each independently represents a hydrogen atom, a halogen atom, a C$_1$-C$_6$ alkyl group, a C$_1$-C$_6$ alkoxy group, or a cyano group;

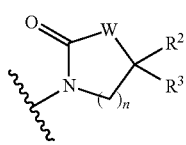
(II)

Y$^3$ represents a hydrogen atom; and
Y$^4$ is represented by —O-M$^2$, formula (V), Y$^a$, or Y$^b$
wherein
M$^2$ is any of the following M$^{2a}$ to M$^{2l}$:

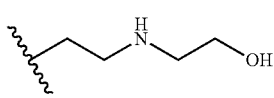
M$^{2a}$

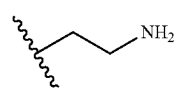
M$^{2b}$

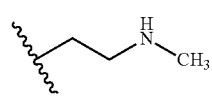
M$^{2c}$

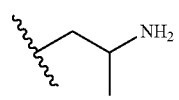
M$^{2d}$

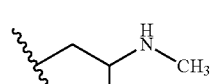
M$^{2e}$

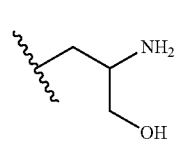
M$^{2f}$

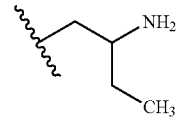
M$^{2g}$

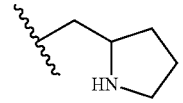
M$^{2h}$

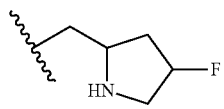
M$^{2i}$

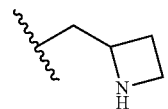
M$^{2j}$

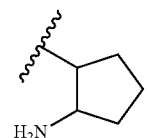
M$^{2k}$

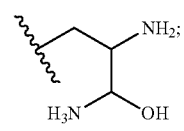
M$^{2l}$ formula (V) is

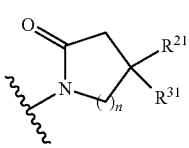
(V)

wherein
n represents 1 or 2; and
R$^{21}$ and R$^{31}$ each independently represents a hydrogen atom, an amino group, a C1-C6 alkyl group, an amino-C1-C6 alkyl group, or a C1-C6 alkylamino group; and
Y$^a$ and Y$^b$ are

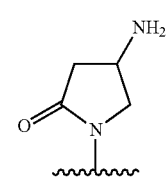
Y$^a$

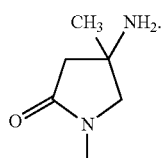
$Y^b$

2. A compound according to claim 1 or a pharmacologically acceptable salt thereof, wherein in the formula (I), Q represents an oxygen atom.

3. A compound according to claim 1 or a pharmacologically acceptable salt thereof, wherein in the formula (I), Q represents $R^aN$, wherein $R^a$ represents a hydrogen atom or a $C_1$-$C_6$ alkyl group.

4. A compound according to claim 1 or a pharmacologically acceptable salt thereof, wherein in the formula (I), G is represented by the following formula (IV):

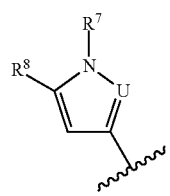
(IV)

wherein

U represents a nitrogen atom or CH;

$R^7$ represents a hydrogen atom or a C1-C6 alkyl group; and $R^8$ represents a hydrogen atom, a C1-C6 alkyl group, or a halogen atom.

5. A compound according to claim 1 or a pharmacologically acceptable salt thereof, wherein in the formula (I), G is any of the following $G^a$ to $G^e$:

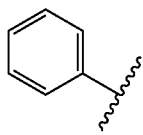
$G^a$

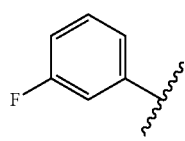
$G^b$

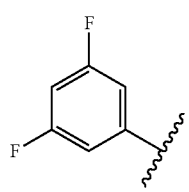
$G^c$

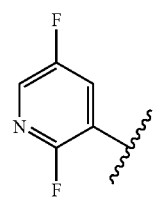
$G^d$

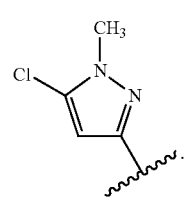
$G^e$

6. A compound according to claim 1 or a pharmacologically acceptable salt thereof, wherein in the formula (I), $Y^4$ represents —O-$M^2$, wherein $M^2$ is any of the following $M^{2a}$ to $M^{2l}$:

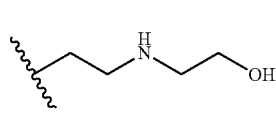
$M^{2a}$

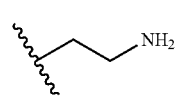
$M^{2b}$

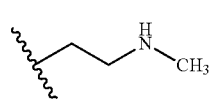
$M^{2c}$

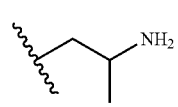
$M^{2d}$

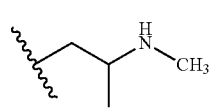
$M^{2e}$

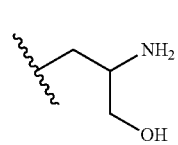
$M^{2f}$

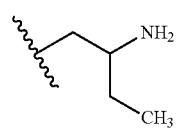
$M^{2g}$

-continued

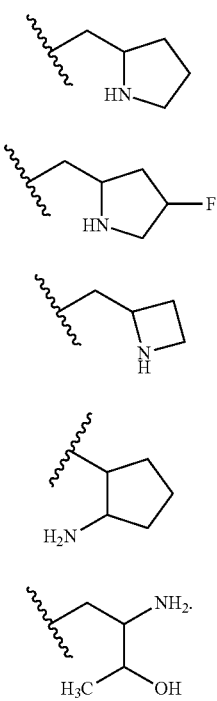

M²ʰ

M²ⁱ

M²ʲ

M²ᵏ

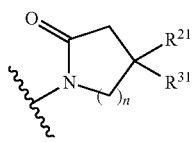

M²ˡ

7. A compound according to claim 1 or a pharmacologically acceptable salt thereof, wherein in the formula (I), Y⁴ is represented by the following formula (V):

(V)

wherein n represents 1 or 2; and $R^{21}$ and $R^{31}$ each independently represents a hydrogen atom, an amino group, a C1-C6 alkyl group, an amino-C1-C6 alkyl group, or a C1-C6 alkylamino group.

8. A compound according to claim 1 or a pharmacologically acceptable salt thereof, wherein in the formula (I), Y⁴ is the following Yᵃ or Yᵇ:

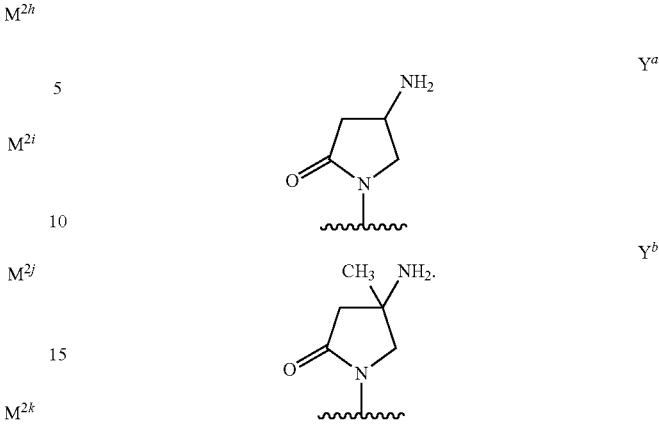

9. A pharmaceutical composition comprising a compound according to claim 1 or a pharmacologically acceptable salt thereof, as an active ingredient.

10. A method for inhibiting proliferation of a cancer cell having a detectable increase in the expression level of ROS1 gene, comprising administering a compound according to claim 1 or a pharmacologically acceptable salt thereof.

11. A method for inhibiting proliferation of a cancer cell having a detectable increase in the expression level of NTRK gene, comprising a compound according to claim 1 or a pharmacologically acceptable salt thereof.

12. A method for inhibiting proliferation of a cancer cell having a detectable expression of ROS1 fusion gene, comprising administering a compound according to claim 1 or a pharmacologically acceptable salt thereof.

13. A method for inhibiting proliferation of a cancer cell having a detectable expression of NTRK fusion gene, comprising administering a compound according to claim 1 or a pharmacologically acceptable salt thereof.

14. A method for inhibiting proliferation of a cancer cell by the inhibition of ROS1 kinase enzyme activity, comprising administering a compound according to claim 1 or a pharmacologically acceptable salt thereof.

15. A method for inhibiting proliferation of a cancer cell by the inhibition of NTRK kinase enzyme activity, comprising a compound according to claim 1 or a pharmacologically acceptable salt thereof.

16. A method for inhibiting ROS1 kinase enzyme activity in a subject, comprising administering a compound according to claim 1 or a pharmacologically acceptable salt thereof.

17. A method for inhibiting NTRK kinase enzyme activity in a subject, comprising administering a compound according to claim 1 or a pharmacologically acceptable salt thereof.

* * * * *

UNITED STATES PATENT AND TRADEMARK OFFICE
CERTIFICATE OF CORRECTION

PATENT NO. : 9,751,887 B2  
APPLICATION NO. : 14/926973  
DATED : September 5, 2017  
INVENTOR(S) : Y. Takeda et al.

Page 1 of 2

It is certified that error appears in the above-identified patent and that said Letters Patent is hereby corrected as shown below:

In the Claims

| Column | Line | Error |
|---|---|---|
| 240 (Claim 1, | 30 Line 27) Formula IV | " 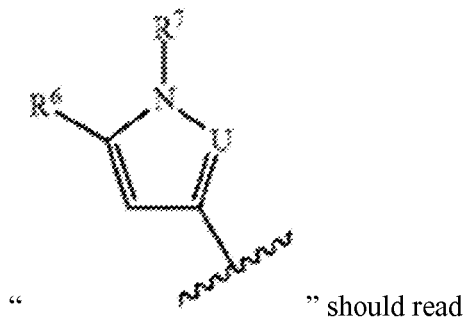 " should read -- 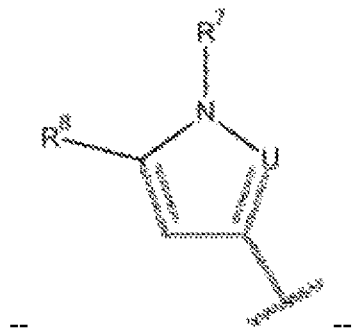 -- |

Signed and Sealed this  
Tenth Day of July, 2018

Andrei Iancu  
*Director of the United States Patent and Trademark Office*

CERTIFICATE OF CORRECTION (continued)
U.S. Pat. No. 9,751,887 B2

242       32  
(Claim 1, Line 162)    " 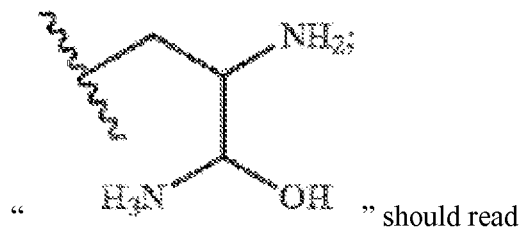 " should read